United States Patent
Matsumoto et al.

(10) Patent No.: US 7,524,841 B2
(45) Date of Patent: *Apr. 28, 2009

(54) 4,4-DISUBSTITUTED PIPERIDINE DERIVATIVES HAVING CCR3 ANTAGONISM

(75) Inventors: Yoshiyuki Matsumoto, Tokyo (JP); Minoru Imai, Tokyo (JP); Yoshiyuki Sawai, Tokyo (JP); Susumu Takeuchi, Tokyo (JP); Akinobu Nakanishi, Tokyo (JP); Kunio Minamizono, Tokyo (JP); Tomonori Yokoyama, Tokyo (JP)

(73) Assignee: Teijin Limited, Osaka (JP)

( * ) Notice: Subject to any disclaimer, the term of this patent is extended or adjusted under 35 U.S.C. 154(b) by 889 days.

This patent is subject to a terminal disclaimer.

(21) Appl. No.: 10/512,339

(22) PCT Filed: Apr. 16, 2003

(86) PCT No.: PCT/JP03/04842

§ 371 (c)(1),
(2), (4) Date: Oct. 22, 2004

(87) PCT Pub. No.: WO03/091245

PCT Pub. Date: Nov. 6, 2003

(65) Prior Publication Data

US 2007/0037851 A1  Feb. 15, 2007

(30) Foreign Application Priority Data

Apr. 25, 2002 (JP) ............................. 2002-123883
Aug. 21, 2002 (JP) ............................. 2002-240508

(51) Int. Cl.
*C07D 487/04* (2006.01)
*C07D 403/12* (2006.01)
*C07D 403/14* (2006.01)
*A61K 31/4523* (2006.01)
*A61K 31/454* (2006.01)
*A61P 11/06* (2006.01)

(52) U.S. Cl. ...................... 514/223.2; 544/12; 544/287; 546/199; 546/201; 546/202; 514/266.21; 514/322; 514/323; 514/324

(58) Field of Classification Search .................. 544/12, 544/287; 546/199, 201, 202; 514/223.2, 514/266.21, 322, 323, 324
See application file for complete search history.

(56) References Cited

FOREIGN PATENT DOCUMENTS

| WO | WO 99/25686 A1 | 5/1999 |
|----|----------------|--------|
| WO | WO 99/37304 A1 | 7/1999 |
| WO | WO 00/53600 A1 | 9/2000 |
| WO | WO 01/07436 A2 | 2/2001 |
| WO | WO 01/10439 A1 | 2/2001 |
| WO | WO 01/32615 A1 | 5/2001 |
| WO | WO 02/068409 A1 | 9/2002 |
| WO | WO 03/028641 A2 | 4/2003 |

*Primary Examiner*—Kahsay Habte
(74) *Attorney, Agent, or Firm*—Sughrue Mion, PLLC

(57) ABSTRACT

The invention provides low molecular compounds having activity which inhibits binding of CCR3 ligands to CCR3 on target cells, i.e. CCR3 antagonists. The invention also provides 4,4-(disubstituted)piperidine derivatives represented by formula (I) below, pharmaceutically acceptable acid adducts thereof, or pharmaceutically acceptable $C_1$-$C_6$ alkyl adducts thereof, as well as pharmaceutical compositions comprising them as effective ingredients, which are useful for treatment or prevention of diseases associated with CCR3, such as asthma and allergic rhinitis.

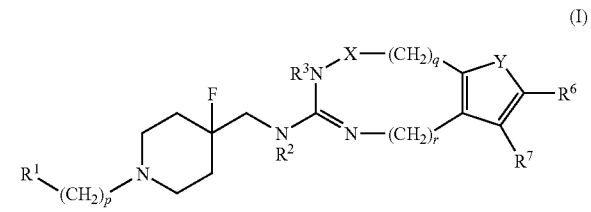

(I)

25 Claims, No Drawings

4,4-DISUBSTITUTED PIPERIDINE DERIVATIVES HAVING CCR3 ANTAGONISM

This is a National Stage of Application No, PCT/JP03/04842 filed on Apr. 16, 2003.

TECHNICAL FIELD

The present invention relates to 4,4-(disubstituted)piperidine derivatives with CCR3 (C—C Chemokine Receptor 3) antagonism. More specifically, the invention relates to CCR3 antagonists with anticipated effects as therapeutic and/or prophylactic agents for allergic conditions such as bronchial asthma, allergic rhinitis, atopic dermatitis, urticaria, contact dermatitis or allergic conjunctivitis, inflammatory bowel diseases such as ulcerative colitis or Crohn's disease, diseases whose major factor is accelerated or sustained increase or tissue infiltration of eosinophils, basophils or activated T cells, such as eosinophilia, eosinophilic gastroenteritis, eosinophilic enteropathy, eosinophilic fasciitis, eosinophilic granuloma, eosinophilic pustular folliculitis, eosinophilic pneumonia or eosinophilic leukemia, or AIDS (Acquired Immune Deficiency Syndrome) which is caused by infection with HIV (Human Immunodeficiency Virus).

BACKGROUND ART

In recent years, the concept that allergic conditions such as bronchial asthma are fundamentally diseases of chronic inflammation has been established, and accumulation of eosinophils at local sites of inflammation is considered to be a major feature thereof (for example, see Busse, W. W. J. Allergy Clin. Immunol. 1998, 102, S17-S22; Fujisawa, T. Gendai Iryou 1999, 31, 1297). For example, administration of anti-adhesion molecule (ICAM-1) antibodies in monkey asthma models inhibits accumulation of eosinophils and suppresses late asthmatic symptoms, suggesting the importance of eosinophils in allergic conditions (Wegner, C. D. et al. Science, 1990, 247, 456).

Eotaxins have been identified as specific chemotactic factors inducing accumulation and/or migration of eosinophils (for example, see Jose, P. J., et al. J. Exp. Med. 1994, 179, 881; Garcia-Zepda, E. A. et al. Nature Med. 1996, 2, 449; Ponath, P. D. et al. J. Clin. Invest. 1996, 97, 604; Kitaura, M. et al. J. Biol. Chem. 1996, 271, 7725). It has also been demonstrated that eotaxins bind to CCR3 expressed on eosinophils, exhibiting an effect of promoting accumulation and/or migration of eosinophils. In addition, chemotactic factors such as eotaxin-2, RANTES (abbreviation for Regulated on Activation, Normal T-cell Expressed and Secreted) antibodies, MCP-2 (abbreviation for Monocyte Chemoattractant Protein-2), MCP-3 (abbreviation for Monocyte Chemoattractant Protein-3), MCP-4 (abbreviation for Monocyte Chemoattractant Protein-4) and the like are also known to exhibit effects similar to those of eotaxins via CCR3, although their potency is weaker than that of eotaxins (for example, see Kitaura, M. et al. J. Biol. Chem. 1996, 271, 7725; Daugherty, B. L. et al. J. Exp. Med. 1996, 183, 2349; Ponath, P. D. et al. J. Exp. Med. 1996, 183, 2437; Hiath, H. et al. J. Clin. Invest. 1997, 99, 178; Patel, V. P. et al. J. Exp. Med. 1997, 185, 1163; Forssmann, U. et al. J. Exp. Med. 185, 2171, 1997).

The reported effects of eotaxins on eosinophils include not only inducing migration of eosinophils, but also effects related to eosinophil activation, such as augmenting expression of adhesion molecule receptor (CD11b) (for example, see Tenscher, K. et al. Blood, 1996, 88, 3195), accelerating production of active oxygen (for example, see Elsner, J. et al. Eur. J. Immunol. 1996, 26, 1919), and promoting release of EDN (Eosinophil-Derived Neurotoxin) (see El-Shazly, et al. Int. Arch. Allergy Immunol. 1998, 117 (suppl.1), 55). Eotaxins have also been reported to accelerate liberation of eosinophils and their precursors from the bone marrow into the blood (for example, see Palframan, R. T. et al. Blood 1998, 91, 2240).

Numerous reports indicate that eotaxins and CCR3 play important roles in allergic conditions such as bronchial asthma. For example, it has been reported that infiltration of eosinophils is suppressed by anti-eotaxin antibodies in mouse asthma models (Gonzalo, J.-A. et al. J. Clin. Invest. 1996, 98, 2332), that infiltration of eosinophils is suppressed by anti-eotaxin antiserum in mouse cutaneous allergy models (Teixeira, M. M. et al. J. Clin. Invest. 1997, 100, 1657), that formation of pulmonary granulomas is suppressed by anti-eotaxin antibodies in mouse models (see Ruth, J. H. et al. J. Immunol. 1998, 161, 4276), that infiltration of eosinophils is suppressed in eotaxin gene-deficient mouse asthma models and interstitial keratitis models (see Rothenberg, M. E. et al. J. Exp. Med. 1997, 185, 785), that expression of eotaxins and CCR3 is augmented on both the genetic and protein level in asthmatic bronchi compared to healthy controls (see Ying, S. et al. Eur. J. Immunol. 1997, 27, 3507), and that eotaxin expression is augmented in nasal subepithelial tissue of chronic sinusitis patients (Am. J. Respir. Cell Mol. Biol. 1997, 17, 683).

Also, based on reports that eotaxins are abundantly expressed at sites of inflammation in the inflammatory bowel diseases of ulcerative colitis and Crohn's disease (see Garcia-Zepda, E. A. et al. Nature Med. 1996, 2, 449), it is believed that eotaxins also play an important role in such inflammatory conditions.

These data strongly suggest that eotaxins, via CCR3-mediated accumulation and activation of eosinophils at lesion sites, are intimately involved in the onset, progression or sustaining of diseases wherein eosinophils are closely associated with developing lesions, including, for example, allergic conditions such as bronchial asthma, allergic rhinitis, atopic dermatitis, urticaria, contact dermatitis or allergic conjunctivitis, inflammatory bowel diseases such as ulcerative colitis or Crohn's disease, and eosinophilia, eosinophilic gastroenteritis, eosinophilic enteropathy, eosinophilic fasciitis, eosinophilic granuloma, eosinophilic pustular folliculitis, eosinophilic pneumonia or eosinophilic leukemia. In addition, since CCR3 is expressed not only on eosinophils but also on basophils and Th2 lymphocytes, and eotaxins induce intracellular calcium ion concentration increase and migration of these cells, it is believed that eotaxins and CCR3 are involved in the onset, progression and sustaining of diseases associated with these cells, such as allergic conditions, also via accumulation and activation of basophils and Th2 lymphocytes (for example, see Sallusto, F. et al. Science 1997, 277, 2005; Gerber, B. O. et al. Current Biol. 1997, 7, 836; Sallusto, F. et al. J. Exp. Med. 1998, 187, 875; Uguccioni, M. et al. J. Clin. Invest. 1997, 100, 1137; Yamada, H. et al. Biochem Biophys. Res. Commun. 1997, 231, 365).

Consequently, compounds which inhibit binding of CCR3 to CCR3 ligands such as eotaxins, or in other words CCR3 antagonists, should inhibit the effects of the CCR3 ligands on target cells and are therefore expected be useful as therapeutic and/or prophylactic agents for allergic conditions and inflammatory bowel disease. Yet, no agents having such activity have been known.

Moreover, it has also been reported that HIV-1 (Human Immunodeficiency Virus-1) may utilize CCR3 to infect host cells, and therefore CCR3 antagonists are also expected to be useful as therapeutic or prophylactic agents for AIDS (Acquired Immune Deficiency Syndrome) caused by HIV infection (for example, see Choe, H. et al. Cell 1996, 85, 1135; Doranz, B. J. et al. Cell 1996, 85, 1149).

Recently, piperidine derivatives (see Patent Specification No. WO9802151, Patent Specification No. WO9804554, Patent Specification No. WO0029377, Patent Specification No. WO0031033, Patent Specification No. WO0035449, Patent Specification No. WO0035451, Patent Specification No. WO0035452, Patent Specification No. WO0035453, Patent Specification No. WO0035454, Patent Specification No. WO0035876, Patent Specification No. WO0035877, Patent Specification No. WO0051607, Patent Specification No. WO0051608, Patent Specification No. WO0051609, Patent Specification No. WO0051610, Patent Specification No. WO0053600, Patent Specification No. WO0058305, Patent Specification No. WO0059497, Patent Specification No. WO0059498, Patent Specification No. WO0059502, Patent Specification No. WO0059503, Patent Specification No. WO0076511, Patent Specification No. WO0076512, Patent Specification No. WO0076513, Patent Specification No. WO0076514, Patent Specification No. WO0076972, Patent Specification No. WO0076973, Patent Specification No. WO0105782, Patent Specification No. WO0114333, Patent Specification No. WO0164216, Patent Specification No. WO0177101, Patent Specification No. WO0192227, Patent Specification No. WO0198268, Patent Specification No. WO0198269, Patent Specification No. WO0198270, Patent Specification No. WO0202525, Patent Specification No. WO0204420), piperazine derivatives (see Patent Specification No. EP0903349, Patent Specification No. WO0034278, Patent Specification No. WO0102381) and other low molecular compounds (see Patent Specification No. WO9955324, Patent Specification No. WO9955330, Patent Specification No. WO0004003, Patent Specification No. WO0027800, Patent Specification No. WO0027835, Patent Specification No. WO0027843, Patent Specification No. WO0031032, Patent Specification No. WO0041685, Patent Specification No. WO0053172, Patent Specification No. WO0109088, Patent Specification No. WO0128987, Patent Specification No. WO0129000), have been reported to exhibit antagonism against CCR3. However, these compounds differ from the compounds of the invention.

Patent Specification No. WO0107436 and Patent Specification No. WO9937304 describe oxopiperazine derivatives having inhibiting activity on Factor Xa, but they do not specifically mention the piperidine derivatives of the invention, nor is it known whether these oxopiperazine derivatives exhibit competitive inhibition for CCR3. Patent Specification No. WO0132615 and Patent Specification No. WO0268409 describe N-substituted piperidine derivatives having NMDA/NR2B antagonism, but they do not specifically mention the 4,4-(disubstituted)piperidine derivatives of the invention, nor is it known whether these N-substituted piperidine derivatives exhibit competitive inhibition for CCR3.

It is an object of the present invention to provide low molecular compounds having activity which inhibits binding of CCR3 ligands to CCR3 on target cells, i.e. CCR3 antagonists.

It is another object of the invention to provide therapeutic and/or prophylactic agents for diseases in which a causal factor is binding of a CCR3 ligand to CCR3 on target cells.

DISCLOSURE OF THE INVENTION

The present invention provides the following:
(1) Compounds represented by the following formula (I):

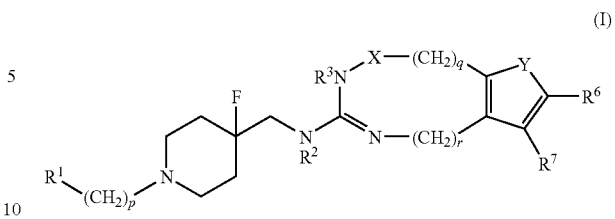

(wherein $R^1$ represents phenyl, $C_3$-$C_8$ cycloalkyl or an aromatic heterocyclic group (having 1-3 atoms selected from the group consisting of oxygen, sulfur and nitrogen as hetero atoms), the phenyl or aromatic heterocyclic group of $R^1$ may optionally fuse with a benzene ring or aromatic heterocyclic group (having 1-3 atoms selected from the group consisting of oxygen, sulfur and nitrogen as hetero atoms) to form a fused ring, the phenyl, $C_3$-$C_8$ cycloalkyl or aromatic heterocyclic group, or fused ring, in $R^1$ may be unsubstituted, or substituted with one or more substituents selected from the group consisting of halogens, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_1$-$C_6$ alkylsulfonyl, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, piperidylcarbonyl, morpholinylcarbonyl, pyrrolidinylcarbonyl, piperazinylcarbonyl, N-methoxycarbamoyl, (formyl)amino and ureido, and the substituent of the phenyl, $C_3$-$C_8$ cycloalkyl or aromatic heterocyclic group, or fused ring, of $R^1$ may be unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, $C_1$-$C_6$ alkylthio, amino, mono($C_1$-$C_6$ alkyl)amino, di($C_1$-$C_6$ alkyl)amino, pyrrolidinyl, piperidyl, $C_3$-$C_7$ lactam, carbamoyl, $C_2$-$C_7$ N-alkylcarbamoyl, $C_2$-$C_7$ alkoxycarbonyl, carboxyl, hydroxy, benzoyl, cyano, trifluoromethyl, halogen and tert-butoxycarbonylamino, provided that when $R^1$ is $C_3$-$C_8$ cycloalkyl, the substituent does not include amino, mono($C_1$-$C_6$ alkyl)amino or di($C_1$-$C_6$ alkyl)amino;

p represents an integer of 1-6;

$R^2$ and $R^3$ may be the same or different and each independently represents hydrogen, $C_1$-$C_6$ alkyl or phenyl, where the $C_1$-$C_6$ alkyl or phenyl group of $R^2$ and $R^3$ may be unsubstituted, or substituted with one or more substituents selected from the group consisting of halogens, hydroxy, $C_1$-$C_6$ alkyl, $C_2$-$C_7$ alkoxycarbonyl, amino, carbamoyl, carboxyl, cyano and $C_1$-$C_6$ alkoxy;

X represents —CO—, —$SO_2$—, —$CH_2$—, —CS— or a single bond;

q represents 0 or 1;

r represents 0 or 1;

Y represents —($R^4$)C=C($R^5$)—, —S— or —$NR^8$—;

$R^4$, $R^5$, $R^6$ and $R^7$ may be the same or different, and each independently represents hydrogen, a halogen, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, phenylsulfonyl, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_4$-$C_{10}$ cycloalkanoylamino, $C_1$-$C_6$ alkenoylamino, $C_1$-$C_6$ alkylsulfonyl, $C_1$-$C_6$ alkylsulfonylamino, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, N-($C_7$-$C_{12}$ phenylalkyl)carbamoyl, piperidylcarbonyl, morpholinylcarbonyl, pyrrolidinylcarbonyl, piperazinylcarbonyl, N-methoxycarbamoyl, sulfamoyl, $C_1$-$C_6$ N-alkylsulfamoyl, (formyl)amino, (thioformyl)amino, ureido or thioureido, where the aforementioned groups of $R^4$, $R^5$, $R^6$ and $R^7$ each may be independently unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, ($C_1$-$C_6$ alkoxy) ($C_1$-$C_6$ alkoxy), phenyl ($C_1$-$C_6$ alkoxy), $C_1$-$C_6$ alkylthio, amino, mono ($C_1$-$C_6$ alkyl)amino, di($C_1$-$C_6$ alkyl) amino, pyrrolidinyl, piperidyl, ($C_2$-$C_7$ alkanoyl)piperidyl, $C_3$-$C_7$ lactam, carbamoyl, $C_2$-$C_7$ N-alkylcarbamoyl, $C_4$-$C_9$ N-cycloalkylcarbamoyl, N-phenylcarbamoyl, N-($C_7$-$C_{12}$ phenylalkyl)carbamoyl, $C_2$-$C_7$ alkanoylamino, $C_2$-$C_7$ alkoxycarbonyl, carboxyl, hydroxy, benzoyl, cyano, trifluoromethyl, halogens, tert-butoxycarbonylamino, $C_1$-$C_6$ alkylsulfonyl and heterocycles or aromatic heterocycles (where a heterocycle or aromatic heterocycle has 1-3 atoms selected from the group consisting of oxygen, sulfur and nitrogen as hetero atoms, and may be substituted with $C_1$-$C_6$ alkyl); and $R^8$ represents hydrogen or $C_1$-$C_6$ alkyl, where the $C_1$-$C_6$ alkyl group of $R^8$ may be unsubstituted, or substituted with one or more substituents selected from the group consisting of halogens, hydroxy, cyano, nitro, carboxyl, carbamoyl, mercapto, guanidino, $C_3$-$C_8$ cycloalkyl, $C_1$-$C_6$ alkoxy, $C_1$-$C_6$ alkylthio, phenyl (where phenyl may be substituted, or substituted with one or more substituents selected from the group consisting of halogens, hydroxy, $C_1$-$C_6$ alkyl, $C_1$-$C_6$ alkoxy and benzyloxy), phenoxy, benzyloxy, benzyloxycarbonyl, $C_2$-$C_7$ alkanoyl, $C_2$-$C_7$ alkoxycarbonyl, $C_2$-$C_7$ alkanoyloxy, $C_2$-$C_7$ alkanoylamino, $C_2$-$C_7$ N-alkylcarbamoyl, $C_2$-$C_6$ alkylsulfonyl, amino, mono($C_1$-$C_6$ alkyl)amino, di($C_1$-$C_6$ alkyl)amino and ureido], pharmaceutically acceptable acid adducts thereof, or pharmaceutically acceptable $C_1$-$C_6$ alkyl adducts thereof;

(2) Compounds according to (1), pharmaceutically acceptable acid adducts thereof, or pharmaceutically acceptable $C_1$-$C_6$ alkyl adducts thereof, wherein X in formula (I) is —$SO_2$—;

(3) Compounds according to (1), pharmaceutically acceptable acid adducts thereof, or pharmaceutically acceptable $C_1$-$C_6$ alkyl adducts thereof, wherein X in formula (I) is —CO—;

(4) Compounds according to (1), pharmaceutically acceptable acid adducts thereof, or pharmaceutically acceptable $C_1$-$C_6$ alkyl adducts thereof, wherein X in formula (I) is —$CH_2$—;

(5) Compounds according to (1), pharmaceutically acceptable acid adducts thereof, or pharmaceutically acceptable $C_1$-$C_6$ alkyl adducts thereof, wherein X in formula (I) is —CS—;

(6) Compounds according to (1), pharmaceutically acceptable acid adducts thereof, or pharmaceutically acceptable $C_1$-$C_6$ alkyl adducts thereof, wherein X in formula (I) is a single bond;

(7) Compounds according to any one of (1) to (6), pharmaceutically acceptable acid adducts thereof, or pharmaceutically acceptable $C_1$-$C_6$ alkyl adducts thereof, wherein Y in formula (I) is —($R^4$)C=C($R^5$)—;

(8) Compounds according to any one of (1) to (6), pharmaceutically acceptable acid adducts thereof, or pharmaceutically acceptable $C_1$-$C_6$ alkyl adducts thereof, wherein Y in formula (I) is —S—;

(9) Compounds according to any one of (1) to (6), pharmaceutically acceptable acid adducts thereof, or pharmaceutically acceptable $C_1$-$C_6$ alkyl adducts thereof, wherein Y in formula (I) is —$NR^8$—;

(10) Compounds according to any one of (1) to (9), pharmaceutically acceptable acid adducts thereof, or pharmaceutically acceptable $C_1$-$C_6$ alkyl adducts thereof, wherein $R^1$ in formula (I) is substituted or unsubstituted phenyl;

(11) Compounds according to any one of (1) to (10), pharmaceutically acceptable acid adducts thereof, or pharmaceutically acceptable $C_1$-$C_6$ alkyl adducts thereof, wherein $R^2$ in formula (I) is hydrogen;

(12) Compounds according to any one of (1) to (11), pharmaceutically acceptable acid adducts thereof, or pharmaceutically acceptable $C_1$-$C_6$ alkyl adducts thereof, wherein $R^3$ in formula (I) is hydrogen;

(13) Compounds according to any one of (1) to (12), pharmaceutically acceptable acid adducts thereof, or pharmaceutically acceptable $C_1$-$C_6$ alkyl adducts thereof, wherein q=0 and r=0 in formula (I);

(14) Compounds according to any one of (1) to (12), pharmaceutically acceptable acid adducts thereof, or pharmaceutically acceptable $C_1$-$C_6$ alkyl adducts thereof, wherein q=1 and r=0 in formula (I);

(15) Compounds according to any one of (1) to (12), pharmaceutically acceptable acid adducts thereof, or pharmaceutically acceptable $C_1$-$C_6$ alkyl adducts thereof, wherein q=0 and r=1 in formula (I);

(16) Compounds according to any one of (1) to (15), pharmaceutically acceptable acid adducts thereof, or pharmaceutically acceptable $C_1$-$C_6$ alkyl adducts thereof, wherein p=1 in formula (I);

(17) Compounds according to (2), pharmaceutically acceptable acid adducts thereof, or pharmaceutically acceptable $C_1$-$C_6$ alkyl adducts thereof, wherein Y is —($R^4$)C=C($R^5$)—, $R^1$ is substituted or unsubstituted phenyl, $R^2$ is hydrogen, $R^3$ is hydrogen, q=0, r=0 and p=1 in formula (I);

(18) Compounds according to (3), pharmaceutically acceptable acid adducts thereof, or pharmaceutically acceptable $C_1$-$C_6$ alkyl adducts thereof, wherein Y is —($R^4$)C=C($R^5$)—, $R^1$ is substituted or unsubstituted phenyl, $R^2$ is hydrogen, $R^3$ is hydrogen, q=0, r=0 and p=1 in formula (I);

(19) Compounds according to (4), pharmaceutically acceptable acid adducts thereof, or pharmaceutically acceptable $C_1$-$C_6$ alkyl adducts thereof, wherein Y is —($R^4$)C=C($R^5$)—, $R^1$ is substituted or unsubstituted phenyl, $R^2$ is hydrogen, $R^3$ is hydrogen, q=0, r=0 and p=1 in formula (I);

(20) Compounds according to (6), pharmaceutically acceptable acid adducts thereof, or pharmaceutically acceptable $C_1$-$C_6$ alkyl adducts thereof, wherein Y is —($R^4$)C=C($R^5$)—, $R^1$ is substituted or unsubstituted phenyl, $R^2$ is hydrogen, $R^3$ is hydrogen, q=0, r=0 and p=1 in formula (I);

(21) Compounds according to any one of (17) to (20), pharmaceutically acceptable acid adducts thereof or pharmaceutically acceptable $C_1$-$C_6$ alkyl adducts thereof, wherein $R^4$ and $R^5$ in formula (I) may be the same or different and each is independently hydrogen, a halogen, hydroxy, cyano, nitro, carboxyl, $C_1$-$C_6$ alkyl, $C_1$-$C_6$ alkoxy, $C_2$-$C_7$ alkoxycarbonyl, $C_2$-$C_7$ alkanoylamino, $C_1$-$C_6$ alkylsulfonyl, amino, carbamoyl, $C_2$-$C_7$ N-alkylcarbamoyl, sulfamoyl or $C_1$-$C_6$ N-alkylsulfamoyl;

(22) Compounds according to any one of (17) to (20), pharmaceutically acceptable acid adducts thereof or pharmaceutically acceptable $C_1$-$C_6$ alkyl adducts thereof, wherein $R^4$ and $R^5$ in formula (I) may be the same or different and each is independently a halogen, hydroxy, cyano, nitro, $C_1$-$C_6$ alkyl, $C_1$-$C_6$ alkoxy, $C_2$-$C_7$ alkoxycarbonyl, $C_1$-$C_6$ alkylsulfonyl or $C_1$-$C_6$ N-alkylsulfamoyl;

(23) A compound according to any one of (17) to (22) wherein the substituents of $R^1$ in formula (I) above may be the same or different and each is independently a halogen, hydroxy, cyano, nitro, $C_1$-$C_6$ alkyl or $C_1$-$C_6$ alkoxy, a pharmaceutically acceptable acid adduct thereof or a pharmaceutically acceptable $C_1$-$C_6$ alkyl adduct thereof.

(24) A pharmaceutical composition with CCR3 antagonism, which comprises as an effective ingredient thereof a compound represented by formula (I) above according to any one of (1) to (23), a pharmaceutically acceptable acid adduct thereof or a pharmaceutically acceptable $C_1$-$C_6$ alkyl adduct thereof.

(25) A prophylactic and/or therapeutic composition for a disease associated with CCR3, which comprises as an effective ingredient thereof a compound represented by formula (I) above according to any one of (1) to (23), a pharmaceutically acceptable acid adduct thereof or a pharmaceutically acceptable $C_1$-$C_6$ alkyl adduct thereof.

(26) A prophylactic and/or therapeutic composition according to (25), wherein said condition is an allergic condition.

(27) A prophylactic and/or therapeutic composition according to (26), wherein said allergic condition is bronchial asthma, allergic rhinitis, atopic dermatitis, urticaria, contact dermatitis or allergic conjunctivitis.

(28) A prophylactic and/or therapeutic composition according to (25), wherein said condition is inflammatory bowel disease.

(29) A prophylactic and/or therapeutic composition according to (25), wherein said condition is AIDS (Acquired Immune Deficiency Syndrome)

(30) Prophylactic and/or therapeutic compositions according to (25), wherein the disease is eosinophilia, eosinophilic gastroenteritis, eosinophilic enteropathy, eosinophilic fasciitis, eosinophilic granuloma, eosinophilic pustular folliculitis, eosinophilic pneumonia or eosinophilic leukemia.

BEST MODE FOR CARRYING OUT THE INVENTION

The number of substituents on the phenyl, $C_3$-$C_8$ cycloalkyl or aromatic heterocyclic group, or fused ring, of $R^1$, and the number of substituents on the substituents of the phenyl, $C_3$-$C_8$ cycloalkyl or aromatic heterocyclic group, or fused ring, of $R^1$ may be any chemically possible number, but it is preferably 0-15, more preferably 0-10 and more preferably 0-7.

The term "$C_3$-$C_8$ cycloalkyl" for $R^1$ means a cyclic alkyl group such as, for example, cyclopropyl, cyclobutyl, cyclopentyl, cyclohexyl, cycloheptyl or cyclooctyl, and as preferred examples there may be mentioned cyclopropyl, cyclopentyl and cyclohexyl.

The term "aromatic heterocyclic group (having 1-3 atoms selected from the group consisting of oxygen, sulfur and nitrogen as hetero atoms)" for $R^1$ means an aromatic heterocyclic group such as, for example, thienyl, furyl, pyrrolyl, imidazolyl, pyrazolyl, oxazolyl, isooxazolyl, thiazolyl, isothiazolyl, pyridyl, pyrimidinyl, triazinyl, triazolyl, oxadiazolyl (furazanyl) or thiadiazolyl, and as preferred examples there may be mentioned thienyl, furyl, pyrrolyl and pyridyl.

The term "fused ring" for $R^1$ means a bicyclic aromatic heterocyclic group formed by fusing the phenyl or aromatic heterocyclic group with a benzene ring or an aromatic heterocyclic group (having 1-3 atoms selected from the group consisting of oxygen, sulfur and nitrogen as hetero atoms) at any possible position, and as preferred examples there may be mentioned naphthyl, indolyl, benzofuranyl, benzothienyl, quinolyl and benzoimidazolyl.

$R^1$ according to the invention is most preferably phenyl, thienyl, furanyl, pyrrolyl, naphthyl, benzothienyl, benzofuranyl or indolyl.

The term "halogen" as a substituent on the phenyl, $C_3$-$C_8$ cycloalkyl or aromatic heterocyclic group, or fused ring, of $R^1$ means fluorine, chlorine, bromine and iodine or the like, and as preferred examples there may be mentioned fluorine, chlorine, bromine or iodine.

The term "$C_1$-$C_6$ alkyl" as a substituent on $R^1$ means a $C_1$-$C_6$ straight-chain or branched alkyl group such as, for example, methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, isohexyl, 2-methylpentyl or 1-ethylbutyl, and as preferred examples there may be mentioned methyl, ethyl, propyl and isopropyl.

The term "$C_3$-$C_8$ cycloalkyl" as a substituent on $R^1$ has the same meaning as "$C_3$-$C_8$ cycloalkyl" for $R^1$ itself, and the same preferred examples may be mentioned.

The term "$C_2$-$C_6$ alkenyl" as a substituent on $R^1$ means a $C_2$-$C_6$ straight-chain or branched alkenyl group such as, for example, vinyl, allyl, 1-propenyl, 2-butenyl, 3-butenyl, 2-methyl-1-propenyl, 4-pentenyl, 5-hexenyl or 4-methyl-3-pentenyl, and as preferred examples there may be mentioned vinyl and 2-methyl-1-propenyl.

The term "$C_1$-$C_6$ alkoxy" as a substituent on $R^1$ means a group comprising a $C_1$-$C_6$ alkyl group and an oxy group, and as preferred examples there may be mentioned methoxy and ethoxy.

The term "$C_1$-$C_6$ alkylthio" as a substituent on $R^1$ means a group comprising a $C_1$-$C_6$ alkyl group and a thio group, and as preferred examples there may be mentioned methylthio and ethylthio.

The term "$C_3$-$C_5$ alkylene" as a substituent on $R^1$ means a $C_3$-$C_5$ divalent alkylene group such as, for example, trimethylene, tetramethylene, pentamethylene or 1-methyltrimethylene, and as preferred examples there may be mentioned trimethylene and tetramethylene.

The term "$C_2$-$C_4$ alkyleneoxy" as a substituent on $R^1$ means a group comprising a $C_2$-$C_4$ divalent alkylene group and an oxy group, such as, for example, ethyleneoxy (—$CH_2CH_2O$—), trimethyleneoxy (—$CH_2CH_2CH_2O$—), tetramethyleneoxy (—$CH_2CH_2CH_2CH_2O$—) or 1,1-dimethylethyleneoxy (—$CH_2C(CH_3)_2O$—), and as preferred examples there may be mentioned ethyleneoxy and trimethyleneoxy.

The term "$C_1$-$C_3$ alkylenedioxy" as a substituent on $R^1$ means a group comprising a $C_1$-$C_3$ divalent alkylene group and two oxy groups, such as, for example, methylenedioxy (—$OCH_2O$—), ethylenedioxy (—$OCH_2CH_2O$—), trimethylenedioxy (—$OCH_2CH_2CH_2O$—) or propylenedioxy (—$OCH_2CH(CH_3)O$—), and as preferred examples there may be mentioned methylenedioxy and ethylenedioxy.

The term "$C_2$-$C_7$ alkanoyl" as a substituent on $R^1$ means a $C_2$-$C_7$ straight-chain or branched alkanoyl group such as, for example, acetyl, propanoyl, butanoyl, pentanoyl, hexanoyl, heptanoyl, isobutyryl, 3-methylbutanoyl, 2-methylbutanoyl, pivaloyl, 4-methylpentanoyl, 3,3-dimethylbutanoyl or 5-methylhexanoyl, and as a preferred example there may be mentioned acetyl.

The term "$C_2$-$C_7$ alkoxycarbonyl" as a substituent on $R^1$ means a group comprising the aforementioned $C_1$-$C_6$ alkoxy group and a carbonyl group, and as preferred examples there may be mentioned methoxycarbonyl and ethoxycarbonyl.

The term "$C_2$-$C_7$ alkanoyloxy" as a substituent on $R^1$ means a group comprising the aforementioned $C_2$-$C_7$ alkanoyl and an oxy group, and as a preferred example there may be mentioned acetyloxy.

The term "$C_2$-$C_7$ alkanoylamino" as a substituent on $R^1$ means a group comprising the aforementioned $C_2$-$C_7$ alkanoyl group and an amino group, and as a preferred example there may be mentioned acetylamino.

The term "$C_1$-$C_6$ alkylsulfonyl" as a substituent on $R^1$ means a group comprising the aforementioned $C_1$-$C_6$ alkyl group and a sulfonyl group, and as a preferred example there may be mentioned methylsulfonyl.

The term "$C_3$-$C_8$ (alkoxycarbonyl)methyl" as a substituent on $R^1$ means a group comprising the aforementioned $C_2$-$C_7$ alkoxycarbonyl group and a methyl group, and as preferred examples there may be mentioned (methoxycarbonyl)methyl and (ethoxycarbonyl)methyl.

The term "mono($C_1$-$C_6$ alkyl)amino as a substituent on $R^1$ means an amino group substituted with the aforementioned $C_1$-$C_6$ alkyl group, and as preferred examples there may be mentioned methylamino and ethylamino.

The term "di($C_1$-$C_6$ alkyl)amino" as a substituent on $R^1$ means an amino group substituted with two identical or different $C_1$-$C_6$ alkyl groups, and as preferred examples there may be mentioned dimethylamino, diethylamino and N-ethyl-N-methylamino.

The term "$C_2$-$C_7$ N-alkylcarbamoyl" as a substituent on $R^1$ means a group comprising the aforementioned $C_1$-$C_6$ alkyl group and a carbamoyl group, and as preferred examples there may be mentioned N-methylcarbamoyl and N-ethylcarbamoyl.

The term "$C_4$-$C_9$ N-cycloalkylcarbamoyl" as a substituent on $R^1$ means a group comprising the aforementioned $C_3$-$C_8$ cycloalkyl group and a carbamoyl group, and as preferred examples there may be mentioned N-cyclopentylcarbamoyl and N-cyclohexylcarbamoyl.

The term "piperidylcarbonyl" as a substituent on $R^1$ means a group resulting from bonding a piperidine group and a carbonyl group, and as a preferred example there may be mentioned (1-piperidyl)carbonyl.

The term "morpholinylcarbonyl" as a substituent on $R^1$ means a group resulting from bonding a morpholine group and a carbonyl group, and as a preferred example there may be mentioned (1-morpholinyl)carbonyl.

The term "pyrrolidinylcarbonyl" as a substituent on $R^1$ means a group resulting from bonding a pyrrolidine group and a carbonyl group, and as a preferred example there may be mentioned (1-pyrrolidinyl)carbonyl.

The term "piperazinylcarbonyl" as a substituent on $R^1$ means a group resulting from bonding a piperazine group and a carbonyl group, and as a preferred example there may be mentioned (1-piperazinyl)carbonyl.

As particularly preferred substituents on $R^1$ there may be mentioned halogens, hydroxy, cyano, nitro, $C_1$-$C_6$ alkyl and $C_1$-$C_6$ alkoxy.

The term "$C_2$-$C_6$ alkynyl" as a substituent further substituting the substituent on the phenyl, $C_3$-$C_8$ cycloalkyl or aromatic heterocyclic group, or fused ring, of $R^1$, means a $C_2$-$C_6$ alkynyl group such as, for example, ethynyl, methylethynyl and ethylethynyl, and as a preferred example there may be mentioned ethynyl.

The term "$C_3$-$C_8$ cycloalkenyl" as a substituent further substituting the substituent on $R^1$ means a $C_3$-$C_8$ cyclic alkenyl group such as, for example, cyclopentenyl, cyclohexenyl or 1,3-cyclohexadienyl, and as a preferred example there may be mentioned cyclohexenyl.

The term "$C_3$-$C_7$ lactam" as a substituent further substituting the substituent on $R^1$ means a group derived by removing one hydrogen from a cyclic amide group such as, for example, 3-propanelactam, 4-butanelactam, 5-pentanelactam or 6-hexanelactam, and as a preferred example there may be mentioned "a group derived by removing one hydrogen from 4-butanelactam".

The $C_1$-$C_6$ alkyl, $C_2$-$C_6$ alkenyl, $C_1$-$C_6$ alkoxy, $C_1$-$C_6$ alkylthio, $C_3$-$C_5$ alkylene, $C_3$-$C_8$ cycloalkyl, mono($C_1$-$C_6$ alkyl)amino, di($C_1$-$C_6$ alkyl)amino, $C_2$-$C_7$ alkoxycarbonyl or $C_2$-$C_7$ N-alkylcarbamoyl groups as substituents further substituting the substituent on $R^1$ have the same definitions as the substituents on $R^1$, and the same preferred examples may be mentioned.

In formula (I), p represents an integer of 1-6, and preferably 1 or 3.

The number of substituents on the $C_1$-$C_6$ alkyl or phenyl group of $R^2$ and $R^3$ according to the invention may be any chemically possible number, but it is preferably 0-13, more preferably 0-10 and more preferably 0-7.

The $C_1$-$C_6$ alkyl group of $R^2$ and $R^3$ has the same definition as the substituent on $R^1$, and the same preferred examples may be mentioned.

The halogen, $C_1$-$C_6$ alkyl, $C_2$-$C_7$ alkoxycarbonyl and $C_1$-$C_6$ alkoxy groups as substituents on the $C_1$-$C_6$ alkyl or phenyl group of $R^2$ and $R^3$ have the same definitions as the substituents on $R^1$, and the same preferred examples may be mentioned.

Either $R^2$ and $R^3$ of formula (I) preferably represents hydrogen, and most preferably both represent hydrogen.

In formula (I), X represents —CO—, —$SO_2$—, —$CH_2$—, —CS— or a single bond, all of which may be mentioned as preferred examples. Here, —CO— represents carbonyl, —$SO_2$— represents sulfonyl and —CS— represents thiocarbonyl.

In formula (I), q represents 0 or 1, and r represents 0 or 1. The cases where q=0 and r=0, q=1 and r=0, and q=0 and r=1 may be mentioned as preferred examples.

In formula (I), Y represents —($R^4$)C=C($R^5$)—, —S— or —$NR^8$—, all of which may be mentioned as preferred examples.

The number of substituents on the groups for $R^4$, $R^5$, $R^6$ and $R^7$ according to the invention may be any chemically possible number, but it is preferably 0-15, more preferably 0-10 and more preferably 0-7.

The $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, $C_2$-$C_7$ alkanoyl, $C_2$-$C_7$ alkoxycarbonyl, piperidylcarbonyl, morpholinylcarbonyl, pyrrolidinylcarbonyl, piperazinylcarbonyl, $C_2$-$C_7$ alkanoyloxy, $C_2$-$C_7$ alkanoylamino, $C_1$-$C_6$ alkylsulfonyl, $C_3$-$C_8$ (alkoxycarbonyl)methyl, mono($C_1$-$C_6$ alkyl)amino, di($C_1$-$C_6$ alkyl)amino, carbamoyl, $C_2$-$C_7$ N-alkylcarbamoyl or $C_4$-$C_9$ N-cycloalkylcarbamoyl groups for $R^4$, $R^5$, $R^6$ and $R^7$ have the same respective definitions as the substituents on $R^1$ or the substituents further substituting those substituents, and the same preferred examples may be mentioned.

The term "$C_4$-$C_{10}$ cycloalkanoylamino" for $R^4$, $R^5$, $R^6$ and $R^7$ means a group comprising a $C_4$-$C_{10}$ cycloalkanoyl group and an amino group, and as preferred examples there may be mentioned cyclopropanoylamino, cyclobutanoylamino, cyclopentanoylamino and cyclohexanoylamino.

The term "$C_3$-$C_7$ alkenoylamino" for $R^4$, $R^5$, $R^6$ and $R^7$ means a group comprising a $C_3$-$C_7$ alkenoyl group and an amino group, and as a preferred example there may be mentioned acryloyl.

The term "$C_1$-$C_6$ alkylsulfonylamino" for $R^4$, $R^5$, $R^6$ and $R^7$ means a group comprising a $C_1$-$C_6$ alkylsulfonyl group and an amino group, and as preferred examples there may be mentioned methylsulfonylamino, ethylsulfonylamino, propylsulfonylamino and butylsulfonylamino.

The term "N-($C_7$-$C_{12}$ phenylalkyl)carbamoyl" for $R^4$, $R^5$, $R^6$ and R means a group comprising a carbamoyl group and a $C_7$-$C_{12}$ phenylalkyl group, and as preferred examples there may be mentioned phenylmethylcarbamoyl and phenylethylcarbamoyl.

The term "$C_1$-$C_6$ N-alkylsulfamoyl" for $R^4$, $R^5$, $R^6$ and $R^7$ means a group comprising a $C_1$-$C_6$ alkyl group having the same definition as "$C_1$-$C_6$ alkyl" as a substituent on $R^1$, and a sulfamoyl group, and as preferred examples there may be mentioned N-methylsulfamoyl and N,N-dimethylsulfamoyl.

As particularly preferred groups for $R^4$, $R^5$, $R^6$ and $R^7$ there may be mentioned halogens, hydroxy, cyano, nitro, $C_1$-$C_6$ alkyl, $C_1$-$C_6$ alkoxy, $C_2$-$C_7$ alkoxycarbonyl, $C_1$-$C_6$ alkylsulfonyl and $C_1$-$C_6$ N-alkylsulfamoyl.

The $C_1$-$C_6$ alkyl, $C_2$-$C_6$ alkenyl, $C_2$-$C_6$ alkynyl, $C_3$-$C_5$ alkylene, $C_3$-$C_8$ cycloalkyl, $C_3$-$C_8$ cycloalkenyl, $C_1$-$C_6$ alkoxy, $C_1$-$C_6$ alkylthio, mono($C_1$-$C_6$ alkyl)amino, di($C_1$-$C_6$ alkyl)amino, $C_3$-$C_7$ lactam, $C_2$-$C_7$ N-alkylcarbamoyl, $C_4$-$C_9$ N-cycloalkylcarbamoyl, N—($C_7$-$C_{12}$ phenylalkyl)carbamoyl or $C_2$-$C_7$ alkoxycarbonyl groups as substituents on $R^4$, $R^5$, $R^6$ and $R^7$ have the same respective definitions as the substituents on $R^1$, as the substituents further substituting those substituents or as $R^4$, $R^5$, $R^6$ and $R^7$ themselves, and the same preferred examples may be mentioned.

The term "($C_1$-$C_6$ alkoxy)($C_1$-$C_6$ alkoxy)" as a substituent on $R^4$, $R^5$, $R^6$ and $R^7$ means a group comprising a $C_1$-$C_6$ alkoxy group and a $C_1$-$C_6$ alkoxy group, and as preferred examples there may be mentioned methoxymethoxy, methoxyethoxy and ethoxyethoxy.

The term "phenyl($C_1$-$C_6$ alkoxy)" as a substituent on $R^4$, $R^5$, $R^6$ and $R^7$ means a group comprising a phenyl group and a $C_1$-$C_6$ alkoxy group, and as preferred examples there may be mentioned benzyloxy, phenylethoxy and phenylpropoxy.

The term "($C_2$-$C_7$ alkanoyl)piperidyl" as a substituent on $R^4$, $R^5$, $R^6$ and $R^7$ means a group comprising a $C_2$-$C_7$ alkanoyl group and a piperidyl group, and as a preferred example there may be mentioned 1-(acetyl)-4-piperidyl.

The number of substituents on the $C_1$-$C_6$ alkyl group for $R^8$ and the number of substituents on the phenyl group as a substituent on the $C_1$-$C_6$ alkyl group for $R^8$ according to the invention may be any chemically possible number, but it is preferably 0-15, more preferably 0-10 and more preferably 0-7.

The $C_1$-$C_6$ alkyl group for $R^8$ has the same definition as the substituent on $R^1$, and the same preferred examples may be mentioned.

The halogen, $C_3$-$C_8$ cycloalkyl, $C_1$-$C_6$ alkoxy, $C_1$-$C_6$ alkylthio, $C_2$-$C_7$ alkanoyl, $C_2$-$C_7$ alkoxycarbonyl, $C_2$-$C_7$ alkanoyloxy, $C_2$-$C_7$ alkanoylamino, $C_2$-$C_7$ N-alkylcarbamoyl, $C_2$-$C_6$ alkylsulfohyl, mono($C_1$-$C_6$ alkyl)amino and di($C_1$-$C_6$ alkyl) amino groups as substituents on the $C_1$-$C_6$ alkyl group for $R^8$ have the same respective definitions as the substituents of $R^1$, and the same preferred examples may be mentioned.

The terms "halogen", "$C_1$-$C_6$ alkyl" and "$C_1$-$C_6$ alkoxy" as substituents on the phenyl group substituting the $C_1$-$C_6$ alkyl group of $R^8$ have the same definitions as the substituents on $R^1$, and the same preferred examples may be mentioned.

As preferred examples of 4,4-(disubstituted)piperidine derivatives of formula (I) there may be mentioned compounds containing the substituents listed in Tables 1 to 8 below. The compound numbers are listed in the columns titled "Compd. No." in Tables 1 to 8.

Table 1 lists preferred examples of compounds wherein X=single bond, q=0, r=0 and Y=—($R^4$)C=C($R^5$)—. Table 2 lists preferred examples of compounds wherein X=—CO—, q=0, r=0 and Y=—($R^4$)C=C($R^5$)—. Table 3 lists preferred examples of compounds wherein X=—$SO_2$—, q=0, r=0 and Y=—($R^4$)C=C($R^5$)—. Table 4 lists preferred examples of compounds wherein X=—$CH_2$—, q=0, r=0 and Y=—($R^4$)C=C($R^5$)—. Table 5 lists preferred examples of compounds wherein X=—CO—, q=0, r=0 and Y=—S—. Table 6 lists preferred examples of compounds wherein X=—CO—, q=0, r=0 and Y=—N($R^8$)—. Table 7 lists preferred examples of compounds wherein X=—CO—, q=1, r=0 and Y=—($R^4$)C=C($R^5$)—. Table 8 lists preferred examples of compounds wherein X=—CS—, q=0, r=0 and Y=—($R^4$)C=C($R^5$)—.

TABLE 1

| X = Single Bond, q = 0, r = 0, Y = —(R4)C=C(R5)— | | | | | | |
|---|---|---|---|---|---|---|
| Compound No. 1- R1—(CH2)p— | R2 | R3 | R4 | R5 | R6 | R7 |
| 1  (2,4-dichloro-6-hydroxyphenyl) | H | H | H | COOMe | H | H |
| 2  (4-chloro-2-hydroxyphenyl) | H | H | H | COOMe | H | H |

TABLE 1-continued

| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 3 | naphthalen-1-ylmethyl | H | H | H | COOMe | H | H |
| 4 | 3-phenylpropyl | H | H | H | COOMe | H | H |
| 5 | (1-methyl-1H-indol-3-yl)methyl | H | H | H | COOMe | H | H |
| 6 | benzo[b]thiophen-3-ylmethyl | H | H | H | COOMe | H | H |
| 7 | 3,4-dichlorobenzyl | H | H | H | H | H | H |
| 8 | 3,4-dichlorobenzyl | H | H | H | Cl | H | H |
| 9 | naphthalen-1-ylmethyl | H | H | H | H | H | H |
| 10 | naphthalen-1-ylmethyl | H | H | H | Cl | H | H |
| 11 | 2-chlorobenzyl | H | H | H | H | H | H |
| 12 | 3-chlorobenzyl | H | H | H | H | H | H |

TABLE 1-continued
| | X = Single Bond, q = 0, r = 0, Y = —(R4)C═C(R5)— | | | | | | |
|---|---|---|---|---|---|---|---|
| Compound No. | 1- R1—(CH2)p— | R2 | R3 | R4 | R5 | R6 | R7 |
| 13 | 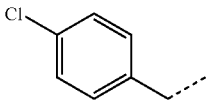 | H | H | H | H | H | H |
| 14 | 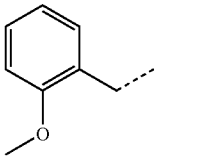 | H | H | H | H | H | H |
| 15 | 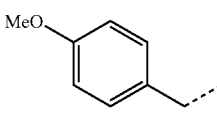 | H | H | H | H | H | H |
| 16 | 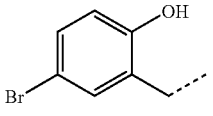 | H | H | H | H | H | H |
| 17 | 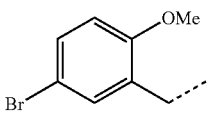 | H | H | H | H | H | H |
| 18 | 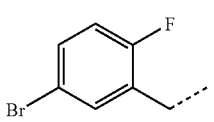 | H | H | H | H | H | H |
| 19 | 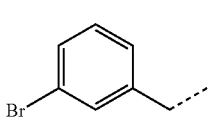 | H | H | H | H | H | H |
| 20 |  | H | H | H | H | H | H |
| 21 | 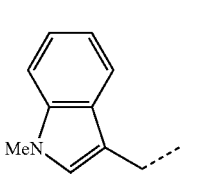 | H | H | H | H | H | H |
| 22 | 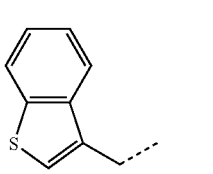 | H | H | H | H | H | H |
| 23 | 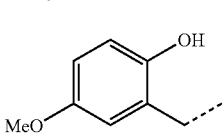 | H | H | H | H | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 24 3-nitrobenzyl | H | H | H | H | H | H |
| 25 3-methoxybenzyl | H | H | H | H | H | H |
| 26 naphthalen-2-ylmethyl | H | H | H | H | H | H |
| 27 benzyl | H | H | H | H | H | H |
| 28 phenethyl | H | H | H | H | H | H |
| 29 (3-bromo-5-chloro-2-hydroxyphenyl)methyl | H | H | H | H | H | H |
| 30 (5-cyano-2-hydroxyphenyl)methyl | H | H | H | H | H | H |
| 31 (3-chloro-2-hydroxy-5-trifluoromethylphenyl)methyl | H | H | H | H | H | H |
| 32 (5-chloro-2-hydroxy-3-trifluoromethylphenyl)methyl | H | H | H | H | H | H |
| 33 (3-chloro-2-hydroxyphenyl)methyl | H | H | H | H | H | H |
| 34 4-methylbenzyl | H | H | H | H | H | H |

TABLE 1-continued
| | X = Single Bond, q = 0, r = 0, Y = —(R4)C=C(R5)— | | | | | | |
|---|---|---|---|---|---|---|---|
| Compound No. 1- | R1—(CH2)p— | R2 | R3 | R4 | R5 | R6 | R7 |
| 35 | 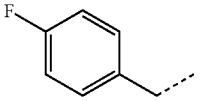 | H | H | H | H | H | H |
| 36 | 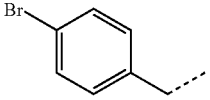 | H | H | H | H | H | H |
| 37 | 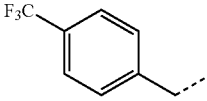 | H | H | H | H | H | H |
| 38 | 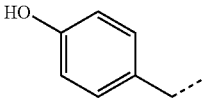 | H | H | H | H | H | H |
| 39 | 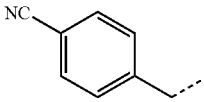 | H | H | H | H | H | H |
| 40 | 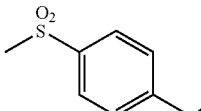 | H | H | H | H | H | H |
| 41 | 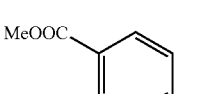 | H | H | H | H | H | H |
| 42 | 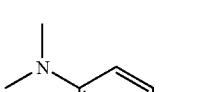 | H | H | H | H | H | H |
| 43 | 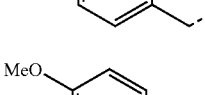 | H | H | H | H | H | H |
| 44 | 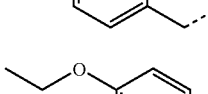 | H | H | H | H | H | H |
| 45 | 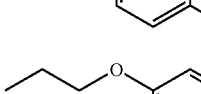 | H | H | H | H | H | H |
| 46 | 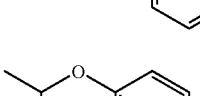 | H | H | H | H | H | H |

TABLE 1-continued

| X = Single Bond, q = 0, r = 0, Y = —(R4)C=C(R5)— | | | | | | |
|---|---|---|---|---|---|---|
| Compound No. 1- R1—(CH2)p— | R2 | R3 | R4 | R5 | R6 | R7 |
| 47 (4-isopropylbenzyl) | H | H | H | H | H | H |
| 48 (4-benzyloxybenzyl) | H | H | H | H | H | H |
| 49 (4-phenoxybenzyl) | H | H | H | H | H | H |
| 50 (biphenyl-4-ylmethyl) | H | H | H | H | H | H |
| 51 (4-acetamidobenzyl) | H | H | H | H | H | H |
| 52 (2-propylbenzyl) | H | H | H | H | H | H |
| 53 (2-benzyloxybenzyl) | H | H | H | H | H | H |
| 54 (2-methylbenzyl) | H | H | H | H | H | H |
| 55 (2-cyanobenzyl) | H | H | H | H | H | H |

TABLE 1-continued

| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 56 | 2-chlorobenzyl | H | H | H | H | H | H |
| 57 | 2-methoxybenzyl | H | H | H | H | H | H |
| 58 | 2-ethoxybenzyl | H | H | H | H | H | H |
| 59 | 2-phenylbenzyl | H | H | H | H | H | H |
| 60 | 3-trifluoromethylbenzyl | H | H | H | H | H | H |
| 61 | 3-chloro-2-fluorobenzyl | H | H | H | H | H | H |
| 62 | 3,5-dichlorobenzyl | H | H | H | H | H | H |
| 63 | 3-methylbenzyl | H | H | H | H | H | H |
| 64 | 3-fluoro-5-trifluoromethylbenzyl | H | H | H | H | H | H |

TABLE 1-continued

X = Single Bond, q = 0, r = 0, Y = —(R4)C=C(R5)—

| Compound No. | 1- R1—(CH2)p— | R2 | R3 | R4 | R5 | R6 | R7 |
|---|---|---|---|---|---|---|---|
| 65 | 3-F₃CO-C₆H₄-CH₂- | H | H | H | H | H | H |
| 66 | 4-F,5-MeO-C₆H₃-CH₂- | H | H | H | H | H | H |
| 67 | 4-F,5-O₂N-C₆H₃-CH₂- | H | H | H | H | H | H |
| 68 | 4-O₂N-C₆H₄-CH₂- | H | H | H | H | H | H |
| 69 | 3-F,2-Me-C₆H₃-CH₂- | H | H | H | H | H | H |
| 70 | 3-F₃CS-C₆H₄-CH₂- | H | H | H | H | H | H |
| 71 | 2,5-Cl₂-C₆H₃-CH₂- | H | H | H | H | H | H |
| 72 | 3-F₂HC-C₆H₄-CH₂- | H | H | H | H | H | H |
| 73 | 2-F-C₆H₄-CH₂- | H | H | H | H | H | H |
| 74 | 2-O₂N-C₆H₄-CH₂- | H | H | H | H | H | H |
| 75 | 2-HOOC-C₆H₄-CH₂- | H | H | H | H | H | H |
| 76 | 4-Br,3-EtO-C₆H₃-CH₂- | H | H | H | H | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 77 (2,3-dimethylphenyl-CH2—) | H | H | H | H | H | H |
| 78 (3-fluorophenyl-CH2—) | H | H | H | H | H | H |
| 79 (2,4-dichlorophenyl-CH2—) | H | H | H | H | H | H |
| 80 (3-cyanophenyl-CH2—) | H | H | H | H | H | H |
| 81 (3-hydroxyphenyl-CH2—) | H | H | H | H | H | H |
| 82 (3-ethoxyphenyl-CH2—) | H | H | H | H | H | H |
| 83 (4-chloro-3-nitrophenyl-CH2—) | H | H | H | H | H | H |
| 84 (2,3-dichlorophenyl-CH2—) | H | H | H | H | H | H |
| 85 (2,3-difluoro-4-methylphenyl-CH2—) | H | H | H | H | H | H |
| 86 (3-bromo-4-fluorophenyl-CH2—) | H | H | H | H | H | H |
| 87 (2-fluoro-3-trifluoromethylphenyl-CH2—) | H | H | H | H | H | H |

TABLE 1-continued

| X = Single Bond, q = 0, r = 0, Y = —(R4)C=C(R5)— | | | | | | |
|---|---|---|---|---|---|---|
| Compound No. 1- R1—(CH2)p— | R2 | R3 | R4 | R5 | R6 | R7 |
| 88 (2-chloro-4-hydroxyphenyl)methyl | H | H | H | H | H | H |
| 89 (2,3-difluorophenyl)methyl | H | H | H | H | H | H |
| 90 (3-bromo-4-methoxyphenyl)methyl | H | H | H | H | H | H |
| 91 (2-ethoxy-3-methoxyphenyl)methyl | H | H | H | H | H | H |
| 92 (4-methoxy-2,3-dimethylphenyl)methyl | H | H | H | H | H | H |
| 93 (2-benzyloxy-3-methoxyphenyl)methyl | H | H | H | H | H | H |
| 94 (2-chloro-5-nitrophenyl)methyl | H | H | H | H | H | H |
| 95 [3-(4-methoxyphenoxy)phenyl]methyl | H | H | H | H | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 96 | H | H | H | H | H | H |
| 97 | H | H | H | H | H | H |
| 98 | H | H | H | H | H | H |
| 99 | H | H | H | H | H | H |
| 100 | H | H | H | H | H | H |
| 101 | H | H | H | H | H | H |
| 102 | H | H | H | H | H | H |
| 103 | H | H | H | H | H | H |
| 104 | H | H | H | H | H | H |

TABLE 1-continued

X = Single Bond, q = 0, r = 0, Y = —(R4)C=C(R5)—

| Compound No. 1- R1—(CH2)p— | R1—(CH2)p— structure | R2 | R3 | R4 | R5 | R6 | R7 |
|---|---|---|---|---|---|---|---|
| 105 | HO-CH2CH2-O-(3-phenyl)-CH2- | H | H | H | H | H | H |
| 106 | 2,3,4-trimethoxyphenyl (MeO, OMe, OMe)-CH2- | H | H | H | H | H | H |
| 107 | 2-fluoro-3-phenoxyphenyl-CH2- | H | H | H | H | H | H |
| 108 | 3,4-dimethoxy-2-carboxyphenyl (MeO, OMe, COOH)-CH2- | H | H | H | H | H | H |
| 109 | 4-chloro-2-nitrophenyl (Cl, NO2)-CH2- | H | H | H | H | H | H |
| 110 | 3,5-dihydroxyphenyl (HO, OH)-CH2- | H | H | H | H | H | H |
| 111 | 4-methoxy-3-benzyloxyphenyl-CH2- | H | H | H | H | H | H |
| 112 | 3,4-diethoxyphenyl (EtO, EtO)-CH2- | H | H | H | H | H | H |
| 113 | 3-carboxyphenyl (HOOC)-CH2- | H | H | H | H | H | H |
| 114 | 4-methoxy-3-hydroxyphenyl (OMe, HO)-CH2- | H | H | H | H | H | H |
| 115 | 2-nitro-3-hydroxyphenyl (O2N, HO)-CH2- | H | H | H | H | H | H |

TABLE 1-continued

| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 116 | 3,5-bis(trifluoromethyl)benzyl | H | H | H | H | H | H |
| 117 | 2-methoxy-3-nitrobenzyl | H | H | H | H | H | H |
| 118 | (4-methylnaphthalen-1-yl)methyl | H | H | H | H | H | H |
| 119 | (1,7-dimethyl-1H-indol-3-yl)methyl | H | H | H | H | H | H |
| 120 | (7-methoxynaphthalen-1-yl)methyl | H | H | H | H | H | H |
| 121 | benzofuran-2-ylmethyl | H | H | H | H | H | H |
| 122 | (1,2-dimethyl-1H-indol-3-yl)methyl | H | H | H | H | H | H |
| 123 | quinolin-2-yl | H | H | H | H | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 124 (7-hydroxyquinolin-8-yl) | H | H | H | H | H | H |
| 125 (7-acetoxyquinolin-8-yl) | H | H | H | H | H | H |
| 126 (1-hydroxynaphthalen-2-yl)methyl | H | H | H | H | H | H |
| 127 (1H-indol-7-yl)methyl | H | H | H | H | H | H |
| 128 (quinolin-4-yl)methyl | H | H | H | H | H | H |
| 129 (5-methyl-1-methyl-1H-indol-3-yl)methyl | H | H | H | H | H | H |
| 130 (phenanthren-9-yl)methyl | H | H | H | H | H | H |

TABLE 1-continued

X = Single Bond, q = 0, r = 0, Y = —(R4)C═C(R5)—

| Compound No. 1- R1—(CH2)p— | R2 | R3 | R4 | R5 | R6 | R7 |
|---|---|---|---|---|---|---|
| 131 (2-methyl-naphthalen-1-yl-methyl) | H | H | H | H | H | H |
| 132 (2-ethoxy-naphthalen-1-yl-methyl) | H | H | H | H | H | H |
| 133 (1H-indol-3-yl-methyl) | H | H | H | H | H | H |
| 134 (6-methyl-1-methyl-1H-indol-3-yl-methyl) | H | H | H | H | H | H |
| 135 (1-methyl-1H-indol-2-yl-methyl) | H | H | H | H | H | H |
| 136 (4-methyl-1-methyl-1H-indol-3-yl-methyl) | H | H | H | H | H | H |
| 137 (2,5-dimethyl-1-methyl-1H-indol-3-yl-methyl) | H | H | H | H | H | H |
| 138 (5-methoxy-1-methyl-1H-indol-3-yl-methyl) | H | H | H | H | H | H |

TABLE 1-continued

X = Single Bond, q = 0, r = 0, Y = —(R4)C═C(R5)—

| Compound No. 1- R1—(CH2)p— | | R2 | R3 | R4 | R5 | R6 | R7 |
|---|---|---|---|---|---|---|---|
| 139 | 4-methylbenzothiophen-3-ylmethyl | H | H | H | H | H | H |
| 140 | 1-methylbenzimidazol-2-ylmethyl | H | H | H | H | H | H |
| 141 | 1-methyl-2-phenylindol-3-ylmethyl | H | H | H | H | H | H |
| 142 | 1-acetylindol-3-ylmethyl | H | H | H | H | H | H |
| 143 | quinolin-2-ylmethyl | H | H | H | H | H | H |
| 144 | 6-methoxy-1-methylindol-3-ylmethyl | H | H | H | H | H | H |
| 145 | 3-methylbenzothiophen-2-ylmethyl | H | H | H | H | H | H |
| 146 | 4-methoxynaphth-1-ylmethyl | H | H | H | H | H | H |

TABLE 1-continued

X = Single Bond, q = 0, r = 0, Y = —(R4)C═C(R5)—

| Compound No. 1- R1—(CH2)p— | | R2 | R3 | R4 | R5 | R6 | R7 |
|---|---|---|---|---|---|---|---|
| 147 | (phenanthrenyl) | H | H | H | H | H | H |
| 148 | MeO-naphthyl | H | H | H | H | H | H |
| 149 | bromo-naphthyl | H | H | H | H | H | H |
| 150 | dimethylamino-naphthyl | H | H | H | H | H | H |
| 151 | benzodioxinyl | H | H | H | H | H | H |
| 152 | dimethyl-chromanyl | H | H | H | H | H | H |
| 153 | dihydrobenzofuranyl | H | H | H | H | H | H |
| 154 | N-ethyl-carbazolyl | H | H | H | H | H | H |
| 155 | benzodioxolyl | H | H | H | H | H | H |

TABLE 1-continued
X = Single Bond, q = 0, r = 0, Y = —(R4)C═C(R5)—
| Compound No. 1- R1—(CH2)p— | | R2 | R3 | R4 | R5 | R6 | R7 |
|---|---|---|---|---|---|---|---|
| 156 | 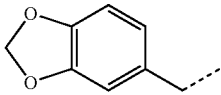 | H | H | H | H | H | H |
| 157 | 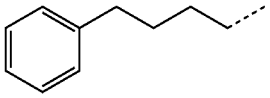 | H | H | H | H | H | H |
| 158 | 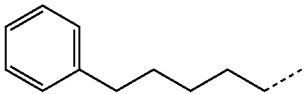 | H | H | H | H | H | H |
| 159 | 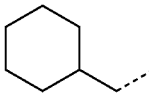 | H | H | H | H | H | H |
| 160 | 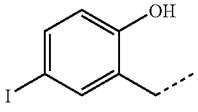 | H | H | H | H | H | H |
| 161 | 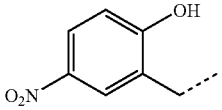 | H | H | H | H | H | H |
| 162 | 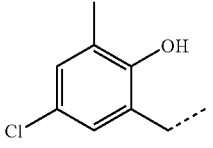 | H | H | H | H | H | H |
| 163 | 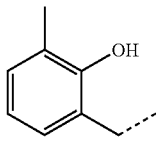 | H | H | H | H | H | H |
| 164 | 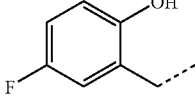 | H | H | H | H | H | H |
| 165 | 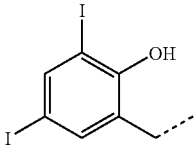 | H | H | H | H | H | H |
| 166 | 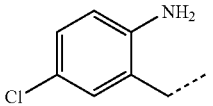 | H | H | H | H | H | H |
| 167 | 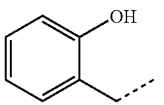 | H | H | H | H | H | H |

TABLE 1-continued

X = Single Bond, q = 0, r = 0, Y = —(R4)C═C(R5)—

| Compound No. 1- R1—(CH2)p— | | R2 | R3 | R4 | R5 | R6 | R7 |
|---|---|---|---|---|---|---|---|
| 168 | 2-aminobenzyl | H | H | H | H | H | H |
| 169 | 4-tert-butyl-2-hydroxybenzyl | H | H | H | H | H | H |
| 170 | 2-hydroxy-4-trifluoromethoxybenzyl | H | H | H | H | H | H |
| 171 | 3-methoxy-2-hydroxybenzyl | H | H | H | H | H | H |
| 172 | 2,3-dihydroxybenzyl | H | H | H | H | H | H |
| 173 | 3-ethoxy-2-hydroxybenzyl | H | H | H | H | H | H |
| 174 | 3-carboxy-2-hydroxybenzyl | H | H | H | H | H | H |
| 175 | 3-tert-butyl-2-hydroxybenzyl | H | H | H | H | H | H |
| 176 | furan-2-ylmethyl | H | H | H | H | H | H |
| 177 | oxazol-2-ylmethyl | H | H | H | H | H | H |

TABLE 1-continued
| | X = Single Bond, q = 0, r = 0, Y = —(R4)C═C(R5)— | | | | | | |
|---|---|---|---|---|---|---|---|
| Compound No. 1- R1—(CH2)p— | | R2 | R3 | R4 | R5 | R6 | R7 |
| 178 | 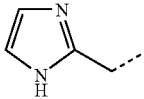 | H | H | H | H | H | H |
| 179 | 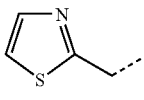 | H | H | H | H | H | H |
| 180 | 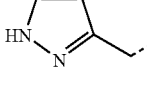 | H | H | H | H | H | H |
| 181 | 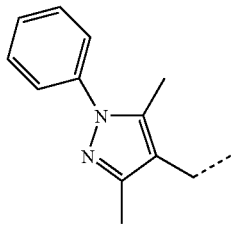 | H | H | H | H | H | H |
| 182 | 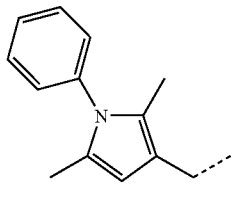 | H | H | H | H | H | H |
| 183 | 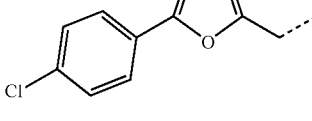 | H | H | H | H | H | H |
| 184 | 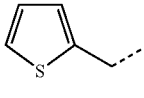 | H | H | H | H | H | H |
| 185 | 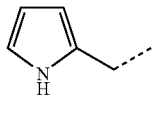 | H | H | H | H | H | H |
| 186 | 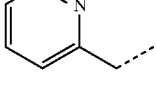 | H | H | H | H | H | H |
| 187 | 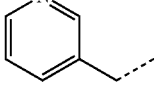 | H | H | H | H | H | H |
| 188 | 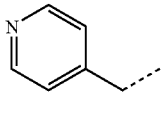 | H | H | H | H | H | H |

TABLE 1-continued
X = Single Bond, q = 0, r = 0, Y = —(R4)C=C(R5)—
| Compound No. 1- R1—(CH2)p— | | R2 | R3 | R4 | R5 | R6 | R7 |
|---|---|---|---|---|---|---|---|
| 189 | 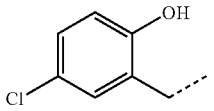 | H | H | H | Cl | H | H |
| 190 | 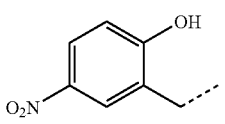 | H | H | H | Cl | H | H |
| 191 | 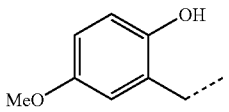 | H | H | H | Cl | H | H |
| 192 | 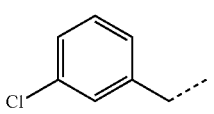 | H | H | H | Cl | H | H |
| 193 | 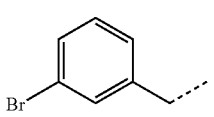 | H | H | H | Cl | H | H |
| 194 | 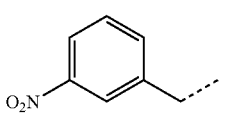 | H | H | H | Cl | H | H |
| 195 | 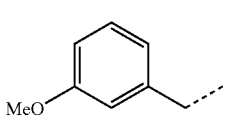 | H | H | H | Cl | H | H |
| 196 | 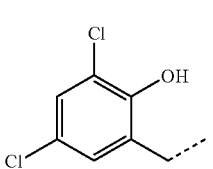 | H | H | H | Cl | H | H |
| 197 | 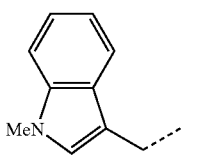 | H | H | H | CL | H | H |
| 198 | 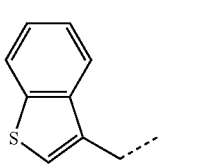 | H | H | H | Cl | H | H |
| 199 | 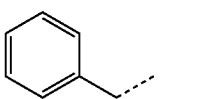 | H | H | H | Cl | H | H |

TABLE 1-continued
X = Single Bond, q = 0, r = 0, Y = —(R4)C=C(R5)—
| Compound No. 1- R1—(CH2)p— | | R2 | R3 | R4 | R5 | R6 | R7 |
|---|---|---|---|---|---|---|---|
| 200 | 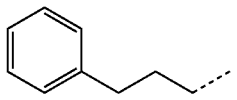 | H | H | H | Cl | H | H |
| 201 | 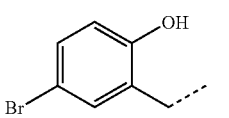 | H | H | H | Cl | H | H |
| 202 | 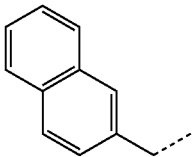 | H | H | H | Cl | H | H |
| 203 | 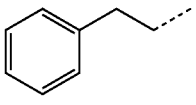 | H | H | H | Cl | H | H |
| 204 | 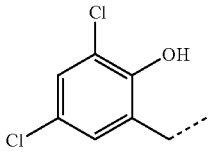 | H | H | Cl | H | H | H |
| 205 | 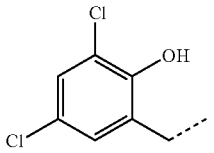 | H | H | H | OMe | H | H |
| 206 | 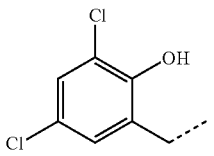 | H | H | H | OCF3 | H | H |
| 207 | 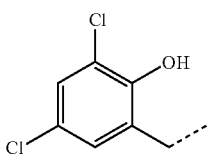 | H | H | COOMe | H | H | H |
| 208 | 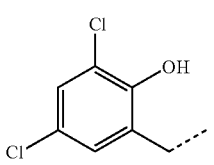 | H | H | H | CF3 | H | H |
| 209 | 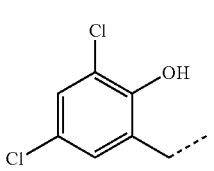 | H | H | H | Me | H | H |

TABLE 1-continued
X = Single Bond, q = 0, r = 0, Y = —(R4)C═C(R5)—
| Compound No. 1- R1—(CH2)p— | | R2 | R3 | R4 | R5 | R6 | R7 |
|---|---|---|---|---|---|---|---|
| 210 | 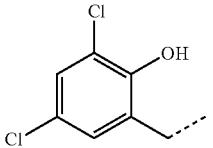 | H | H | H | F | H | H |
| 211 | 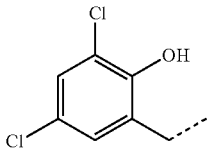 | H | H | H | OH | H | H |
| 212 | 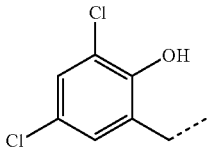 | H | H | H | NO2 | H | H |
| 213 | 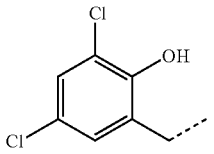 | H | H | H | F | F | H |
| 214 | 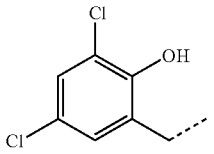 | H | H | F | H | H | H |
| 215 |  | H | H | Me | H | H | H |
| 216 | 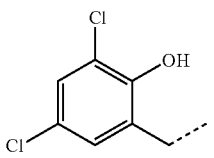 | H | H | H | CN | H | H |
| 217 | 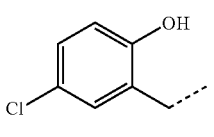 | H | H | Cl | H | H | H |
| 218 | 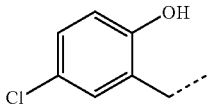 | H | H | H | OMe | H | H |
| 219 | 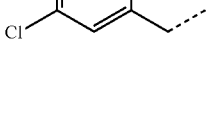 | H | H | H | OCF3 | H | H |

TABLE 1-continued

X = Single Bond, q = 0, r = 0, Y = —(R4)C=C(R5)—

| Compound No. 1- R1—(CH2)p— | | R2 | R3 | R4 | R5 | R6 | R7 |
|---|---|---|---|---|---|---|---|
| 220 | 4-Cl-2-(CH2)-phenol (OH at 1, Cl at 4) | H | H | COOMe | H | H | H |
| 221 | 4-Cl-2-(CH2)-phenol | H | H | H | CF3 | H | H |
| 222 | 4-Cl-2-(CH2)-phenol | H | H | H | Me | H | H |
| 223 | 4-Cl-2-(CH2)-phenol | H | H | H | F | H | H |
| 224 | 1-naphthylmethyl | H | H | Cl | H | H | H |
| 225 | 1-naphthylmethyl | H | H | H | OMe | H | H |
| 226 | 1-naphthylmethyl | H | H | H | OCF3 | H | H |
| 227 | 1-naphthylmethyl | H | H | COOMe | H | H | H |
| 228 | 1-naphthylmethyl | H | H | H | CF3 | H | H |
| 229 | 1-naphthylmethyl | H | H | H | Me | H | H |

TABLE 1-continued
| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 230 | 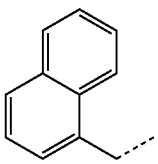 | H | H | H | F | H | H |
| 231 | 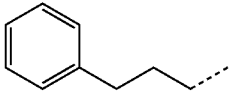 | H | H | Cl | H | H | H |
| 232 | 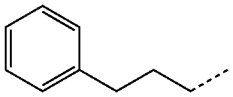 | H | H | H | OMe | H | H |
| 233 | 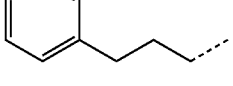 | H | H | H | OCF3 | H | H |
| 234 | 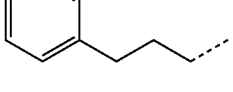 | H | H | COOMe | H | H | H |
| 235 | 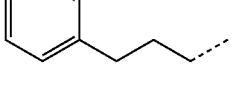 | H | H | H | CF3 | H | H |
| 236 | 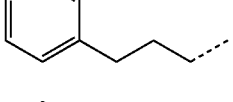 | H | H | H | Me | H | H |
| 237 | 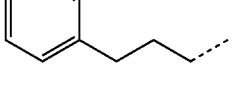 | H | H | H | F | H | H |
| 238 | 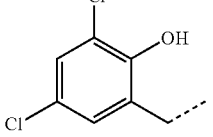 | H | H | OMe | H | H | H |
| 239 | 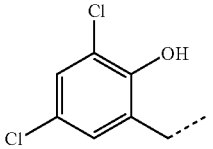 | H | H | CF3 | H | H | H |
| 240 | 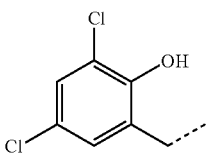 | H | H | OH | H | H | H |

TABLE 1-continued
X = Single Bond, q = 0, r = 0, Y = —(R4)C═C(R5)—
| Compound No. 1- R1—(CH2)p— | | R2 | R3 | R4 | R5 | R6 | R7 |
|---|---|---|---|---|---|---|---|
| 241 | 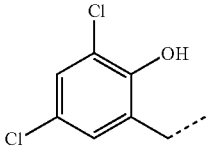 | H | H | OCF3 | H | H | H |
| 242 | 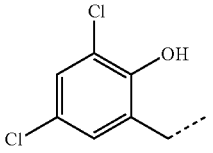 | H | H | NO2 | H | H | H |
| 243 | 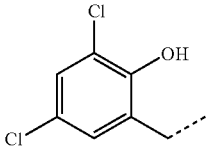 | H | H | CN | H | H | H |
| 244 | 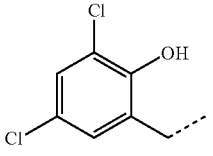 | H | H | Br | H | H | H |
| 245 | 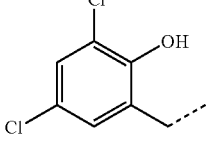 | H | H | H | Br | H | H |
| 246 | 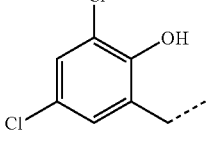 | H | H | COOH | H | H | H |
| 247 | 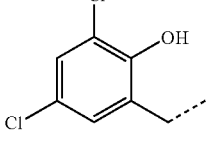 | H | H | H | COOH | H | H |
| 248 | 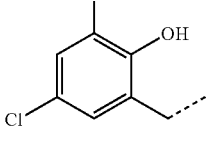 | H | H | NHCOMe | H | H | H |
| 249 | 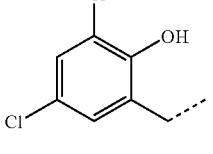 | H | H | H | NHCOMe | H | H |

TABLE 1-continued
| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 250 | 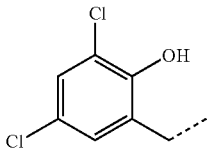 | H | H | SO2NH2 | H | H | H |
| 251 | 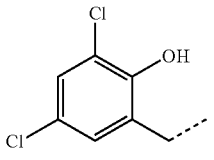 | H | H | H | SO2NH2 | H | H |
| 252 | 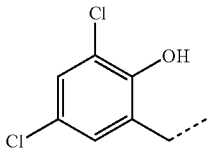 | H | H | Me | Me | H | H |
| 253 | 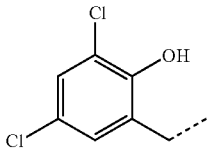 | H | H | Me | H | Me | H |
| 254 | 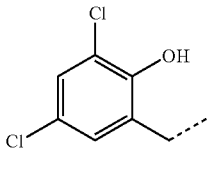 | H | H | H | Me | Me | H |
| 255 | 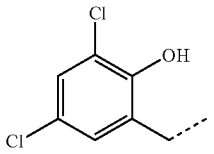 | H | H | F | F | H | H |
| 256 | 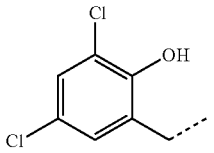 | H | H | F | H | F | H |
| 257 | 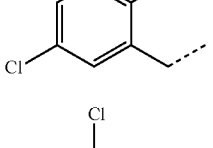 | H | H | H | F | F | H |
| 258 | 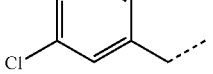 | H | H | Cl | Cl | H | H |

TABLE 1-continued

X = Single Bond, q = 0, r = 0, Y = —(R4)C=C(R5)—

| Compound No. 1- R1—(CH2)p— | | R2 | R3 | R4 | R5 | R6 | R7 |
|---|---|---|---|---|---|---|---|
| 259 | 2,4-dichloro-6-hydroxybenzyl | H | H | Cl | H | Cl | H |
| 260 | 2,4-dichloro-6-hydroxybenzyl | H | H | H | Cl | Cl | H |
| 261 | 2,4-dichloro-6-hydroxybenzyl | H | H | Me | F | H | H |
| 262 | 2,4-dichloro-6-hydroxybenzyl | H | H | Me | Cl | H | H |
| 263 | 2,4-dichloro-6-hydroxybenzyl | H | H | Me | OH | H | H |
| 264 | 2,4-dichloro-6-hydroxybenzyl | H | H | Me | OMe | H | H |
| 265 | 2,4-dichloro-6-hydroxybenzyl | H | H | F | Me | H | H |
| 266 | 2,4-dichloro-6-hydroxybenzyl | H | H | F | Cl | H | H |
| 267 | 2,4-dichloro-6-hydroxybenzyl | H | H | F | OH | H | H |

TABLE 1-continued

| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 268 | 2,4-dichloro-6-hydroxybenzyl | H | H | F | OMe | H | H |
| 269 | 2,4-dichloro-6-hydroxybenzyl | H | H | Cl | Me | H | H |
| 270 | 2,4-dichloro-6-hydroxybenzyl | H | H | Cl | F | H | H |
| 271 | 2,4-dichloro-6-hydroxybenzyl | H | H | Cl | OH | H | H |
| 272 | 2,4-dichloro-6-hydroxybenzyl | H | H | Cl | OMe | H | H |
| 273 | 4-chloro-2-hydroxybenzyl | H | H | H | H | H | COOMe |
| 274 | 4-chloro-2-hydroxybenzyl | H | H | F | H | H | H |
| 275 | 4-chloro-2-hydroxybenzyl | H | H | Me | H | H | H |
| 276 | 4-chloro-2-hydroxybenzyl | H | H | OMe | H | H | H |
| 277 | 4-chloro-2-hydroxybenzyl | H | H | CF3 | H | H | H |

TABLE 1-continued

X = Single Bond, q = 0, r = 0, Y = —(R4)C=C(R5)—

| Compound No. | 1- R1—(CH2)p— | R2 | R3 | R4 | R5 | R6 | R7 |
|---|---|---|---|---|---|---|---|
| 278 | 4-Cl-2-(OH)-C6H3-CH2— | H | H | OH | H | H | H |
| 279 | 4-Cl-2-(OH)-C6H3-CH2— | H | H | H | OH | H | H |
| 280 | 4-Cl-2-(OH)-C6H3-CH2— | H | H | OCF3 | H | H | H |
| 281 | 4-Cl-2-(OH)-C6H3-CH2— | H | H | NO2 | H | H | H |
| 282 | 4-Cl-2-(OH)-C6H3-CH2— | H | H | H | NO2 | H | H |
| 283 | 4-Cl-2-(OH)-C6H3-CH2— | H | H | CN | H | H | H |
| 284 | 4-Cl-2-(OH)-C6H3-CH2— | H | H | H | CN | H | H |
| 285 | 4-Cl-2-(OH)-C6H3-CH2— | H | H | Br | H | H | H |
| 286 | 4-Cl-2-(OH)-C6H3-CH2— | H | H | H | Br | H | H |
| 287 | 4-Cl-2-(OH)-C6H3-CH2— | H | H | COOH | H | H | H |
| 288 | 4-Cl-2-(OH)-C6H3-CH2— | H | H | H | COOH | H | H |
| 289 | 4-Cl-2-(OH)-C6H3-CH2— | H | H | NHCOMe | H | H | H |

TABLE 1-continued

X = Single Bond, q = 0, r = 0, Y = —(R4)C=C(R5)—

| Compound No. 1- R1—(CH2)p— | | R2 | R3 | R4 | R5 | R6 | R7 |
|---|---|---|---|---|---|---|---|
| 290 | 4-Cl-2-(CH2)-phenol | H | H | H | NHCOMe | H | H |
| 291 | 4-Cl-2-(CH2)-phenol | H | H | SO2NH2 | H | H | H |
| 292 | 4-Cl-2-(CH2)-phenol | H | H | H | SO2NH2 | H | H |
| 293 | 4-Cl-2-(CH2)-phenol | H | H | Me | Me | H | H |
| 294 | 4-Cl-2-(CH2)-phenol | H | H | Me | H | Me | H |
| 295 | 4-Cl-2-(CH2)-phenol | H | H | H | Me | Me | H |
| 296 | 4-Cl-2-(CH2)-phenol | H | H | F | F | H | H |
| 297 | 4-Cl-2-(CH2)-phenol | H | H | F | H | F | H |
| 298 | 4-Cl-2-(CH2)-phenol | H | H | H | F | F | H |
| 299 | 4-Cl-2-(CH2)-phenol | H | H | Cl | Cl | H | H |
| 300 | 4-Cl-2-(CH2)-phenol | H | H | Cl | H | Cl | H |
| 301 | 4-Cl-2-(CH2)-phenol | H | H | H | Cl | Cl | H |

TABLE 1-continued
X = Single Bond, q = 0, r = 0, Y = —(R4)C=C(R5)—
| Compound No. 1- R1—(CH2)p— | | R2 | R3 | R4 | R5 | R6 | R7 |
|---|---|---|---|---|---|---|---|
| 302 | 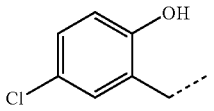 | H | H | Me | F | H | H |
| 303 | 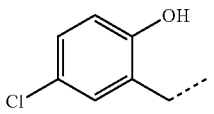 | H | H | Me | Cl | H | H |
| 304 | 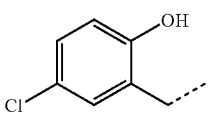 | H | H | Me | OH | H | H |
| 305 | 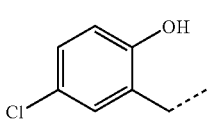 | H | H | Me | OMe | H | H |
| 306 | 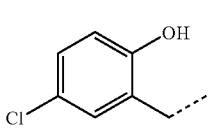 | H | H | H | H | H | H |
| 307 | 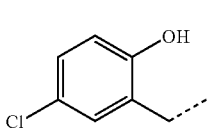 | H | H | F | Cl | H | H |
| 308 | 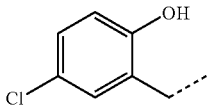 | H | H | F | OH | H | H |
| 309 |  | H | H | F | OMe | H | H |
| 310 |  | H | H | Cl | Me | H | H |
| 311 | 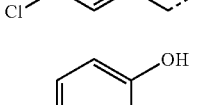 | H | H | Cl | F | H | H |
| 312 |  | H | H | Cl | OH | H | H |
| 313 | 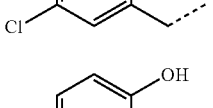 | H | H | Cl | OMe | H | H |

TABLE 1-continued
X = Single Bond, q = 0, r = 0, Y = —(R4)C═C(R5)—
| Compound No. 1- R1—(CH2)p— | | R2 | R3 | R4 | R5 | R6 | R7 |
|---|---|---|---|---|---|---|---|
| 314 | 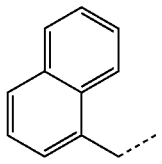 | H | H | F | H | H | H |
| 315 | 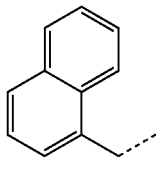 | H | H | Me | H | H | H |
| 316 | 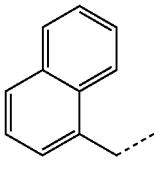 | H | H | OMe | H | H | H |
| 317 | 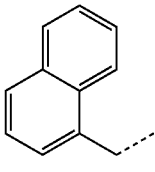 | H | H | CF3 | H | H | H |
| 318 | 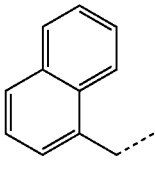 | H | H | OH | H | H | H |
| 319 | 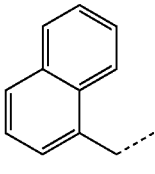 | H | H | H | OH | H | H |
| 320 | 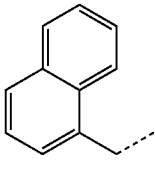 | H | H | OCF3 | H | H | H |
| 321 | 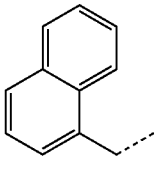 | H | H | NO2 | H | H | H |
| 322 | 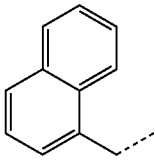 | H | H | H | NO2 | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 323 naphthalen-1-ylmethyl | H | H | CN | H | H | H |
| 324 naphthalen-1-ylmethyl | H | H | H | CN | H | H |
| 325 naphthalen-1-ylmethyl | H | H | Br | H | H | H |
| 326 naphthalen-1-ylmethyl | H | H | H | Br | H | H |
| 327 naphthalen-1-ylmethyl | H | H | COOH | H | H | H |
| 328 naphthalen-1-ylmethyl | H | H | H | COOH | H | H |
| 329 naphthalen-1-ylmethyl | H | H | NHCOMe | H | H | H |
| 330 naphthalen-1-ylmethyl | H | H | H | NHCOMe | H | H |

TABLE 1-continued
X = Single Bond, q = 0, r = 0, Y = —(R4)C═C(R5)—
| Compound No. 1- R1—(CH2)p— | | R2 | R3 | R4 | R5 | R6 | R7 |
|---|---|---|---|---|---|---|---|
| 331 | 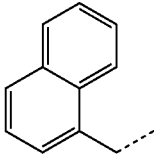 | H | H | SO2NH2 | H | H | H |
| 332 | 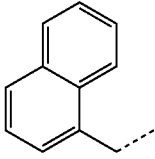 | H | H | H | SO2NH2 | H | H |
| 333 | 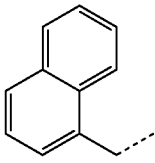 | H | H | Me | Me | H | H |
| 334 | 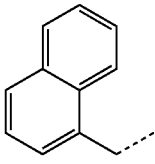 | H | H | Me | H | Me | H |
| 335 | 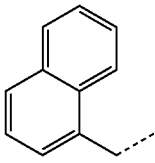 | H | H | H | Me | Me | H |
| 336 | 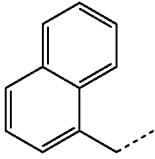 | H | H | F | F | H | H |
| 337 | 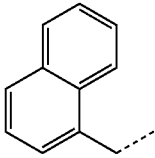 | H | H | F | H | F | H |
| 338 | 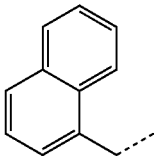 | H | H | H | F | F | H |
| 339 | 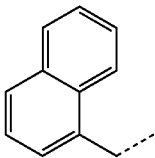 | H | H | Cl | Cl | H | H |

TABLE 1-continued

| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 340 | naphthyl-CH2 | H | H | Cl | H | Cl | H |
| 341 | naphthyl-CH2 | H | H | H | Cl | Cl | H |
| 342 | naphthyl-CH2 | H | H | Me | F | H | H |
| 343 | naphthyl-CH2 | H | H | Me | Cl | H | H |
| 344 | naphthyl-CH2 | H | H | Me | OH | H | H |
| 345 | naphthyl-CH2 | H | H | Me | OMe | H | H |
| 346 | naphthyl-CH2 | H | H | F | Me | H | H |
| 347 | naphthyl-CH2 | H | H | F | Cl | H | H |

TABLE 1-continued

X = Single Bond, q = 0, r = 0, Y = —(R4)C═C(R5)—

| Compound No. 1- R1—(CH2)p— | | R2 | R3 | R4 | R5 | R6 | R7 |
|---|---|---|---|---|---|---|---|
| 348 | naphthyl-CH2 | H | H | F | OH | H | H |
| 349 | naphthyl-CH2 | H | H | F | OMe | H | H |
| 350 | naphthyl-CH2 | H | H | Cl | Me | H | H |
| 351 | naphthyl-CH2 | H | H | Cl | F | H | H |
| 352 | naphthyl-CH2 | H | H | Cl | OH | H | H |
| 353 | naphthyl-CH2 | H | H | Cl | OMe | H | H |
| 354 | 4-Br-2-OH-C6H3-CH2 | H | H | Cl | H | H | H |
| 355 | 4-Br-2-OH-C6H3-CH2 | H | H | H | OMe | H | H |
| 356 | 4-Br-2-OH-C6H3-CH2 | H | H | H | COOMe | H | H |
| 357 | 4-Br-2-OH-C6H3-CH2 | H | H | H | H | COOMe | H |

TABLE 1-continued
X = Single Bond, q = 0, r = 0, Y = —(R4)C=C(R5)—
| Compound No. 1- R1—(CH2)p— | | R2 | R3 | R4 | R5 | R6 | R7 |
|---|---|---|---|---|---|---|---|
| 358 | 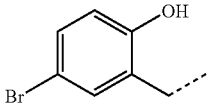 | H | H | H | OCF3 | H | H |
| 359 | 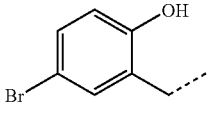 | H | H | COOMe | H | H | H |
| 360 | 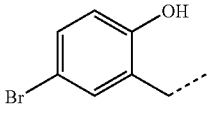 | H | H | H | CF3 | H | H |
| 361 | 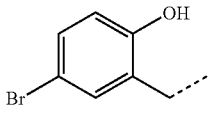 | H | H | H | Me | H | H |
| 362 | 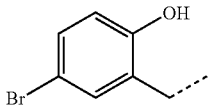 | H | H | H | F | H | H |
| 363 | 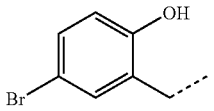 | H | H | H | OH | H | H |
| 364 | 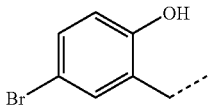 | H | H | H | NO2 | H | H |
| 365 | 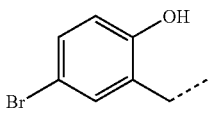 | H | H | H | F | F | H |
| 366 | 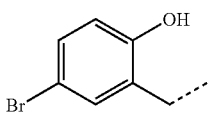 | H | H | F | H | H | H |
| 367 | 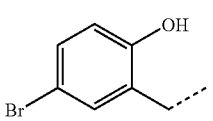 | H | H | Me | H | H | H |
| 368 | 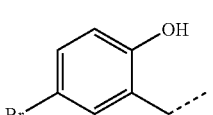 | H | H | H | CN | H | H |
| 369 | 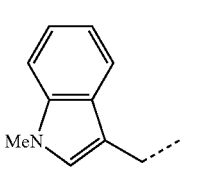 | H | H | Cl | H | H | H |

TABLE 1-continued

| | X = Single Bond, q = 0, r = 0, Y = —(R4)C=C(R5)— | | | | | |
|---|---|---|---|---|---|---|
| Compound No. 1- R1—(CH2)p— | R2 | R3 | R4 | R5 | R6 | R7 |
| 370 (3-methylindole, N-Me) | H | H | H | OMe | H | H |
| 371 (3-methylindole, N-Me) | H | H | H | OCF3 | H | H |
| 372 (3-methylindole, N-Me) | H | H | COOMe | H | H | H |
| 373 (3-methylindole, N-Me) | H | H | H | CF3 | H | H |
| 374 (3-methylindole, N-Me) | H | H | H | Me | H | H |
| 375 (3-methylindole, N-Me) | H | H | H | F | H | H |
| 376 (3-methylindole, N-Me) | H | H | H | OH | H | H |
| 377 (3-methylindole, N-Me) | H | H | H | NO2 | H | H |
| 378 (3-methylindole, N-Me) | H | H | H | F | F | H |

TABLE 1-continued

| | X = Single Bond, q = 0, r = 0, Y = —(R4)C=C(R5)— | | | | | |
|---|---|---|---|---|---|---|
| Compound No. 1- R1—(CH2)p— | | R2 | R3 | R4 | R5 | R6 | R7 |
| 379 | 3-(1-methylindolyl)methyl | H | H | F | H | H | H |
| 380 | 3-(1-methylindolyl)methyl | H | H | Me | H | H | H |
| 381 | 3-(1-methylindolyl)methyl | H | H | H | CN | H | H |
| 382 | 3-benzothienyl methyl | H | H | Cl | H | H | H |
| 383 | 3-benzothienyl methyl | H | H | H | OMe | H | H |
| 384 | 3-benzothienyl methyl | H | H | H | OCF3 | H | H |
| 385 | 3-benzothienyl methyl | H | H | COOMe | H | H | H |
| 386 | 3-benzothienyl methyl | H | H | H | CF3 | H | H |
| 387 | 3-benzothienyl methyl | H | H | H | Me | H | H |

TABLE 1-continued

X = Single Bond, q = 0, r = 0, Y = —(R4)C═C(R5)—

| Compound No. 1- R1—(CH2)p— | R2 | R3 | R4 | R5 | R6 | R7 |
|---|---|---|---|---|---|---|
| 388 (benzothiophen-3-ylmethyl) | H | H | H | F | H | H |
| 389 (benzothiophen-3-ylmethyl) | H | H | H | OH | H | H |
| 390 (benzothiophen-3-ylmethyl) | H | H | H | NO2 | H | H |
| 391 (benzothiophen-3-ylmethyl) | H | H | H | F | F | H |
| 392 (benzothiophen-3-ylmethyl) | H | H | F | H | H | H |
| 393 (benzothiophen-3-ylmethyl) | H | H | Me | H | H | H |
| 394 (benzothiophen-3-ylmethyl) | H | H | H | CN | H | H |
| 395 (3,5-dichloro-2-hydroxybenzyl) | H | Me | H | H | H | H |
| 396 (5-chloro-2-hydroxybenzyl) | H | Me | H | H | H | H |

TABLE 1-continued

| | X = Single Bond, q = 0, r = 0, Y = —(R4)C=C(R5)— | | | | | | |
|---|---|---|---|---|---|---|---|
| Compound No. 1- | R1—(CH2)p— | R2 | R3 | R4 | R5 | R6 | R7 |
| 397 | 1-naphthylmethyl | H | Me | H | H | H | H |
| 398 | 3-phenylpropyl | H | Me | H | H | H | H |
| 399 | 4-chloro-2-fluoro-3-hydroxybenzyl(2-OH) | H | H | H | H | H | H |
| 400 | 4-chloro-2-fluoro-3-hydroxybenzyl | H | H | F | H | H | H |
| 401 | 4-chloro-2-fluoro-3-hydroxybenzyl | H | H | Cl | H | H | H |
| 402 | 4-chloro-2-fluoro-3-hydroxybenzyl | H | H | Me | H | H | H |
| 403 | 4-chloro-2-fluoro-3-hydroxybenzyl | H | H | Et | H | H | H |
| 404 | 4-chloro-2-fluoro-3-hydroxybenzyl | H | H | OMe | H | H | H |
| 405 | 4-chloro-2-fluoro-3-hydroxybenzyl | H | H | OEt | H | H | H |

TABLE 1-continued

| | X = Single Bond, q = 0, r = 0, Y = —(R4)C=C(R5)— | | | | | | |
|---|---|---|---|---|---|---|---|
| Compound No. | 1- R1—(CH2)p— | R2 | R3 | R4 | R5 | R6 | R7 |
| 406 | 4-Cl, 2-F, 3-OH-benzyl | H | H | CF3 | H | H | H |
| 407 | 4-Cl, 2-F, 3-OH-benzyl | H | H | OCF3 | H | H | H |
| 408 | 4-Cl, 2-F, 3-OH-benzyl | H | H | NO2 | H | H | H |
| 409 | 4-Cl, 2-F, 3-OH-benzyl | H | H | NH2 | H | H | H |
| 410 | 4-Cl, 2-F, 3-OH-benzyl | H | H | OH | H | H | H |
| 411 | 4-Cl, 2-F, 3-OH-benzyl | H | H | CN | H | H | H |
| 412 | 4-Cl, 2-F, 3-OH-benzyl | H | H | COMe | H | H | H |
| 413 | 4-Cl, 2-F, 3-OH-benzyl | H | H | COOMe | H | H | H |
| 414 | 4-Cl, 2-F, 3-OH-benzyl | H | H | H | F | H | H |

TABLE 1-continued

| | X = Single Bond, q = 0, r = 0, Y = —(R4)C═C(R5)— | | | | | | |
|---|---|---|---|---|---|---|---|
| Compound No. | 1- R1—(CH2)p— | R2 | R3 | R4 | R5 | R6 | R7 |
| 415 | 4-Cl, 2-F, 6-OH-benzyl | H | H | H | Cl | H | H |
| 416 | 4-Cl, 2-F, 6-OH-benzyl | H | H | H | Me | H | H |
| 417 | 4-Cl, 2-F, 6-OH-benzyl | H | H | H | Et | H | H |
| 418 | 4-Cl, 2-F, 6-OH-benzyl | H | H | H | OMe | H | H |
| 419 | 4-Cl, 2-F, 6-OH-benzyl | H | H | H | OEt | H | H |
| 420 | 4-Cl, 2-F, 6-OH-benzyl | H | H | H | CF3 | H | H |
| 421 | 4-Cl, 2-F, 6-OH-benzyl | H | H | H | OCF3 | H | H |
| 422 | 4-Cl, 2-F, 6-OH-benzyl | H | H | H | NO2 | H | H |
| 423 | 4-Cl, 2-F, 6-OH-benzyl | H | H | H | NH2 | H | H |

TABLE 1-continued

| | X = Single Bond, q = 0, r = 0, Y = —(R4)C=C(R5)— | | | | | | |
|---|---|---|---|---|---|---|---|
| Compound No. 1- R1—(CH2)p— | | R2 | R3 | R4 | R5 | R6 | R7 |
| 424 | 4-Cl, 2-F, 3-OH-phenyl | H | H | H | OH | H | H |
| 425 | 4-Cl, 2-F, 3-OH-phenyl | H | H | H | CN | H | H |
| 426 | 4-Cl, 2-F, 3-OH-phenyl | H | H | H | COMe | H | H |
| 427 | 4-Cl, 2-F, 3-OH-phenyl | H | H | H | COOMe | H | H |
| 428 | 4-Cl, 2-F, 3-OH-phenyl | H | H | F | F | H | H |
| 429 | 4-Cl, 2-F, 3-OH-phenyl | H | H | F | Cl | H | H |
| 430 | 4-Cl, 2-F, 3-OH-phenyl | H | H | F | Me | H | H |
| 431 | 4-Cl, 2-F, 3-OH-phenyl | H | H | F | Et | H | H |
| 432 | 4-Cl, 2-F, 3-OH-phenyl | H | H | F | OMe | H | H |

TABLE 1-continued

| | X = Single Bond, q = 0, r = 0, Y = —(R4)C=C(R5)— | | | | | | |
|---|---|---|---|---|---|---|---|
| Compound No. | 1- R1—(CH2)p— | R2 | R3 | R4 | R5 | R6 | R7 |
| 433 | 4-Cl, 2-F, 3-OH-benzyl (F, OH, Cl substituted) | H | H | F | OEt | H | H |
| 434 | 4-Cl, 2-F, 3-OH-benzyl | H | H | F | CF3 | H | H |
| 435 | 4-Cl, 2-F, 3-OH-benzyl | H | H | F | OCF3 | H | H |
| 436 | 4-Cl, 2-F, 3-OH-benzyl | H | H | Cl | F | H | H |
| 437 | 4-Cl, 2-F, 3-OH-benzyl | H | H | Cl | Cl | H | H |
| 438 | 4-Cl, 2-F, 3-OH-benzyl | H | H | Cl | Me | H | H |
| 439 | 4-Cl, 2-F, 3-OH-benzyl | H | H | Cl | Et | H | H |
| 440 | 4-Cl, 2-F, 3-OH-benzyl | H | H | Cl | OMe | H | H |
| 441 | 4-Cl, 2-F, 3-OH-benzyl | H | H | Cl | OEt | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 442 (4-Cl, 2-F, phenol-6-CH<) | H | H | Cl | CF3 | H | H |
| 443 (4-Cl, 2-F, phenol-6-CH<) | H | H | Cl | OCF3 | H | H |
| 444 (4-Cl, 2-F, phenol-6-CH<) | H | H | Me | F | H | H |
| 445 (4-Cl, 2-F, phenol-6-CH<) | H | H | Me | Cl | H | H |
| 446 (4-Cl, 2-F, phenol-6-CH<) | H | H | Me | Me | H | H |
| 447 (4-Cl, 2-F, phenol-6-CH<) | H | H | Me | Et | H | H |
| 448 (4-Cl, 2-F, phenol-6-CH<) | H | H | Me | OMe | H | H |
| 449 (4-Cl, 2-F, phenol-6-CH<) | H | H | Me | OEt | H | H |
| 450 (4-Cl, 2-F, phenol-6-CH<) | H | H | Me | CF3 | H | H |

TABLE 1-continued

X = Single Bond, q = 0, r = 0, Y = —(R4)C=C(R5)—

| Compound No. 1- R1—(CH2)p— | R2 | R3 | R4 | R5 | R6 | R7 |
|---|---|---|---|---|---|---|
| 451 (4-Cl, 2-F, 6-OH phenyl) | H | H | Me | OCF3 | H | H |
| 452 (4-Cl, 2-F, 6-OH phenyl) | H | H | OMe | F | H | H |
| 453 (4-Cl, 2-F, 6-OH phenyl) | H | H | OMe | Cl | H | H |
| 454 (4-Cl, 2-F, 6-OH phenyl) | H | H | OMe | Me | H | H |
| 455 (4-Cl, 2-F, 6-OH phenyl) | H | H | OMe | Et | H | H |
| 456 (4-Cl, 2-F, 6-OH phenyl) | H | H | OMe | OMe | H | H |
| 457 (4-Cl, 2-F, 6-OH phenyl) | H | H | OMe | OEt | H | H |
| 458 (4-Cl, 2-F, 6-OH phenyl) | H | H | OMe | CF3 | H | H |
| 459 (4-Cl, 2-F, 6-OH phenyl) | H | H | OMe | OCF3 | H | H |

TABLE 2

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 1 | 2,4-dichloro-6-hydroxyphenyl-CH2- (Cl, OH, Cl on phenyl) | H | H | H | H | H | H |
| 2 | 4-chloro-2-hydroxyphenyl-CH2- | H | H | H | H | H | H |
| 3 | naphthalen-1-yl-CH2- | H | H | H | H | H | H |
| 4 | phenyl-(CH2)3- | H | H | H | H | H | H |
| 5 | 3,4-dichlorophenyl-CH2- | H | H | H | H | H | H |
| 6 | 3,4-dichlorophenyl-CH2- | H | H | H | Cl | H | H |
| 7 | naphthalen-1-yl-CH2- | H | H | H | Cl | H | H |
| 8 | 2-chlorophenyl-CH2- | H | H | H | H | H | H |
| 9 | 3-chlorophenyl-CH2- | H | H | H | H | H | H |
| 10 | 4-chlorophenyl-CH2- | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 11 | 2-methoxybenzyl | H | H | H | H | H | H |
| 12 | 4-methoxybenzyl | H | H | H | H | H | H |
| 13 | 5-bromo-2-hydroxybenzyl | H | H | H | H | H | H |
| 14 | 5-bromo-2-methoxybenzyl | H | H | H | H | H | H |
| 15 | 5-bromo-2-fluorobenzyl | H | H | H | H | H | H |
| 16 | 3-bromobenzyl | H | H | H | H | H | H |
| 17 | 3-chloro-4-fluorobenzyl | H | H | H | H | H | H |
| 18 | (1-methyl-1H-indol-3-yl)methyl | H | H | H | H | H | H |
| 19 | benzo[b]thiophen-3-ylmethyl | H | H | H | H | H | H |
| 20 | 2-hydroxy-4-methoxybenzyl | H | H | H | H | H | H |
| 21 | 3-nitrobenzyl | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 22 | 3-MeO-C6H4-CH2— | H | H | H | H | H | H |
| 23 | naphthalen-2-yl-CH2— | H | H | H | H | H | H |
| 24 | C6H5-CH2— | H | H | H | H | H | H |
| 25 | C6H5-CH2CH2— | H | H | H | H | H | H |
| 26 | 3-Br-4-OH-5-Cl-C6H2-CH2— | H | H | H | H | H | H |
| 27 | 3-CN-6-OH-C6H3-CH2— | H | H | H | H | H | H |
| 28 | 3-Cl-4-OH-5-CF3-C6H2-CH2— | H | H | H | H | H | H |
| 29 | 3-CF3-4-OH-5-Cl-C6H2-CH2— | H | H | H | H | H | H |
| 30 | 2-Cl-6-OH-C6H3-CH2— | H | H | H | H | H | H |
| 31 | 4-Me-C6H4-CH2— | H | H | H | H | H | H |
| 32 | 4-F-C6H4-CH2— | H | H | H | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 33 | 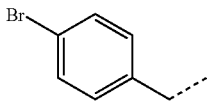 | H | H | H | H | H | H |
| 34 | 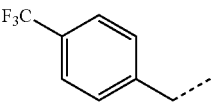 | H | H | H | H | H | H |
| 35 | 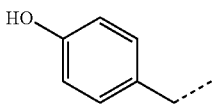 | H | H | H | H | H | H |
| 36 | 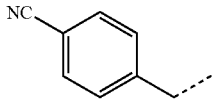 | H | H | H | H | H | H |
| 37 | 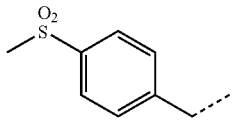 | H | H | H | H | H | H |
| 38 | 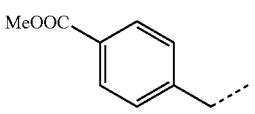 | H | H | H | H | H | H |
| 39 | 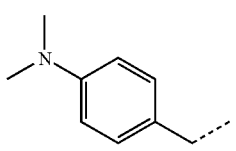 | H | H | H | H | H | H |
| 40 | 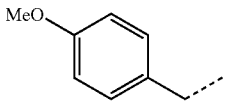 | H | H | H | H | H | H |
| 41 | 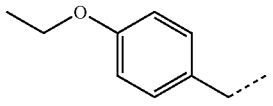 | H | H | H | H | H | H |
| 42 | 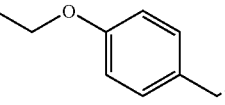 | H | H | H | H | H | H |
| 43 | 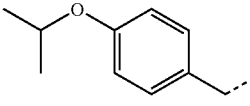 | H | H | H | H | H | H |
| 44 | 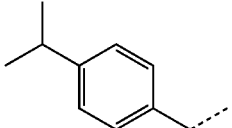 | H | H | H | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 45 | 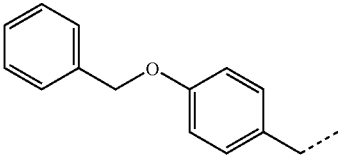 | H | H | H | H | H | H |
| 46 | 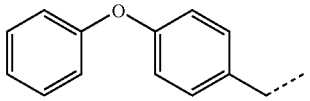 | H | H | H | H | H | H |
| 47 | 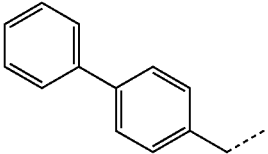 | H | H | H | H | H | H |
| 48 | 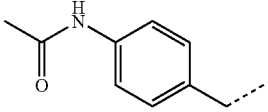 | H | H | H | H | H | H |
| 49 | 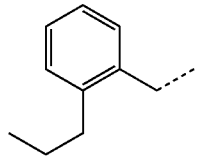 | H | H | H | H | H | H |
| 50 | 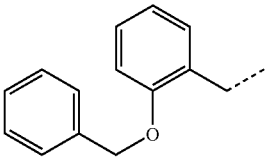 | H | H | H | H | H | H |
| 51 | 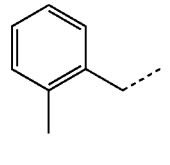 | H | H | H | H | H | H |
| 52 | 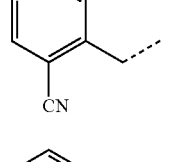 | H | H | H | H | H | H |
| 53 | 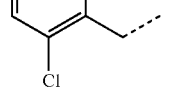 | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 54 | 2-methoxybenzyl | H | H | H | H | H | H |
| 55 | 2-ethoxybenzyl | H | H | H | H | H | H |
| 56 | 2-biphenylmethyl | H | H | H | H | H | H |
| 57 | 3-(trifluoromethyl)benzyl | H | H | H | H | H | H |
| 58 | 3-chloro-2-fluorobenzyl | H | H | H | H | H | H |
| 59 | 3,5-dichlorobenzyl | H | H | H | H | H | H |
| 60 | 3-methylbenzyl | H | H | H | H | H | H |
| 61 | 3-fluoro-5-(trifluoromethyl)benzyl | H | H | H | H | H | H |
| 62 | 3-(trifluoromethoxy)benzyl | H | H | H | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 63 | 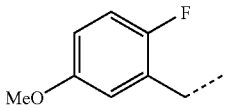 | H | H | H | H | H | H |
| 64 | 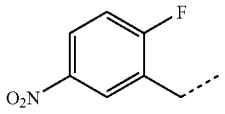 | H | H | H | H | H | H |
| 65 | 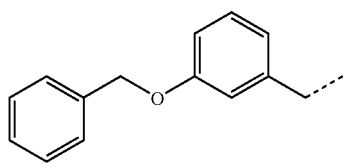 | H | H | H | H | H | H |
| 66 | 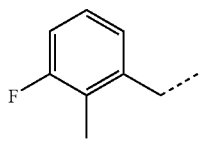 | H | H | H | H | H | H |
| 67 | 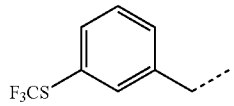 | H | H | H | H | H | H |
| 68 | 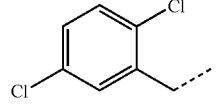 | H | H | H | H | H | H |
| 69 | 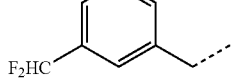 | H | H | H | H | H | H |
| 70 | 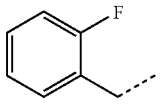 | H | H | H | H | H | H |
| 71 | 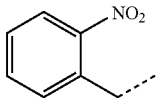 | H | H | H | H | H | H |
| 72 | 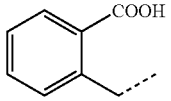 | H | H | H | H | H | H |
| 73 | 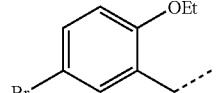 | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 74 | 2,3-dimethylphenyl-CH2— | H | H | H | H | H | H |
| 75 | 3-fluorophenyl-CH2— | H | H | H | H | H | H |
| 76 | 2,4-dichlorophenyl-CH2— | H | H | H | H | H | H |
| 77 | 3-cyanophenyl-CH2— | H | H | H | H | H | H |
| 78 | 3-hydroxyphenyl-CH2— | H | H | H | H | H | H |
| 79 | 3-ethoxyphenyl-CH2— | H | H | H | H | H | H |
| 80 | 4-chloro-3-nitrophenyl-CH2— | H | H | H | H | H | H |
| 81 | 2,3-dichlorophenyl-CH2— | H | H | H | H | H | H |
| 82 | 2,3-difluoro-4-methylphenyl-CH2— | H | H | H | H | H | H |
| 83 | 3-bromo-4-fluorophenyl-CH2— | H | H | H | H | H | H |
| 84 | 2-fluoro-3-(trifluoromethyl)phenyl-CH2— | H | H | H | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 85 | 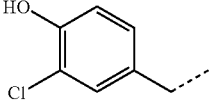 | H | H | H | H | H | H |
| 86 | 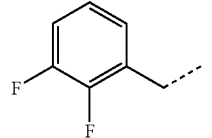 | H | H | H | H | H | H |
| 87 | 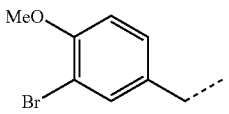 | H | H | H | H | H | H |
| 88 | 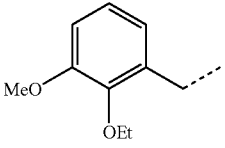 | H | H | H | H | H | H |
| 89 | 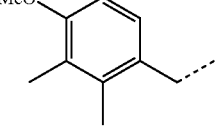 | H | H | H | H | H | H |
| 90 | 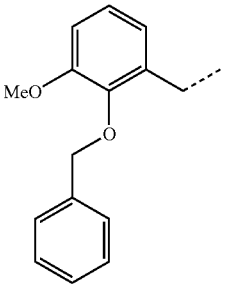 | H | H | H | H | H | H |
| 91 | 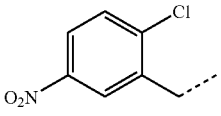 | H | H | H | H | H | H |
| 92 | 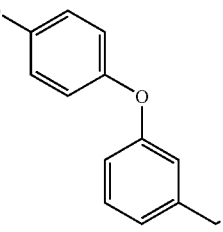 | H | H | H | H | H | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 93 | 4-methylphenoxy-phenyl | H | H | H | H | H | H |
| 94 | 4-chlorophenoxy-phenyl | H | H | H | H | H | H |
| 95 | 3-benzyloxyphenyl | H | H | H | H | H | H |
| 96 | 3-phenoxyphenyl | H | H | H | H | H | H |
| 97 | 2-methoxy-3-hydroxyphenyl (MeO, HO) | H | H | H | H | H | H |
| 98 | 3-CF3-2-Cl-phenyl | H | H | H | H | H | H |
| 99 | 4-hydroxy-3-nitrophenyl (HO, O2N) | H | H | H | H | H | H |
| 100 | 2,3-dimethoxyphenyl (OMe, OMe) | H | H | H | H | H | H |
| 101 | 4-EtO, 3-Me, 2-OEt-phenyl | H | H | H | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 102 | 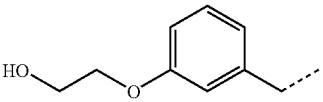 | H | H | H | H | H | H |
| 103 | 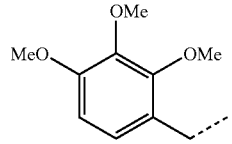 | H | H | H | H | H | H |
| 104 | 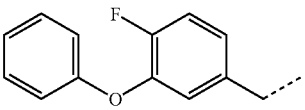 | H | H | H | H | H | H |
| 105 | 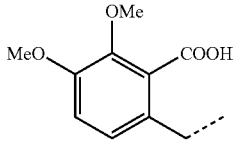 | H | H | H | H | H | H |
| 106 | 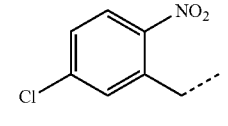 | H | H | H | H | H | H |
| 107 | 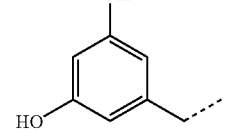 | H | H | H | H | H | H |
| 108 | 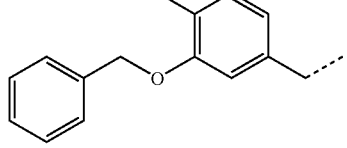 | H | H | H | H | H | H |
| 109 | 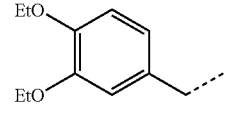 | H | H | H | H | H | H |
| 110 | 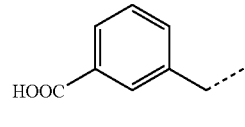 | H | H | H | H | H | H |
| 111 | 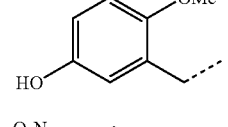 | H | H | H | H | H | H |
| 112 | 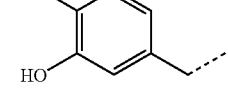 | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 113 | 3,5-bis(trifluoromethyl)benzyl | H | H | H | H | H | H |
| 114 | 2-methoxy-3-nitrobenzyl | H | H | H | H | H | H |
| 115 | (4-methylnaphthalen-1-yl)methyl | H | H | H | H | H | H |
| 116 | (1,7-dimethyl-1H-indol-3-yl)methyl | H | H | H | H | H | H |
| 117 | (2-methoxynaphthalen-1-yl)methyl | H | H | H | H | H | H |
| 118 | benzofuran-2-ylmethyl | H | H | H | H | H | H |
| 119 | (1,2-dimethyl-1H-indol-3-yl)methyl | H | H | H | H | H | H |
| 120 | quinolin-8-ylmethyl | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 121 | 2-hydroxynaphthalen-1-ylmethyl | H | H | H | H | H | H |
| 122 | 2-acetoxynaphthalen-1-ylmethyl | H | H | H | H | H | H |
| 123 | 1-hydroxynaphthalen-2-ylmethyl | H | H | H | H | H | H |
| 124 | 1H-indol-7-ylmethyl | H | H | H | H | H | H |
| 125 | quinolin-4-ylmethyl | H | H | H | H | H | H |
| 126 | 1,5-dimethyl-1H-indol-3-ylmethyl | H | H | H | H | H | H |
| 127 | anthracen-9-ylmethyl | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 128 | 2-methyl-1-naphthylmethyl | H | H | H | H | H | H |
| 129 | 2-ethoxy-1-naphthylmethyl | H | H | H | H | H | H |
| 130 | 1H-indol-3-ylmethyl | H | H | H | H | H | H |
| 131 | 1-methyl-1H-indol-3-ylmethyl | H | H | H | H | H | H |
| 132 | 1-methyl-1H-indol-2-ylmethyl | H | H | H | H | H | H |
| 133 | 4-methyl-1-methyl-1H-indol-3-ylmethyl | H | H | H | H | H | H |
| 134 | 2,5-dimethyl-1-methyl-1H-indol-3-ylmethyl | H | H | H | H | H | H |
| 135 | 5-methoxy-1-methyl-1H-indol-2-ylmethyl | H | H | H | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 136 | 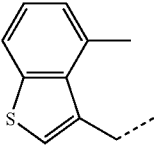 | H | H | H | H | H | H |
| 137 | 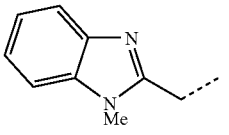 | H | H | H | H | H | H |
| 138 | 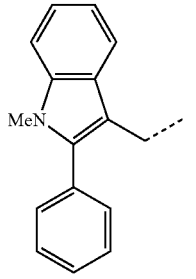 | H | H | H | H | H | H |
| 139 | 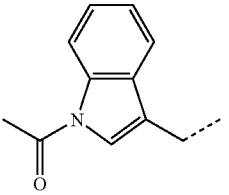 | H | H | H | H | H | H |
| 140 | 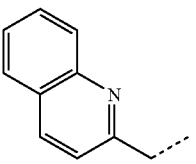 | H | H | H | H | H | H |
| 141 | 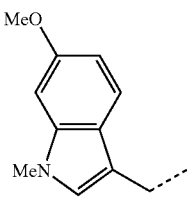 | H | H | H | H | H | H |
| 142 | 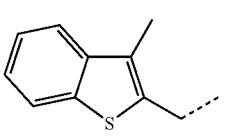 | H | H | H | H | H | H |
| 143 | 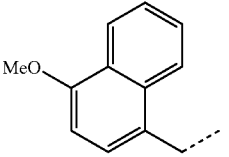 | H | H | H | H | H | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 144 | phenanthrenyl-CH2 | H | H | H | H | H | H |
| 145 | 6-methoxynaphth-2-yl-CH2 | H | H | H | H | H | H |
| 146 | 1-bromonaphth-2-yl-CH2 | H | H | H | H | H | H |
| 147 | 4-(dimethylamino)naphth-1-yl-CH2 | H | H | H | H | H | H |
| 148 | 2,3-dihydro-1,4-benzodioxin-6-yl-CH2 | H | H | H | H | H | H |
| 149 | 2,2-dimethylchroman-6-yl-CH2 | H | H | H | H | H | H |
| 150 | 2,3-dihydrobenzofuran-5-yl-CH2 | H | H | H | H | H | H |
| 151 | 9-ethylcarbazol-3-yl-CH2 | H | H | H | H | H | H |
| 152 | benzo[1,3]dioxol-4-yl-CH2 | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 153 | benzo[1,3]dioxol-5-ylmethyl | H | H | H | H | H | H |
| 154 | 4-phenylbutyl | H | H | H | H | H | H |
| 155 | 5-phenylpentyl | H | H | H | H | H | H |
| 156 | cyclohexylmethyl | H | H | H | H | H | H |
| 157 | 5-iodo-2-hydroxybenzyl | H | H | H | H | H | H |
| 158 | 5-nitro-2-hydroxybenzyl | H | H | H | H | H | H |
| 159 | 5-chloro-3-methyl-2-hydroxybenzyl | H | H | H | H | H | H |
| 160 | 3-methyl-2-hydroxybenzyl | H | H | H | H | H | H |
| 161 | 5-fluoro-2-hydroxybenzyl | H | H | H | H | H | H |
| 162 | 3,5-diiodo-2-hydroxybenzyl | H | H | H | H | H | H |
| 163 | 5-chloro-2-aminobenzyl | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 164 | 2-hydroxyphenyl-CH2- | H | H | H | H | H | H |
| 165 | 2-aminophenyl-CH2- | H | H | H | H | H | H |
| 166 | 4-tert-butyl-2-hydroxyphenyl-CH2- | H | H | H | H | H | H |
| 167 | 4-trifluoromethoxy-2-hydroxyphenyl-CH2- | H | H | H | H | H | H |
| 168 | 3-methoxy-2-hydroxyphenyl-CH2- | H | H | H | H | H | H |
| 169 | 2,3-dihydroxyphenyl-CH2- | H | H | H | H | H | H |
| 170 | 3-ethoxy-2-hydroxyphenyl-CH2- | H | H | H | H | H | H |
| 171 | 3-carboxy-2-hydroxyphenyl-CH2- | H | H | H | H | H | H |
| 172 | 3-tert-butyl-2-hydroxyphenyl-CH2- | H | H | H | H | H | H |
| 173 | furan-2-yl-CH2- | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 174 | oxazol-2-yl | H | H | H | H | H | H |
| 175 | 1H-imidazol-2-yl | H | H | H | H | H | H |
| 176 | thiazol-2-yl | H | H | H | H | H | H |
| 177 | 1H-pyrazol-3-yl | H | H | H | H | H | H |
| 178 | 3,5-dimethyl-1-phenyl-1H-pyrazol-4-yl | H | H | H | H | H | H |
| 179 | 2,5-dimethyl-1-phenyl-1H-pyrrol-3-yl | H | H | H | H | H | H |
| 180 | 5-(4-chlorophenyl)furan-2-yl | H | H | H | H | H | H |
| 181 | thiophen-2-yl | H | H | H | H | H | H |
| 182 | 1H-pyrrol-2-yl | H | H | H | H | H | H |
| 183 | pyridin-2-yl | H | H | H | H | H | H |
| 184 | pyridin-3-yl | H | H | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 185 | 4-pyridylmethyl | H | H | H | H | H | H |
| 186 | 5-chloro-2-hydroxybenzyl | H | H | H | Cl | H | H |
| 187 | 5-nitro-2-hydroxybenzyl | H | H | H | Cl | H | H |
| 188 | 5-methoxy-2-hydroxybenzyl | H | H | H | Cl | H | H |
| 189 | 3-chlorobenzyl | H | H | H | Cl | H | H |
| 190 | 3-bromobenzyl | H | H | H | Cl | H | H |
| 191 | 3-nitrobenzyl | H | H | H | Cl | H | H |
| 192 | 3-methoxybenzyl | H | H | H | Cl | H | H |
| 193 | 3,5-dichloro-2-hydroxybenzyl | H | H | H | Cl | H | H |
| 194 | (1-methylindol-3-yl)methyl | H | H | H | Cl | H | H |
| 195 | (benzothiophen-3-yl)methyl | H | H | H | Cl | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 196 | benzyl | H | H | H | Cl | H | H |
| 197 | 3-phenylpropyl | H | H | H | Cl | H | H |
| 198 | 4-bromo-2-hydroxybenzyl | H | H | H | Cl | H | H |
| 199 | 2-naphthylmethyl | H | H | H | Cl | H | H |
| 200 | 2-phenylethyl | H | H | H | Cl | H | H |
| 201 | 3,5-dichloro-2-hydroxybenzyl | H | H | Cl | H | H | H |
| 202 | 3,5-dichloro-2-hydroxybenzyl | H | H | H | OMe | H | H |
| 203 | 3,5-dichloro-2-hydroxybenzyl | H | H | H | COOMe | H | H |
| 204 | 3,5-dichloro-2-hydroxybenzyl | H | H | H | H | Cl | H |
| 205 | 3,5-dichloro-2-hydroxybenzyl | H | H | H | H | COOMe | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 206 | 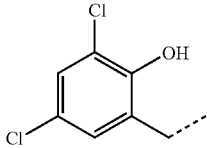 | H | H | H | H | H | Cl |
| 207 | 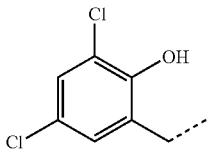 | H | H | H | OCF3 | H | H |
| 208 | 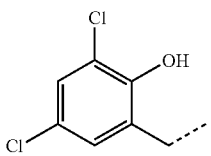 | H | H | COOMe | H | H | H |
| 209 | 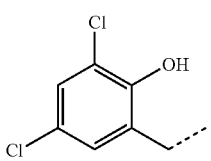 | H | H | H | CF3 | H | H |
| 210 | 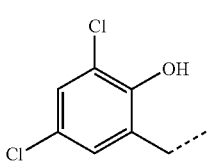 | H | H | H | Me | H | H |
| 211 | 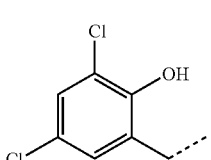 | H | H | H | F | H | H |
| 212 | 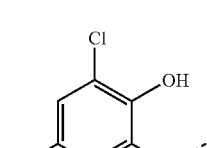 | H | H | H | OH | H | H |
| 213 | 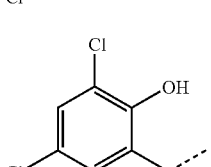 | H | H | H | NO2 | H | H |
| 214 | 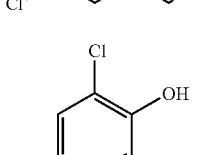 | H | H | H | F | F | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 215 | 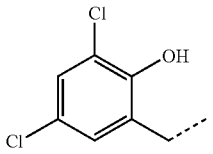 | H | H | F | H | H | H |
| 216 | 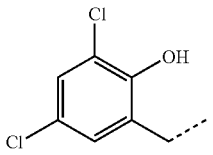 | H | H | Me | H | H | H |
| 217 | 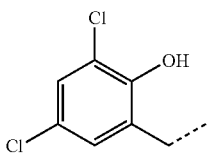 | H | H | H | CN | H | H |
| 218 | 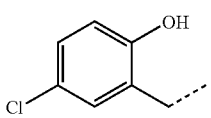 | H | H | Cl | H | H | H |
| 219 | 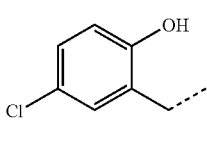 | H | H | H | OMe | H | H |
| 220 | 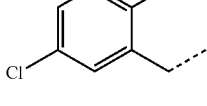 | H | H | H | COOMe | H | H |
| 221 | 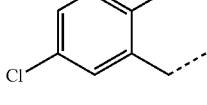 | H | H | H | H | Cl | H |
| 222 | 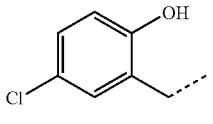 | H | H | H | H | COOMe | H |
| 223 | 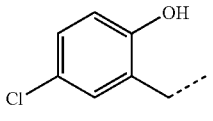 | H | H | H | H | H | Cl |
| 224 | 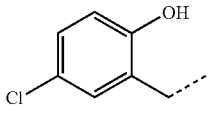 | H | H | H | OCF3 | H | H |
| 225 | 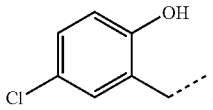 | H | H | COOMe | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 226 | 4-Cl-2-OH-phenyl-CH2 | H | H | H | CF3 | H | H |
| 227 | 4-Cl-2-OH-phenyl-CH2 | H | H | H | Me | H | H |
| 228 | 4-Cl-2-OH-phenyl-CH2 | H | H | H | F | H | H |
| 229 | naphth-1-yl-CH2 | H | H | Cl | H | H | H |
| 230 | naphth-1-yl-CH2 | H | H | H | OMe | H | H |
| 231 | naphth-1-yl-CH2 | H | H | H | COOMe | H | H |
| 232 | naphth-1-yl-CH2 | H | H | H | H | Cl | H |
| 233 | naphth-1-yl-CH2 | H | H | H | H | COOMe | H |
| 234 | naphth-1-yl-CH2 | H | H | H | H | H | Cl |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 235 | naphthyl-CH2 | H | H | H | OCF3 | H | H |
| 236 | naphthyl-CH2 | H | H | COOMe | H | H | H |
| 237 | naphthyl-CH2 | H | H | H | CF3 | H | H |
| 238 | naphthyl-CH2 | H | H | H | Me | H | H |
| 239 | naphthyl-CH2 | H | H | H | F | H | H |
| 240 | phenyl-(CH2)3 | H | H | Cl | H | H | H |
| 241 | phenyl-(CH2)3 | H | H | H | OMe | H | H |
| 242 | phenyl-(CH2)3 | H | H | H | COOMe | H | H |
| 243 | phenyl-(CH2)3 | H | H | H | H | Cl | H |
| 244 | phenyl-(CH2)3 | H | H | H | H | COOMe | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 245 | 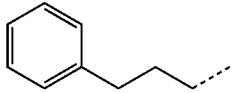 | H | H | H | H | H | Cl |
| 246 | 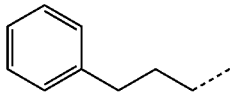 | H | H | H | OCF3 | H | H |
| 247 | 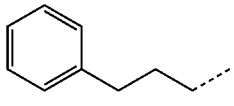 | H | H | COOMe | H | H | H |
| 248 | 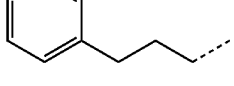 | H | H | H | CF3 | H | H |
| 249 | 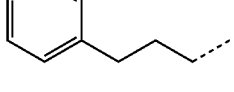 | H | H | H | Me | H | H |
| 250 | 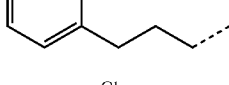 | H | H | H | F | H | H |
| 251 | 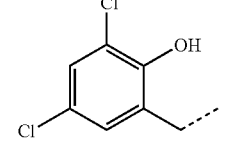 | H | H | H | H | H | COOMe |
| 252 | 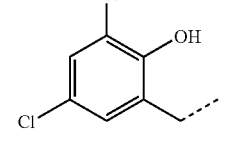 | H | H | H | H | F | H |
| 253 | 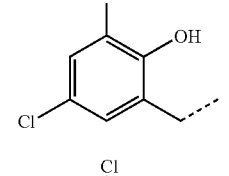 | H | H | H | H | H | F |
| 254 | 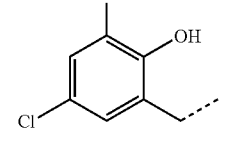 | H | H | H | H | Me | H |
| 255 | 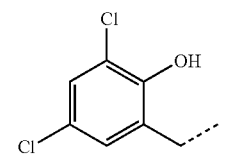 | H | H | H | H | H | Me |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 256 | 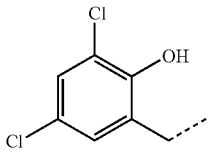 | H | H | OMe | H | H | H |
| 257 | 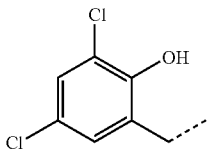 | H | H | H | H | OMe | H |
| 258 | 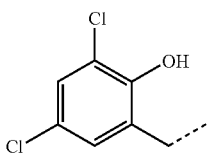 | H | H | H | H | H | OMe |
| 259 | 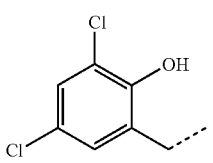 | H | H | CF3 | H | H | H |
| 260 | 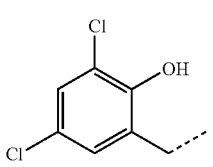 | H | H | H | H | CF3 | H |
| 261 | 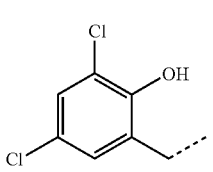 | H | H | H | H | H | CF3 |
| 262 | 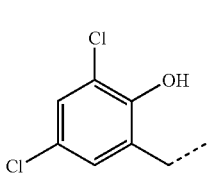 | H | H | OH | H | H | H |
| 263 | 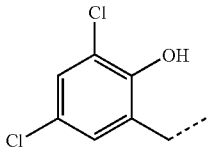 | H | H | H | H | OH | H |
| 264 | 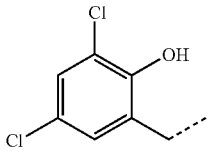 | H | H | H | H | H | OH |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 265 | 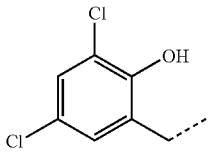 | H | H | OCF3 | H | H | H |
| 266 | 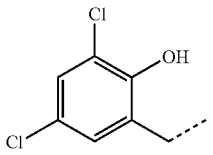 | H | H | H | H | OCF3 | H |
| 267 | 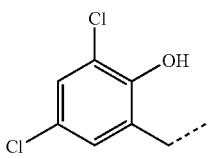 | H | H | H | H | H | OCF3 |
| 268 | 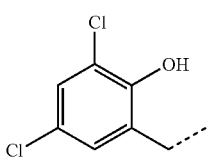 | H | H | NO2 | H | H | H |
| 269 | 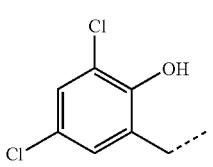 | H | H | H | H | NO2 | H |
| 270 | 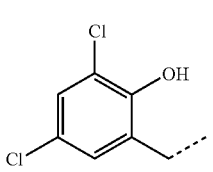 | H | H | H | H | H | NO2 |
| 271 | 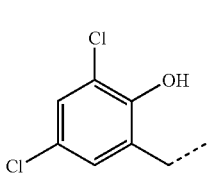 | H | H | CN | H | H | H |
| 272 | 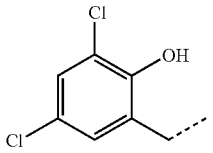 | H | H | H | H | CN | H |
| 273 | 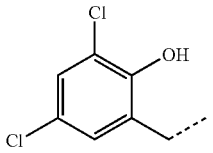 | H | H | H | H | H | CN |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 274 | 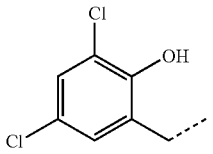 | H | H | Br | H | H | H |
| 275 | 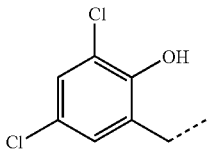 | H | H | H | Br | H | H |
| 276 | 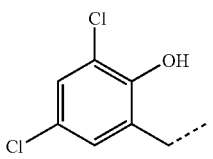 | H | H | H | H | Br | H |
| 277 | 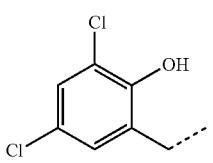 | H | H | H | H | H | Br |
| 278 | 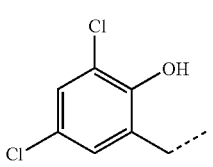 | H | H | COOH | H | H | H |
| 279 | 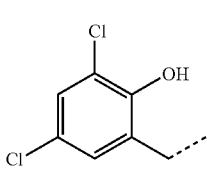 | H | H | H | COOH | H | H |
| 280 | 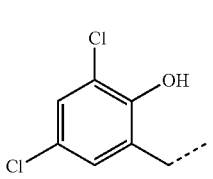 | H | H | H | H | COOH | H |
| 281 | 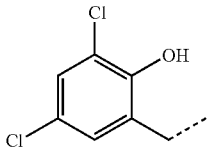 | H | H | H | H | H | COOH |
| 282 | 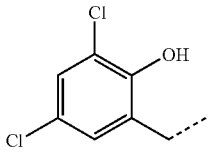 | H | H | NHCOMe | H | H | H |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 283 | 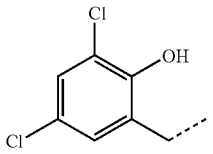 | H | H | H | NHCOMe | H | H |
| 284 | 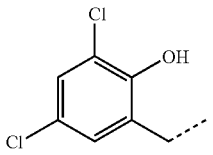 | H | H | H | H | NHCOMe | H |
| 285 | 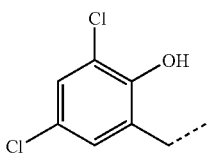 | H | H | H | H | H | NHCOMe |
| 286 | 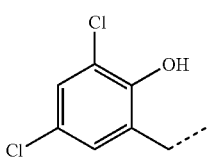 | H | H | SO2NH2 | H | H | H |
| 287 | 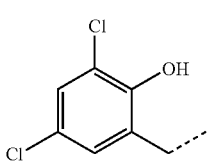 | H | H | H | SO2NH2H | H | H |
| 288 | 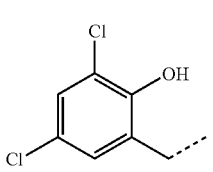 | H | H | H | H | SO2NH2H | H |
| 289 | 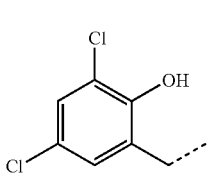 | H | H | H | H | H | SO2NH2 |
| 290 | 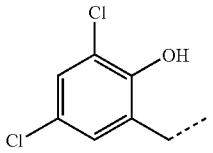 | H | H | Me | Me | H | H |
| 291 | 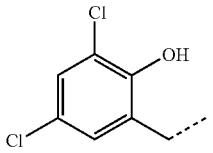 | H | H | Me | H | Me | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 292 | 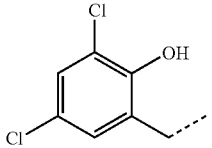 | H | H | H | Me | Me | H |
| 293 | 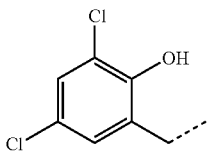 | H | H | F | F | H | H |
| 294 | 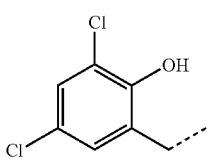 | H | H | F | H | F | H |
| 295 | 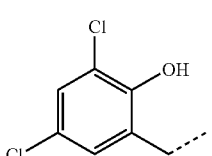 | H | H | H | F | F | H |
| 296 | 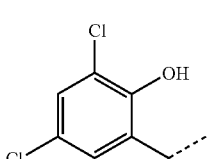 | H | H | Cl | Cl | H | H |
| 297 | 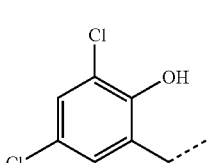 | H | H | Cl | H | Cl | H |
| 298 | 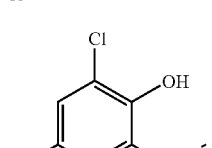 | H | H | H | Cl | Cl | H |
| 299 | 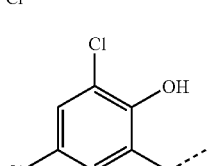 | H | H | Me | F | H | H |
| 300 | 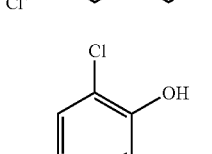 | H | H | Me | Cl | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 301 | 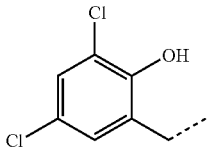 | H | H | Me | OH | H | H |
| 302 | 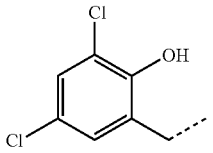 | H | H | Me | OMe | H | H |
| 303 | 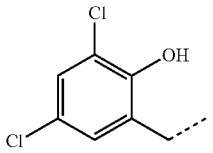 | H | H | F | Me | H | H |
| 304 | 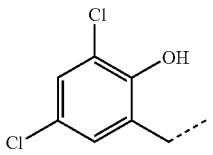 | H | H | F | Cl | H | H |
| 305 | 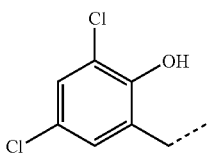 | H | H | F | OH | H | H |
| 306 | 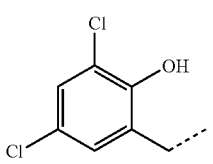 | H | H | F | OMe | H | H |
| 307 | 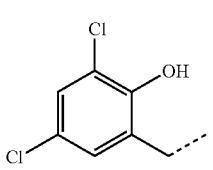 | H | H | Cl | Me | H | H |
| 308 | 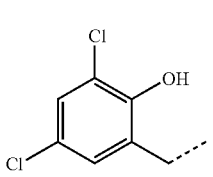 | H | H | Cl | F | H | H |
| 309 | 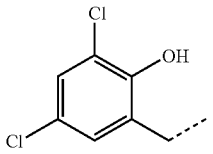 | H | H | Cl | OH | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 310 | 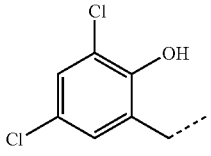 | H | H | Cl | OMe | H | H |
| 311 | 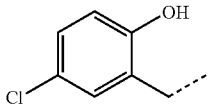 | H | H | H | H | H | COOMe |
| 312 | 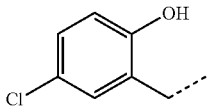 | H | H | F | H | H | H |
| 313 | 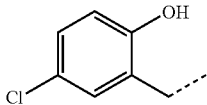 | H | H | H | H | F | H |
| 314 | 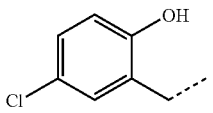 | H | H | H | H | H | F |
| 315 | 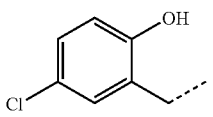 | H | H | Me | H | H | H |
| 316 | 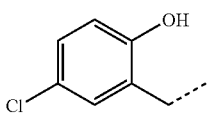 | H | H | H | H | Me | H |
| 317 | 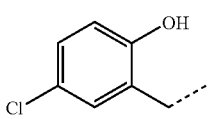 | H | H | H | H | H | Me |
| 318 | 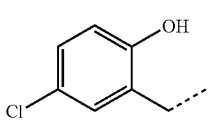 | H | H | OMe | H | H | H |
| 319 | 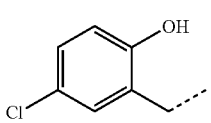 | H | H | H | H | OMe | H |
| 320 | 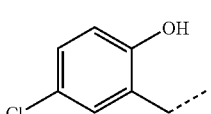 | H | H | H | H | H | OMe |
| 321 | 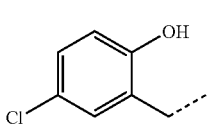 | H | H | CF3 | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 322 | 4-Cl, 2-OH-benzyl | H | H | H | H | CF3 | H |
| 323 | 4-Cl, 2-OH-benzyl | H | H | H | H | H | CF3 |
| 324 | 4-Cl, 2-OH-benzyl | H | H | OH | H | H | H |
| 325 | 4-Cl, 2-OH-benzyl | H | H | H | OH | H | H |
| 326 | 4-Cl, 2-OH-benzyl | H | H | H | H | OH | H |
| 327 | 4-Cl, 2-OH-benzyl | H | H | H | H | H | OH |
| 328 | 4-Cl, 2-OH-benzyl | H | H | OCF3 | H | H | H |
| 329 | 4-Cl, 2-OH-benzyl | H | H | H | H | OCF3 | H |
| 330 | 4-Cl, 2-OH-benzyl | H | H | H | H | H | OCF3 |
| 331 | 4-Cl, 2-OH-benzyl | H | H | NO2 | H | H | H |
| 332 | 4-Cl, 2-OH-benzyl | H | H | H | NO2 | H | H |
| 333 | 4-Cl, 2-OH-benzyl | H | H | H | H | NO2 | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 334 | 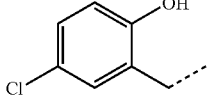 | H | H | H | H | H | NO2 |
| 335 | 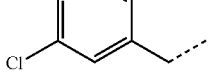 | H | H | CN | H | H | H |
| 336 | 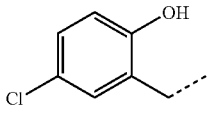 | H | H | H | CN | H | H |
| 337 | 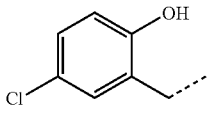 | H | H | H | H | CN | H |
| 338 | 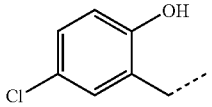 | H | H | H | H | H | CN |
| 339 | 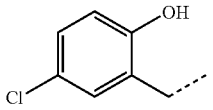 | H | H | Br | H | H | H |
| 340 | 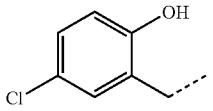 | H | H | H | Br | H | H |
| 341 | 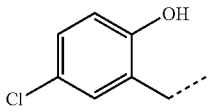 | H | H | H | H | Br | H |
| 342 | 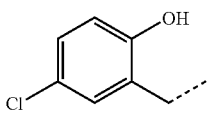 | H | H | H | H | H | Br |
| 343 | 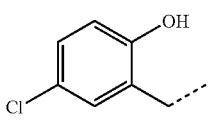 | H | H | COOH | H | H | H |
| 344 | 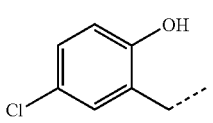 | H | H | H | COOH | H | H |
| 345 | 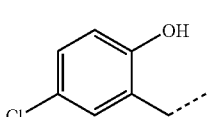 | H | H | H | H | COOH | H |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 346 | 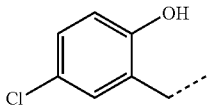 | H | H | H | H | H | COOH |
| 347 |  | H | H | NHCOMe | H | H | H |
| 348 | 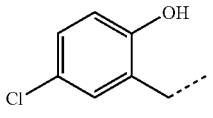 | H | H | H | NHCOMe | H | H |
| 349 | 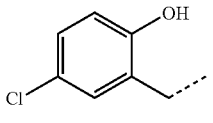 | H | H | H | H | NHCOMe | H |
| 350 | 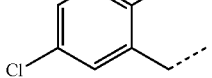 | H | H | H | H | H | NHCOMe |
| 351 | 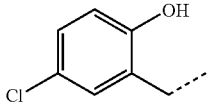 | H | H | SO2NH2 | H | H | H |
| 352 | 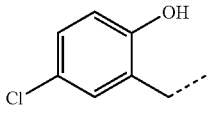 | H | H | H | SO2NH2 | H | H |
| 353 | 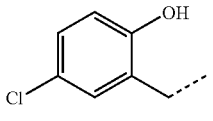 | H | H | H | H | SO2NH2 | H |
| 354 | 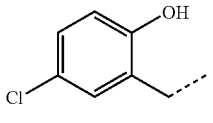 | H | H | H | H | H | SO2NH2 |
| 355 | 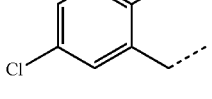 | H | H | Me | Me | H | H |
| 356 | 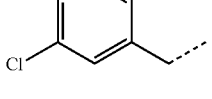 | H | H | Me | H | Me | H |
| 357 | 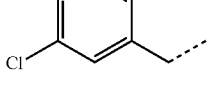 | H | H | H | Me | Me | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 358 | 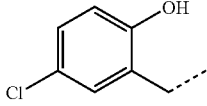 | H | H | F | F | H | H |
| 359 | 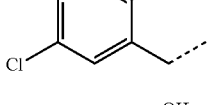 | H | H | F | H | F | H |
| 360 | 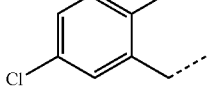 | H | H | H | F | F | H |
| 361 | 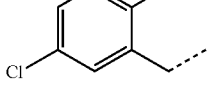 | H | H | Cl | Cl | H | H |
| 362 | 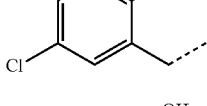 | H | H | Cl | H | Cl | H |
| 363 | 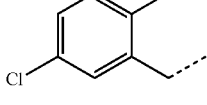 | H | H | H | Cl | Cl | H |
| 364 | 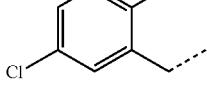 | H | H | Me | F | H | H |
| 365 | 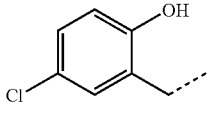 | H | H | Me | Cl | H | H |
| 366 | 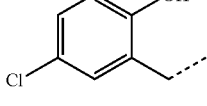 | H | H | Me | OH | H | H |
| 367 | 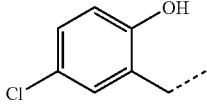 | H | H | Me | OMe | H | H |
| 368 | 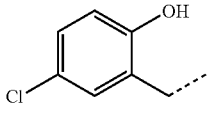 | H | H | F | Me | H | H |
| 369 | 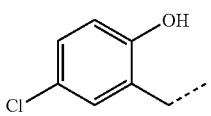 | H | H | F | Cl | H | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 370 | 4-Cl-2-(CH2)-phenol | H | H | F | OH | H | H |
| 371 | 4-Cl-2-(CH2)-phenol | H | H | F | OMe | H | H |
| 372 | 4-Cl-2-(CH2)-phenol | H | H | Cl | Me | H | H |
| 373 | 4-Cl-2-(CH2)-phenol | H | H | Cl | F | H | H |
| 374 | 4-Cl-2-(CH2)-phenol | H | H | Cl | OH | H | H |
| 375 | 4-Cl-2-(CH2)-phenol | H | H | Cl | OMe | H | H |
| 376 | naphth-1-ylmethyl | H | H | H | H | H | COOMe |
| 377 | naphth-1-ylmethyl | H | H | F | H | H | H |
| 378 | naphth-1-ylmethyl | H | H | H | H | F | H |
| 379 | naphth-1-ylmethyl | H | H | H | H | H | F |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 380 | 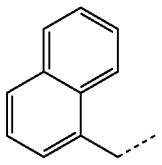 | H | H | Me | H | H | H |
| 381 | 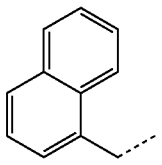 | H | H | H | H | Me | H |
| 382 |  | H | H | H | H | H | Me |
| 383 | 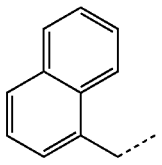 | H | H | OMe | H | H | H |
| 384 | 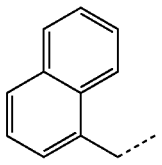 | H | H | H | H | OMe | H |
| 385 | 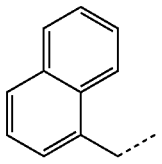 | H | H | H | H | H | OMe |
| 386 | 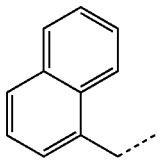 | H | H | CF3 | H | H | H |
| 387 |  | H | H | H | H | CF3 | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 388 | naphthalen-1-ylmethyl | H | H | H | H | H | CF3 |
| 389 | naphthalen-1-ylmethyl | H | H | OH | H | H | H |
| 390 | naphthalen-1-ylmethyl | H | H | H | OH | H | H |
| 391 | naphthalen-1-ylmethyl | H | H | H | H | OH | H |
| 392 | naphthalen-1-ylmethyl | H | H | H | H | H | OH |
| 393 | naphthalen-1-ylmethyl | H | H | OCF3 | H | H | H |
| 394 | naphthalen-1-ylmethyl | H | H | H | H | OCF3 | H |
| 395 | naphthalen-1-ylmethyl | H | H | H | H | H | OCF3 |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 396 | naphthyl-CH | H | H | NO2 | H | H | H |
| 397 | naphthyl-CH | H | H | H | NO2 | H | H |
| 398 | naphthyl-CH | H | H | H | H | NO2 | H |
| 399 | naphthyl-CH | H | H | H | H | H | NO2 |
| 400 | naphthyl-CH | H | H | CN | H | H | H |
| 401 | naphthyl-CH | H | H | H | CN | H | H |
| 402 | naphthyl-CH | H | H | H | H | CN | H |
| 403 | naphthyl-CH | H | H | H | H | H | CN |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 404 | naphthyl-CH | H | H | Br | H | H | H |
| 405 | naphthyl-CH | H | H | H | Br | H | H |
| 406 | naphthyl-CH | H | H | H | H | Br | H |
| 407 | naphthyl-CH | H | H | H | H | H | Br |
| 408 | naphthyl-CH | H | H | COOH | H | H | H |
| 409 | naphthyl-CH | H | H | H | COOH | H | H |
| 410 | naphthyl-CH | H | H | H | H | COOH | H |
| 411 | naphthyl-CH | H | H | H | H | H | COOH |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 412 | naphthyl-CH | H | H | NHCOMe | H | H | H |
| 413 | naphthyl-CH | H | H | H | NHCOMe | H | H |
| 414 | naphthyl-CH | H | H | H | H | NHCOMe | H |
| 415 | naphthyl-CH | H | H | H | H | H | NHCOMe |
| 416 | naphthyl-CH | H | H | SO2NH2 | H | H | H |
| 417 | naphthyl-CH | H | H | H | SO2NH2 | H | H |
| 418 | naphthyl-CH | H | H | H | H | SO2NH2 | H |
| 419 | naphthyl-CH | H | H | H | H | H | SO2NH2 |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 420 | 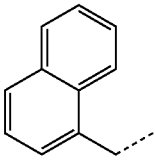 | H | H | Me | Me | H | H |
| 421 | 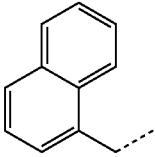 | H | H | Me | H | Me | H |
| 422 | 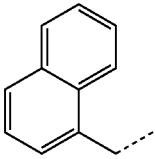 | H | H | H | Me | Me | H |
| 423 | 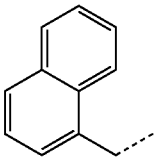 | H | H | F | F | H | H |
| 424 | 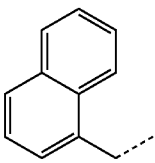 | H | H | F | H | F | H |
| 425 | 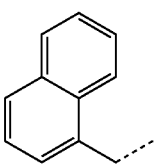 | H | H | H | F | F | H |
| 426 | 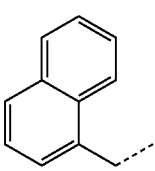 | H | H | Cl | Cl | H | H |
| 427 | 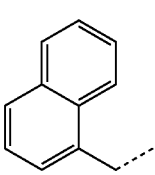 | H | H | Cl | H | Cl | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 428 | 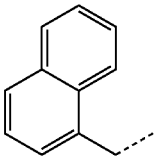 | H | H | H | Cl | Cl | H |
| 429 | 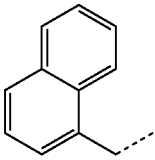 | H | H | Me | F | H | H |
| 430 | 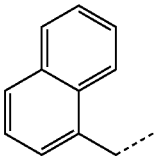 | H | H | Me | Cl | H | H |
| 431 | 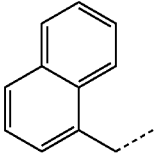 | H | H | Me | OH | H | H |
| 432 | 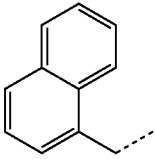 | H | H | Me | OMe | H | H |
| 433 | 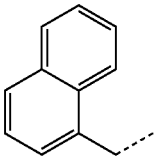 | H | H | F | Me | H | H |
| 434 | 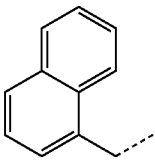 | H | H | F | Cl | H | H |
| 435 | 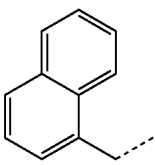 | H | H | F | OH | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 436 | naphthalen-1-ylmethyl | H | H | F | OMe | H | H |
| 437 | naphthalen-1-ylmethyl | H | H | Cl | Me | H | H |
| 438 | naphthalen-1-ylmethyl | H | H | Cl | F | H | H |
| 439 | naphthalen-1-ylmethyl | H | H | Cl | OH | H | H |
| 440 | naphthalen-1-ylmethyl | H | H | Cl | OMe | H | H |
| 441 | 4-bromo-2-hydroxybenzyl | H | H | Cl | H | H | H |
| 442 | 4-bromo-2-hydroxybenzyl | H | H | H | OMe | H | H |
| 443 | 4-bromo-2-hydroxybenzyl | H | H | H | COOMe | H | H |
| 444 | 4-bromo-2-hydroxybenzyl | H | H | H | H | Cl | H |
| 445 | 4-bromo-2-hydroxybenzyl | H | H | H | H | COOMe | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 446 | 4-Br, 2-(CH2)-phenol | H | H | H | H | H | Cl |
| 447 | 4-Br, 2-(CH2)-phenol | H | H | H | OCF3 | H | H |
| 448 | 4-Br, 2-(CH2)-phenol | H | H | COOMe | H | H | H |
| 449 | 4-Br, 2-(CH2)-phenol | H | H | H | CF3 | H | H |
| 450 | 4-Br, 2-(CH2)-phenol | H | H | H | Me | H | H |
| 451 | 4-Br, 2-(CH2)-phenol | H | H | H | F | H | H |
| 452 | 4-Br, 2-(CH2)-phenol | H | H | H | OH | H | H |
| 453 | 4-Br, 2-(CH2)-phenol | H | H | H | NO2 | H | H |
| 454 | 4-Br, 2-(CH2)-phenol | H | H | H | F | F | H |
| 455 | 4-Br, 2-(CH2)-phenol | H | H | F | H | H | H |
| 456 | 4-Br, 2-(CH2)-phenol | H | H | Me | H | H | H |
| 457 | 4-Br, 2-(CH2)-phenol | H | H | H | CN | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 458 | 3-(1-methylindolyl)methyl | H | H | Cl | H | H | H |
| 459 | 3-(1-methylindolyl)methyl | H | H | H | OMe | H | H |
| 460 | 3-(1-methylindolyl)methyl | H | H | H | COOMe | H | H |
| 461 | 3-(1-methylindolyl)methyl | H | H | H | H | Cl | H |
| 462 | 3-(1-methylindolyl)methyl | H | H | H | H | COOMe | H |
| 463 | 3-(1-methylindolyl)methyl | H | H | H | H | H | Cl |
| 464 | 3-(1-methylindolyl)methyl | H | H | H | OCF3 | H | H |
| 465 | 3-(1-methylindolyl)methyl | H | H | COOMe | H | H | H |
| 466 | 3-(1-methylindolyl)methyl | H | H | H | CF3 | H | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 467 | 1-methylindol-3-yl | H | H | H | Me | H | H |
| 468 | 1-methylindol-3-yl | H | H | H | F | H | H |
| 469 | 1-methylindol-3-yl | H | H | H | OH | H | H |
| 470 | 1-methylindol-3-yl | H | H | H | NO2 | H | H |
| 471 | 1-methylindol-3-yl | H | H | H | F | F | H |
| 472 | 1-methylindol-3-yl | H | H | F | H | H | H |
| 473 | 1-methylindol-3-yl | H | H | Me | H | H | H |
| 474 | 1-methylindol-3-yl | H | H | H | CN | H | H |
| 475 | benzothiophen-3-yl | H | H | Cl | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 476 | benzothiophen-3-yl | H | H | H | OMe | H | H |
| 477 | benzothiophen-3-yl | H | H | H | COOMe | H | H |
| 478 | benzothiophen-3-yl | H | H | H | H | Cl | H |
| 479 | benzothiophen-3-yl | H | H | H | H | COOMe | H |
| 480 | benzothiophen-3-yl | H | H | H | H | H | Cl |
| 481 | benzothiophen-3-yl | H | H | H | OCF3 | H | H |
| 482 | benzothiophen-3-yl | H | H | COOMe | H | H | H |
| 483 | benzothiophen-3-yl | H | H | H | CF3 | H | H |
| 484 | benzothiophen-3-yl | H | H | H | Me | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 485 | 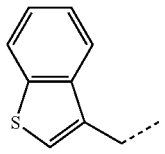 | H | H | H | F | H | H |
| 486 | 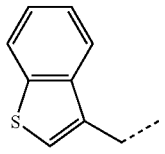 | H | H | H | OH | H | H |
| 487 | 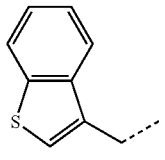 | H | H | H | NO2 | H | H |
| 488 | 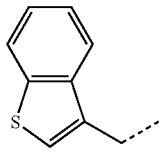 | H | H | H | F | F | H |
| 489 | 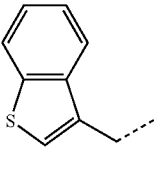 | H | H | F | H | H | H |
| 490 | 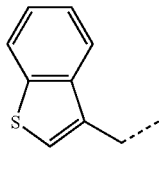 | H | H | Me | H | H | H |
| 491 | 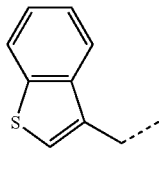 | H | H | H | CN | H | H |
| 492 | 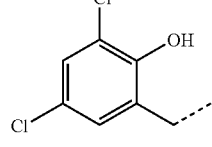 | H | Me | H | H | H | H |
| 493 | 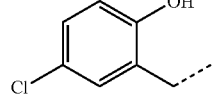 | H | Me | H | H | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 494 | 1-naphthylmethyl | H | Me | H | H | H | H |
| 495 | 3-phenylpropyl | H | Me | H | H | H | H |
| 496 | 5-chloro-3-fluoro-2-hydroxybenzyl | H | H | H | H | H | H |
| 497 | 5-chloro-3-fluoro-2-hydroxybenzyl | H | H | F | H | H | H |
| 498 | 5-chloro-3-fluoro-2-hydroxybenzyl | H | H | Cl | H | H | H |
| 499 | 5-chloro-3-fluoro-2-hydroxybenzyl | H | H | Me | H | H | H |
| 500 | 5-chloro-3-fluoro-2-hydroxybenzyl | H | H | Et | H | H | H |
| 501 | 5-chloro-3-fluoro-2-hydroxybenzyl | H | H | OMe | H | H | H |
| 502 | 5-chloro-3-fluoro-2-hydroxybenzyl | H | H | OEt | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 503 | 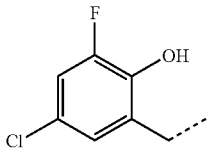 | H | H | CF3 | H | H | H |
| 504 | 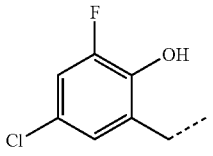 | H | H | OCF3 | H | H | H |
| 505 | 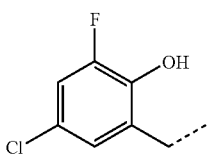 | H | H | NO2 | H | H | H |
| 506 | 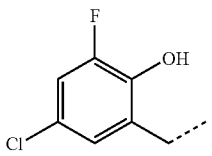 | H | H | NH2 | H | H | H |
| 507 | 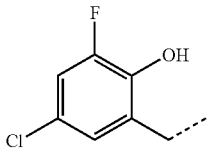 | H | H | OH | H | H | H |
| 508 | 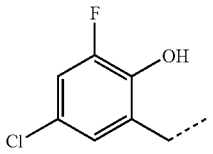 | H | H | CN | H | H | H |
| 509 | 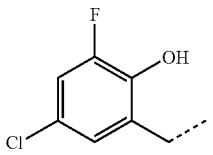 | H | H | COMe | H | H | H |
| 510 | 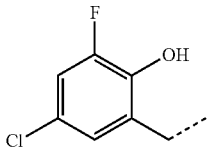 | H | H | COOMe | H | H | H |
| 511 | 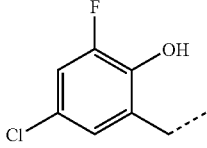 | H | H | H | F | H | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 512 | 4-Cl-2-F-6-OH-C6H2-CH2- | H | H | H | Cl | H | H |
| 513 | 4-Cl-2-F-6-OH-C6H2-CH2- | H | H | H | Me | H | H |
| 514 | 4-Cl-2-F-6-OH-C6H2-CH2- | H | H | H | Et | H | H |
| 515 | 4-Cl-2-F-6-OH-C6H2-CH2- | H | H | H | OMe | H | H |
| 516 | 4-Cl-2-F-6-OH-C6H2-CH2- | H | H | H | OEt | H | H |
| 517 | 4-Cl-2-F-6-OH-C6H2-CH2- | H | H | H | CF3 | H | H |
| 518 | 4-Cl-2-F-6-OH-C6H2-CH2- | H | H | H | OCF3 | H | H |
| 519 | 4-Cl-2-F-6-OH-C6H2-CH2- | H | H | H | NO2 | H | H |
| 520 | 4-Cl-2-F-6-OH-C6H2-CH2- | H | H | H | NH2 | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 521 | 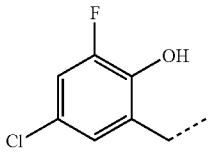 | H | H | H | OH | H | H |
| 522 | 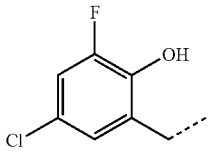 | H | H | H | CN | H | H |
| 523 | 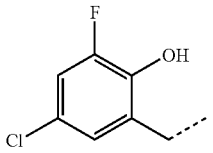 | H | H | H | COMe | H | H |
| 524 | 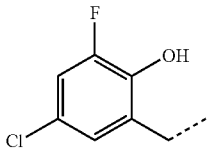 | H | H | H | COOMe | H | H |
| 525 | 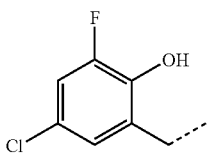 | H | H | F | F | H | H |
| 526 | 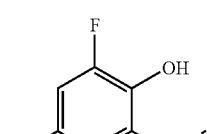 | H | H | F | Cl | H | H |
| 527 | 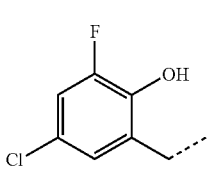 | H | H | F | Me | H | H |
| 528 |  | H | H | F | Et | H | H |
| 529 |  | H | H | F | OMe | H | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 530 | 4-Cl-2-F-6-OH-phenyl-CH2 | H | H | F | OEt | H | H |
| 531 | 4-Cl-2-F-6-OH-phenyl-CH2 | H | H | F | CF3 | H | H |
| 532 | 4-Cl-2-F-6-OH-phenyl-CH2 | H | H | F | OCF3 | H | H |
| 533 | 4-Cl-2-F-6-OH-phenyl-CH2 | H | H | Cl | F | H | H |
| 534 | 4-Cl-2-F-6-OH-phenyl-CH2 | H | H | Cl | Cl | H | H |
| 535 | 4-Cl-2-F-6-OH-phenyl-CH2 | H | H | Cl | Me | H | H |
| 536 | 4-Cl-2-F-6-OH-phenyl-CH2 | H | H | Cl | Et | H | H |
| 537 | 4-Cl-2-F-6-OH-phenyl-CH2 | H | H | Cl | OMe | H | H |
| 538 | 4-Cl-2-F-6-OH-phenyl-CH2 | H | H | Cl | OEt | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 539 | 4-Cl,2-F,6-OH-phenyl-CH2- | H | H | Cl | CF3 | H | H |
| 540 | 4-Cl,2-F,6-OH-phenyl-CH2- | H | H | Cl | OCF3 | H | H |
| 541 | 4-Cl,2-F,6-OH-phenyl-CH2- | H | H | Me | F | H | H |
| 542 | 4-Cl,2-F,6-OH-phenyl-CH2- | H | H | Me | Cl | H | H |
| 543 | 4-Cl,2-F,6-OH-phenyl-CH2- | H | H | Me | Me | H | H |
| 544 | 4-Cl,2-F,6-OH-phenyl-CH2- | H | H | Me | Et | H | H |
| 545 | 4-Cl,2-F,6-OH-phenyl-CH2- | H | H | Me | OMe | H | H |
| 546 | 4-Cl,2-F,6-OH-phenyl-CH2- | H | H | Me | OEt | H | H |
| 547 | 4-Cl,2-F,6-OH-phenyl-CH2- | H | H | Me | CF3 | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 548 | 4-Cl-2-F-6-OH-phenyl-CH2 | H | H | Me | OCF3 | H | H |
| 549 | 4-Cl-2-F-6-OH-phenyl-CH2 | H | H | OMe | F | H | H |
| 550 | 4-Cl-2-F-6-OH-phenyl-CH2 | H | H | OMe | Cl | H | H |
| 551 | 4-Cl-2-F-6-OH-phenyl-CH2 | H | H | OMe | Me | H | H |
| 552 | 4-Cl-2-F-6-OH-phenyl-CH2 | H | H | OMe | Et | H | H |
| 553 | 4-Cl-2-F-6-OH-phenyl-CH2 | H | H | OMe | OMe | H | H |
| 554 | 4-Cl-2-F-6-OH-phenyl-CH2 | H | H | OMe | OEt | H | H |
| 555 | 4-Cl-2-F-6-OH-phenyl-CH2 | H | H | OMe | CF3 | H | H |
| 556 | 4-Cl-2-F-6-OH-phenyl-CH2 | H | H | OMe | OCF3 | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 557 | 4-Cl-2-OMe-6-OH-phenyl | H | H | H | H | H | H |
| 558 | 4-Cl-2-OMe-6-OH-phenyl | H | H | F | H | H | H |
| 559 | 4-Cl-2-OMe-6-OH-phenyl | H | H | Cl | H | H | H |
| 560 | 4-Cl-2-OMe-6-OH-phenyl | H | H | Me | H | H | H |
| 561 | 4-Cl-2-OMe-6-OH-phenyl | H | H | Et | H | H | H |
| 562 | 4-Cl-2-OMe-6-OH-phenyl | H | H | OMe | H | H | H |
| 563 | 4-Cl-2-OMe-6-OH-phenyl | H | H | H | F | H | H |
| 564 | 4-Cl-2-OMe-6-OH-phenyl | H | H | H | Cl | H | H |
| 565 | 4-Cl-2-OMe-6-OH-phenyl | H | H | H | Me | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 566 | 4-Cl-2-OMe-phenol-6-yl-CH | H | H | H | Et | H | H |
| 567 | 4-Cl-2-OMe-phenol-6-yl-CH | H | H | H | OMe | H | H |
| 568 | 4-Cl-2-OMe-phenol-6-yl-CH | H | H | F | F | H | H |
| 569 | 4-Cl-2-OMe-phenol-6-yl-CH | H | H | F | Cl | H | H |
| 570 | 4-Cl-2-OMe-phenol-6-yl-CH | H | H | F | Me | H | H |
| 571 | 4-Cl-2-OMe-phenol-6-yl-CH | H | H | F | Et | H | H |
| 572 | 4-Cl-2-OMe-phenol-6-yl-CH | H | H | F | OMe | H | H |
| 573 | 4-Cl-2-OMe-phenol-6-yl-CH | H | H | Cl | F | H | H |
| 574 | 4-Cl-2-OMe-phenol-6-yl-CH | H | H | Cl | Cl | H | H |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 575 | 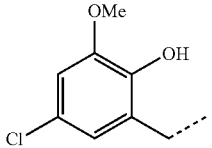 | H | H | Cl | Me | H | H |
| 576 | 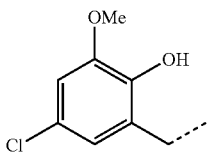 | H | H | Cl | Et | H | H |
| 577 | 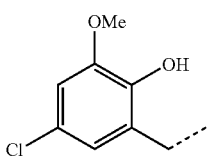 | H | H | Cl | OMe | H | H |
| 578 | 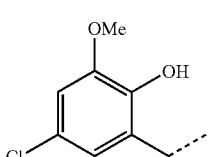 | H | H | Me | F | H | H |
| 579 | 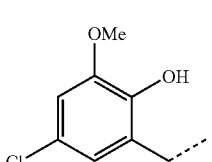 | H | H | Me | Cl | H | H |
| 580 | 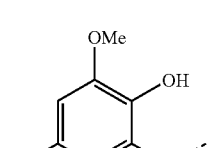 | H | H | Me | Me | H | H |
| 581 | 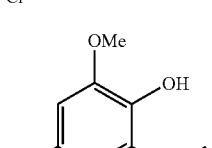 | H | H | Me | Et | H | H |
| 582 | 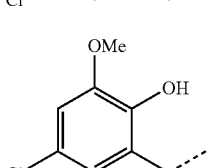 | H | H | Me | OMe | H | H |
| 583 | 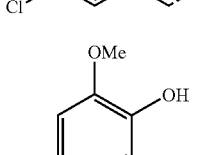 | H | H | Et | F | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 584 | 4-Cl-2-OMe-phenol (6-CH2) | H | H | Et | Cl | H | H |
| 585 | 4-Cl-2-OMe-phenol (6-CH2) | H | H | Et | Me | H | H |
| 586 | 4-Cl-2-OMe-phenol (6-CH2) | H | H | Et | Et | H | H |
| 587 | 4-Cl-2-OMe-phenol (6-CH2) | H | H | Et | OMe | H | H |
| 588 | 4-Cl-2-OMe-phenol (6-CH2) | H | H | OMe | F | H | H |
| 589 | 4-Cl-2-OMe-phenol (6-CH2) | H | H | OMe | Cl | H | H |
| 590 | 4-Cl-2-OMe-phenol (6-CH2) | H | H | OMe | Me | H | H |
| 591 | 4-Cl-2-OMe-phenol (6-CH2) | H | H | OMe | Et | H | H |
| 592 | 4-Cl-2-OMe-phenol (6-CH2) | H | H | OMe | OMe | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 593 | 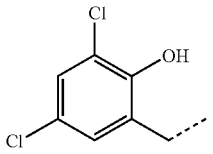 | H | H | Me | CN | H | H |
| 594 | 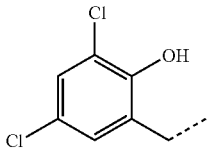 | H | H | H | CN | Me | H |
| 595 | 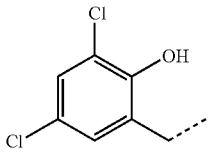 | H | H | H | CN | H | Me |
| 596 | 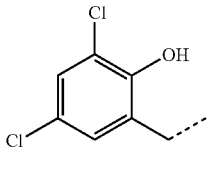 | H | H | Me | Br | H | H |
| 597 | 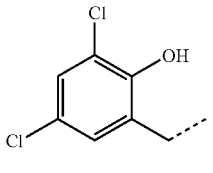 | H | H | H | Br | Me | H |
| 598 | 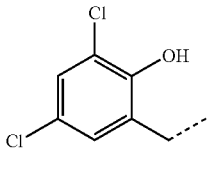 | H | H | H | Br | H | Me |
| 599 | 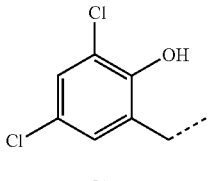 | H | H | Me | H | F | H |
| 600 | 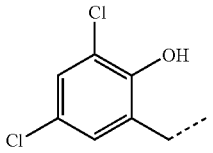 | H | H | Me | H | H | F |
| 601 | 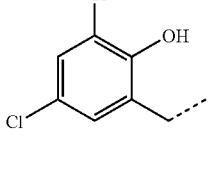 | H | H | F | H | Me | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 602 | 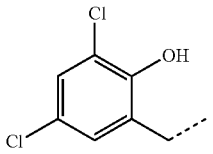 | H | H | F | H | H | Me |
| 603 | 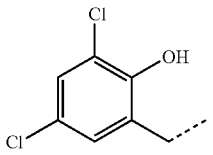 | H | H | Me | H | H | Me |
| 604 | 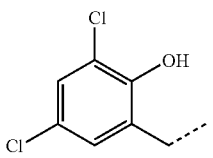 | H | H | H | OMe | Me | H |
| 605 | 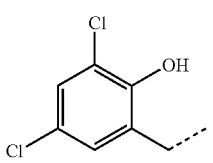 | H | H | H | OH | Me | H |
| 606 | 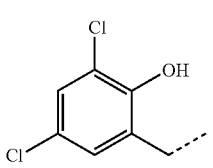 | H | H | NH2 | H | H | H |
| 607 | 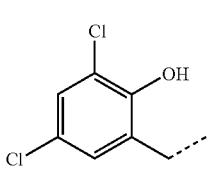 | H | H | H | NH2 | H | H |
| 608 | 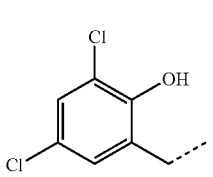 | H | H | H | H | NH2 | H |
| 609 | 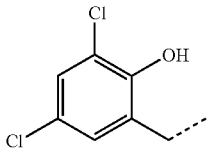 | H | H | Et | H | H | H |
| 610 | 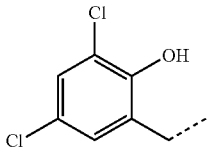 | H | H | H | Et | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 611 | 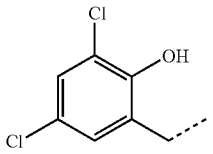 | H | H | H | H | Et | H |
| 612 | 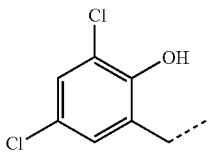 | H | H | iPr | H | H | H |
| 613 | 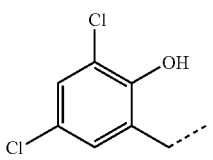 | H | H | H | iPr | H | H |
| 614 | 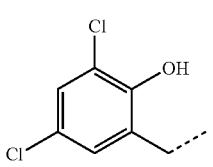 | H | H | H | H | iPr | H |
| 615 | 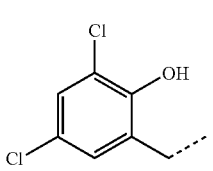 | H | H | Ph | H | H | H |
| 616 | 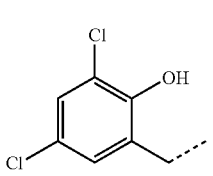 | H | H | H | Ph | H | H |
| 617 | 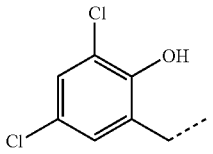 | H | H | H | H | Ph | H |
| 618 | 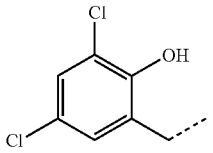 | H | H | OEt | H | H | H |
| 619 | 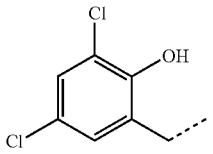 | H | H | H | OEt | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 620 | 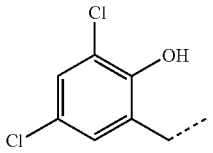 | H | H | H | H | OEt | H |
| 621 | 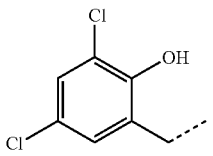 | H | H | OiPr | H | H | H |
| 622 | 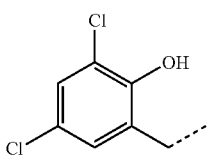 | H | H | H | OiPr | H | H |
| 623 | 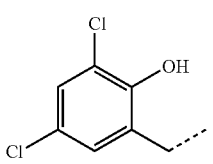 | H | H | H | H | OiPr | H |
| 624 | 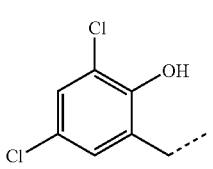 | H | H | OPh | H | H | H |
| 625 | 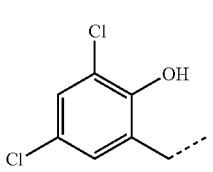 | H | H | H | OPh | H | H |
| 626 | 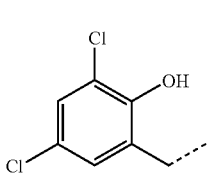 | H | H | H | H | OPh | H |
| 627 | 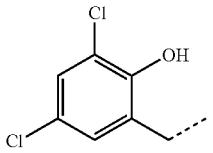 | H | H | SO2Me | H | H | H |
| 628 | 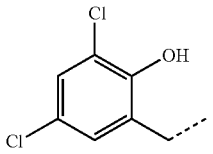 | H | H | H | SO2Me | H | H |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 629 | 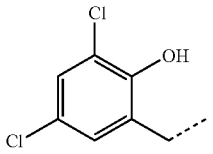 | H | H | H | H | SO2Me | H |
| 630 | 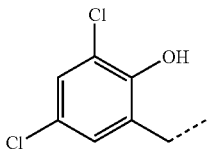 | H | H | SO2Et | H | H | H |
| 631 | 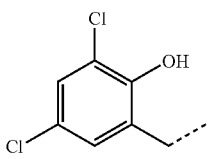 | H | H | H | SO2Et | H | H |
| 632 | 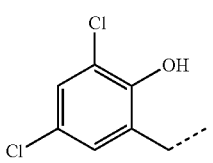 | H | H | H | H | SO2Et | H |
| 633 | 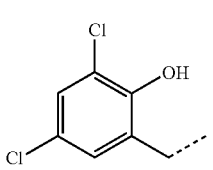 | H | H | SO2iPr | H | H | H |
| 634 | 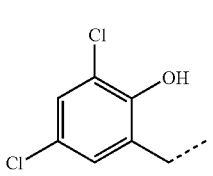 | H | H | H | SO2iPr | H | H |
| 635 | 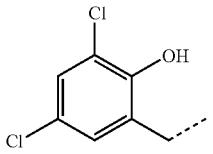 | H | H | H | H | SO2iPr | H |
| 636 | 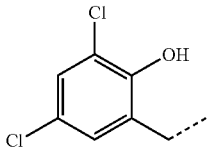 | H | H | SO2Ph | H | H | H |
| 637 | 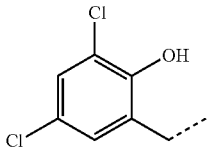 | H | H | H | SO2Ph | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 638 | 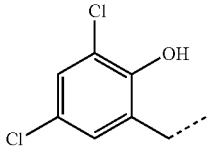 | H | H | H | H | SO2Ph | H |
| 639 | 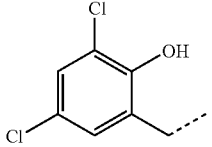 | H | H | SO2Me | H | H | H |
| 640 | 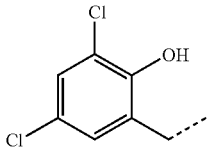 | H | H | SO2Me | H | Me | H |
| 641 | 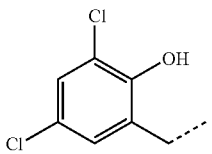 | H | H | Me | SO2Me | H | H |
| 642 | 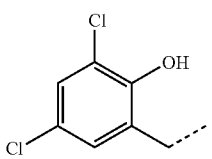 | H | H | H | SO2Me | Me | H |
| 643 | 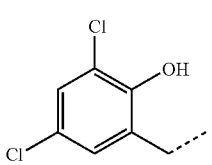 | H | H | SO2Me | F | H | H |
| 644 | 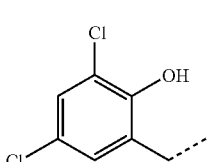 | H | H | SO2Me | H | F | H |
| 645 | 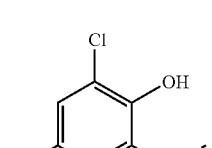 | H | H | F | SO2Me | H | H |
| 646 | 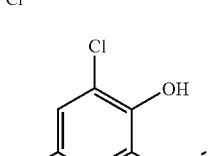 | H | H | H | SO2Me | F | H |

TABLE 2-continued
X = —CO—, q = 0, r = 0, Y = —(R4)C═C(R5)—
| Compound No. 2 | R1—(CH2)p— | R2 | R3 | R4 | R5 | R6 | R7 |
|---|---|---|---|---|---|---|---|
| 647 | 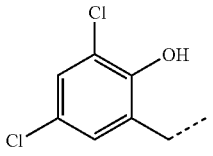 | H | H | SO2NMe2 | H | H | H |
| 648 | 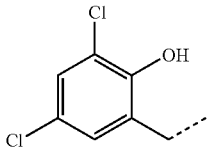 | H | H | H | SO2NMe2 | H | H |
| 649 | 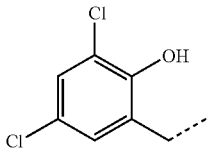 | H | H | H | H | SO2NMe2 | H |
| 650 | 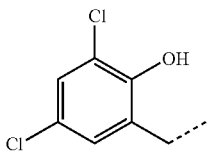 | H | H | SO2Et2 | H | H | H |
| 651 | 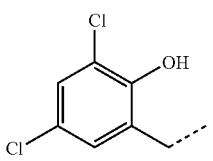 | H | H | H | SO2Et2 | H | H |
| 652 | 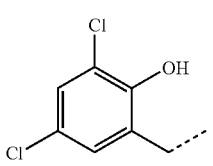 | H | H | H | H | SO2Et2 | H |
| 653 | 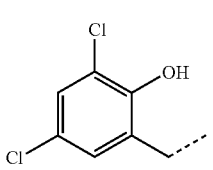 | H | H | SO2NMeH2 | Me | H | H |
| 654 | 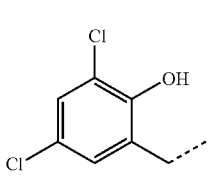 | H | H | SO2NMeH2 | H | Me | H |
| 655 | 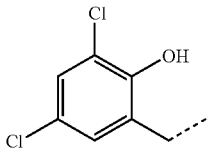 | H | H | Me | SO2NMe2 | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 656 | 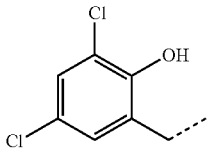 | H | H | H | SO2NMe2 | Me | H |
| 657 | 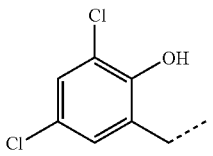 | H | H | SO2NMeH2 | F | H | H |
| 658 | 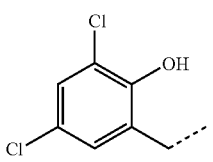 | H | H | SO2NMeH2 | H | F | H |
| 659 | 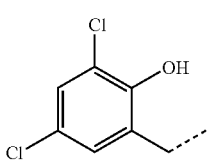 | H | H | F | SO2NMe2 | H | H |
| 660 | 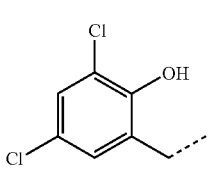 | H | H | H | SO2NMe2 | F | H |
| 661 | 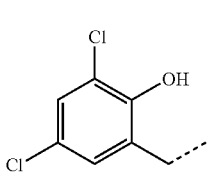 | H | H | NHCOEt | H | H | H |
| 662 | 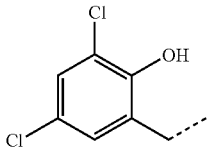 | H | H | H | NHCOEt | H | H |
| 663 | 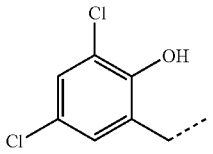 | H | H | H | H | NHCOEt | H |
| 664 | 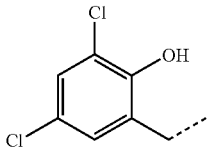 | H | H | NHCOiPr | H | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 665 | 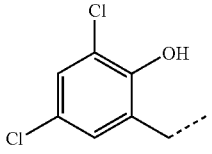 | H | H | H | NHCOiPr | H | H |
| 666 | 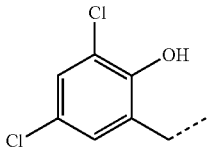 | H | H | H | H | NHCOiPr | H |
| 667 | 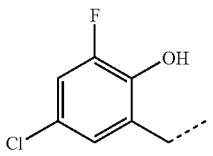 | H | H | Me | CN | H | H |
| 668 | 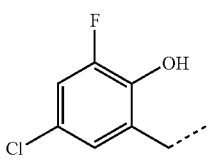 | H | H | H | CN | Me | H |
| 669 | 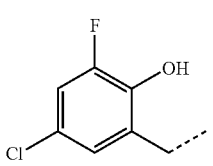 | H | H | H | CN | H | Me |
| 670 | 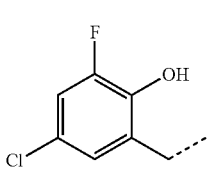 | H | H | Me | Br | H | H |
| 671 | 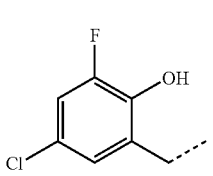 | H | H | H | Br | Me | H |
| 672 | 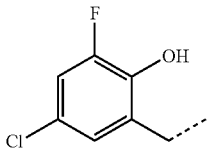 | H | H | H | Br | H | Me |
| 673 | 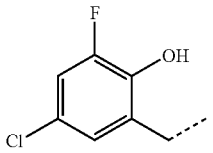 | H | H | Me | H | F | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 674 | 4-Cl-2-F-6-(OH)-phenyl | H | H | Me | H | H | F |
| 675 | 4-Cl-2-F-6-(OH)-phenyl | H | H | F | H | Me | H |
| 676 | 4-Cl-2-F-6-(OH)-phenyl | H | H | F | H | H | Me |
| 677 | 4-Cl-2-F-6-(OH)-phenyl | H | H | Me | H | H | Me |
| 678 | 4-Cl-2-F-6-(OH)-phenyl | H | H | H | OMe | Me | H |
| 679 | 4-Cl-2-F-6-(OH)-phenyl | H | H | H | OH | Me | H |
| 680 | 4-Cl-2-F-6-(OH)-phenyl | H | H | NH2 | H | H | H |
| 681 | 4-Cl-2-F-6-(OH)-phenyl | H | H | H | NH2 | H | H |
| 682 | 4-Cl-2-F-6-(OH)-phenyl | H | H | H | H | NH2 | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 683 | 4-Cl-2-F-6-(OH)-C6H2-CH2- | H | H | Et | H | H | H |
| 684 | 4-Cl-2-F-6-(OH)-C6H2-CH2- | H | H | H | Et | H | H |
| 685 | 4-Cl-2-F-6-(OH)-C6H2-CH2- | H | H | H | H | Et | H |
| 686 | 4-Cl-2-F-6-(OH)-C6H2-CH2- | H | H | iPr | H | H | H |
| 687 | 4-Cl-2-F-6-(OH)-C6H2-CH2- | H | H | H | iPr | H | H |
| 688 | 4-Cl-2-F-6-(OH)-C6H2-CH2- | H | H | H | H | iPr | H |
| 689 | 4-Cl-2-F-6-(OH)-C6H2-CH2- | H | H | Ph | H | H | H |
| 690 | 4-Cl-2-F-6-(OH)-C6H2-CH2- | H | H | H | Ph | H | H |
| 691 | 4-Cl-2-F-6-(OH)-C6H2-CH2- | H | H | H | H | Ph | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 692 | 4-Cl-2-F-6-(OH)-phenyl-CH2 | H | H | OEt | H | H | H |
| 693 | 4-Cl-2-F-6-(OH)-phenyl-CH2 | H | H | H | OEt | H | H |
| 694 | 4-Cl-2-F-6-(OH)-phenyl-CH2 | H | H | H | H | OEt | H |
| 695 | 4-Cl-2-F-6-(OH)-phenyl-CH2 | H | H | OiPr | H | H | H |
| 696 | 4-Cl-2-F-6-(OH)-phenyl-CH2 | H | H | H | OiPr | H | H |
| 697 | 4-Cl-2-F-6-(OH)-phenyl-CH2 | H | H | H | H | OiPr | H |
| 698 | 4-Cl-2-F-6-(OH)-phenyl-CH2 | H | H | OPh | H | H | H |
| 699 | 4-Cl-2-F-6-(OH)-phenyl-CH2 | H | H | H | OPh | H | H |
| 700 | 4-Cl-2-F-6-(OH)-phenyl-CH2 | H | H | H | H | OPh | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 701 | 4-Cl-2-F-6-OH-phenyl | H | H | SO2Me | H | H | H |
| 702 | 4-Cl-2-F-6-OH-phenyl | H | H | H | SO2Me | H | H |
| 703 | 4-Cl-2-F-6-OH-phenyl | H | H | H | H | SO2Me | H |
| 704 | 4-Cl-2-F-6-OH-phenyl | H | H | SO2Et | H | H | H |
| 705 | 4-Cl-2-F-6-OH-phenyl | H | H | H | SO2Et | H | H |
| 706 | 4-Cl-2-F-6-OH-phenyl | H | H | H | H | SO2Et | H |
| 707 | 4-Cl-2-F-6-OH-phenyl | H | H | SO2iPr | H | H | H |
| 708 | 4-Cl-2-F-6-OH-phenyl | H | H | H | SO2iPr | H | H |
| 709 | 4-Cl-2-F-6-OH-phenyl | H | H | H | H | SO2iPr | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 710 | 4-Cl, 2-F, 6-OH benzyl | H | H | SO2Ph | H | H | H |
| 711 | 4-Cl, 2-F, 6-OH benzyl | H | H | H | SO2Ph | H | H |
| 712 | 4-Cl, 2-F, 6-OH benzyl | H | H | H | H | SO2Ph | H |
| 713 | 4-Cl, 2-F, 6-OH benzyl | H | H | SO2Me | Me | H | H |
| 714 | 4-Cl, 2-F, 6-OH benzyl | H | H | SO2Me | H | Me | H |
| 715 | 4-Cl, 2-F, 6-OH benzyl | H | H | Me | SO2Me | H | H |
| 716 | 4-Cl, 2-F, 6-OH benzyl | H | H | H | SO2Me | Me | H |
| 717 | 4-Cl, 2-F, 6-OH benzyl | H | H | SO2Me | F | H | H |
| 718 | 4-Cl, 2-F, 6-OH benzyl | H | H | SO2Me | H | F | H |

TABLE 2-continued

X = —CO—, q = 0, r = 0, Y = —(R4)C═C(R5)—

| Compound No. 2 | R1—(CH2)p— | R2 | R3 | R4 | R5 | R6 | R7 |
|---|---|---|---|---|---|---|---|
| 719 | 4-Cl-2-F-6-(CH2)-phenol (F, OH, Cl substituted benzyl) | H | H | F | SO2Me | H | H |
| 720 | 4-Cl-2-F-6-(CH2)-phenol | H | H | H | SO2Me | F | H |
| 721 | 4-Cl-2-F-6-(CH2)-phenol | H | H | SO2NMe2 | H | H | H |
| 722 | 4-Cl-2-F-6-(CH2)-phenol | H | H | H | SO2NMe2 | H | H |
| 723 | 4-Cl-2-F-6-(CH2)-phenol | H | H | H | H | SO2NMe2 | H |
| 724 | 4-Cl-2-F-6-(CH2)-phenol | H | H | SO2Et2 | H | H | H |
| 725 | 4-Cl-2-F-6-(CH2)-phenol | H | H | H | SO2Et2 | H | H |
| 726 | 4-Cl-2-F-6-(CH2)-phenol | H | H | H | H | SO2Et2 | H |
| 727 | 4-Cl-2-F-6-(CH2)-phenol | H | H | SO2NMe2 | Me | H | H |

TABLE 2-continued

X = —CO—, q = 0, r = 0, Y = —(R4)C=C(R5)—

| Compound No. 2 | R1—(CH2)p— | R2 | R3 | R4 | R5 | R6 | R7 |
|---|---|---|---|---|---|---|---|
| 728 | 4-Cl-2-F-phenol-6-yl-CH2 | H | H | SO2NMe2 | H | Me | H |
| 729 | 4-Cl-2-F-phenol-6-yl-CH2 | H | H | Me | SO2NMe2 | H | H |
| 730 | 4-Cl-2-F-phenol-6-yl-CH2 | H | H | H | SO2NMe2 | Me | H |
| 731 | 4-Cl-2-F-phenol-6-yl-CH2 | H | H | SO2NMe2 | F | H | H |
| 732 | 4-Cl-2-F-phenol-6-yl-CH2 | H | H | SO2NMe2 | H | F | H |
| 733 | 4-Cl-2-F-phenol-6-yl-CH2 | H | H | F | SO2NMe2 | H | H |
| 734 | 4-Cl-2-F-phenol-6-yl-CH2 | H | H | H | SO2NMe2 | F | H |
| 735 | 4-Cl-2-F-phenol-6-yl-CH2 | H | H | NHCOEt | H | H | H |
| 736 | 4-Cl-2-F-phenol-6-yl-CH2 | H | H | H | NHCOEt | H | H |

TABLE 2-continued
X = —CO—, q = 0, r = 0, Y = —(R4)C=C(R5)—
| Compound No. 2 | R1—(CH2)p— | R2 | R3 | R4 | R5 | R6 | R7 |
|---|---|---|---|---|---|---|---|
| 737 | 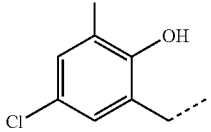 | H | H | H | H | NHCOEt | H |
| 738 | 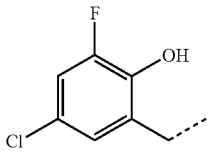 | H | H | NHCOiPr | H | H | H |
| 739 | 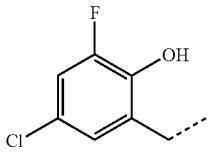 | H | H | H | NHCOiPr | H | H |
| 740 | 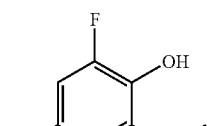 | H | H | H | H | NHCOiPr | H |
| 741 | 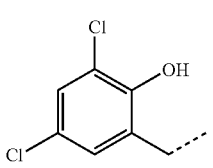 | H | H | F | H | H | F |
| 742 | 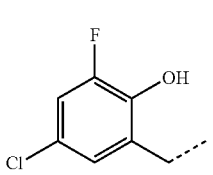 | H | H | F | H | H | F |
TABLE 3
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 1 | 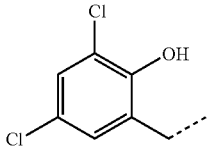 | H | H | H | H | H | H |
| 2 | 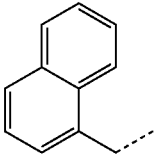 | H | H | H | H | H | H |

TABLE 3-continued

| | X = —SO2—, q = 0, r = 0, Y = —(R4)C=C(R5)— | | | | | | |
|---|---|---|---|---|---|---|---|
| Compound No. 3 | R1—(CH2)p— | R2 | R3 | R4 | R5 | R6 | R7 |
| 3 | 4-Cl, 2-OH-phenyl-CH2— | H | H | H | H | H | H |
| 4 | phenyl-CH2CH2CH=CH2 (but-3-enyl-phenyl) | H | H | H | H | H | H |
| 5 | 3,5-diCl, 2-OH-phenyl-CH2— | H | H | H | Me | H | H |
| 6 | 4-Cl, 2-OH-phenyl-CH2— | H | H | H | Me | H | H |
| 7 | naphth-1-yl-CH2— | H | H | H | Me | H | H |
| 8 | 3,5-diCl, 2-OH-phenyl-CH2— | H | H | H | F | H | H |
| 9 | 4-Cl, 2-OH-phenyl-CH2— | H | H | H | F | H | H |
| 10 | naphth-1-yl-CH2— | H | H | H | F | H | H |
| 11 | 3,4-diCl-phenyl-CH2— | H | H | H | H | H | H |
| 12 | 3,4-diCl-phenyl-CH2— | H | H | H | Cl | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 13 | 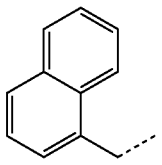 | H | H | H | Cl | H | H |
| 14 | 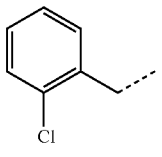 | H | H | H | H | H | H |
| 15 | 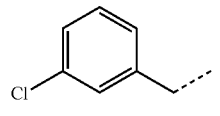 | H | H | H | H | H | H |
| 16 | 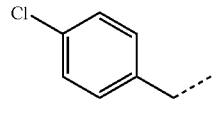 | H | H | H | H | H | H |
| 17 | 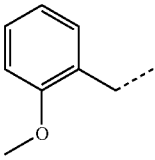 | H | H | H | H | H | H |
| 18 | 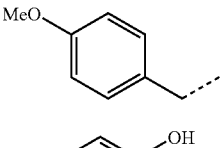 | H | H | H | H | H | H |
| 19 | 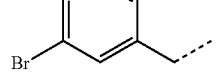 | H | H | H | H | H | H |
| 20 | 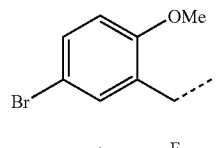 | H | H | H | H | H | H |
| 21 | 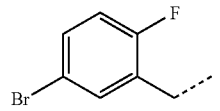 | H | H | H | H | H | H |
| 22 | 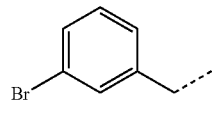 | H | H | H | H | H | H |
| 23 | 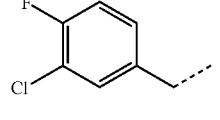 | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 24 | 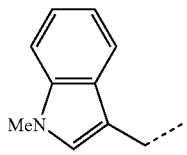 | H | H | H | H | H | H |
| 25 | 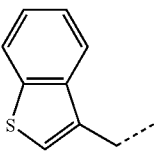 | H | H | H | H | H | H |
| 26 | 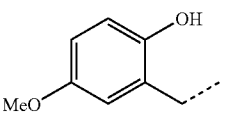 | H | H | H | H | H | H |
| 27 | 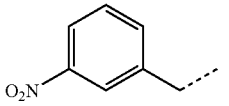 | H | H | H | H | H | H |
| 28 | 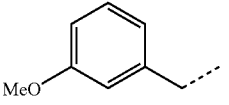 | H | H | H | H | H | H |
| 29 | 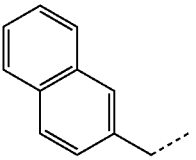 | H | H | H | H | H | H |
| 30 | 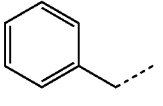 | H | H | H | H | H | H |
| 31 | 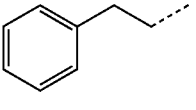 | H | H | H | H | H | H |
| 32 | 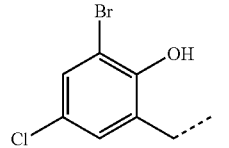 | H | H | H | H | H | H |
| 33 | 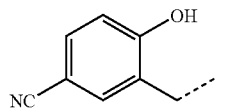 | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 34 | 2-Cl, 6-OH, 4-CF3 benzyl | H | H | H | H | H | H |
| 35 | 2-CF3, 6-OH, 4-Cl benzyl | H | H | H | H | H | H |
| 36 | 2-Cl, 6-OH benzyl | H | H | H | H | H | H |
| 37 | 4-methyl benzyl | H | H | H | H | H | H |
| 38 | 4-F benzyl | H | H | H | H | H | H |
| 39 | 4-Br benzyl | H | H | H | H | H | H |
| 40 | 4-CF3 benzyl | H | H | H | H | H | H |
| 41 | 4-OH benzyl | H | H | H | H | H | H |
| 42 | 4-CN benzyl | H | H | H | H | H | H |
| 43 | 4-SO2Me benzyl | H | H | H | H | H | H |
| 44 | 4-COOMe benzyl | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 45 | 4-(dimethylamino)benzyl | H | H | H | H | H | H |
| 46 | 4-methoxybenzyl | H | H | H | H | H | H |
| 47 | 4-ethoxybenzyl | H | H | H | H | H | H |
| 48 | 4-propoxybenzyl | H | H | H | H | H | H |
| 49 | 4-isopropoxybenzyl | H | H | H | H | H | H |
| 50 | 4-isopropylbenzyl | H | H | H | H | H | H |
| 51 | 4-(benzyloxy)benzyl | H | H | H | H | H | H |
| 52 | 4-phenoxybenzyl | H | H | H | H | H | H |
| 53 | biphenyl-4-ylmethyl | H | H | H | H | H | H |
| 54 | 4-acetamidobenzyl | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 55 | 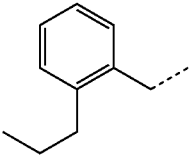 | H | H | H | H | H | H |
| 56 | 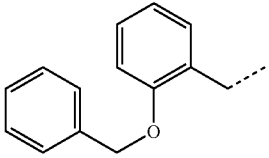 | H | H | H | H | H | H |
| 57 | 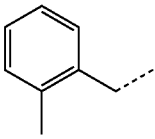 | H | H | H | H | H | H |
| 58 | 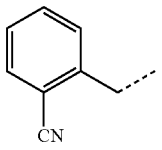 | H | H | H | H | H | H |
| 59 | 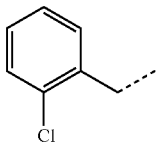 | H | H | H | H | H | H |
| 60 | 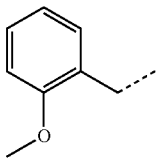 | H | H | H | H | H | H |
| 61 | 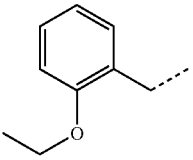 | H | H | H | H | H | H |
| 62 | 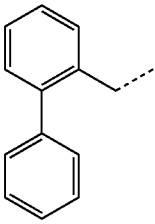 | H | H | H | H | H | H |
| 63 | 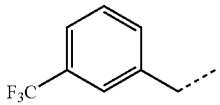 | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 64 | 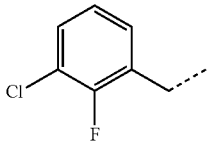 | H | H | H | H | H | H |
| 65 | 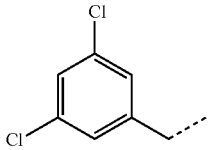 | H | H | H | H | H | H |
| 66 | 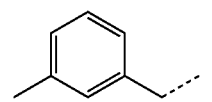 | H | H | H | H | H | H |
| 67 | 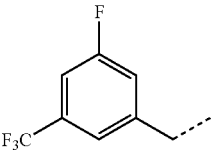 | H | H | H | H | H | H |
| 68 | 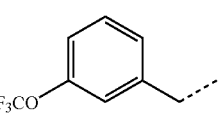 | H | H | H | H | H | H |
| 69 | 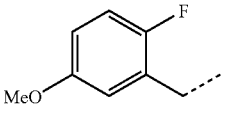 | H | H | H | H | H | H |
| 70 | 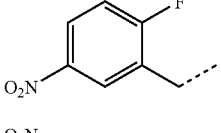 | H | H | H | H | H | H |
| 71 | 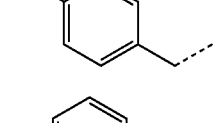 | H | H | H | H | H | H |
| 72 | 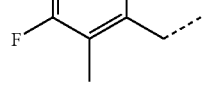 | H | H | H | H | H | H |
| 73 | 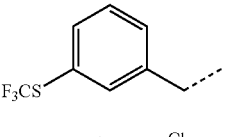 | H | H | H | H | H | H |
| 74 | 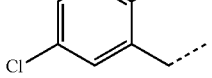 | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 75 | 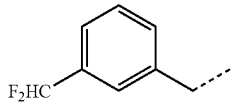 | H | H | H | H | H | H |
| 76 | 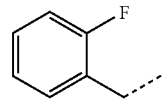 | H | H | H | H | H | H |
| 77 | 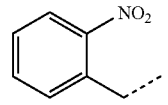 | H | H | H | H | H | H |
| 78 | 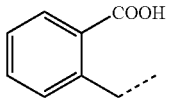 | H | H | H | H | H | H |
| 79 | 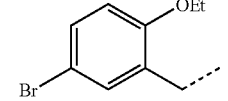 | H | H | H | H | H | H |
| 80 | 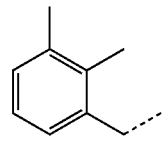 | H | H | H | H | H | H |
| 81 | 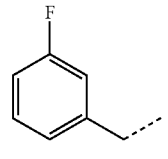 | H | H | H | H | H | H |
| 82 | 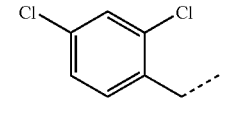 | H | H | H | H | H | H |
| 83 | 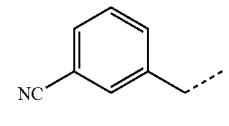 | H | H | H | H | H | H |
| 84 | 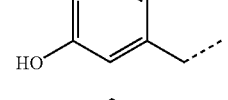 | H | H | H | H | H | H |
| 85 | 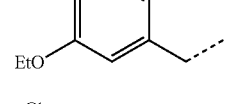 | H | H | H | H | H | H |
| 86 | 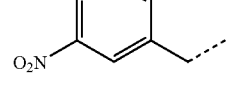 | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 87 | 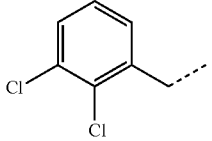 | H | H | H | H | H | H |
| 88 | 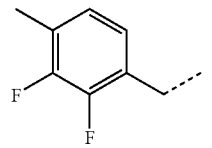 | H | H | H | H | H | H |
| 89 | 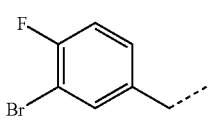 | H | H | H | H | H | H |
| 90 | 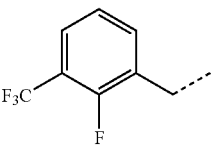 | H | H | H | H | H | H |
| 91 | 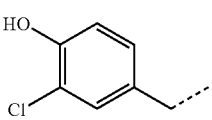 | H | H | H | H | H | H |
| 92 | 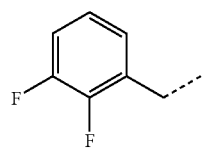 | H | H | H | H | H | H |
| 93 | 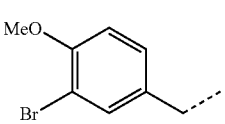 | H | H | H | H | H | H |
| 94 | 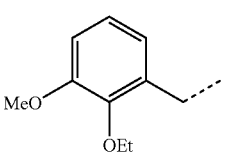 | H | H | H | H | H | H |
| 95 | 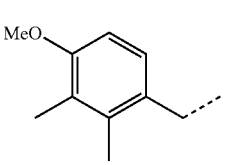 | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 96 | 2-MeO, 3-(OBn)phenyl | H | H | H | H | H | H |
| 97 | 4-Cl, 3-NO2 (O2N at 5?) phenyl (4-Cl-3-nitrophenyl... actually shown: Cl para, O2N meta) | H | H | H | H | H | H |
| 98 | 3-(4-MeO-phenoxy)phenyl | H | H | H | H | H | H |
| 99 | 3-(4-methylphenoxy)phenyl | H | H | H | H | H | H |
| 100 | 3-(4-Cl-phenoxy)phenyl | H | H | H | H | H | H |
| 101 | 3-(benzyloxy)phenyl | H | H | H | H | H | H |
| 102 | 3-phenoxyphenyl | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 103 | 3-hydroxy-4-methoxybenzyl | H | H | H | H | H | H |
| 104 | 2-chloro-3-(trifluoromethyl)benzyl | H | H | H | H | H | H |
| 105 | 4-hydroxy-3-nitrobenzyl | H | H | H | H | H | H |
| 106 | 2,3-dimethoxybenzyl | H | H | H | H | H | H |
| 107 | 2,4-diethoxy-3-methylbenzyl | H | H | H | H | H | H |
| 108 | 3-(2-hydroxyethoxy)benzyl | H | H | H | H | H | H |
| 109 | 2,3,4-trimethoxybenzyl | H | H | H | H | H | H |
| 110 | 4-fluoro-3-phenoxybenzyl | H | H | H | H | H | H |
| 111 | 2-carboxy-3,4-dimethoxybenzyl | H | H | H | H | H | H |
| 112 | 4-chloro-2-nitrobenzyl | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 113 | 3,5-dihydroxyphenyl-CH2— | H | H | H | H | H | H |
| 114 | 4-MeO-3-(benzyloxy)phenyl-CH2— | H | H | H | H | H | H |
| 115 | 3,4-diethoxyphenyl-CH2— | H | H | H | H | H | H |
| 116 | 3-carboxyphenyl-CH2— | H | H | H | H | H | H |
| 117 | 4-MeO-3-hydroxyphenyl-CH2— | H | H | H | H | H | H |
| 118 | 4-nitro-3-hydroxyphenyl-CH2— | H | H | H | H | H | H |
| 119 | 3,5-bis(trifluoromethyl)phenyl-CH2— | H | H | H | H | H | H |
| 120 | 3-MeO-2-nitrophenyl-CH2— | H | H | H | H | H | H |
| 121 | 4-methylnaphthalen-1-yl-CH2— | H | H | H | H | H | H |
| 122 | 1-methyl-7-methyl-1H-indol-3-yl-CH2— | H | H | H | H | H | H |

TABLE 3-continued

X = —SO2—, q = 0, r = 0, Y = —(R4)C═C(R5)—

| Compound No. 3 | R1—(CH2)p— | R2 | R3 | R4 | R5 | R6 | R7 |
|---|---|---|---|---|---|---|---|
| 123 | 1-(2-methoxynaphthyl)methyl | H | H | H | H | H | H |
| 124 | benzofuran-2-ylmethyl | H | H | H | H | H | H |
| 125 | (1-methyl-2-methylindol-3-yl)methyl | H | H | H | H | H | H |
| 126 | quinolin-8-ylmethyl | H | H | H | H | H | H |
| 127 | 1-(2-hydroxynaphthyl)methyl | H | H | H | H | H | H |
| 128 | 1-(2-acetoxynaphthyl)methyl | H | H | H | H | H | H |
| 129 | 2-(1-hydroxynaphthyl)methyl | H | H | H | H | H | H |
| 130 | (1H-indol-7-yl)methyl | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 131 | quinolin-4-ylmethyl | H | H | H | H | H | H |
| 132 | (5-methyl-1-methyl-1H-indol-3-yl)methyl | H | H | H | H | H | H |
| 133 | anthracen-9-ylmethyl | H | H | H | H | H | H |
| 134 | (2-methylnaphthalen-1-yl)methyl | H | H | H | H | H | H |
| 135 | (2-ethoxynaphthalen-1-yl)methyl | H | H | H | H | H | H |
| 136 | (1H-indol-3-yl)methyl | H | H | H | H | H | H |
| 137 | (6-methyl-1-methyl-1H-indol-3-yl)methyl | H | H | H | H | H | H |

TABLE 3-continued

| | X = —SO2—, q = 0, r = 0, Y = —(R4)C=C(R5)— | | | | | | |
|---|---|---|---|---|---|---|---|
| Compound No. 3 | R1—(CH2)p— | R2 | R3 | R4 | R5 | R6 | R7 |
| 138 | 2-(1-methylindol-2-yl)methyl | H | H | H | H | H | H |
| 139 | (1,4-dimethylindol-3-yl)methyl | H | H | H | H | H | H |
| 140 | (1,2,5-trimethylindol-3-yl)methyl | H | H | H | H | H | H |
| 141 | (5-methoxy-1-methylindol-3-yl)methyl | H | H | H | H | H | H |
| 142 | (4-methylbenzothiophen-3-yl)methyl | H | H | H | H | H | H |
| 143 | (1-methylbenzimidazol-2-yl)methyl | H | H | H | H | H | H |
| 144 | (1-methyl-2-phenylindol-3-yl)methyl | H | H | H | H | H | H |

TABLE 3-continued

X = —SO2—, q = 0, r = 0, Y = —(R4)C═C(R5)—

| Compound No. 3 | R1—(CH2)p— | R2 | R3 | R4 | R5 | R6 | R7 |
|---|---|---|---|---|---|---|---|
| 145 | 1-acetylindol-3-yl | H | H | H | H | H | H |
| 146 | quinolin-2-yl | H | H | H | H | H | H |
| 147 | 6-methoxy-1-methylindol-3-yl | H | H | H | H | H | H |
| 148 | 3-methylbenzothiophen-2-yl | H | H | H | H | H | H |
| 149 | 4-methoxynaphth-1-yl | H | H | H | H | H | H |
| 150 | phenanthren-9-yl | H | H | H | H | H | H |
| 151 | 6-methoxyquinolin-2-yl | H | H | H | H | H | H |
| 152 | 1-bromonaphth-2-yl | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 153 | 4-(dimethylamino)naphthalen-1-ylmethyl | H | H | H | H | H | H |
| 154 | 2,3-dihydro-1,4-benzodioxin-6-ylmethyl | H | H | H | H | H | H |
| 155 | 2,2-dimethylchroman-6-ylmethyl | H | H | H | H | H | H |
| 156 | 2,3-dihydrobenzofuran-5-ylmethyl | H | H | H | H | H | H |
| 157 | 9-ethyl-9H-carbazol-3-ylmethyl | H | H | H | H | H | H |
| 158 | benzo[1,3]dioxol-4-ylmethyl | H | H | H | H | H | H |
| 159 | benzo[1,3]dioxol-5-ylmethyl | H | H | H | H | H | H |
| 160 | 3-phenylpropyl | H | H | H | H | H | H |
| 161 | 4-phenylbutyl | H | H | H | H | H | H |
| 162 | cyclohexylmethyl | H | H | H | H | H | H |
| 163 | 2-hydroxy-5-iodobenzyl | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 164 | 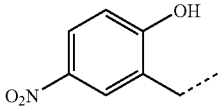 | H | H | H | H | H | H |
| 165 | 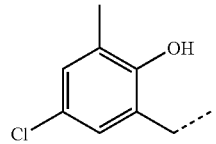 | H | H | H | H | H | H |
| 166 | 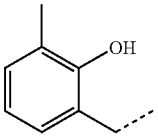 | H | H | H | H | H | H |
| 167 | 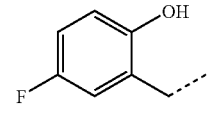 | H | H | H | H | H | H |
| 168 | 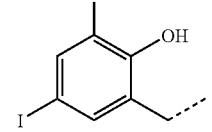 | H | H | H | H | H | H |
| 169 | 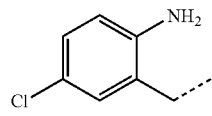 | H | H | H | H | H | H |
| 170 | 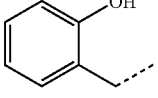 | H | H | H | H | H | H |
| 171 | 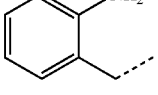 | H | H | H | H | H | H |
| 172 | 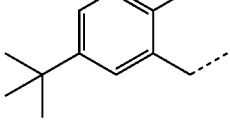 | H | H | H | H | H | H |
| 173 | 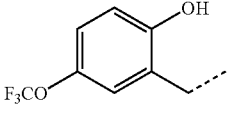 | H | H | H | H | H | H |
| 174 | 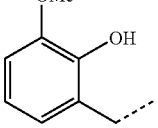 | H | H | H | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 175 | 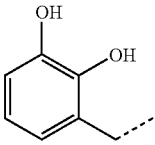 | H | H | H | H | H | H |
| 176 | 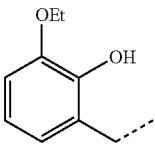 | H | H | H | H | H | H |
| 177 | 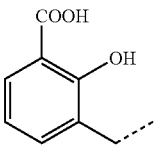 | H | H | H | H | H | H |
| 178 | 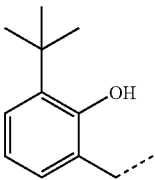 | H | H | H | H | H | H |
| 179 | 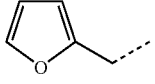 | H | H | H | H | H | H |
| 180 | 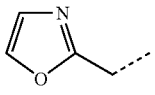 | H | H | H | H | H | H |
| 181 | 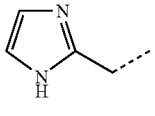 | H | H | H | H | H | H |
| 182 | 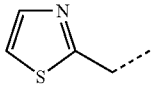 | H | H | H | H | H | H |
| 183 | 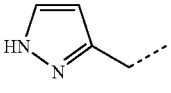 | H | H | H | H | H | H |
| 184 | 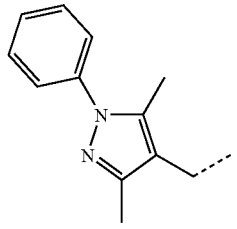 | H | H | H | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 185 | 1-phenyl-2,5-dimethyl-pyrrol-3-ylmethyl | H | H | H | H | H | H |
| 186 | 5-(4-chlorophenyl)-furan-2-ylmethyl | H | H | H | H | H | H |
| 187 | thiophen-2-ylmethyl | H | H | H | H | H | H |
| 188 | 1H-pyrrol-2-ylmethyl | H | H | H | H | H | H |
| 189 | pyridin-2-ylmethyl | H | H | H | H | H | H |
| 190 | pyridin-3-ylmethyl | H | H | H | H | H | H |
| 191 | pyridin-4-ylmethyl | H | H | H | H | H | H |
| 192 | 4-chloro-2-hydroxyphenylmethyl | H | H | H | Cl | H | H |
| 193 | 4-nitro-2-hydroxyphenylmethyl | H | H | H | Cl | H | H |
| 194 | 4-methoxy-2-hydroxyphenylmethyl | H | H | H | Cl | H | H |
| 195 | 3-chlorophenylmethyl | H | H | H | Cl | H | H |
| 196 | 3-bromophenylmethyl | H | H | H | Cl | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 197 | 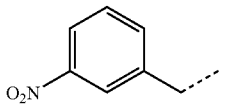 | H | H | H | Cl | H | H |
| 198 | 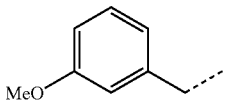 | H | H | H | Cl | H | H |
| 199 | 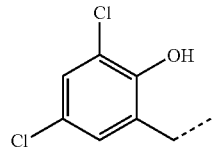 | H | H | H | Cl | H | H |
| 200 | 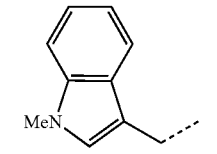 | H | H | H | Cl | H | H |
| 201 | 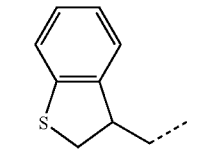 | H | H | H | Cl | H | H |
| 202 | 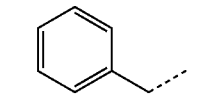 | H | H | H | Cl | H | H |
| 203 | 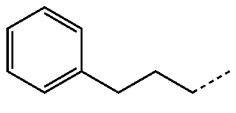 | H | H | H | Cl | H | H |
| 204 | 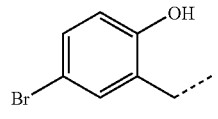 | H | H | H | Cl | H | H |
| 205 | 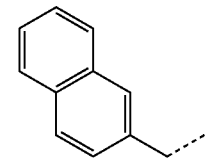 | H | H | H | Cl | H | H |
| 206 | 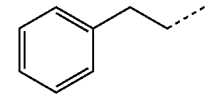 | H | H | H | Cl | H | H |
| 207 | 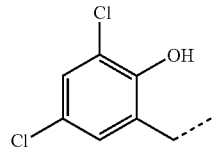 | H | H | Cl | H | H | H |

TABLE 3-continued

X = —SO2—, q = 0, r = 0, Y = —(R4)C═C(R5)—

| Compound No. 3 | R1—(CH2)p— | R2 | R3 | R4 | R5 | R6 | R7 |
|---|---|---|---|---|---|---|---|
| 208 | 2,4-dichloro-6-hydroxybenzyl | H | H | H | OMe | H | H |
| 209 | 2,4-dichloro-6-hydroxybenzyl | H | H | H | COOMe | H | H |
| 210 | 2,4-dichloro-6-hydroxybenzyl | H | H | H | H | Cl | H |
| 211 | 2,4-dichloro-6-hydroxybenzyl | H | H | H | H | COOMe | H |
| 212 | 2,4-dichloro-6-hydroxybenzyl | H | H | H | H | H | Cl |
| 213 | 2,4-dichloro-6-hydroxybenzyl | H | H | H | OCF3 | H | H |
| 214 | 2,4-dichloro-6-hydroxybenzyl | H | H | COOMe | H | H | H |
| 215 | 2,4-dichloro-6-hydroxybenzyl | H | H | H | CF3 | H | H |
| 216 | 2,4-dichloro-6-hydroxybenzyl | H | H | H | OH | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 217 | 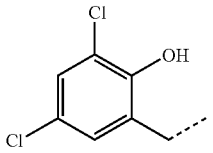 | H | H | H | NO2 | H | H |
| 218 | 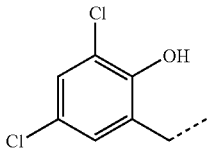 | H | H | H | F | F | H |
| 219 | 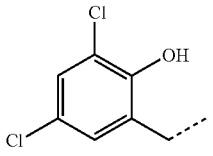 | H | H | F | H | H | H |
| 220 | 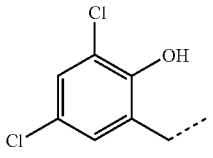 | H | H | Me | H | H | H |
| 221 | 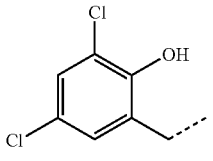 | H | H | H | CN | H | H |
| 222 | 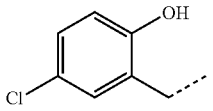 | H | H | Cl | H | H | H |
| 223 |  | H | H | H | OMe | H | H |
| 224 | 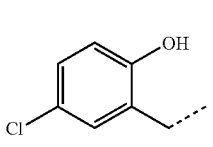 | H | H | H | COOMe | H | H |
| 225 |  | H | H | H | H | Cl | H |
| 226 | 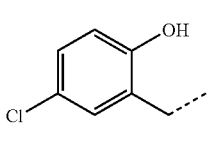 | H | H | H | H | COOMe | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 227 | 4-Cl, 2-OH phenyl | H | H | H | H | H | Cl |
| 228 | 4-Cl, 2-OH phenyl | H | H | H | OCF3 | H | H |
| 229 | 4-Cl, 2-OH phenyl | H | H | COOMe | H | H | H |
| 230 | 4-Cl, 2-OH phenyl | H | H | H | CF3 | H | H |
| 231 | 4-Cl, 2-OH phenyl | H | H | H | OH | H | H |
| 232 | 4-Cl, 2-OH phenyl | H | H | H | NO2 | H | H |
| 233 | 4-Cl, 2-OH phenyl | H | H | H | F | F | H |
| 234 | 4-Cl, 2-OH phenyl | H | H | F | H | H | H |
| 235 | 4-Cl, 2-OH phenyl | H | H | Me | H | H | H |
| 236 | 4-Cl, 2-OH phenyl | H | H | H | CN | H | H |
| 237 | 1-naphthyl | H | H | Cl | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 238 | naphthyl-CH2– | H | H | H | OMe | H | H |
| 239 | naphthyl-CH2– | H | H | H | COOMe | H | H |
| 240 | naphthyl-CH2– | H | H | H | H | Cl | H |
| 241 | naphthyl-CH2– | H | H | H | H | COOMe | H |
| 242 | naphthyl-CH2– | H | H | H | H | H | Cl |
| 243 | naphthyl-CH2– | H | H | H | OCF3 | H | H |
| 244 | naphthyl-CH2– | H | H | COOMe | H | H | H |
| 245 | naphthyl-CH2– | H | H | H | CF3 | H | H |

TABLE 3-continued
X = —SO2—, q = 0, r = 0, Y = —(R4)C═C(R5)—
| Compound No. 3 | R1—(CH2)p— | R2 | R3 | R4 | R5 | R6 | R7 |
|---|---|---|---|---|---|---|---|
| 246 | 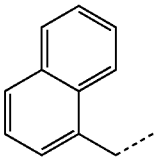 | H | H | H | OH | H | H |
| 247 | 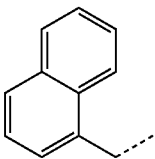 | H | H | H | NO2 | H | H |
| 248 | 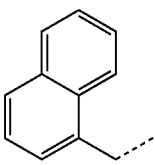 | H | H | H | F | F | H |
| 249 | 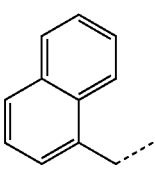 | H | H | F | H | H | H |
| 250 | 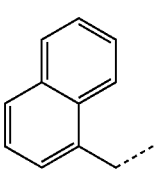 | H | H | Me | H | H | H |
| 251 | 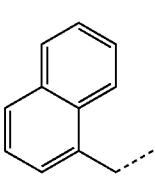 | H | H | H | CN | H | H |
| 252 | 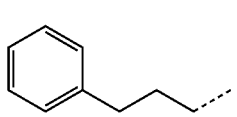 | H | H | Cl | H | H | H |
| 253 | 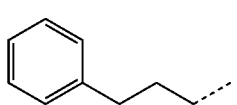 | H | H | H | OMe | H | H |
| 254 | 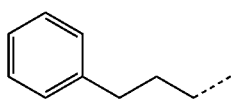 | H | H | H | COOMe | H | H |
| 255 | 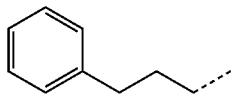 | H | H | H | H | Cl | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 256 | PhCH2CH2— | H | H | H | H | COOMe | H |
| 257 | PhCH2CH2— | H | H | H | H | H | Cl |
| 258 | PhCH2CH2— | H | H | H | OCF3 | H | H |
| 259 | PhCH2CH2— | H | H | COOMe | H | H | H |
| 260 | PhCH2CH2— | H | H | H | CF3 | H | H |
| 261 | PhCH2CH2— | H | H | H | Me | H | H |
| 262 | PhCH2CH2— | H | H | H | F | H | H |
| 263 | PhCH2CH2— | H | H | H | OH | H | H |
| 264 | PhCH2CH2— | H | H | H | NO2 | H | H |
| 265 | PhCH2CH2— | H | H | H | F | F | H |
| 266 | PhCH2CH2— | H | H | F | H | H | H |
| 267 | PhCH2CH2— | H | H | Me | H | H | H |
| 268 | PhCH2CH2— | H | H | H | CN | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 269 | 2,4-dichloro-6-hydroxyphenyl-CH2 | H | H | H | H | H | COOMe |
| 270 | 2,4-dichloro-6-hydroxyphenyl-CH2 | H | H | H | H | F | H |
| 271 | 2,4-dichloro-6-hydroxyphenyl-CH2 | H | H | H | H | H | F |
| 272 | 2,4-dichloro-6-hydroxyphenyl-CH2 | H | H | H | H | Me | H |
| 273 | 2,4-dichloro-6-hydroxyphenyl-CH2 | H | H | H | H | H | Me |
| 274 | 2,4-dichloro-6-hydroxyphenyl-CH2 | H | H | OMe | H | H | H |
| 275 | 2,4-dichloro-6-hydroxyphenyl-CH2 | H | H | H | H | OMe | H |
| 276 | 2,4-dichloro-6-hydroxyphenyl-CH2 | H | H | H | H | H | OMe |
| 277 | 2,4-dichloro-6-hydroxyphenyl-CH2 | H | H | CF3 | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 278 | 2,4-dichloro-6-hydroxyphenyl | H | H | H | H | CF3 | H |
| 279 | 2,4-dichloro-6-hydroxyphenyl | H | H | H | H | H | CF3 |
| 280 | 2,4-dichloro-6-hydroxyphenyl | H | H | OH | H | H | H |
| 281 | 2,4-dichloro-6-hydroxyphenyl | H | H | H | H | OH | H |
| 282 | 2,4-dichloro-6-hydroxyphenyl | H | H | H | H | H | OH |
| 283 | 2,4-dichloro-6-hydroxyphenyl | H | H | OCF3 | H | H | H |
| 284 | 2,4-dichloro-6-hydroxyphenyl | H | H | H | H | OCF3 | H |
| 285 | 2,4-dichloro-6-hydroxyphenyl | H | H | H | H | H | OCF3 |
| 286 | 2,4-dichloro-6-hydroxyphenyl | H | H | NO2 | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 287 | 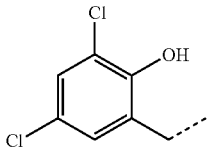 | H | H | H | H | NO2 | H |
| 288 | 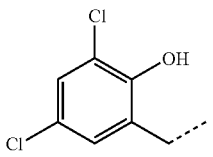 | H | H | H | H | H | NO2 |
| 289 | 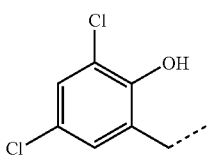 | H | H | CN | H | H | H |
| 290 | 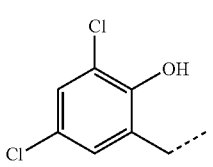 | H | H | H | H | CN | H |
| 291 | 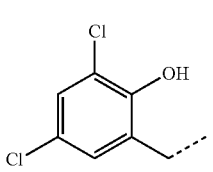 | H | H | H | H | H | CN |
| 292 | 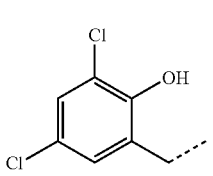 | H | H | Br | H | H | H |
| 293 | 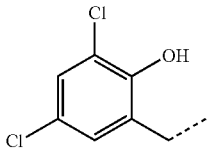 | H | H | H | Br | H | H |
| 294 | 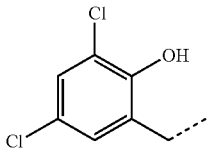 | H | H | H | H | Br | H |
| 295 | 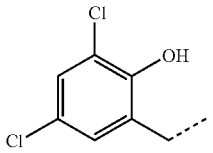 | H | H | H | H | H | Br |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 296 | 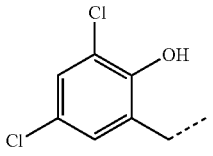 | H | H | COOH | H | H | H |
| 297 | 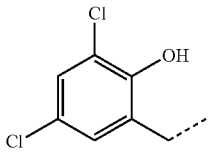 | H | H | H | COOH | H | H |
| 298 | 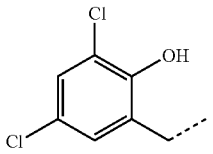 | H | H | H | H | COOH | H |
| 299 | 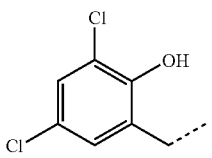 | H | H | H | H | H | COOH |
| 300 | 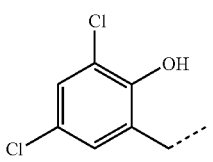 | H | H | NHCOMe | H | H | H |
| 301 | 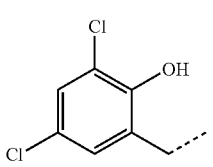 | H | H | H | NHCOMe | H | H |
| 302 | 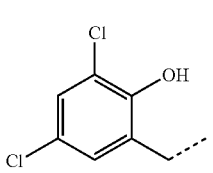 | H | H | H | H | NHCOMe | H |
| 303 | 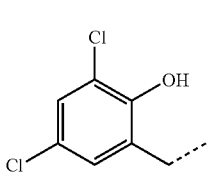 | H | H | H | H | H | NHCOMe |
| 304 | 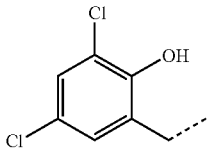 | H | H | SO2NH2 | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 305 | 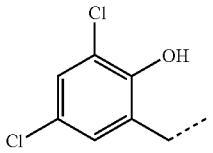 | H | H | H | SO2NH2 | H | H |
| 306 | 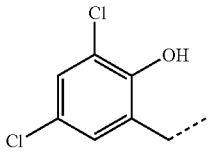 | H | H | H | H | SO2NH2 | H |
| 307 | 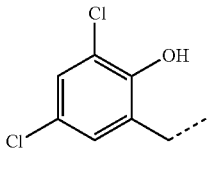 | H | H | H | H | H | SO2NH2 |
| 308 | 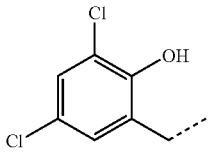 | H | H | Me | Me | H | H |
| 309 | 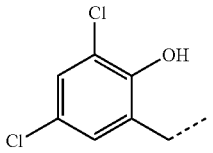 | H | H | Me | H | Me | H |
| 310 | 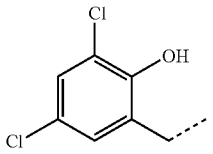 | H | H | H | Me | Me | H |
| 311 |  | H | H | F | F | H | H |
| 312 |  | H | H | F | H | F | H |
| 313 |  | H | H | H | F | F | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 314 | 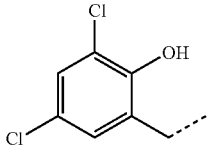 | H | H | Cl | Cl | H | H |
| 315 | 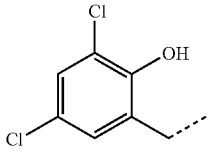 | H | H | Cl | H | Cl | H |
| 316 | 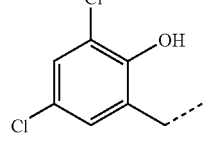 | H | H | H | Cl | Cl | H |
| 317 | 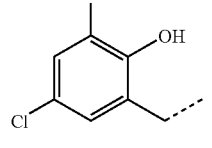 | H | H | Me | F | H | H |
| 318 | 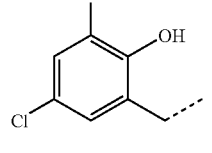 | H | H | Me | Cl | H | H |
| 319 | 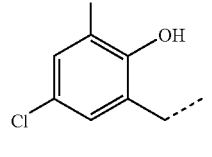 | H | H | Me | OH | H | H |
| 320 | 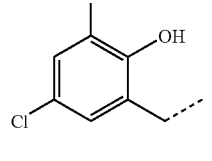 | H | H | Me | OMe | H | H |
| 321 | 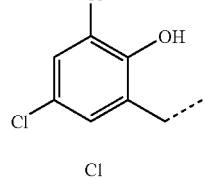 | H | H | F | Me | H | H |
| 322 | 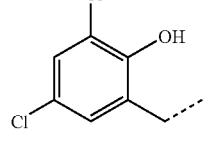 | H | H | F | Cl | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 323 | 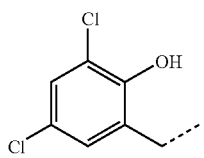 | H | H | F | OH | H | H |
| 324 | 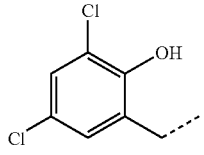 | H | H | F | OMe | H | H |
| 325 | 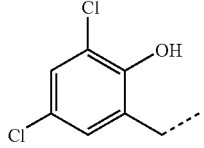 | H | H | Cl | Me | H | H |
| 326 | 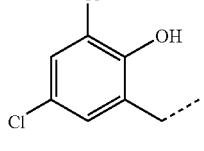 | H | H | Cl | F | H | H |
| 327 | 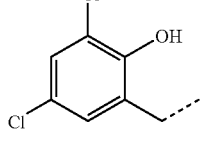 | H | H | Cl | OH | H | H |
| 328 | 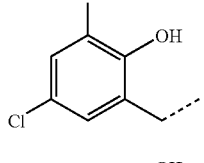 | H | H | Cl | OMe | H | H |
| 329 | 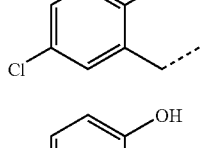 | H | H | H | H | H | COOMe |
| 330 | 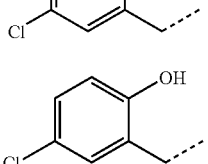 | H | H | H | H | F | H |
| 331 | 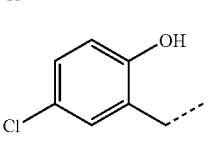 | H | H | H | H | H | F |
| 332 |  | H | H | H | H | Me | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 333 | 4-Cl-2-(CH2)-phenol | H | H | H | H | H | Me |
| 334 | 4-Cl-2-(CH2)-phenol | H | H | OMe | H | H | H |
| 335 | 4-Cl-2-(CH2)-phenol | H | H | H | H | OMe | H |
| 336 | 4-Cl-2-(CH2)-phenol | H | H | H | H | H | OMe |
| 337 | 4-Cl-2-(CH2)-phenol | H | H | CF3 | H | H | H |
| 338 | 4-Cl-2-(CH2)-phenol | H | H | H | H | CF3 | H |
| 339 | 4-Cl-2-(CH2)-phenol | H | H | H | H | H | CF3 |
| 340 | 4-Cl-2-(CH2)-phenol | H | H | OH | H | H | H |
| 341 | 4-Cl-2-(CH2)-phenol | H | H | H | H | OH | H |
| 342 | 4-Cl-2-(CH2)-phenol | H | H | H | H | H | OH |
| 343 | 4-Cl-2-(CH2)-phenol | H | H | OCF3 | H | H | H |
| 344 | 4-Cl-2-(CH2)-phenol | H | H | H | H | OCF3 | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 345 | 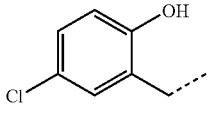 | H | H | H | H | H | OCF3 |
| 346 | 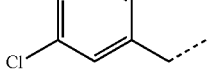 | H | H | NO2 | H | H | H |
| 347 | 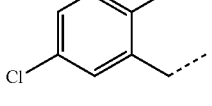 | H | H | H | H | NO2 | H |
| 348 | 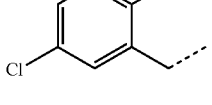 | H | H | H | H | H | NO2 |
| 349 | 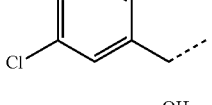 | H | H | CN | H | H | H |
| 350 | 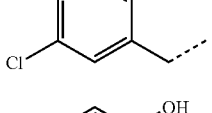 | H | H | H | H | CN | H |
| 351 | 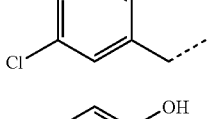 | H | H | H | H | H | CN |
| 352 | 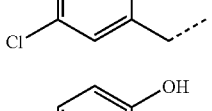 | H | H | Br | H | H | H |
| 353 | 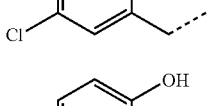 | H | H | H | Br | H | H |
| 354 | 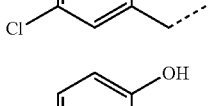 | H | H | H | H | Br | H |
| 355 | 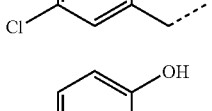 | H | H | H | H | H | Br |
| 356 | 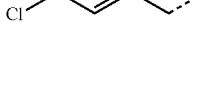 | H | H | COOH | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 357 | 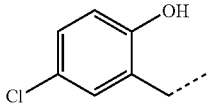 | H | H | H | COOH | H | H |
| 358 | 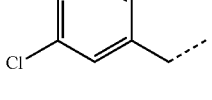 | H | H | H | H | COOH | H |
| 359 | 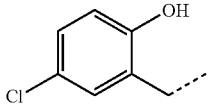 | H | H | H | H | H | COOH |
| 360 | 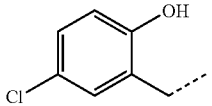 | H | H | NHCOMe | H | H | H |
| 361 | 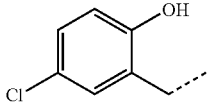 | H | H | H | NHCOMe | H | H |
| 362 | 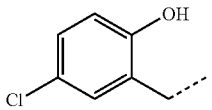 | H | H | H | H | NHCOMe | H |
| 363 | 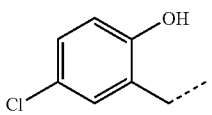 | H | H | H | H | H | NHCOMe |
| 364 | 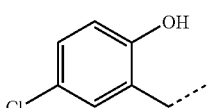 | H | H | SO2NH2 | H | H | H |
| 365 | 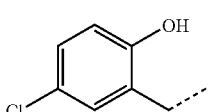 | H | H | H | SO2NH2 | H | H |
| 366 | 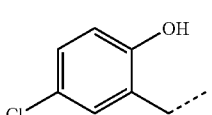 | H | H | H | H | SO2NH2 | H |
| 367 | 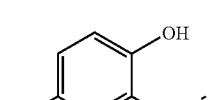 | H | H | H | H | H | SO2NH2 |
| 368 | 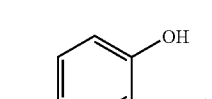 | H | H | Me | Me | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 369 | 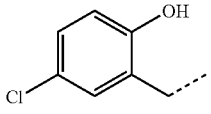 | H | H | Me | H | Me | H |
| 370 | 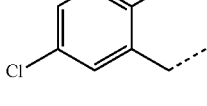 | H | H | H | Me | Me | H |
| 371 | 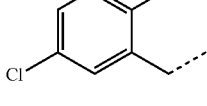 | H | H | F | F | H | H |
| 372 | 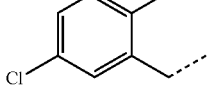 | H | H | F | H | F | H |
| 373 | 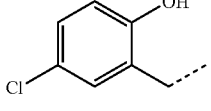 | H | H | H | F | F | H |
| 374 | 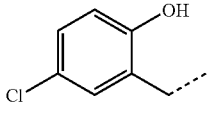 | H | H | Cl | Cl | H | H |
| 375 | 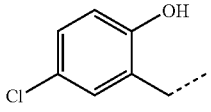 | H | H | Cl | H | Cl | H |
| 376 | 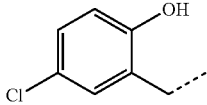 | H | H | H | Cl | Cl | H |
| 377 | 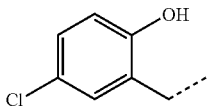 | H | H | Me | F | H | H |
| 378 | 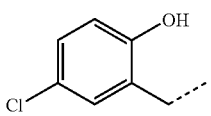 | H | H | Me | Cl | H | H |
| 379 | 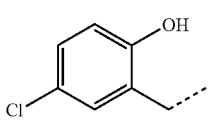 | H | H | Me | OH | H | H |
| 380 | 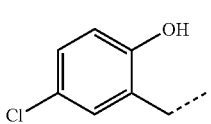 | H | H | Me | OMe | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 381 | 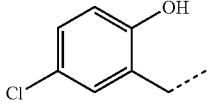 | H | H | F | Me | H | H |
| 382 | 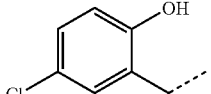 | H | H | F | Cl | H | H |
| 383 | 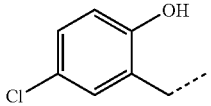 | H | H | F | OH | H | H |
| 384 | 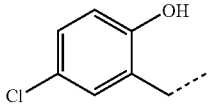 | H | H | F | OMe | H | H |
| 385 | 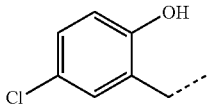 | H | H | Cl | Me | H | H |
| 386 | 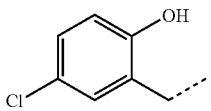 | H | H | Cl | F | H | H |
| 387 | 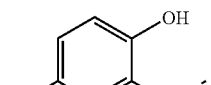 | H | H | Cl | OH | H | H |
| 388 | 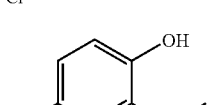 | H | H | Cl | OMe | H | H |
| 389 | 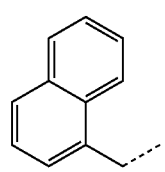 | H | H | H | H | H | COOMe |
| 390 | 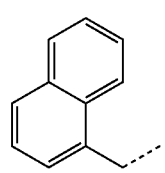 | H | H | H | H | F | H |
| 391 | 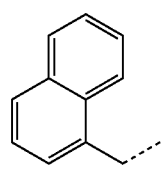 | H | H | H | H | H | F |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 392 | 1-naphthylmethyl | H | H | H | H | Me | H |
| 393 | 1-naphthylmethyl | H | H | H | H | H | Me |
| 394 | 1-naphthylmethyl | H | H | OMe | H | H | H |
| 395 | 1-naphthylmethyl | H | H | H | H | OMe | H |
| 396 | 1-naphthylmethyl | H | H | H | H | H | OMe |
| 397 | 1-naphthylmethyl | H | H | CF3 | H | H | H |
| 398 | 1-naphthylmethyl | H | H | H | H | CF3 | H |
| 399 | 1-naphthylmethyl | H | H | H | H | H | CF3 |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 400 | naphthyl-CH2 | H | H | OH | H | H | H |
| 401 | naphthyl-CH2 | H | H | H | H | OH | H |
| 402 | naphthyl-CH2 | H | H | H | H | H | OH |
| 403 | naphthyl-CH2 | H | H | OCF3 | H | H | H |
| 404 | naphthyl-CH2 | H | H | H | H | OCF3 | H |
| 405 | naphthyl-CH2 | H | H | H | H | H | OCF3 |
| 406 | naphthyl-CH2 | H | H | NO2 | H | H | H |
| 407 | naphthyl-CH2 | H | H | H | H | NO2 | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 408 | naphthalen-1-ylmethyl | H | H | H | H | H | NO2 |
| 409 | naphthalen-1-ylmethyl | H | H | CN | H | H | H |
| 410 | naphthalen-1-ylmethyl | H | H | H | H | CN | H |
| 411 | naphthalen-1-ylmethyl | H | H | H | H | H | CN |
| 412 | naphthalen-1-ylmethyl | H | H | Br | H | H | H |
| 413 | naphthalen-1-ylmethyl | H | H | H | Br | H | H |
| 414 | naphthalen-1-ylmethyl | H | H | H | H | Br | H |
| 415 | naphthalen-1-ylmethyl | H | H | H | H | H | Br |

TABLE 3-continued
X = —SO2—, q = 0, r = 0, Y = —(R4)C═C(R5)—
| Compound No. 3 | R1—(CH2)p— | R2 | R3 | R4 | R5 | R6 | R7 |
|---|---|---|---|---|---|---|---|
| 416 | 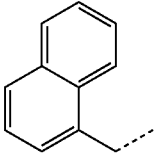 | H | H | COOH | H | H | H |
| 417 | 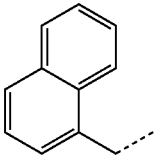 | H | H | H | COOH | H | H |
| 418 | 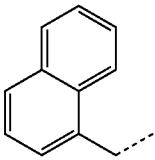 | H | H | H | H | COOH | H |
| 419 | 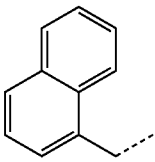 | H | H | H | H | H | COOH |
| 420 | 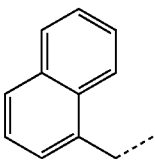 | H | H | NHCOMe | H | H | H |
| 421 | 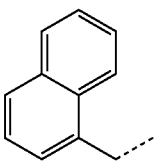 | H | H | H | NHCOMe | H | H |
| 422 | 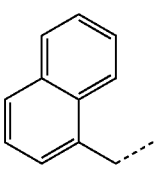 | H | H | H | H | NHCOMe | H |
| 423 | 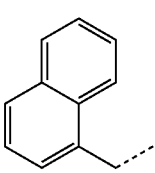 | H | H | H | H | H | NHCOMe |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 424 | naphthalen-1-ylmethyl | H | H | SO2NH2 | H | H | H |
| 425 | naphthalen-1-ylmethyl | H | H | H | SO2NH2 | H | H |
| 426 | naphthalen-1-ylmethyl | H | H | H | H | SO2NH2 | H |
| 427 | naphthalen-1-ylmethyl | H | H | H | H | H | SO2NH2 |
| 428 | naphthalen-1-ylmethyl | H | H | Me | Me | H | H |
| 429 | naphthalen-1-ylmethyl | H | H | Me | H | Me | H |
| 430 | naphthalen-1-ylmethyl | H | H | H | Me | Me | H |
| 431 | naphthalen-1-ylmethyl | H | H | F | F | H | H |

TABLE 3-continued

X = —SO2—, q = 0, r = 0, Y = —(R4)C═C(R5)—

| Compound No. 3 | R1—(CH2)p— | R2 | R3 | R4 | R5 | R6 | R7 |
|---|---|---|---|---|---|---|---|
| 432 | 1-naphthylmethyl | H | H | F | H | F | H |
| 433 | 1-naphthylmethyl | H | H | H | F | F | H |
| 434 | 1-naphthylmethyl | H | H | Cl | Cl | H | H |
| 435 | 1-naphthylmethyl | H | H | Cl | H | Cl | H |
| 436 | 1-naphthylmethyl | H | H | H | Cl | Cl | H |
| 437 | 1-naphthylmethyl | H | H | Me | F | H | H |
| 438 | 1-naphthylmethyl | H | H | Me | Cl | H | H |
| 439 | 1-naphthylmethyl | H | H | Me | OH | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 440 | naphthalen-1-ylmethyl | H | H | Me | OMe | H | H |
| 441 | naphthalen-1-ylmethyl | H | H | F | Me | H | H |
| 442 | naphthalen-1-ylmethyl | H | H | F | Cl | H | H |
| 443 | naphthalen-1-ylmethyl | H | H | F | OH | H | H |
| 444 | naphthalen-1-ylmethyl | H | H | F | OMe | H | H |
| 445 | naphthalen-1-ylmethyl | H | H | Cl | Me | H | H |
| 446 | naphthalen-1-ylmethyl | H | H | Cl | F | H | H |
| 447 | naphthalen-1-ylmethyl | H | H | Cl | OH | H | H |

TABLE 3-continued

X = —SO2—, q = 0, r = 0, Y = —(R4)C═C(R5)—

| Compound No. 3 | R1—(CH2)p— | R2 | R3 | R4 | R5 | R6 | R7 |
|---|---|---|---|---|---|---|---|
| 448 | naphthalen-1-ylmethyl | H | H | Cl | OMe | H | H |
| 449 | 4-bromo-2-hydroxybenzyl | H | H | Cl | H | H | H |
| 450 | 4-bromo-2-hydroxybenzyl | H | H | H | OMe | H | H |
| 451 | 4-bromo-2-hydroxybenzyl | H | H | H | COOMe | H | H |
| 452 | 4-bromo-2-hydroxybenzyl | H | H | H | H | Cl | H |
| 453 | 4-bromo-2-hydroxybenzyl | H | H | H | H | COOMe | H |
| 454 | 4-bromo-2-hydroxybenzyl | H | H | H | H | H | Cl |
| 455 | 4-bromo-2-hydroxybenzyl | H | H | H | OCF3 | H | H |
| 456 | 4-bromo-2-hydroxybenzyl | H | H | COOMe | H | H | H |
| 457 | 4-bromo-2-hydroxybenzyl | H | H | H | CF3 | H | H |
| 458 | 4-bromo-2-hydroxybenzyl | H | H | H | Me | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 459 | 5-Br-2-OH-C6H3-CH2- | H | H | H | F | H | H |
| 460 | 5-Br-2-OH-C6H3-CH2- | H | H | H | OH | H | H |
| 461 | 5-Br-2-OH-C6H3-CH2- | H | H | H | NO2 | H | H |
| 462 | 5-Br-2-OH-C6H3-CH2- | H | H | H | F | F | H |
| 463 | 5-Br-2-OH-C6H3-CH2- | H | H | F | H | H | H |
| 464 | 5-Br-2-OH-C6H3-CH2- | H | H | Me | H | H | H |
| 465 | 5-Br-2-OH-C6H3-CH2- | H | H | H | CN | H | H |
| 466 | (1-Me-indol-3-yl)-CH2- | H | H | Cl | H | H | H |
| 467 | (1-Me-indol-3-yl)-CH2- | H | H | H | OMe | H | H |
| 468 | (1-Me-indol-3-yl)-CH2- | H | H | H | COOMe | H | H |
| 469 | (1-Me-indol-3-yl)-CH2- | H | H | H | H | Cl | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 470 | 1-Me-indol-3-yl-CH2 | H | H | H | H | COOMe | H |
| 471 | 1-Me-indol-3-yl-CH2 | H | H | H | H | H | Cl |
| 472 | 1-Me-indol-3-yl-CH2 | H | H | H | OCF3 | H | H |
| 473 | 1-Me-indol-3-yl-CH2 | H | H | COOMe | H | H | H |
| 474 | 1-Me-indol-3-yl-CH2 | H | H | H | CF3 | H | H |
| 475 | 1-Me-indol-3-yl-CH2 | H | H | H | Me | H | H |
| 476 | 1-Me-indol-3-yl-CH2 | H | H | H | F | H | H |
| 477 | 1-Me-indol-3-yl-CH2 | H | H | H | OH | H | H |
| 478 | 1-Me-indol-3-yl-CH2 | H | H | H | NO2 | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 479 | 3-(1-methylindolyl)methyl | H | H | H | F | F | H |
| 480 | 3-(1-methylindolyl)methyl | H | H | F | H | H | H |
| 481 | 3-(1-methylindolyl)methyl | H | H | Me | H | H | H |
| 482 | 3-(1-methylindolyl)methyl | H | H | H | CN | H | H |
| 483 | 3-benzothienyl methyl | H | H | Cl | H | H | H |
| 484 | 3-benzothienyl methyl | H | H | H | OMe | H | H |
| 485 | 3-benzothienyl methyl | H | H | H | COOMe | H | H |
| 486 | 3-benzothienyl methyl | H | H | H | H | Cl | H |
| 487 | 3-benzothienyl methyl | H | H | H | H | COOMe | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 488 | 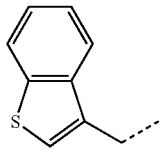 | H | H | H | H | H | Cl |
| 489 | 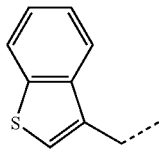 | H | H | H | OCF3 | H | H |
| 490 | 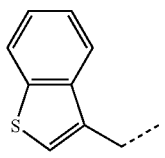 | H | H | COOMe | H | H | H |
| 491 | 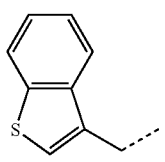 | H | H | H | CF3 | H | H |
| 492 | 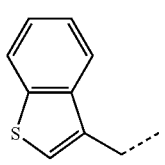 | H | H | H | Me | H | H |
| 493 | 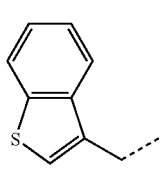 | H | H | H | F | H | H |
| 494 | 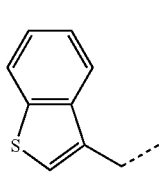 | H | H | H | OH | H | H |
| 495 | 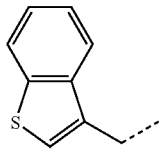 | H | H | H | NO2 | H | H |
| 496 | 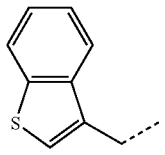 | H | H | H | F | F | H |

TABLE 3-continued
X = —SO2—, q = 0, r = 0, Y = —(R4)C═C(R5)—
| Compound No. 3 | R1—(CH2)p— | R2 | R3 | R4 | R5 | R6 | R7 |
|---|---|---|---|---|---|---|---|
| 497 | 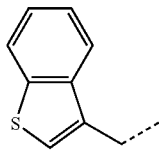 | H | H | F | H | H | H |
| 498 | 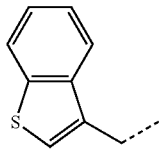 | H | H | Me | H | H | H |
| 499 | 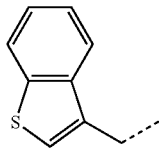 | H | H | H | CN | H | H |
| 500 | 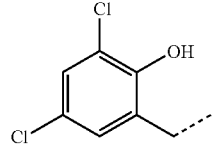 | H | Me | H | H | H | H |
| 501 | 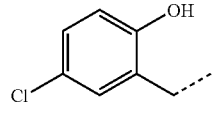 | H | Me | H | H | H | H |
| 502 | 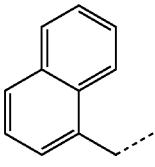 | H | Me | H | H | H | H |
| 503 | 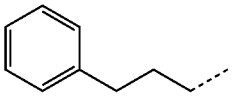 | H | Me | H | H | H | H |
| 504 | 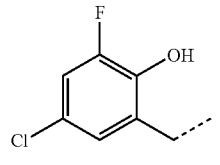 | H | H | H | H | H | H |
| 505 | 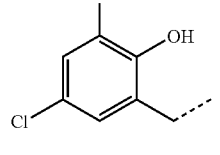 | H | H | F | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 506 | 4-chloro-2-fluoro-6-hydroxybenzyl | H | H | Cl | H | H | H |
| 507 | 4-chloro-2-fluoro-6-hydroxybenzyl | H | H | Me | H | H | H |
| 508 | 4-chloro-2-fluoro-6-hydroxybenzyl | H | H | Et | H | H | H |
| 509 | 4-chloro-2-fluoro-6-hydroxybenzyl | H | H | OMe | H | H | H |
| 510 | 4-chloro-2-fluoro-6-hydroxybenzyl | H | H | OEt | H | H | H |
| 511 | 4-chloro-2-fluoro-6-hydroxybenzyl | H | H | CF3 | H | H | H |
| 512 | 4-chloro-2-fluoro-6-hydroxybenzyl | H | H | OCF3 | H | H | H |
| 513 | 4-chloro-2-fluoro-6-hydroxybenzyl | H | H | NO2 | H | H | H |
| 514 | 4-chloro-2-fluoro-6-hydroxybenzyl | H | H | NH2 | H | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 515 | 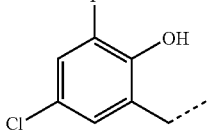 | H | H | OH | H | H | H |
| 516 | 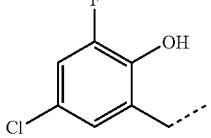 | H | H | CN | H | H | H |
| 517 | 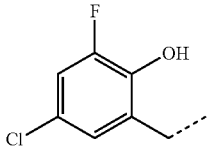 | H | H | COMe | H | H | H |
| 518 | 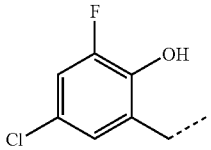 | H | H | COOMe | H | H | H |
| 519 | 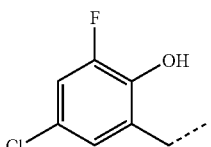 | H | H | H | F | H | H |
| 520 | 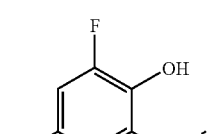 | H | H | H | Cl | H | H |
| 521 | 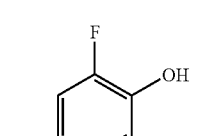 | H | H | H | Me | H | H |
| 522 | 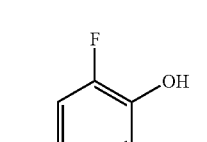 | H | H | H | Et | H | H |
| 523 | 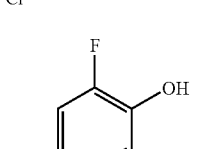 | H | H | H | OMe | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 524 | 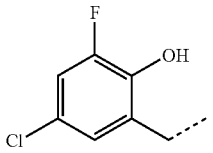 | H | H | H | OEt | H | H |
| 525 | 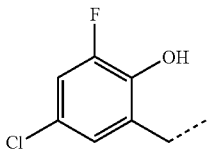 | H | H | H | CF3 | H | H |
| 526 | 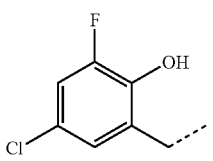 | H | H | H | OCF3 | H | H |
| 527 | 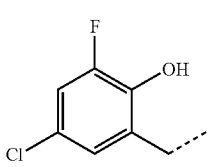 | H | H | H | NO2 | H | H |
| 528 | 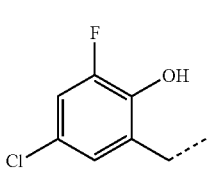 | H | H | H | NH2 | H | H |
| 529 | 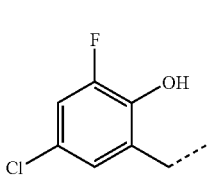 | H | H | H | OH | H | H |
| 530 | 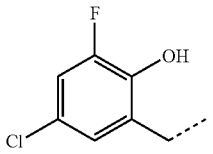 | H | H | H | CN | H | H |
| 531 |  | H | H | H | COMe | H | H |
| 532 |  | H | H | H | COOMe | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 533 | 4-Cl-2-F-6-OH-phenyl-CH2- | H | H | F | F | H | H |
| 534 | 4-Cl-2-F-6-OH-phenyl-CH2- | H | H | F | Cl | H | H |
| 535 | 4-Cl-2-F-6-OH-phenyl-CH2- | H | H | F | Me | H | H |
| 536 | 4-Cl-2-F-6-OH-phenyl-CH2- | H | H | F | Et | H | H |
| 537 | 4-Cl-2-F-6-OH-phenyl-CH2- | H | H | F | OMe | H | H |
| 538 | 4-Cl-2-F-6-OH-phenyl-CH2- | H | H | F | OEt | H | H |
| 539 | 4-Cl-2-F-6-OH-phenyl-CH2- | H | H | F | CF3 | H | H |
| 540 | 4-Cl-2-F-6-OH-phenyl-CH2- | H | H | F | OCF3 | H | H |
| 541 | 4-Cl-2-F-6-OH-phenyl-CH2- | H | H | Cl | F | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 542 | 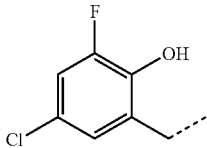 | H | H | Cl | Cl | H | H |
| 543 |  | H | H | Cl | Me | H | H |
| 544 | 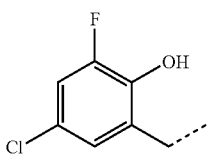 | H | H | Cl | Et | H | H |
| 545 | 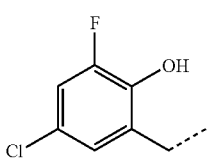 | H | H | Cl | OMe | H | H |
| 546 | 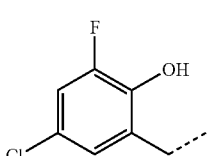 | H | H | Cl | OEt | H | H |
| 547 | 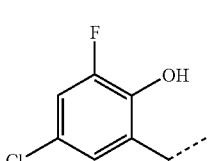 | H | H | Cl | CF3 | H | H |
| 548 | 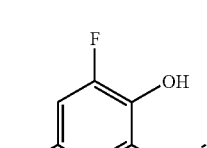 | H | H | Cl | OCF3 | H | H |
| 549 | 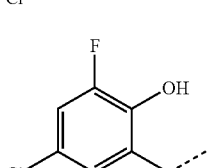 | H | H | Me | F | H | H |
| 550 | 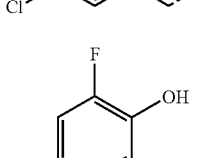 | H | H | Me | Cl | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 551 | 4-Cl-2-F-6-OH-phenyl | H | H | Me | Me | H | H |
| 552 | 4-Cl-2-F-6-OH-phenyl | H | H | Me | Et | H | H |
| 553 | 4-Cl-2-F-6-OH-phenyl | H | H | Me | OMe | H | H |
| 554 | 4-Cl-2-F-6-OH-phenyl | H | H | Me | OEt | H | H |
| 555 | 4-Cl-2-F-6-OH-phenyl | H | H | Me | CF3 | H | H |
| 556 | 4-Cl-2-F-6-OH-phenyl | H | H | Me | OCF3 | H | H |
| 557 | 4-Cl-2-F-6-OH-phenyl | H | H | OMe | F | H | H |
| 558 | 4-Cl-2-F-6-OH-phenyl | H | H | OMe | Cl | H | H |
| 559 | 4-Cl-2-F-6-OH-phenyl | H | H | OMe | Me | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 560 | 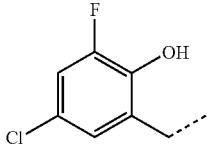 | H | H | OMe | Et | H | H |
| 561 | 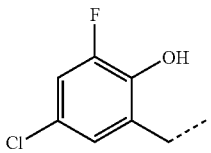 | H | H | OMe | OMe | H | H |
| 562 | 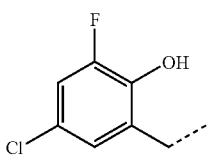 | H | H | OMe | OEt | H | H |
| 563 | 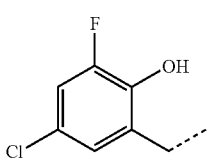 | H | H | OMe | CF3 | H | H |
| 564 | 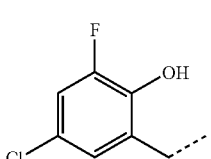 | H | H | OMe | OCF3 | H | H |
| 565 | 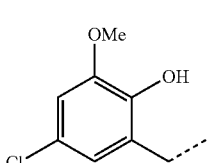 | H | H | H | H | H | H |
| 566 | 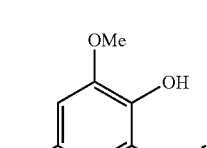 | H | H | F | H | H | H |
| 567 | 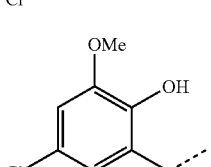 | H | H | Cl | H | H | H |
| 568 | 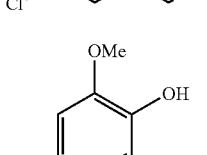 | H | H | Me | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 569 | 4-Cl, 6-OMe, 2-OH phenyl | H | H | Et | H | H | H |
| 570 | 4-Cl, 6-OMe, 2-OH phenyl | H | H | OMe | H | H | H |
| 571 | 4-Cl, 6-OMe, 2-OH phenyl | H | H | H | F | H | H |
| 572 | 4-Cl, 6-OMe, 2-OH phenyl | H | H | H | Cl | H | H |
| 573 | 4-Cl, 6-OMe, 2-OH phenyl | H | H | H | Me | H | H |
| 574 | 4-Cl, 6-OMe, 2-OH phenyl | H | H | H | Et | H | H |
| 575 | 4-Cl, 6-OMe, 2-OH phenyl | H | H | H | OMe | H | H |
| 576 | 4-Cl, 6-OMe, 2-OH phenyl | H | H | F | F | H | H |
| 577 | 4-Cl, 6-OMe, 2-OH phenyl | H | H | F | Cl | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 578 | 4-Cl-2-OMe-6-OH-phenyl-CH2- | H | H | F | Me | H | H |
| 579 | 4-Cl-2-OMe-6-OH-phenyl-CH2- | H | H | F | Et | H | H |
| 580 | 4-Cl-2-OMe-6-OH-phenyl-CH2- | H | H | F | OMe | H | H |
| 581 | 4-Cl-2-OMe-6-OH-phenyl-CH2- | H | H | Cl | F | H | H |
| 582 | 4-Cl-2-OMe-6-OH-phenyl-CH2- | H | H | Cl | Cl | H | H |
| 583 | 4-Cl-2-OMe-6-OH-phenyl-CH2- | H | H | Cl | Me | H | H |
| 584 | 4-Cl-2-OMe-6-OH-phenyl-CH2- | H | H | Cl | Et | H | H |
| 585 | 4-Cl-2-OMe-6-OH-phenyl-CH2- | H | H | Cl | OMe | H | H |
| 586 | 4-Cl-2-OMe-6-OH-phenyl-CH2- | H | H | Me | F | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 587 | 4-Cl-2-OMe-6-OH-benzyl | H | H | Me | Cl | H | H |
| 588 | 4-Cl-2-OMe-6-OH-benzyl | H | H | Me | Me | H | H |
| 589 | 4-Cl-2-OMe-6-OH-benzyl | H | H | Me | Et | H | H |
| 590 | 4-Cl-2-OMe-6-OH-benzyl | H | H | Me | OMe | H | H |
| 591 | 4-Cl-2-OMe-6-OH-benzyl | H | H | Et | F | H | H |
| 592 | 4-Cl-2-OMe-6-OH-benzyl | H | H | Et | Cl | H | H |
| 593 | 4-Cl-2-OMe-6-OH-benzyl | H | H | Et | Me | H | H |
| 594 | 4-Cl-2-OMe-6-OH-benzyl | H | H | Et | Et | H | H |
| 595 | 4-Cl-2-OMe-6-OH-benzyl | H | H | Et | OMe | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 596 | 4-Cl-2-OMe-phenol-6-yl-CH2 | H | H | OMe | F | H | H |
| 597 | 4-Cl-2-OMe-phenol-6-yl-CH2 | H | H | OMe | Cl | H | H |
| 598 | 4-Cl-2-OMe-phenol-6-yl-CH2 | H | H | OMe | Me | H | H |
| 599 | 4-Cl-2-OMe-phenol-6-yl-CH2 | H | H | OMe | Et | H | H |
| 600 | 4-Cl-2-OMe-phenol-6-yl-CH2 | H | H | OMe | OMe | H | H |
| 601 | 2,4-diCl-phenol-6-yl-CH2 | H | H | Me | CN | H | H |
| 602 | 2,4-diCl-phenol-6-yl-CH2 | H | H | H | CN | Me | H |
| 603 | 2,4-diCl-phenol-6-yl-CH2 | H | H | H | CN | H | Me |
| 604 | 2,4-diCl-phenol-6-yl-CH2 | H | H | Me | Br | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 605 | 2,4-dichloro-6-hydroxyphenyl-CH2 | H | H | H | Br | Me | H |
| 606 | 2,4-dichloro-6-hydroxyphenyl-CH2 | H | H | H | Br | H | Me |
| 607 | 2,4-dichloro-6-hydroxyphenyl-CH2 | H | H | Me | H | F | H |
| 608 | 2,4-dichloro-6-hydroxyphenyl-CH2 | H | H | Me | H | H | F |
| 609 | 2,4-dichloro-6-hydroxyphenyl-CH2 | H | H | F | H | Me | H |
| 610 | 2,4-dichloro-6-hydroxyphenyl-CH2 | H | H | F | H | H | Me |
| 611 | 2,4-dichloro-6-hydroxyphenyl-CH2 | H | H | Me | H | H | Me |
| 612 | 2,4-dichloro-6-hydroxyphenyl-CH2 | H | H | H | OMe | Me | H |
| 613 | 2,4-dichloro-6-hydroxyphenyl-CH2 | H | H | H | O | Me | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 614 | 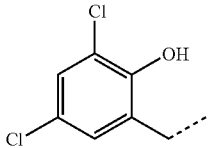 | H | H | NH2 | H | H | H |
| 615 | 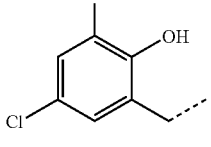 | H | H | H | NH2 | H | H |
| 616 | 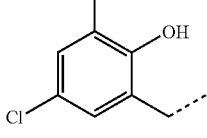 | H | H | H | H | NH2 | H |
| 617 | 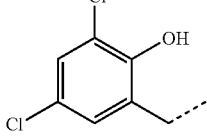 | H | H | Et | H | H | H |
| 618 | 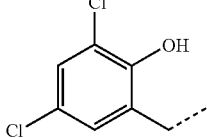 | H | H | H | Et | H | H |
| 619 | 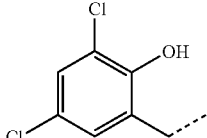 | H | H | H | H | Et | H |
| 620 | 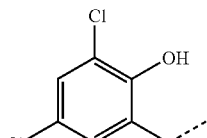 | H | H | iPr | H | H | H |
| 621 | 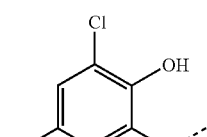 | H | H | H | iPr | H | H |
| 622 | 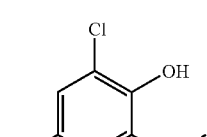 | H | H | H | H | iPr | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 623 | 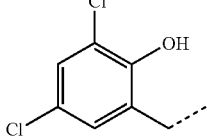 | H | H | Ph | H | H | H |
| 624 | 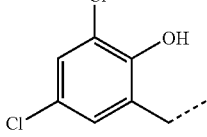 | H | H | H | Ph | H | H |
| 625 | 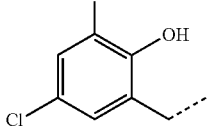 | H | H | H | H | Ph | H |
| 626 | 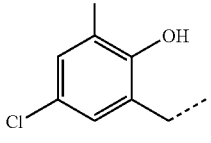 | H | H | OEt | H | H | H |
| 627 | 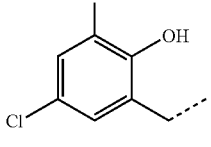 | H | H | H | OEt | H | H |
| 628 | 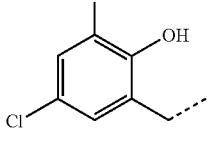 | H | H | H | H | OEt | H |
| 629 | 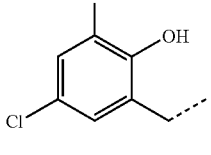 | H | H | OiPr | H | H | H |
| 630 | 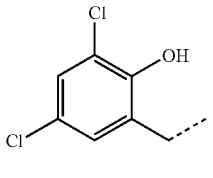 | H | H | H | OiPr | H | H |
| 631 | 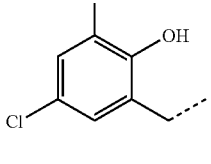 | H | H | H | H | OiPr | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 632 | 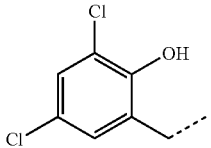 | H | H | OPh | H | H | H |
| 633 | 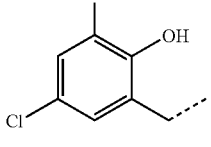 | H | H | H | OPh | H | H |
| 634 | 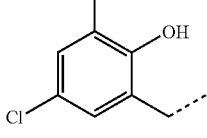 | H | H | H | H | OPh | H |
| 635 | 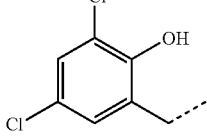 | H | H | SO2Me | H | H | H |
| 636 | 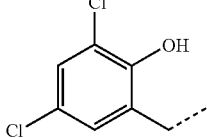 | H | H | H | SO2Me | H | H |
| 637 | 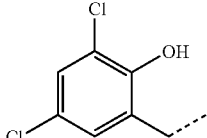 | H | H | H | H | SO2Me | H |
| 638 | 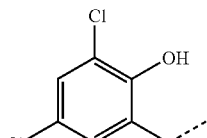 | H | H | SO2Et | H | H | H |
| 639 | 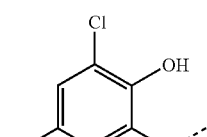 | H | H | H | SO2Et | H | H |
| 640 | 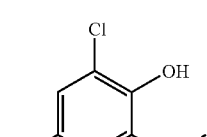 | H | H | H | H | SO2Et | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 641 | 2,4-dichloro-6-hydroxyphenyl | H | H | SO2iPr | H | H | H |
| 642 | 2,4-dichloro-6-hydroxyphenyl | H | H | H | SO2iPr | H | H |
| 643 | 2,4-dichloro-6-hydroxyphenyl | H | H | H | H | SO2iPr | H |
| 644 | 2,4-dichloro-6-hydroxyphenyl | H | H | SO2Ph | H | H | H |
| 645 | 2,4-dichloro-6-hydroxyphenyl | H | H | H | SO2Ph | H | H |
| 646 | 2,4-dichloro-6-hydroxyphenyl | H | H | H | H | SO2Ph | H |
| 647 | 2,4-dichloro-6-hydroxyphenyl | H | H | SO2Me | H | H | H |
| 648 | 2,4-dichloro-6-hydroxyphenyl | H | H | SO2Me | H | Me | H |
| 649 | 2,4-dichloro-6-hydroxyphenyl | H | H | Me | SO2Me | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 650 | 2,4-dichloro-6-hydroxyphenyl-CH2- | H | H | H | SO2Me | H | H |
| 651 | 2,4-dichloro-6-hydroxyphenyl-CH2- | H | H | SO2Me | F | H | H |
| 652 | 2,4-dichloro-6-hydroxyphenyl-CH2- | H | H | SO2Me | H | F | H |
| 653 | 2,4-dichloro-6-hydroxyphenyl-CH2- | H | H | F | SO2Me | H | H |
| 654 | 2,4-dichloro-6-hydroxyphenyl-CH2- | H | H | H | SO2Me | F | H |
| 655 | 2,4-dichloro-6-hydroxyphenyl-CH2- | H | H | SO2NMe2 | H | H | H |
| 656 | 2,4-dichloro-6-hydroxyphenyl-CH2- | H | H | H | SO2NMe2 | H | H |
| 657 | 2,4-dichloro-6-hydroxyphenyl-CH2- | H | H | H | H | SO2NMe2 | H |
| 658 | 2,4-dichloro-6-hydroxyphenyl-CH2- | H | H | SO2Et2 | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 659 | 2,4-dichloro-6-hydroxyphenyl-CH2 | H | H | H | SO2Et2 | H | H |
| 660 | 2,4-dichloro-6-hydroxyphenyl-CH2 | H | H | H | H | SO2Et2 | H |
| 661 | 2,4-dichloro-6-hydroxyphenyl-CH2 | H | H | SO2NMe2 | Me | H | H |
| 662 | 2,4-dichloro-6-hydroxyphenyl-CH2 | H | H | SO2NMe2 | H | Me | H |
| 663 | 2,4-dichloro-6-hydroxyphenyl-CH2 | H | H | Me | SO2NMe2 | H | H |
| 664 | 2,4-dichloro-6-hydroxyphenyl-CH2 | H | H | H | SO2NMe2 | Me | H |
| 665 | 2,4-dichloro-6-hydroxyphenyl-CH2 | H | H | SO2NMe2 | F | H | H |
| 666 | 2,4-dichloro-6-hydroxyphenyl-CH2 | H | H | SO2NMe2 | H | F | H |
| 667 | 2,4-dichloro-6-hydroxyphenyl-CH2 | H | H | F | SO2NMe2 | H | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 668 | 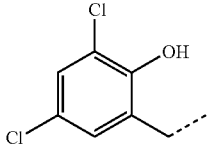 | H | H | H | SO2NMe2 | F | H |
| 669 | 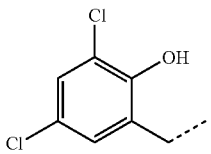 | H | H | NHCOEt | H | H | H |
| 670 | 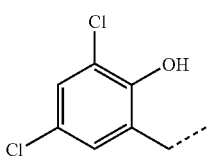 | H | H | H | NHCOEt | H | H |
| 671 | 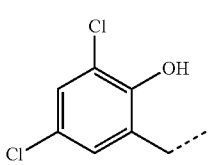 | H | H | H | H | NHCOEt | H |
| 672 | 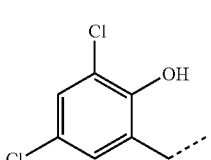 | H | H | NHCOiPr | H | H | H |
| 673 | 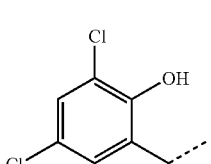 | H | H | H | NHCOiPr | H | H |
| 674 | 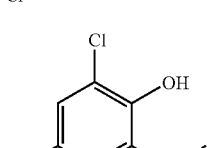 | H | H | H | H | NHCOiPr | H |
| 675 | 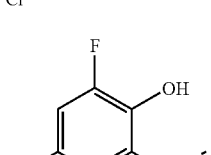 | H | H | Me | CN | H | H |
| 676 | 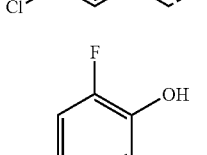 | H | H | H | CN | Me | H |

TABLE 3-continued
X = —SO2—, q = 0, r = 0, Y = —(R4)C=C(R5)—
| Compound No. 3 | R1—(CH2)p— | R2 | R3 | R4 | R5 | R6 | R7 |
|---|---|---|---|---|---|---|---|
| 677 | 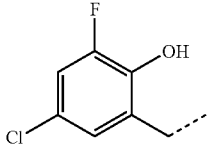 | H | H | H | CN | H | Me |
| 678 | 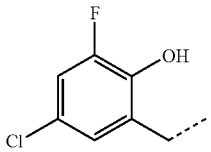 | H | H | Me | Br | H | H |
| 679 | 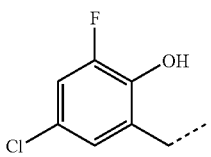 | H | H | H | Br | Me | H |
| 680 | 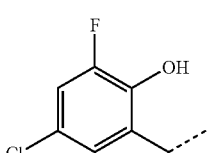 | H | H | H | Br | H | Me |
| 681 | 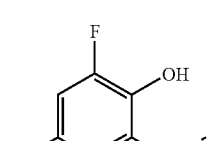 | H | H | Me | H | F | H |
| 682 | 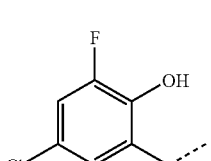 | H | H | Me | H | H | F |
| 683 | 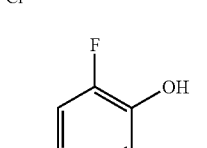 | H | H | F | H | Me | H |
| 684 | 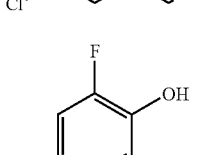 | H | H | F | H | H | Me |
| 685 | 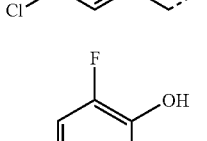 | H | H | Me | H | H | Me |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 686 | 4-Cl, 2-F, 6-OH-benzyl | H | H | H | OMe | Me | H |
| 687 | 4-Cl, 2-F, 6-OH-benzyl | H | H | H | OH | Me | H |
| 688 | 4-Cl, 2-F, 6-OH-benzyl | H | H | NH2 | H | H | H |
| 689 | 4-Cl, 2-F, 6-OH-benzyl | H | H | H | NH2 | H | H |
| 690 | 4-Cl, 2-F, 6-OH-benzyl | H | H | H | H | NH2 | H |
| 691 | 4-Cl, 2-F, 6-OH-benzyl | H | H | Et | H | H | H |
| 692 | 4-Cl, 2-F, 6-OH-benzyl | H | H | H | Et | H | H |
| 693 | 4-Cl, 2-F, 6-OH-benzyl | H | H | H | H | Et | H |
| 694 | 4-Cl, 2-F, 6-OH-benzyl | H | H | iPr | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 695 | 4-Cl-2-F-6-OH-phenyl-CH2- | H | H | H | iPr | H | H |
| 696 | 4-Cl-2-F-6-OH-phenyl-CH2- | H | H | H | H | iPr | H |
| 697 | 4-Cl-2-F-6-OH-phenyl-CH2- | H | H | Ph | H | H | H |
| 698 | 4-Cl-2-F-6-OH-phenyl-CH2- | H | H | H | Ph | H | H |
| 699 | 4-Cl-2-F-6-OH-phenyl-CH2- | H | H | H | H | Ph | H |
| 700 | 4-Cl-2-F-6-OH-phenyl-CH2- | H | H | OEt | H | H | H |
| 701 | 4-Cl-2-F-6-OH-phenyl-CH2- | H | H | H | OEt | H | H |
| 702 | 4-Cl-2-F-6-OH-phenyl-CH2- | H | H | H | H | OEt | H |
| 703 | 4-Cl-2-F-6-OH-phenyl-CH2- | H | H | OiPr | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 704 | 4-Cl, 2-F, 3-OH-benzyl | H | H | H | OiPr | H | H |
| 705 | 4-Cl, 2-F, 3-OH-benzyl | H | H | H | H | OiPr | H |
| 706 | 4-Cl, 2-F, 3-OH-benzyl | H | H | OPh | H | H | H |
| 707 | 4-Cl, 2-F, 3-OH-benzyl | H | H | H | OPh | H | H |
| 708 | 4-Cl, 2-F, 3-OH-benzyl | H | H | H | H | OPh | H |
| 709 | 4-Cl, 2-F, 3-OH-benzyl | H | H | SO2Me | H | H | H |
| 710 | 4-Cl, 2-F, 3-OH-benzyl | H | H | H | SO2Me | H | H |
| 711 | 4-Cl, 2-F, 3-OH-benzyl | H | H | H | H | SO2Me | H |
| 712 | 4-Cl, 2-F, 3-OH-benzyl | H | H | SO2Et | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 713 | 4-Cl, 2-F, 6-OH benzyl | H | H | H | SO2Et | H | H |
| 714 | 4-Cl, 2-F, 6-OH benzyl | H | H | H | H | SO2Et | H |
| 715 | 4-Cl, 2-F, 6-OH benzyl | H | H | SO2iPr | H | H | H |
| 716 | 4-Cl, 2-F, 6-OH benzyl | H | H | H | SO2iPr | H | H |
| 717 | 4-Cl, 2-F, 6-OH benzyl | H | H | H | H | SO2iPr | H |
| 718 | 4-Cl, 2-F, 6-OH benzyl | H | H | SO2Ph | H | H | H |
| 719 | 4-Cl, 2-F, 6-OH benzyl | H | H | H | SO2Ph | H | H |
| 720 | 4-Cl, 2-F, 6-OH benzyl | H | H | H | H | SO2Ph | H |
| 721 | 4-Cl, 2-F, 6-OH benzyl | H | H | SO2Me | H | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 722 | 4-Cl-2-F-6-(OH)-phenyl-CH2- | H | H | SO2Me | H | Me | H |
| 723 | 4-Cl-2-F-6-(OH)-phenyl-CH2- | H | H | Me | SO2Me | H | H |
| 724 | 4-Cl-2-F-6-(OH)-phenyl-CH2- | H | H | H | SO2Me | Me | H |
| 725 | 4-Cl-2-F-6-(OH)-phenyl-CH2- | H | H | SO2Me | F | H | H |
| 726 | 4-Cl-2-F-6-(OH)-phenyl-CH2- | H | H | SO2Me | H | F | H |
| 727 | 4-Cl-2-F-6-(OH)-phenyl-CH2- | H | H | F | SO2Me | H | H |
| 728 | 4-Cl-2-F-6-(OH)-phenyl-CH2- | H | H | H | SO2Me | F | H |
| 729 | 4-Cl-2-F-6-(OH)-phenyl-CH2- | H | H | SO2NMe2 | H | H | H |
| 730 | 4-Cl-2-F-6-(OH)-phenyl-CH2- | H | H | H | SO2NMe2 | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 731 | 4-Cl-2-F-6-(OH)-benzyl | H | H | H | H | SO2NMe2 | H |
| 732 | 4-Cl-2-F-6-(OH)-benzyl | H | H | SO2Et2 | H | H | H |
| 733 | 4-Cl-2-F-6-(OH)-benzyl | H | H | H | SO2Et2 | H | H |
| 734 | 4-Cl-2-F-6-(OH)-benzyl | H | H | H | H | SO2Et2 | H |
| 735 | 4-Cl-2-F-6-(OH)-benzyl | H | H | SO2NMe2 | Me | H | H |
| 736 | 4-Cl-2-F-6-(OH)-benzyl | H | H | SO2NMe2 | H | Me | H |
| 737 | 4-Cl-2-F-6-(OH)-benzyl | H | H | Me | SO2NMe2 | H | H |
| 738 | 4-Cl-2-F-6-(OH)-benzyl | H | H | H | SO2NMe2 | Me | H |
| 739 | 4-Cl-2-F-6-(OH)-benzyl | H | H | SO2NMe2 | F | H | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 740 | 4-Cl, 2-F, 3-OH-benzyl | H | H | SO2NMe2 | H | F | H |
| 741 | 4-Cl, 2-F, 3-OH-benzyl | H | H | F | SO2NMe2 | H | H |
| 742 | 4-Cl, 2-F, 3-OH-benzyl | H | H | H | SO2NMe2 | F | H |
| 743 | 4-Cl, 2-F, 3-OH-benzyl | H | H | NHCOEt | H | H | H |
| 744 | 4-Cl, 2-F, 3-OH-benzyl | H | H | H | NHCOEt | H | H |
| 745 | 4-Cl, 2-F, 3-OH-benzyl | H | H | H | H | NHCOEt | H |
| 746 | 4-Cl, 2-F, 3-OH-benzyl | H | H | NHCOiPr | H | H | H |
| 747 | 4-Cl, 2-F, 3-OH-benzyl | H | H | H | NHCOiPr | H | H |
| 748 | 4-Cl, 2-F, 3-OH-benzyl | H | H | H | H | NHCOiPr | H |

TABLE 3-continued

X = —SO2—, q = 0, r = 0, Y = —(R4)C=C(R5)—

| Compound No. 3 | R1—(CH2)p— | R2 | R3 | R4 | R5 | R6 | R7 |
|---|---|---|---|---|---|---|---|
| 749 | 2,4-dichloro-6-hydroxyphenyl (Cl, Cl, OH) | H | H | F | H | H | F |
| 750 | 4-chloro-2-fluoro-6-hydroxyphenyl (F, Cl, OH) | H | H | F | H | H | F |

TABLE 4

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 1 | 3,4-dichlorophenyl | H | H | H | H | H | H |
| 2 | 2,4-dichloro-6-hydroxyphenyl | H | H | H | H | H | H |
| 3 | 4-chloro-2-hydroxyphenyl | H | H | H | H | H | H |
| 4 | naphthalen-1-yl | H | H | H | H | H | H |
| 5 | phenyl-(CH2)2— | H | H | H | H | H | H |
| 6 | 2,4-dichloro-6-hydroxyphenyl | H | H | H | OCF3 | H | H |
| 7 | 2,4-dichloro-6-hydroxyphenyl | H | H | H | Cl | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 8 | 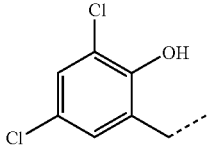 | H | H | H | Me | H | H |
| 9 | 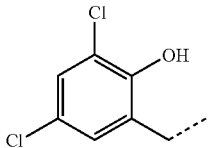 | H | H | H | F | H | H |
| 10 | 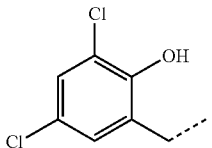 | H | H | Me | H | H | H |
| 11 | 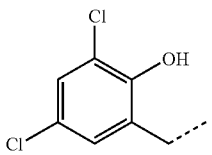 | H | H | H | OH | H | H |
| 12 | 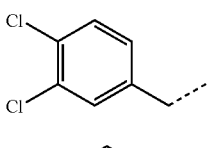 | H | H | H | Cl | H | H |
| 13 | 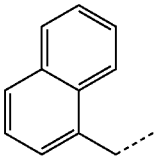 | H | H | H | Cl | H | H |
| 14 | 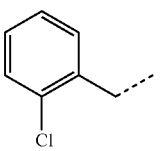 | H | H | H | H | H | H |
| 15 | 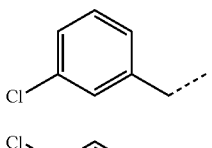 | H | H | H | H | H | H |
| 16 | 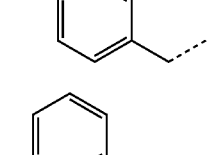 | H | H | H | H | H | H |
| 17 | 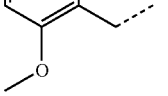 | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 18 | 4-MeO-C6H4-CH2- | H | H | H | H | H | H |
| 19 | 4-Br-2-OH-C6H3-CH2- | H | H | H | H | H | H |
| 20 | 4-Br-2-OMe-C6H3-CH2- | H | H | H | H | H | H |
| 21 | 4-Br-2-F-C6H3-CH2- | H | H | H | H | H | H |
| 22 | 3-Br-C6H4-CH2- | H | H | H | H | H | H |
| 23 | 3-Cl-4-F-C6H3-CH2- | H | H | H | H | H | H |
| 24 | (1-Me-indol-3-yl)-CH2- | H | H | H | H | H | H |
| 25 | (benzothiophen-3-yl)-CH2- | H | H | H | H | H | H |
| 26 | 4-MeO-2-OH-C6H3-CH2- | H | H | H | H | H | H |
| 27 | 3-O2N-C6H4-CH2- | H | H | H | H | H | H |
| 28 | 3-MeO-C6H4-CH2- | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 29 | 2-naphthylmethyl | H | H | H | H | H | H |
| 30 | benzyl | H | H | H | H | H | H |
| 31 | phenethyl | H | H | H | H | H | H |
| 32 | 3-bromo-5-chloro-2-hydroxybenzyl | H | H | H | H | H | H |
| 33 | 4-cyano-2-hydroxybenzyl (NC, OH) | H | H | H | H | H | H |
| 34 | 3-chloro-2-hydroxy-5-(trifluoromethyl)benzyl | H | H | H | H | H | H |
| 35 | 5-chloro-2-hydroxy-3-(trifluoromethyl)benzyl | H | H | H | H | H | H |
| 36 | 3-chloro-2-hydroxybenzyl | H | H | H | H | H | H |
| 37 | 4-methylbenzyl | H | H | H | H | H | H |
| 38 | 4-fluorobenzyl | H | H | H | H | H | H |
| 39 | 4-bromobenzyl | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 40 | 4-(F₃C)-C₆H₄-CH₂- | H | H | H | H | H | H |
| 41 | 4-(HO)-C₆H₄-CH₂- | H | H | H | H | H | H |
| 42 | 4-(NC)-C₆H₄-CH₂- | H | H | H | H | H | H |
| 43 | 4-(MeSO₂)-C₆H₄-CH₂- | H | H | H | H | H | H |
| 44 | 4-(MeOOC)-C₆H₄-CH₂- | H | H | H | H | H | H |
| 45 | 4-(Me₂N)-C₆H₄-CH₂- | H | H | H | H | H | H |
| 46 | 4-(MeO)-C₆H₄-CH₂- | H | H | H | H | H | H |
| 47 | 4-(EtO)-C₆H₄-CH₂- | H | H | H | H | H | H |
| 48 | 4-(n-PrO)-C₆H₄-CH₂- | H | H | H | H | H | H |
| 49 | 4-(i-PrO)-C₆H₄-CH₂- | H | H | H | H | H | H |
| 50 | 4-(i-Pr)-C₆H₄-CH₂- | H | H | H | H | H | H |
| 51 | 4-(PhCH₂O)-C₆H₄-CH₂- | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 52 | 4-phenoxyphenyl | H | H | H | H | H | H |
| 53 | 4-biphenyl | H | H | H | H | H | H |
| 54 | 4-acetamidophenyl | H | H | H | H | H | H |
| 55 | 2-propylphenyl | H | H | H | H | H | H |
| 56 | 2-(benzyloxy)phenyl | H | H | H | H | H | H |
| 57 | 2-methylphenyl | H | H | H | H | H | H |
| 58 | 2-cyanophenyl | H | H | H | H | H | H |
| 59 | 2-chlorophenyl | H | H | H | H | H | H |
| 60 | 2-methoxyphenyl | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 61 | 2-ethoxybenzyl | H | H | H | H | H | H |
| 62 | 2-phenylbenzyl (biphenyl) | H | H | H | H | H | H |
| 63 | 3-(trifluoromethyl)benzyl | H | H | H | H | H | H |
| 64 | 3-chloro-2-fluorobenzyl | H | H | H | H | H | H |
| 65 | 3,5-dichlorobenzyl | H | H | H | H | H | H |
| 66 | 3-methylbenzyl | H | H | H | H | H | H |
| 67 | 3-fluoro-5-(trifluoromethyl)benzyl | H | H | H | H | H | H |
| 68 | 3-(trifluoromethoxy)benzyl | H | H | H | H | H | H |
| 69 | 2-fluoro-5-methoxybenzyl | H | H | H | H | H | H |
| 70 | 2-fluoro-5-nitrobenzyl | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 71 | 4-O2N-C6H4-CH2- | H | H | H | H | H | H |
| 72 | 2-F,3-methyl-C6H3-CH2- | H | H | H | H | H | H |
| 73 | 3-(F3CS)-C6H4-CH2- | H | H | H | H | H | H |
| 74 | 2,5-Cl2-C6H3-CH2- | H | H | H | H | H | H |
| 75 | 3-(F2HC)-C6H4-CH2- | H | H | H | H | H | H |
| 76 | 2-F-C6H4-CH2- | H | H | H | H | H | H |
| 77 | 2-NO2-C6H4-CH2- | H | H | H | H | H | H |
| 78 | 2-COOH-C6H4-CH2- | H | H | H | H | H | H |
| 79 | 4-Br,2-OEt-C6H3-CH2- | H | H | H | H | H | H |
| 80 | 2,3-dimethyl-C6H3-CH2- | H | H | H | H | H | H |
| 81 | 3-F-C6H4-CH2- | H | H | H | H | H | H |
| 82 | 2,4-Cl2-C6H3-CH2- | H | H | H | H | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 83 | 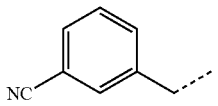 | H | H | H | H | H | H |
| 84 | 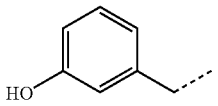 | H | H | H | H | H | H |
| 85 | 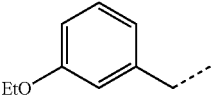 | H | H | H | H | H | H |
| 86 | 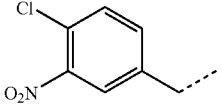 | H | H | H | H | H | H |
| 87 | 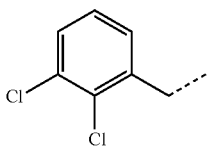 | H | H | H | H | H | H |
| 88 | 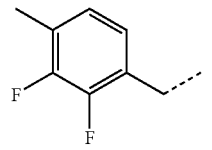 | H | H | H | H | H | H |
| 89 | 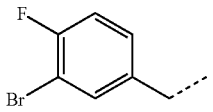 | H | H | H | H | H | H |
| 90 | 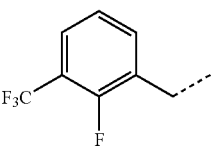 | H | H | H | H | H | H |
| 91 | 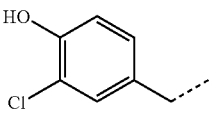 | H | H | H | H | H | H |
| 92 | 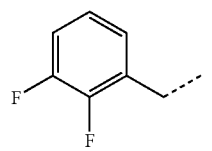 | H | H | H | H | H | H |
| 93 | 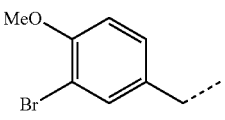 | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 94 | 2-MeO, 3-OEt benzyl | H | H | H | H | H | H |
| 95 | 4-MeO, 2,3-dimethyl benzyl | H | H | H | H | H | H |
| 96 | 3-MeO, 2-(benzyloxy) benzyl | H | H | H | H | H | H |
| 97 | 2-Cl, 5-NO2 benzyl | H | H | H | H | H | H |
| 98 | 3-(4-methoxyphenoxy)benzyl | H | H | H | H | H | H |
| 99 | 3-(4-methylphenoxy)benzyl | H | H | H | H | H | H |
| 100 | 3-(4-chlorophenoxy)benzyl | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 101 | 3-(benzyloxy)benzyl | H | H | H | H | H | H |
| 102 | 3-phenoxybenzyl | H | H | H | H | H | H |
| 103 | 4-methoxy-3-hydroxybenzyl | H | H | H | H | H | H |
| 104 | 2-chloro-3-(trifluoromethyl)benzyl | H | H | H | H | H | H |
| 105 | 4-hydroxy-3-nitrobenzyl | H | H | H | H | H | H |
| 106 | 2,3-dimethoxybenzyl | H | H | H | H | H | H |
| 107 | 4-ethoxy-2-ethoxy-3-methylbenzyl | H | H | H | H | H | H |
| 108 | 3-(2-hydroxyethoxy)benzyl | H | H | H | H | H | H |
| 109 | 2,3,4-trimethoxybenzyl | H | H | H | H | H | H |
| 110 | 2-fluoro-3-phenoxybenzyl | H | H | H | H | H | H |

TABLE 4-continued
| | X = —CH2—, q = 0, r = 0, Y = —(R4)C=C(R5)— | | | | | | |
|---|---|---|---|---|---|---|---|
| Compound No. 4 | R1—(CH2)p— | R2 | R3 | R4 | R5 | R6 | R7 |
| 111 | 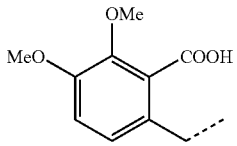 | H | H | H | H | H | H |
| 112 | 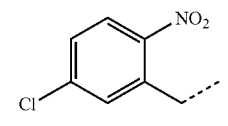 | H | H | H | H | H | H |
| 113 | 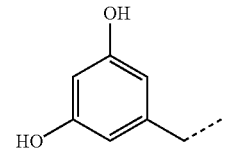 | H | H | H | H | H | H |
| 114 | 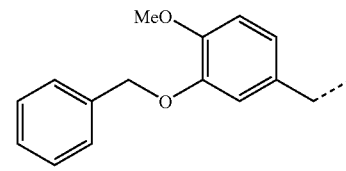 | H | H | H | H | H | H |
| 115 | 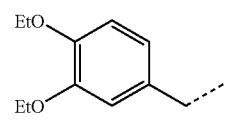 | H | H | H | H | H | H |
| 116 | 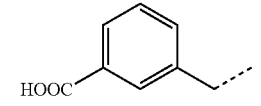 | H | H | H | H | H | H |
| 117 | 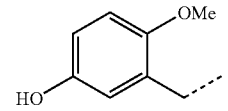 | H | H | H | H | H | H |
| 118 | 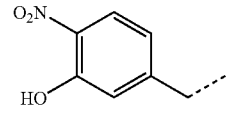 | H | H | H | H | H | H |
| 119 | 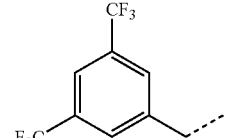 | H | H | H | H | H | H |
| 120 | 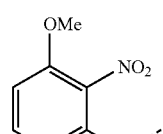 | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 121 | 4-methyl-naphthalen-1-ylmethyl | H | H | H | H | H | H |
| 122 | 7-methyl-1-methyl-1H-indol-3-ylmethyl | H | H | H | H | H | H |
| 123 | 2-methoxy-naphthalen-1-ylmethyl | H | H | H | H | H | H |
| 124 | benzofuran-2-ylmethyl | H | H | H | H | H | H |
| 125 | 2-methyl-1-methyl-1H-indol-3-ylmethyl | H | H | H | H | H | H |
| 126 | quinolin-8-ylmethyl | H | H | H | H | H | H |
| 127 | 2-hydroxy-naphthalen-1-ylmethyl | H | H | H | H | H | H |
| 128 | 2-acetoxy-naphthalen-1-ylmethyl | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 129 | 1-hydroxy-naphthalen-2-ylmethyl | H | H | H | H | H | H |
| 130 | 1H-indol-7-ylmethyl | H | H | H | H | H | H |
| 131 | quinolin-4-ylmethyl | H | H | H | H | H | H |
| 132 | 1,5-dimethyl-1H-indol-3-ylmethyl | H | H | H | H | H | H |
| 133 | anthracen-9-ylmethyl | H | H | H | H | H | H |
| 134 | 2-methyl-naphthalen-1-ylmethyl | H | H | H | H | H | H |
| 135 | 2-ethoxy-naphthalen-1-ylmethyl | H | H | H | H | H | H |
| 136 | 1H-indol-3-ylmethyl | H | H | H | H | H | H |

TABLE 4-continued

X = —CH2—, q = 0, r = 0, Y = —(R4)C═C(R5)—

| Compound No. 4 | R1—(CH2)p— | R2 | R3 | R4 | R5 | R6 | R7 |
|---|---|---|---|---|---|---|---|
| 137 | 6-methyl-1-methylindol-3-yl-CH2 | H | H | H | H | H | H |
| 138 | 1-methylindol-2-yl-CH2 | H | H | H | H | H | H |
| 139 | 4-methyl-1-methylindol-3-yl-CH2 | H | H | H | H | H | H |
| 140 | 2,5-dimethyl-1-methylindol-3-yl-CH2 | H | H | H | H | H | H |
| 141 | 5-methoxy-1-methylindol-3-yl-CH2 | H | H | H | H | H | H |
| 142 | 4-methylbenzothiophen-3-yl-CH2 | H | H | H | H | H | H |
| 143 | 1-methylbenzimidazol-2-yl-CH2 | H | H | H | H | H | H |
| 144 | 1-methyl-2-phenylindol-3-yl-CH2 | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 145 | 1-acetyl-indol-3-yl | H | H | H | H | H | H |
| 146 | quinolin-2-yl | H | H | H | H | H | H |
| 147 | 6-methoxy-1-methyl-indol-3-yl | H | H | H | H | H | H |
| 148 | 3-methyl-benzothiophen-2-yl | H | H | H | H | H | H |
| 149 | 4-methoxy-naphthalen-1-yl | H | H | H | H | H | H |
| 150 | phenanthren-9-yl | H | H | H | H | H | H |
| 151 | 6-methoxy-naphthalen-2-yl | H | H | H | H | H | H |
| 152 | 1-bromo-naphthalen-2-yl | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 153 | *4-(dimethylamino)naphthalen-1-ylmethyl* | H | H | H | H | H | H |
| 154 | *2,3-dihydro-1,4-benzodioxin-6-ylmethyl* | H | H | H | H | H | H |
| 155 | *2,2-dimethylchroman-6-ylmethyl* | H | H | H | H | H | H |
| 156 | *2,3-dihydrobenzofuran-5-ylmethyl* | H | H | H | H | H | H |
| 157 | *9-ethylcarbazol-3-ylmethyl* | H | H | H | H | H | H |
| 158 | *benzo[1,3]dioxol-4-ylmethyl* | H | H | H | H | H | H |
| 159 | *benzo[1,3]dioxol-5-ylmethyl* | H | H | H | H | H | H |
| 160 | *4-phenylbutyl* | H | H | H | H | H | H |
| 161 | *5-phenylpentyl* | H | H | H | H | H | H |
| 162 | *cyclohexylmethyl* | H | H | H | H | H | H |
| 163 | *2-hydroxy-5-iodobenzyl* | H | H | H | H | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 164 | 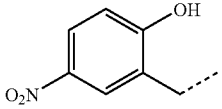 | H | H | H | H | H | H |
| 165 | 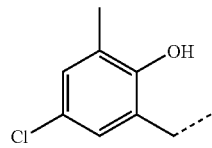 | H | H | H | H | H | H |
| 166 | 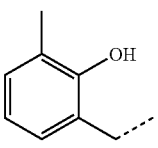 | H | H | H | H | H | H |
| 167 | 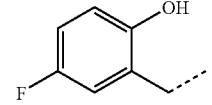 | H | H | H | H | H | H |
| 168 | 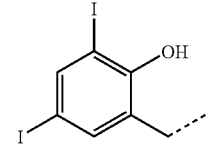 | H | H | H | H | H | H |
| 169 | 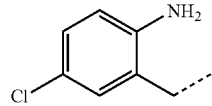 | H | H | H | H | H | H |
| 170 | 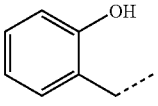 | H | H | H | H | H | H |
| 171 | 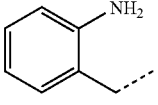 | H | H | H | H | H | H |
| 172 | 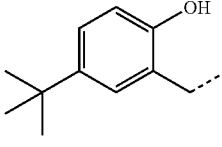 | H | H | H | H | H | H |
| 173 | 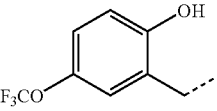 | H | H | H | H | H | H |
| 174 | 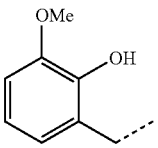 | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 175 | 2,3-dihydroxyphenyl-CH2— | H | H | H | H | H | H |
| 176 | 3-ethoxy-2-hydroxyphenyl-CH2— | H | H | H | H | H | H |
| 177 | 3-carboxy-2-hydroxyphenyl-CH2— | H | H | H | H | H | H |
| 178 | 3-tert-butyl-2-hydroxyphenyl-CH2— | H | H | H | H | H | H |
| 179 | furan-2-yl-CH2— | H | H | H | H | H | H |
| 180 | oxazol-2-yl-CH2— | H | H | H | H | H | H |
| 181 | 1H-imidazol-2-yl-CH2— | H | H | H | H | H | H |
| 182 | thiazol-2-yl-CH2— | H | H | H | H | H | H |
| 183 | 1H-pyrazol-3-yl-CH2— | H | H | H | H | H | H |
| 184 | 3,5-dimethyl-1-phenyl-1H-pyrazol-4-yl-CH2— | H | H | H | H | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 185 | 1-phenyl-2-methyl-pyrrol-3-yl | H | H | H | H | H | H |
| 186 | 5-(4-chlorophenyl)furan-2-yl | H | H | H | H | H | H |
| 187 | thiophen-2-yl | H | H | H | H | H | H |
| 188 | pyrrol-2-yl | H | H | H | H | H | H |
| 189 | pyridin-2-yl | H | H | H | H | H | H |
| 190 | pyridin-3-yl | H | H | H | H | H | H |
| 191 | pyridin-4-yl | H | H | H | H | H | H |
| 192 | 4-chloro-2-hydroxyphenyl | H | H | H | Cl | H | H |
| 193 | 2-hydroxy-4-nitrophenyl | H | H | H | Cl | H | H |
| 194 | 2-hydroxy-4-methoxyphenyl | H | H | H | Cl | H | H |
| 195 | 3-chlorophenyl | H | H | H | Cl | H | H |
| 196 | 3-bromophenyl | H | H | H | Cl | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 197 | 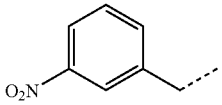 | H | H | H | Cl | H | H |
| 198 | 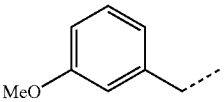 | H | H | H | Cl | H | H |
| 199 | 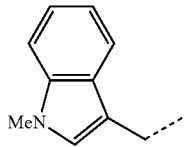 | H | H | H | Cl | H | H |
| 200 | 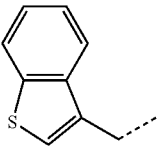 | H | H | H | Cl | H | H |
| 201 | 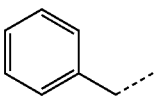 | H | H | H | Cl | H | H |
| 202 | 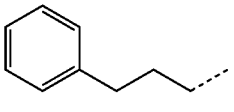 | H | H | H | Cl | H | H |
| 203 | 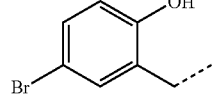 | H | H | H | Cl | H | H |
| 204 | 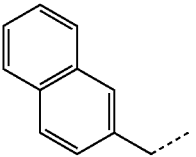 | H | H | H | Cl | H | H |
| 205 | 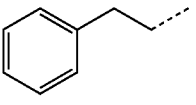 | H | H | H | Cl | H | H |
| 206 | 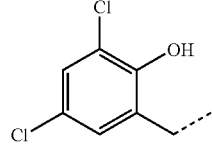 | H | H | Cl | H | H | H |
| 207 | 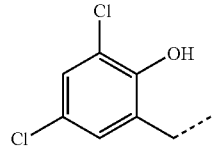 | H | H | H | OMe | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 208 | 2,4-dichloro-6-hydroxyphenyl-CH2 | H | H | H | COOMe | H | H |
| 209 | 2,4-dichloro-6-hydroxyphenyl-CH2 | H | H | H | H | Cl | H |
| 210 | 2,4-dichloro-6-hydroxyphenyl-CH2 | H | H | H | H | COOMe | H |
| 211 | 2,4-dichloro-6-hydroxyphenyl-CH2 | H | H | H | H | H | Cl |
| 212 | 2,4-dichloro-6-hydroxyphenyl-CH2 | H | H | COOMe | H | H | H |
| 213 | 2,4-dichloro-6-hydroxyphenyl-CH2 | H | H | H | CF3 | H | H |
| 214 | 2,4-dichloro-6-hydroxyphenyl-CH2 | H | H | H | NO2 | H | H |
| 215 | 2,4-dichloro-6-hydroxyphenyl-CH2 | H | H | H | F | F | H |
| 216 | 2,4-dichloro-6-hydroxyphenyl-CH2 | H | H | F | H | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 217 | 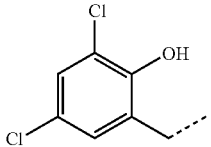 | H | H | H | CN | H | H |
| 218 | 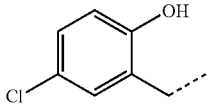 | H | H | Cl | H | H | H |
| 219 | 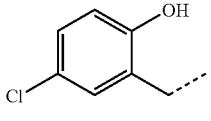 | H | H | H | OMe | H | H |
| 220 | 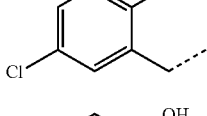 | H | H | H | COOMe | H | H |
| 221 | 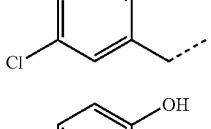 | H | H | H | H | Cl | H |
| 222 | 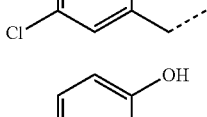 | H | H | H | H | COOMe | H |
| 223 | 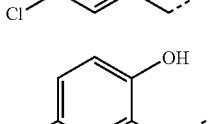 | H | H | H | H | H | Cl |
| 224 | 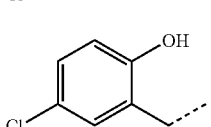 | H | H | H | OCF3 | H | H |
| 225 | 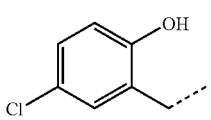 | H | H | COOMe | H | H | H |
| 226 | 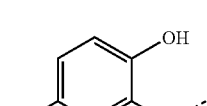 | H | H | H | CF3 | H | H |
| 227 | 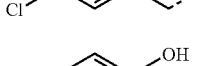 | H | H | H | Me | H | H |
| 228 | 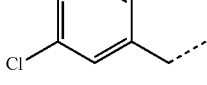 | H | H | H | F | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 229 | 4-Cl-2-OH-C6H3-CH2- | H | H | H | OH | H | H |
| 230 | 4-Cl-2-OH-C6H3-CH2- | H | H | H | NO2 | H | H |
| 231 | 4-Cl-2-OH-C6H3-CH2- | H | H | H | F | F | H |
| 232 | 4-Cl-2-OH-C6H3-CH2- | H | H | F | H | H | H |
| 233 | 4-Cl-2-OH-C6H3-CH2- | H | H | Me | H | H | H |
| 234 | 4-Cl-2-OH-C6H3-CH2- | H | H | H | CN | H | H |
| 235 | 1-naphthyl-CH2- | H | H | Cl | H | H | H |
| 236 | 1-naphthyl-CH2- | H | H | H | OMe | H | H |
| 237 | 1-naphthyl-CH2- | H | H | H | COOMe | H | H |
| 238 | 1-naphthyl-CH2- | H | H | H | H | Cl | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 239 | naphthyl-CH2- | H | H | H | H | COOMe | H |
| 240 | naphthyl-CH2- | H | H | H | H | H | Cl |
| 241 | naphthyl-CH2- | H | H | H | OCF3 | H | H |
| 242 | naphthyl-CH2- | H | H | COOMe | H | H | H |
| 243 | naphthyl-CH2- | H | H | H | CF3 | H | H |
| 244 | naphthyl-CH2- | H | H | H | Me | H | H |
| 245 | naphthyl-CH2- | H | H | H | F | H | H |
| 246 | naphthyl-CH2- | H | H | H | OH | H | H |
| 247 | naphthyl-CH2- | H | H | H | NO2 | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 248 | 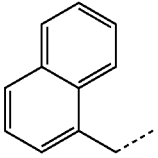 | H | H | H | F | F | H |
| 249 | 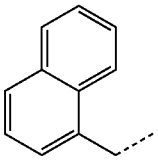 | H | H | F | H | H | H |
| 250 | 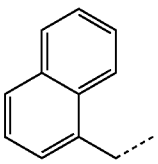 | H | H | Me | H | H | H |
| 251 | 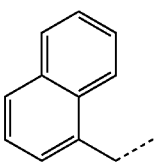 | H | H | H | CN | H | H |
| 252 | 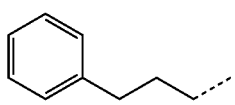 | H | H | Cl | H | H | H |
| 253 | 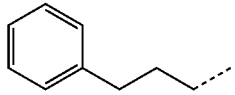 | H | H | H | OMe | H | H |
| 254 | 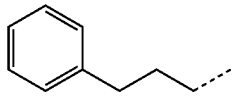 | H | H | H | COOMe | H | H |
| 255 | 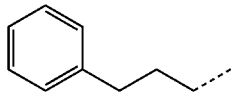 | H | H | H | H | Cl | H |
| 256 | 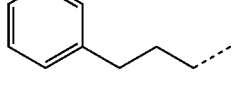 | H | H | H | H | COOMe | H |
| 257 | 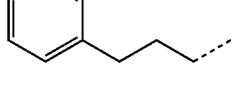 | H | H | H | H | H | Cl |
| 258 | 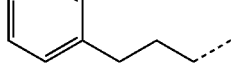 | H | H | H | OCF3 | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 259 | PhCH2CH2— | H | H | COOMe | H | H | H |
| 260 | PhCH2CH2— | H | H | H | CF3 | H | H |
| 261 | PhCH2CH2— | H | H | H | Me | H | H |
| 262 | PhCH2CH2— | H | H | H | F | H | H |
| 263 | PhCH2CH2— | H | H | H | OH | H | H |
| 264 | PhCH2CH2— | H | H | H | NO2 | H | H |
| 265 | PhCH2CH2— | H | H | H | F | F | H |
| 266 | PhCH2CH2— | H | H | F | H | H | H |
| 267 | PhCH2CH2— | H | H | Me | H | H | H |
| 268 | PhCH2CH2— | H | H | H | CN | H | H |
| 269 | 2,4-dichloro-6-hydroxybenzyl | H | H | H | H | H | COOMe |
| 270 | 2,4-dichloro-6-hydroxybenzyl | H | H | H | H | F | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 271 | 2,4-dichloro-6-hydroxyphenyl-CH2 | H | H | H | H | H | F |
| 272 | 2,4-dichloro-6-hydroxyphenyl-CH2 | H | H | H | H | Me | H |
| 273 | 2,4-dichloro-6-hydroxyphenyl-CH2 | H | H | H | H | H | Me |
| 274 | 2,4-dichloro-6-hydroxyphenyl-CH2 | H | H | OMe | H | H | H |
| 275 | 2,4-dichloro-6-hydroxyphenyl-CH2 | H | H | H | H | OMe | H |
| 276 | 2,4-dichloro-6-hydroxyphenyl-CH2 | H | H | H | H | H | OMe |
| 277 | 2,4-dichloro-6-hydroxyphenyl-CH2 | H | H | CF3 | H | H | H |
| 278 | 2,4-dichloro-6-hydroxyphenyl-CH2 | H | H | H | H | CF3 | H |
| 279 | 2,4-dichloro-6-hydroxyphenyl-CH2 | H | H | H | H | H | CF3 |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 280 | 2,4-dichloro-6-hydroxyphenyl-CH2— (Cl, OH, Cl) | H | H | OH | H | H | H |
| 281 | 2,4-dichloro-6-hydroxyphenyl-CH2— | H | H | H | H | OH | H |
| 282 | 2,4-dichloro-6-hydroxyphenyl-CH2— | H | H | H | H | H | OH |
| 283 | 2,4-dichloro-6-hydroxyphenyl-CH2— | H | H | OCF3 | H | H | H |
| 284 | 2,4-dichloro-6-hydroxyphenyl-CH2— | H | H | H | H | OCF3 | H |
| 285 | 2,4-dichloro-6-hydroxyphenyl-CH2— | H | H | H | H | H | OCF3 |
| 286 | 2,4-dichloro-6-hydroxyphenyl-CH2— | H | H | NO2 | H | H | H |
| 287 | 2,4-dichloro-6-hydroxyphenyl-CH2— | H | H | H | H | NO2 | H |
| 288 | 2,4-dichloro-6-hydroxyphenyl-CH2— | H | H | H | H | H | NO2 |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 289 | 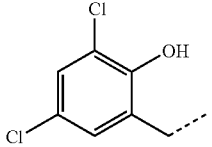 | H | H | CN | H | H | H |
| 290 | 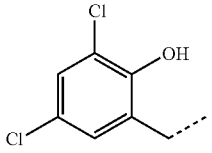 | H | H | H | H | CN | H |
| 291 | 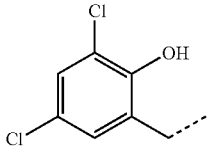 | H | H | H | H | H | CN |
| 292 | 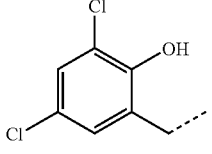 | H | H | Br | H | H | H |
| 293 | 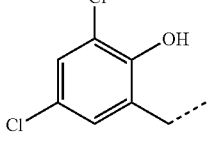 | H | H | H | Br | H | H |
| 294 | 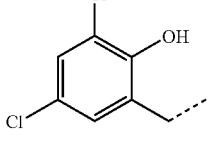 | H | H | H | H | Br | H |
| 295 | 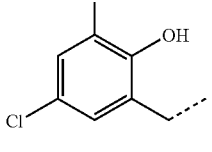 | H | H | H | H | H | Br |
| 296 | 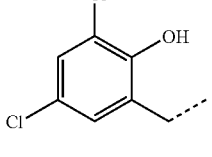 | H | H | COOH | H | H | H |
| 297 | 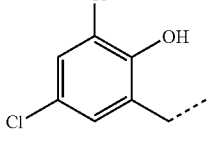 | H | H | H | COOH | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 298 | 2,4-dichloro-6-(CH2)-phenol | H | H | H | H | COOH | H |
| 299 | 2,4-dichloro-6-(CH2)-phenol | H | H | H | H | H | COOH |
| 300 | 2,4-dichloro-6-(CH2)-phenol | H | H | NHCOMe | H | H | H |
| 301 | 2,4-dichloro-6-(CH2)-phenol | H | H | H | NHCOMe | H | H |
| 302 | 2,4-dichloro-6-(CH2)-phenol | H | H | H | H | NHCOMe | H |
| 303 | 2,4-dichloro-6-(CH2)-phenol | H | H | H | H | H | NHCOMe |
| 304 | 2,4-dichloro-6-(CH2)-phenol | H | H | SO2NH2 | H | H | H |
| 305 | 2,4-dichloro-6-(CH2)-phenol | H | H | H | SO2NH2 | H | H |
| 306 | 2,4-dichloro-6-(CH2)-phenol | H | H | H | H | SO2NH2 | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 307 | 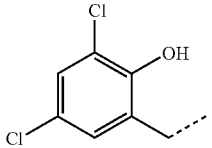 | H | H | H | H | H | SO2NH2 |
| 308 | 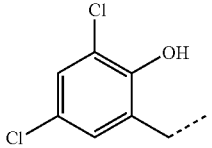 | H | H | Me | Me | H | H |
| 309 | 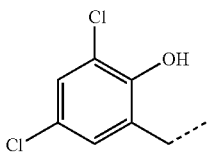 | H | H | Me | H | Me | H |
| 310 | 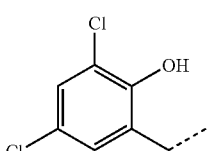 | H | H | H | Me | Me | H |
| 311 | 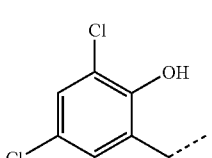 | H | H | F | F | H | H |
| 312 | 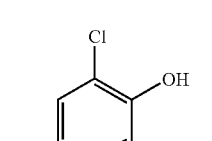 | H | H | F | H | F | H |
| 313 | 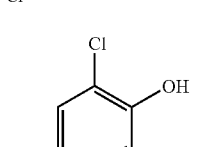 | H | H | H | F | F | H |
| 314 | 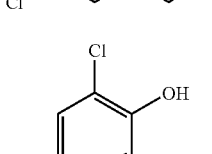 | H | H | Cl | Cl | H | H |
| 315 | 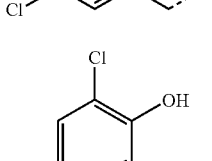 | H | H | Cl | H | Cl | H |

TABLE 4-continued

X = —CH2—, q = 0, r = 0, Y = —(R4)C═C(R5)—

| Compound No. 4 | R1—(CH2)p— | R2 | R3 | R4 | R5 | R6 | R7 |
|---|---|---|---|---|---|---|---|
| 316 | 2,4-dichloro-6-hydroxyphenylmethyl | H | H | H | Cl | Cl | H |
| 317 | 2,4-dichloro-6-hydroxyphenylmethyl | H | H | Me | F | H | H |
| 318 | 2,4-dichloro-6-hydroxyphenylmethyl | H | H | Me | Cl | H | H |
| 319 | 2,4-dichloro-6-hydroxyphenylmethyl | H | H | Me | OH | H | H |
| 320 | 2,4-dichloro-6-hydroxyphenylmethyl | H | H | Me | OMe | H | H |
| 321 | 2,4-dichloro-6-hydroxyphenylmethyl | H | H | F | Me | H | H |
| 322 | 2,4-dichloro-6-hydroxyphenylmethyl | H | H | F | Cl | H | H |
| 323 | 2,4-dichloro-6-hydroxyphenylmethyl | H | H | F | OH | H | H |
| 324 | 2,4-dichloro-6-hydroxyphenylmethyl | H | H | F | OMe | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 325 | 2,4-dichloro-6-(CH2)-phenol | H | H | Cl | Me | H | H |
| 326 | 2,4-dichloro-6-(CH2)-phenol | H | H | Cl | F | H | H |
| 327 | 2,4-dichloro-6-(CH2)-phenol | H | H | Cl | OH | H | H |
| 328 | 2,4-dichloro-6-(CH2)-phenol | H | H | Cl | OMe | H | H |
| 329 | 4-chloro-2-(CH2)-phenol | H | H | H | H | H | COOMe |
| 330 | 4-chloro-2-(CH2)-phenol | H | H | H | H | F | H |
| 331 | 4-chloro-2-(CH2)-phenol | H | H | H | H | H | F |
| 332 | 4-chloro-2-(CH2)-phenol | H | H | H | H | Me | H |
| 333 | 4-chloro-2-(CH2)-phenol | H | H | H | H | H | Me |
| 334 | 4-chloro-2-(CH2)-phenol | H | H | OMe | H | H | H |
| 335 | 4-chloro-2-(CH2)-phenol | H | H | H | H | OMe | H |

TABLE 4-continued
X = —CH2—, q = 0, r = 0, Y = —(R4)C═C(R5)—
| Compound No. 4 | R1—(CH2)p— | R2 | R3 | R4 | R5 | R6 | R7 |
|---|---|---|---|---|---|---|---|
| 336 | 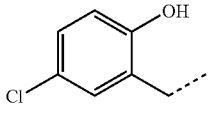 | H | H | H | H | H | OMe |
| 337 | 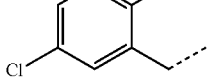 | H | H | CF3 | H | H | H |
| 338 | 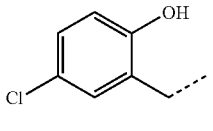 | H | H | H | H | CF3 | H |
| 339 | 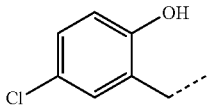 | H | H | H | H | H | CF3 |
| 340 | 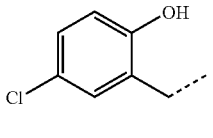 | H | H | OH | H | H | H |
| 341 | 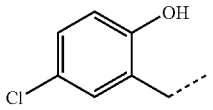 | H | H | H | H | OH | H |
| 342 | 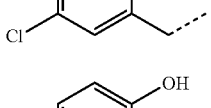 | H | H | H | H | H | OH |
| 343 | 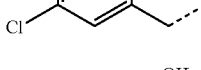 | H | H | OCF3 | H | H | H |
| 344 | 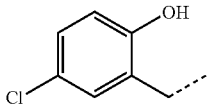 | H | H | H | H | OCF3 | H |
| 345 |  | H | H | H | H | H | OCF3 |
| 346 | 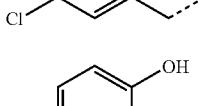 | H | H | NO2 | H | H | H |
| 347 |  | H | H | H | H | NO2 | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 348 | 4-Cl-2-(OH)-C6H3-CH2- | H | H | H | H | H | NO2 |
| 349 | 4-Cl-2-(OH)-C6H3-CH2- | H | H | CN | H | H | H |
| 350 | 4-Cl-2-(OH)-C6H3-CH2- | H | H | H | H | CN | H |
| 351 | 4-Cl-2-(OH)-C6H3-CH2- | H | H | H | H | H | CN |
| 352 | 4-Cl-2-(OH)-C6H3-CH2- | H | H | Br | H | H | H |
| 353 | 4-Cl-2-(OH)-C6H3-CH2- | H | H | H | Br | H | H |
| 354 | 4-Cl-2-(OH)-C6H3-CH2- | H | H | H | H | Br | H |
| 355 | 4-Cl-2-(OH)-C6H3-CH2- | H | H | H | H | H | Br |
| 356 | 4-Cl-2-(OH)-C6H3-CH2- | H | H | COOH | H | H | H |
| 357 | 4-Cl-2-(OH)-C6H3-CH2- | H | H | H | COOH | H | H |
| 358 | 4-Cl-2-(OH)-C6H3-CH2- | H | H | H | H | COOH | H |
| 359 | 4-Cl-2-(OH)-C6H3-CH2- | H | H | H | H | H | COOH |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 360 | 4-Cl, 2-OH benzyl | H | H | NHCOMe | H | H | H |
| 361 | 4-Cl, 2-OH benzyl | H | H | H | NHCOMe | H | H |
| 362 | 4-Cl, 2-OH benzyl | H | H | H | H | NHCOMe | H |
| 363 | 4-Cl, 2-OH benzyl | H | H | H | H | H | NHCOMe |
| 364 | 4-Cl, 2-OH benzyl | H | H | SO2NH2 | H | H | H |
| 365 | 4-Cl, 2-OH benzyl | H | H | H | SO2NH2 | H | H |
| 366 | 4-Cl, 2-OH benzyl | H | H | H | H | SO2NH2 | H |
| 367 | 4-Cl, 2-OH benzyl | H | H | H | H | H | SO2NH2 |
| 368 | 4-Cl, 2-OH benzyl | H | H | Me | Me | H | H |
| 369 | 4-Cl, 2-OH benzyl | H | H | Me | H | Me | H |
| 370 | 4-Cl, 2-OH benzyl | H | H | H | Me | Me | H |
| 371 | 4-Cl, 2-OH benzyl | H | H | F | F | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 372 | 5-Cl-2-OH-benzyl | H | H | F | H | F | H |
| 373 | 5-Cl-2-OH-benzyl | H | H | H | F | F | H |
| 374 | 5-Cl-2-OH-benzyl | H | H | Cl | Cl | H | H |
| 375 | 5-Cl-2-OH-benzyl | H | H | Cl | H | Cl | H |
| 376 | 5-Cl-2-OH-benzyl | H | H | H | Cl | Cl | H |
| 377 | 5-Cl-2-OH-benzyl | H | H | Me | F | H | H |
| 378 | 5-Cl-2-OH-benzyl | H | H | Me | Cl | H | H |
| 379 | 5-Cl-2-OH-benzyl | H | H | Me | OH | H | H |
| 380 | 5-Cl-2-OH-benzyl | H | H | Me | OMe | H | H |
| 381 | 5-Cl-2-OH-benzyl | H | H | F | Me | H | H |
| 382 | 5-Cl-2-OH-benzyl | H | H | F | Cl | H | H |
| 383 | 5-Cl-2-OH-benzyl | H | H | F | OH | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 384 | 4-Cl-2-OH-phenyl | H | H | F | OMe | H | H |
| 385 | 4-Cl-2-OH-phenyl | H | H | Cl | Me | H | H |
| 386 | 4-Cl-2-OH-phenyl | H | H | Cl | F | H | H |
| 387 | 4-Cl-2-OH-phenyl | H | H | Cl | OH | H | H |
| 388 | 4-Cl-2-OH-phenyl | H | H | Cl | OMe | H | H |
| 389 | 1-naphthyl | H | H | H | H | H | COOMe |
| 390 | 1-naphthyl | H | H | H | H | F | H |
| 391 | 1-naphthyl | H | H | H | H | H | F |
| 392 | 1-naphthyl | H | H | H | H | Me | H |
| 393 | 1-naphthyl | H | H | H | H | H | Me |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 394 | naphthalen-1-ylmethyl | H | H | OMe | H | H | H |
| 395 | naphthalen-1-ylmethyl | H | H | H | H | OMe | H |
| 396 | naphthalen-1-ylmethyl | H | H | H | H | H | OMe |
| 397 | naphthalen-1-ylmethyl | H | H | CF3 | H | H | H |
| 398 | naphthalen-1-ylmethyl | H | H | H | H | CF3 | H |
| 399 | naphthalen-1-ylmethyl | H | H | H | H | H | CF3 |
| 400 | naphthalen-1-ylmethyl | H | H | OH | H | H | H |
| 401 | naphthalen-1-ylmethyl | H | H | H | H | OH | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 402 | 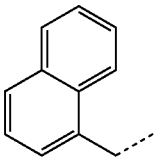 | H | H | H | H | H | OH |
| 403 | 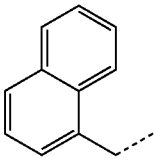 | H | H | OCF3 | H | H | H |
| 404 | 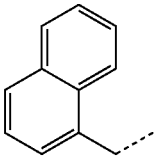 | H | H | H | H | OCF3 | H |
| 405 | 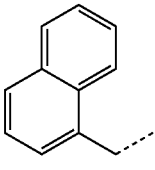 | H | H | H | H | H | OCF3 |
| 406 | 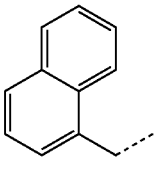 | H | H | NO2 | H | H | H |
| 407 | 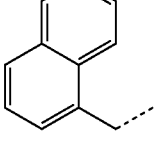 | H | H | H | H | NO2 | H |
| 408 | 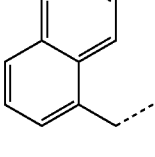 | H | H | H | H | H | NO2 |
| 409 | 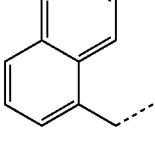 | H | H | CN | H | H | H |

TABLE 4-continued

X = —CH2—, q = 0, r = 0, Y = —(R4)C═C(R5)—

| Compound No. 4 | R1—(CH2)p— | R2 | R3 | R4 | R5 | R6 | R7 |
|---|---|---|---|---|---|---|---|
| 410 | naphthyl-CH2 | H | H | H | H | CN | H |
| 411 | naphthyl-CH2 | H | H | H | H | H | CN |
| 412 | naphthyl-CH2 | H | H | Br | H | H | H |
| 413 | naphthyl-CH2 | H | H | H | Br | H | H |
| 414 | naphthyl-CH2 | H | H | H | H | Br | H |
| 415 | naphthyl-CH2 | H | H | H | H | H | Br |
| 416 | naphthyl-CH2 | H | H | COOH | H | H | H |
| 417 | naphthyl-CH2 | H | H | H | COOH | H | H |
| 418 | naphthyl-CH2 | H | H | H | H | COOH | H |

TABLE 4-continued

X = —CH2—, q = 0, r = 0, Y = —(R4)C═C(R5)—

| Compound No. 4 | R1—(CH2)p— | R2 | R3 | R4 | R5 | R6 | R7 |
|---|---|---|---|---|---|---|---|
| 419 | naphthyl | H | H | H | H | H | COOH |
| 420 | naphthyl | H | H | NHCOMe | H | H | H |
| 421 | naphthyl | H | H | H | NHCOMe | H | H |
| 422 | naphthyl | H | H | H | H | NHCOMe | H |
| 423 | naphthyl | H | H | H | H | H | NHCOMe |
| 424 | naphthyl | H | H | SO2NH2 | H | H | H |
| 425 | naphthyl | H | H | H | SO2NH2 | H | H |
| 426 | naphthyl | H | H | H | H | SO2NH2 | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 427 | naphthyl-CH2- | H | H | H | H | H | SO2NH2 |
| 428 | naphthyl-CH2- | H | H | Me | Me | H | H |
| 429 | naphthyl-CH2- | H | H | Me | H | Me | H |
| 430 | naphthyl-CH2- | H | H | H | Me | Me | H |
| 431 | naphthyl-CH2- | H | H | F | F | H | H |
| 432 | naphthyl-CH2- | H | H | F | H | F | H |
| 433 | naphthyl-CH2- | H | H | H | F | F | H |
| 434 | naphthyl-CH2- | H | H | Cl | Cl | H | H |
| 435 | naphthyl-CH2- | H | H | Cl | H | Cl | H |

TABLE 4-continued

| | X = —CH2—, q = 0, r = 0, Y = —(R4)C=C(R5)— | | | | | | |
|---|---|---|---|---|---|---|---|
| Compound No. 4 | R1—(CH2)p— | R2 | R3 | R4 | R5 | R6 | R7 |
| 436 | naphthyl-CH2 | H | H | H | Cl | Cl | H |
| 437 | naphthyl-CH2 | H | H | Me | F | H | H |
| 438 | naphthyl-CH2 | H | H | Me | Cl | H | H |
| 439 | naphthyl-CH2 | H | H | Me | OH | H | H |
| 440 | naphthyl-CH2 | H | H | Me | OMe | H | H |
| 441 | naphthyl-CH2 | H | H | F | Me | H | H |
| 442 | naphthyl-CH2 | H | H | F | Cl | H | H |
| 443 | naphthyl-CH2 | H | H | F | OH | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 444 | 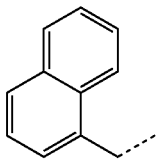 | H | H | F | OMe | H | H |
| 445 | 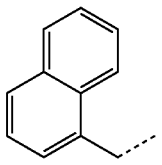 | H | H | Cl | Me | H | H |
| 446 | 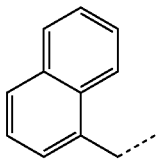 | H | H | Cl | F | H | H |
| 447 | 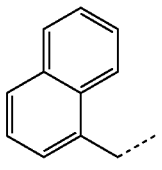 | H | H | Cl | OH | H | H |
| 448 | 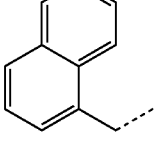 | H | H | Cl | OMe | H | H |
| 449 | 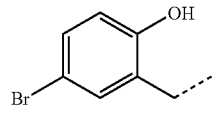 | H | H | Cl | H | H | H |
| 450 | 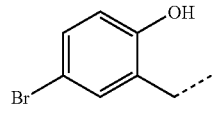 | H | H | H | OMe | H | H |
| 451 | 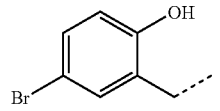 | H | H | H | COOMe | H | H |
| 452 | 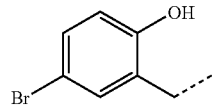 | H | H | H | H | Cl | H |
| 453 | 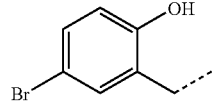 | H | H | H | H | COOMe | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 454 | 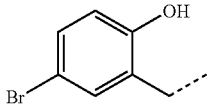 | H | H | H | H | H | Cl |
| 455 | 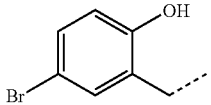 | H | H | H | OCF3 | H | H |
| 456 | 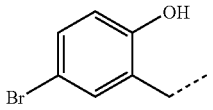 | H | H | COOMe | H | H | H |
| 457 | 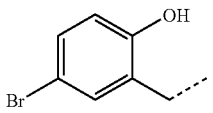 | H | H | H | CF3 | H | H |
| 458 | 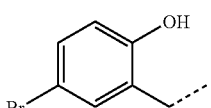 | H | H | H | Me | H | H |
| 459 | 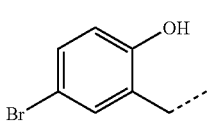 | H | H | H | F | H | H |
| 460 | 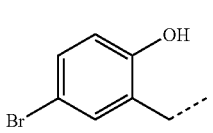 | H | H | H | OH | H | H |
| 461 | 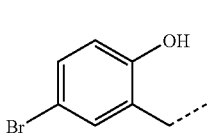 | H | H | H | NO2 | H | H |
| 462 | 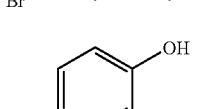 | H | H | H | F | F | H |
| 463 | 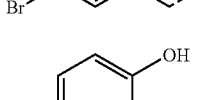 | H | H | F | H | H | H |
| 464 | 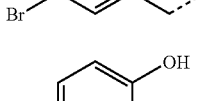 | H | H | Me | H | H | H |
| 465 | 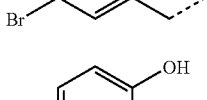 | H | H | H | CN | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 466 | 3-(1-methylindolyl)methyl | H | H | Cl | H | H | H |
| 467 | 3-(1-methylindolyl)methyl | H | H | H | OMe | H | H |
| 468 | 3-(1-methylindolyl)methyl | H | H | H | COOMe | H | H |
| 469 | 3-(1-methylindolyl)methyl | H | H | H | H | Cl | H |
| 470 | 3-(1-methylindolyl)methyl | H | H | H | H | COOMe | H |
| 471 | 3-(1-methylindolyl)methyl | H | H | H | H | H | Cl |
| 472 | 3-(1-methylindolyl)methyl | H | H | H | OCF3 | H | H |
| 473 | 3-(1-methylindolyl)methyl | H | H | COOMe | H | H | H |
| 474 | 3-(1-methylindolyl)methyl | H | H | H | CF3 | H | H |

TABLE 4-continued

| | X = —CH2—, q = 0, r = 0, Y = —(R4)C═C(R5)— | | | | | | |
|---|---|---|---|---|---|---|---|
| Compound No. 4 | R1—(CH2)p— | R2 | R3 | R4 | R5 | R6 | R7 |
| 475 | 3-(N-methylindolyl)methyl | H | H | H | Me | H | H |
| 476 | 3-(N-methylindolyl)methyl | H | H | H | F | H | H |
| 477 | 3-(N-methylindolyl)methyl | H | H | H | OH | H | H |
| 478 | 3-(N-methylindolyl)methyl | H | H | H | NO2 | H | H |
| 479 | 3-(N-methylindolyl)methyl | H | H | H | F | F | H |
| 480 | 3-(N-methylindolyl)methyl | H | H | F | H | H | H |
| 481 | 3-(N-methylindolyl)methyl | H | H | Me | H | H | H |
| 482 | 3-(N-methylindolyl)methyl | H | H | H | CN | H | H |
| 483 | 3-benzothienylmethyl | H | H | Cl | H | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 484 | 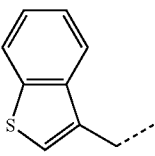 | H | H | H | OMe | H | H |
| 485 | 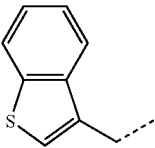 | H | H | H | COOMe | H | H |
| 486 | 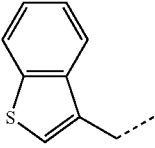 | H | H | H | H | Cl | H |
| 487 | 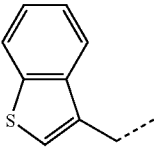 | H | H | H | H | COOMe | H |
| 488 | 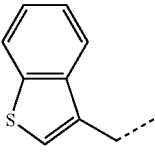 | H | H | H | H | H | Cl |
| 489 | 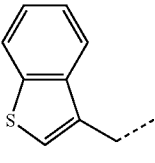 | H | H | H | OCF3 | H | H |
| 490 | 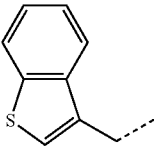 | H | H | COOMe | H | H | H |
| 491 | 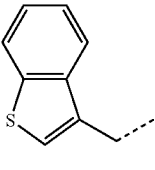 | H | H | H | CF3 | H | H |
| 492 | 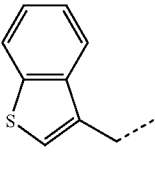 | H | H | H | Me | H | H |

TABLE 4-continued

X = —CH2—, q = 0, r = 0, Y = —(R4)C═C(R5)—

| Compound No. 4 | R1—(CH2)p— | R2 | R3 | R4 | R5 | R6 | R7 |
|---|---|---|---|---|---|---|---|
| 493 | benzothiophen-3-ylmethyl | H | H | H | F | H | H |
| 494 | benzothiophen-3-ylmethyl | H | H | H | OH | H | H |
| 495 | benzothiophen-3-ylmethyl | H | H | H | NO2 | H | H |
| 496 | benzothiophen-3-ylmethyl | H | H | H | F | F | H |
| 497 | benzothiophen-3-ylmethyl | H | H | F | H | H | H |
| 498 | benzothiophen-3-ylmethyl | H | H | Me | H | H | H |
| 499 | benzothiophen-3-ylmethyl | H | H | H | CN | H | H |
| 500 | 2,4-dichloro-6-hydroxyphenylmethyl | H | Me | H | H | H | H |
| 501 | 4-chloro-2-hydroxyphenylmethyl | H | Me | H | H | H | H |

TABLE 4-continued

X = —CH2—, q = 0, r = 0, Y = —(R4)C═C(R5)—

| Compound No. 4 | R1—(CH2)p— | R2 | R3 | R4 | R5 | R6 | R7 |
|---|---|---|---|---|---|---|---|
| 502 | naphthalen-1-ylmethyl | H | Me | H | H | H | H |
| 503 | 3-phenylpropyl | H | Me | H | H | H | H |
| 504 | 4-chloro-2-fluoro-6-hydroxybenzyl | H | H | H | H | H | H |
| 505 | 4-chloro-2-fluoro-6-hydroxybenzyl | H | H | F | H | H | H |
| 506 | 4-chloro-2-fluoro-6-hydroxybenzyl | H | H | Cl | H | H | H |
| 507 | 4-chloro-2-fluoro-6-hydroxybenzyl | H | H | Me | H | H | H |
| 508 | 4-chloro-2-fluoro-6-hydroxybenzyl | H | H | Et | H | H | H |
| 509 | 4-chloro-2-fluoro-6-hydroxybenzyl | H | H | OMe | H | H | H |
| 510 | 4-chloro-2-fluoro-6-hydroxybenzyl | H | H | OEt | H | H | H |

TABLE 4-continued
X = —CH2—, q = 0, r = 0, Y = —(R4)C=C(R5)—
| Compound No. 4 | R1—(CH2)p— | R2 | R3 | R4 | R5 | R6 | R7 |
|---|---|---|---|---|---|---|---|
| 511 | 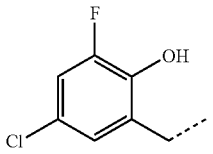 | H | H | CF3 | H | H | H |
| 512 | 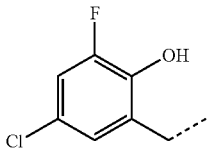 | H | H | OCF3 | H | H | H |
| 513 | 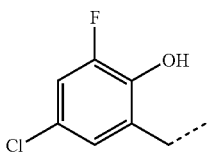 | H | H | NO2 | H | H | H |
| 514 | 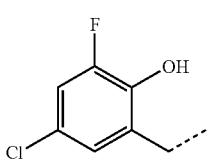 | H | H | NH2 | H | H | H |
| 515 | 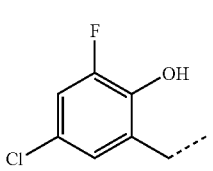 | H | H | OH | H | H | H |
| 516 | 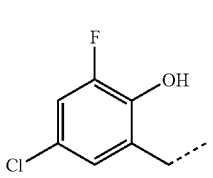 | H | H | CN | H | H | H |
| 517 |  | H | H | COMe | H | H | H |
| 518 |  | H | H | COOMe | H | H | H |
| 519 |  | H | H | H | F | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 520 | 4-Cl, 2-F, 6-(hydroxyphenyl)methyl | H | H | H | Cl | H | H |
| 521 | 4-Cl, 2-F, 6-(hydroxyphenyl)methyl | H | H | H | Me | H | H |
| 522 | 4-Cl, 2-F, 6-(hydroxyphenyl)methyl | H | H | H | Et | H | H |
| 523 | 4-Cl, 2-F, 6-(hydroxyphenyl)methyl | H | H | H | OMe | H | H |
| 524 | 4-Cl, 2-F, 6-(hydroxyphenyl)methyl | H | H | H | OEt | H | H |
| 525 | 4-Cl, 2-F, 6-(hydroxyphenyl)methyl | H | H | H | CF3 | H | H |
| 526 | 4-Cl, 2-F, 6-(hydroxyphenyl)methyl | H | H | H | OCF3 | H | H |
| 527 | 4-Cl, 2-F, 6-(hydroxyphenyl)methyl | H | H | H | NO2 | H | H |
| 528 | 4-Cl, 2-F, 6-(hydroxyphenyl)methyl | H | H | H | NH2 | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 529 | 4-Cl, 2-F, 6-OH-benzyl | H | H | H | OH | H | H |
| 530 | 4-Cl, 2-F, 6-OH-benzyl | H | H | H | CN | H | H |
| 531 | 4-Cl, 2-F, 6-OH-benzyl | H | H | H | COMe | H | H |
| 532 | 4-Cl, 2-F, 6-OH-benzyl | H | H | H | COOMe | H | H |
| 533 | 4-Cl, 2-F, 6-OH-benzyl | H | H | F | F | H | H |
| 534 | 4-Cl, 2-F, 6-OH-benzyl | H | H | F | Cl | H | H |
| 535 | 4-Cl, 2-F, 6-OH-benzyl | H | H | F | Me | H | H |
| 536 | 4-Cl, 2-F, 6-OH-benzyl | H | H | F | Et | H | H |
| 537 | 4-Cl, 2-F, 6-OH-benzyl | H | H | F | OMe | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 538 | 4-Cl, 2-F, 6-OH benzyl | H | H | F | OEt | H | H |
| 539 | 4-Cl, 2-F, 6-OH benzyl | H | H | F | CF3 | H | H |
| 540 | 4-Cl, 2-F, 6-OH benzyl | H | H | F | OCF3 | H | H |
| 541 | 4-Cl, 2-F, 6-OH benzyl | H | H | Cl | F | H | H |
| 542 | 4-Cl, 2-F, 6-OH benzyl | H | H | Cl | Cl | H | H |
| 543 | 4-Cl, 2-F, 6-OH benzyl | H | H | Cl | Me | H | H |
| 544 | 4-Cl, 2-F, 6-OH benzyl | H | H | Cl | Et | H | H |
| 545 | 4-Cl, 2-F, 6-OH benzyl | H | H | Cl | OMe | H | H |
| 546 | 4-Cl, 2-F, 6-OH benzyl | H | H | Cl | OEt | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 547 | 4-Cl, 2-F, 6-(CH2-), phenol | H | H | Cl | CF3 | H | H |
| 548 | 4-Cl, 2-F, 6-(CH2-), phenol | H | H | Cl | OCF3 | H | H |
| 549 | 4-Cl, 2-F, 6-(CH2-), phenol | H | H | Me | F | H | H |
| 550 | 4-Cl, 2-F, 6-(CH2-), phenol | H | H | Me | Cl | H | H |
| 551 | 4-Cl, 2-F, 6-(CH2-), phenol | H | H | Me | Me | H | H |
| 552 | 4-Cl, 2-F, 6-(CH2-), phenol | H | H | Me | Et | H | H |
| 553 | 4-Cl, 2-F, 6-(CH2-), phenol | H | H | Me | OMe | H | H |
| 554 | 4-Cl, 2-F, 6-(CH2-), phenol | H | H | Me | OEt | H | H |
| 555 | 4-Cl, 2-F, 6-(CH2-), phenol | H | H | Me | CF3 | H | H |

TABLE 4-continued

X = —CH2—, q = 0, r = 0, Y = —(R4)C=C(R5)—

| Compound No. 4 | R1—(CH2)p— | R2 | R3 | R4 | R5 | R6 | R7 |
|---|---|---|---|---|---|---|---|
| 556 | 4-Cl, 2-F, 6-OH-phenyl | H | H | Me | OCF3 | H | H |
| 557 | 4-Cl, 2-F, 6-OH-phenyl | H | H | OMe | F | H | H |
| 558 | 4-Cl, 2-F, 6-OH-phenyl | H | H | OMe | Cl | H | H |
| 559 | 4-Cl, 2-F, 6-OH-phenyl | H | H | OMe | Me | H | H |
| 560 | 4-Cl, 2-F, 6-OH-phenyl | H | H | OMe | Et | H | H |
| 561 | 4-Cl, 2-F, 6-OH-phenyl | H | H | OMe | OMe | H | H |
| 562 | 4-Cl, 2-F, 6-OH-phenyl | H | H | OMe | OEt | H | H |
| 563 | 4-Cl, 2-F, 6-OH-phenyl | H | H | OMe | CF3 | H | H |
| 564 | 4-Cl, 2-F, 6-OH-phenyl | H | H | OMe | OCF3 | H | H |

TABLE 5

X = —CO—, q = 0, r = 0, Y = —S—

| Compound No. 5 | R1—(CH2)p— | R2 | R3 | R6 | R7 |
|---|---|---|---|---|---|
| 1 | 2,4-dichloro-6-hydroxybenzyl | H | H | H | H |
| 2 | 3,4-dichlorobenzyl | H | H | H | H |
| 3 | 3,4-dichlorobenzyl | H | H | H | H |
| 4 | naphthalen-1-ylmethyl | H | H | H | H |
| 5 | naphthalen-1-ylmethyl | H | H | H | H |
| 6 | 2-chlorobenzyl | H | H | H | H |
| 7 | 3-chlorobenzyl | H | H | H | H |
| 8 | 4-chlorobenzyl | H | H | H | H |
| 9 | 2-methoxybenzyl | H | H | H | H |
| 10 | 4-methoxybenzyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 11 | phenyl-(CH2)2- | H | H | H | H |
| 12 | 5-chloro-2-hydroxybenzyl | H | H | H | H |
| 13 | 5-bromo-2-hydroxybenzyl | H | H | H | H |
| 14 | 5-bromo-2-methoxybenzyl | H | H | H | H |
| 15 | 5-bromo-2-fluorobenzyl | H | H | H | H |
| 16 | 3-bromobenzyl | H | H | H | H |
| 17 | 3-chloro-4-fluorobenzyl | H | H | H | H |
| 18 | (1-methyl-1H-indol-3-yl)methyl | H | H | H | H |
| 19 | (benzo[b]thiophen-3-yl)methyl | H | H | H | H |
| 20 | 4-methoxy-2-hydroxybenzyl | H | H | H | H |
| 21 | 3-nitrobenzyl | H | H | H | H |
| 22 | 3-methoxybenzyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 23 | 2-naphthylmethyl | H | H | H | H |
| 24 | benzyl | H | H | H | H |
| 25 | phenethyl | H | H | H | H |
| 26 | 3-bromo-5-chloro-2-hydroxybenzyl | H | H | H | H |
| 27 | 5-cyano-2-hydroxybenzyl | H | H | H | H |
| 28 | 3-chloro-5-trifluoromethyl-2-hydroxybenzyl | H | H | H | H |
| 29 | 3-trifluoromethyl-5-chloro-2-hydroxybenzyl | H | H | H | H |
| 30 | 3-chloro-2-hydroxybenzyl | H | H | H | H |
| 31 | 4-methylbenzyl | H | H | H | H |
| 32 | 4-fluorobenzyl | H | H | H | H |

TABLE 5-continued
X = —CO—, q = 0, r = 0, Y = —S—
| Compound No. 5 | R1—(CH2)p— | R2 | R3 | R6 | R7 |
|---|---|---|---|---|---|
| 33 | 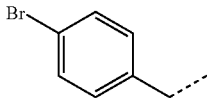 | H | H | H | H |
| 34 | 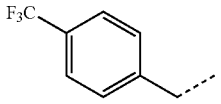 | H | H | H | H |
| 35 | 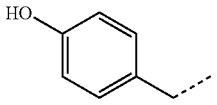 | H | H | H | H |
| 36 | 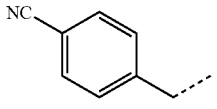 | H | H | H | H |
| 37 | 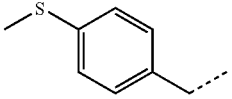 | H | H | H | H |
| 38 | 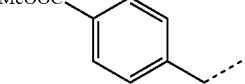 | H | H | H | H |
| 39 | 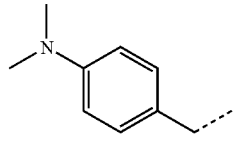 | H | H | H | H |
| 40 | 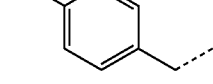 | H | H | H | H |
| 41 | 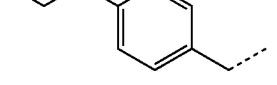 | H | H | H | H |
| 42 | 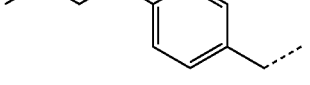 | H | H | H | H |
| 43 |  | H | H | H | H |
| 44 | 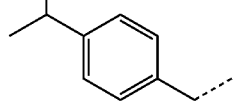 | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 45 | benzyloxy-phenyl-CH2 | H | H | H | H |
| 46 | phenoxy-phenyl-CH2 | H | H | H | H |
| 47 | biphenyl-CH2 | H | H | H | H |
| 48 | 4-acetamidophenyl-CH2 | H | H | H | H |
| 49 | 2-propylphenyl-CH2 | H | H | H | H |
| 50 | 2-benzyloxyphenyl-CH2 | H | H | H | H |
| 51 | 2-methylphenyl-CH2 | H | H | H | H |
| 52 | 2-cyanophenyl-CH2 | H | H | H | H |
| 53 | 2-chlorophenyl-CH2 | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 54 | 2-methoxybenzyl | H | H | H | H |
| 55 | 2-ethoxybenzyl | H | H | H | H |
| 56 | 2-phenylbenzyl (biphenyl-2-ylmethyl) | H | H | H | H |
| 57 | 3-(trifluoromethyl)benzyl | H | H | H | H |
| 58 | 3-chloro-2-fluorobenzyl | H | H | H | H |
| 59 | 3,5-dichlorobenzyl | H | H | H | H |
| 60 | 3-methylbenzyl | H | H | H | H |
| 61 | 3-fluoro-5-(trifluoromethyl)benzyl | H | H | H | H |
| 62 | 3-(trifluoromethoxy)benzyl | H | H | H | H |

TABLE 5-continued
X = —CO—, q = 0, r = 0, Y = —S—
| Compound No. 5 | R1—(CH2)p— | R2 | R3 | R6 | R7 |
|---|---|---|---|---|---|
| 63 | 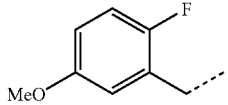 | H | H | H | H |
| 64 | 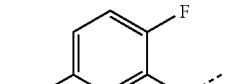 | H | H | H | H |
| 65 | 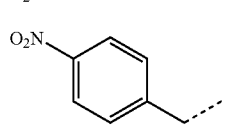 | H | H | H | H |
| 66 | 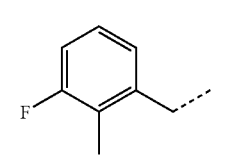 | H | H | H | H |
| 67 | 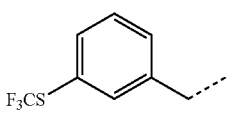 | H | H | H | H |
| 68 | 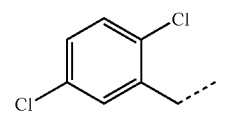 | H | H | H | H |
| 69 | 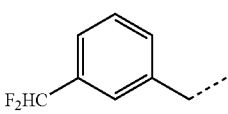 | H | H | H | H |
| 70 | 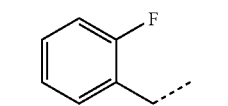 | H | H | H | H |
| 71 | 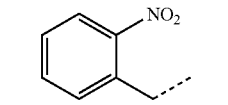 | H | H | H | H |
| 72 | 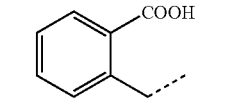 | H | H | H | H |
| 73 | 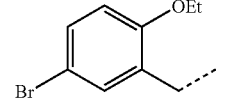 | H | H | H | H |
| 74 | 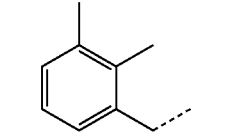 | H | H | H | H |

TABLE 5-continued
X = —CO—, q = 0, r = 0, Y = —S—
| Compound No. 5 | R1—(CH2)p— | R2 | R3 | R6 | R7 |
|---|---|---|---|---|---|
| 75 | 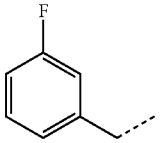 | H | H | H | H |
| 76 | 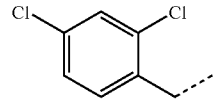 | H | H | H | H |
| 77 | 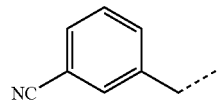 | H | H | H | H |
| 78 | 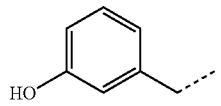 | H | H | H | H |
| 79 | 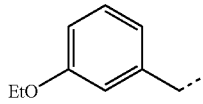 | H | H | H | H |
| 80 | 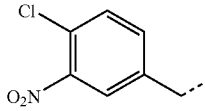 | H | H | H | H |
| 81 | 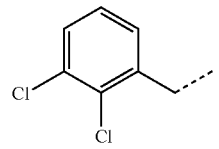 | H | H | H | H |
| 82 | 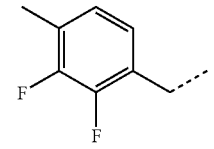 | H | H | H | H |
| 83 | 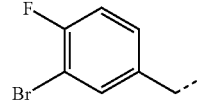 | H | H | H | H |
| 84 | 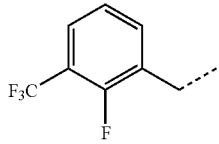 | H | H | H | H |
| 85 | 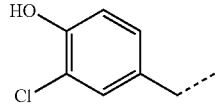 | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 86 | 2,3-difluorophenyl-CH2- | H | H | H | H |
| 87 | 4-MeO-3-Br-phenyl-CH2- | H | H | H | H |
| 88 | 2-MeO-6-OEt-phenyl-CH2- | H | H | H | H |
| 89 | 4-MeO-2,3-dimethyl-phenyl-CH2- | H | H | H | H |
| 90 | 3-MeO-2-(benzyloxy)-phenyl-CH2- | H | H | H | H |
| 91 | 4-Cl-3-NO2-phenyl-CH2- (with O2N at other position) | H | H | H | H |
| 92 | 3-(4-MeO-phenoxy)-phenyl-CH2- | H | H | H | H |
| 93 | 3-(4-methyl-phenoxy)-phenyl-CH2- | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 94 | 4-Cl-C6H4-O-(3-C6H4)- | H | H | H | H |
| 95 | Ph-CH2-O-(3-C6H4)- | H | H | H | H |
| 96 | Ph-O-(3-C6H4)- | H | H | H | H |
| 97 | 3-MeO-5-HO-C6H3- (2-MeO, 5-HO-phenyl) | H | H | H | H |
| 98 | 2-CF3, 3-Cl-C6H3- | H | H | H | H |
| 99 | 4-HO, 3-O2N-C6H3- | H | H | H | H |
| 100 | 2,3-(OMe)2-C6H3- | H | H | H | H |
| 101 | 2-EtO, 3-Me, 4-OEt-C6H2- | H | H | H | H |
| 102 | HO-CH2CH2-O-(3-C6H4)- | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 103 | 2,3-dimethoxy-4-(MeO)benzyl (2,3,4-trimethoxybenzyl) | H | H | H | H |
| 104 | 4-fluoro-3-phenoxybenzyl | H | H | H | H |
| 105 | 2-carboxy-3-methoxy-4-methoxybenzyl | H | H | H | H |
| 106 | 5-chloro-2-nitrobenzyl | H | H | H | H |
| 107 | 3,5-dihydroxybenzyl | H | H | H | H |
| 108 | 3-benzyloxy-4-methoxyphenethyl | H | H | H | H |
| 109 | 3,4-diethoxybenzyl | H | H | H | H |
| 110 | 3-carboxybenzyl | H | H | H | H |
| 111 | 3-hydroxy-4-methoxybenzyl | H | H | H | H |
| 112 | 3-hydroxy-4-nitrobenzyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 113 | 3,5-bis(CF3)benzyl | H | H | H | H |
| 114 | 2-methoxy-3-nitrobenzyl | H | H | H | H |
| 115 | (4-methylnaphthalen-1-yl)methyl | H | H | H | H |
| 116 | (1-methyl-7-methyl-1H-indol-3-yl)methyl | H | H | H | H |
| 117 | (2-methoxynaphthalen-1-yl)methyl | H | H | H | H |
| 118 | benzofuran-2-ylmethyl | H | H | H | H |
| 119 | (1,2-dimethyl-1H-indol-3-yl)methyl | H | H | H | H |
| 120 | quinolin-8-ylmethyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 121 | naphthalen-1-yl-methyl with 2-OH | H | H | H | H |
| 122 | naphthalen-1-yl-methyl with 2-OAc | H | H | H | H |
| 123 | 1-hydroxynaphthalen-2-yl-methyl | H | H | H | H |
| 124 | 1H-indol-7-yl-methyl | H | H | H | H |
| 125 | quinolin-4-yl-methyl | H | H | H | H |
| 126 | 5-methyl-1-methyl-1H-indol-3-yl-methyl | H | H | H | H |
| 127 | anthracen-9-yl-methyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 128 | 2-methylnaphthalen-1-ylmethyl | H | H | H | H |
| 129 | 2-ethoxynaphthalen-1-ylmethyl | H | H | H | H |
| 130 | 1H-indol-3-ylmethyl | H | H | H | H |
| 131 | 6-methyl-1-methyl-1H-indol-3-ylmethyl | H | H | H | H |
| 132 | 1-methyl-1H-indol-2-ylmethyl | H | H | H | H |
| 133 | 4-methyl-1-methyl-1H-indol-3-ylmethyl | H | H | H | H |
| 134 | 2,5-dimethyl-1-methyl-1H-indol-3-ylmethyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 135 | 5-OMe-1-Me-indol-3-yl-CH2 | H | H | H | H |
| 136 | 4-methyl-benzothiophen-3-yl-CH2 | H | H | H | H |
| 137 | 1-Me-benzimidazol-2-yl-CH2 | H | H | H | H |
| 138 | 1-Me-2-phenyl-indol-3-yl-CH2 | H | H | H | H |
| 139 | 1-acetyl-indol-3-yl-CH2 | H | H | H | H |
| 140 | quinolin-2-yl-CH2 | H | H | H | H |
| 141 | 6-OMe-1-Me-indol-3-yl-CH2 | H | H | H | H |
| 142 | 3-methyl-benzothiophen-2-yl-CH2 | H | H | H | H |

TABLE 5-continued
X = —CO—, q = 0, r = 0, Y = —S—
| Compound No. 5 | R1—(CH2)p— | R2 | R3 | R6 | R7 |
|---|---|---|---|---|---|
| 143 | 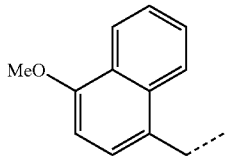 | H | H | H | H |
| 144 | 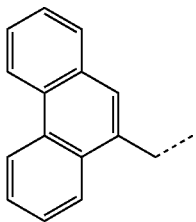 | H | H | H | H |
| 145 | 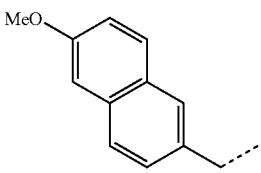 | H | H | H | H |
| 146 | 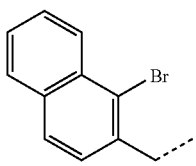 | H | H | H | H |
| 147 | 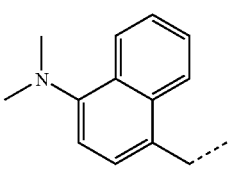 | H | H | H | H |
| 148 | 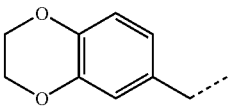 | H | H | H | H |
| 149 | 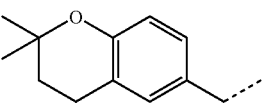 | H | H | H | H |
| 150 | 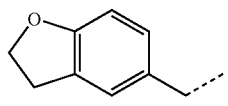 | H | H | H | H |
| 151 | 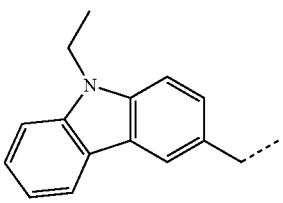 | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 152 | benzo[d][1,3]dioxol-4-ylmethyl | H | H | H | H |
| 153 | benzo[d][1,3]dioxol-5-ylmethyl | H | H | H | H |
| 154 | 3-phenylpropyl | H | H | H | H |
| 155 | 5-phenylpentyl | H | H | H | H |
| 156 | cyclohexylmethyl | H | H | H | H |
| 157 | 5-iodo-2-hydroxybenzyl | H | H | H | H |
| 158 | 5-nitro-2-hydroxybenzyl | H | H | H | H |
| 159 | 5-chloro-3-methyl-2-hydroxybenzyl | H | H | H | H |
| 160 | 3-methyl-2-hydroxybenzyl | H | H | H | H |
| 161 | 5-fluoro-2-hydroxybenzyl | H | H | H | H |
| 162 | 3,5-diiodo-2-hydroxybenzyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 163 | 4-Cl, 2-(CH2—)-aniline (NH2) | H | H | H | H |
| 164 | 2-hydroxybenzyl | H | H | H | H |
| 165 | 2-aminobenzyl | H | H | H | H |
| 166 | 4-tert-butyl-2-hydroxybenzyl | H | H | H | H |
| 167 | 4-trifluoromethoxy-2-hydroxybenzyl | H | H | H | H |
| 168 | 3-methoxy-2-hydroxybenzyl | H | H | H | H |
| 169 | 2,3-dihydroxybenzyl | H | H | H | H |
| 170 | 3-ethoxy-2-hydroxybenzyl | H | H | H | H |
| 171 | 3-carboxy-2-hydroxybenzyl | H | H | H | H |
| 172 | 3-tert-butyl-2-hydroxybenzyl | H | H | H | H |

TABLE 5-continued
X = —CO—, q = 0, r = 0, Y = —S—
| Compound No. 5 | R1—(CH2)p— | R2 | R3 | R6 | R7 |
|---|---|---|---|---|---|
| 173 | 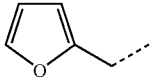 | H | H | H | H |
| 174 | 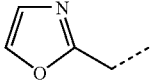 | H | H | H | H |
| 175 | 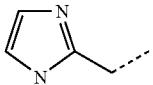 | H | H | H | H |
| 176 | 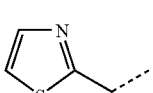 | H | H | H | H |
| 177 | 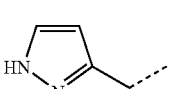 | H | H | H | H |
| 178 | 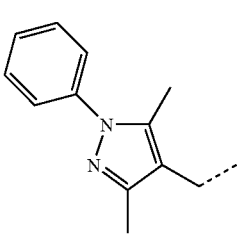 | H | H | H | H |
| 179 | 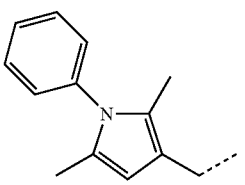 | H | H | H | H |
| 180 | 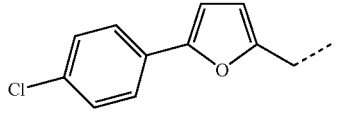 | H | H | H | H |
| 181 | 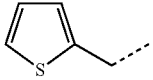 | H | H | H | H |
| 182 | 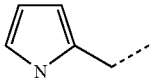 | H | H | H | H |
| 183 | 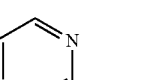 | H | H | H | H |
| 184 | 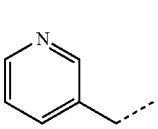 | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 185 | 4-pyridylmethyl | H | H | H | H |
| 186 | 5-chloro-2-hydroxybenzyl | H | H | H | H |
| 187 | 2-hydroxy-5-nitrobenzyl | H | H | H | H |
| 188 | 2-hydroxy-5-methoxybenzyl | H | H | H | H |
| 189 | 3-chlorobenzyl | H | H | H | H |
| 190 | 3-bromobenzyl | H | H | H | H |
| 191 | 3-nitrobenzyl | H | H | H | H |
| 192 | 3-methoxybenzyl | H | H | H | H |
| 193 | 3,5-dichloro-2-hydroxybenzyl | H | H | H | H |
| 194 | (1-methylindol-3-yl)methyl | H | H | H | H |
| 195 | (benzothiophen-3-yl)methyl | H | H | H | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 196 | benzyl | H | H | H | H |
| 197 | 3-phenylpropyl | H | H | H | H |
| 198 | 5-bromo-2-hydroxybenzyl | H | H | H | H |
| 199 | naphthalen-2-ylmethyl | H | H | H | H |
| 200 | 2-phenylethyl | H | H | H | H |
| 201 | 3,5-dichloro-2-hydroxybenzyl | H | H | Cl | H |
| 202 | 3,5-dichloro-2-hydroxybenzyl | H | H | COOMe | H |
| 203 | 3,5-dichloro-2-hydroxybenzyl | H | H | OMe | H |
| 204 | 3,5-dichloro-2-hydroxybenzyl | H | H | OCF3 | H |
| 205 | 3,5-dichloro-2-hydroxybenzyl | H | H | CF3 | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 206 | 2,4-dichloro-6-hydroxyphenyl-CH2 | H | H | Me | H |
| 207 | 2,4-dichloro-6-hydroxyphenyl-CH2 | H | H | F | H |
| 208 | 2,4-dichloro-6-hydroxyphenyl-CH2 | H | H | NO2 | H |
| 209 | 2,4-dichloro-6-hydroxyphenyl-CH2 | H | H | CN | H |
| 210 | 2,4-dichloro-6-hydroxyphenyl-CH2 | H | H | OH | H |
| 211 | 4-chloro-2-hydroxyphenyl-CH2 | H | H | H | H |
| 212 | 4-chloro-2-hydroxyphenyl-CH2 | H | H | Cl | H |
| 213 | 4-chloro-2-hydroxyphenyl-CH2 | H | H | COOMe | H |
| 214 | 4-chloro-2-hydroxyphenyl-CH2 | H | H | OMe | H |
| 215 | 4-chloro-2-hydroxyphenyl-CH2 | H | H | OCF3 | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 216 | 4-Cl-2-hydroxybenzyl | H | H | CF3 | H |
| 217 | 4-Cl-2-hydroxybenzyl | H | H | Me | H |
| 218 | 4-Cl-2-hydroxybenzyl | H | H | F | H |
| 219 | 4-Cl-2-hydroxybenzyl | H | H | NO2 | H |
| 220 | 4-Cl-2-hydroxybenzyl | H | H | CN | H |
| 221 | 4-Cl-2-hydroxybenzyl | H | H | OH | H |
| 222 | 1-naphthylmethyl | H | H | H | H |
| 223 | 1-naphthylmethyl | H | H | Cl | H |
| 224 | 1-naphthylmethyl | H | H | COOMe | H |
| 225 | 1-naphthylmethyl | H | H | OMe | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 226 | naphthalen-1-ylmethyl | H | H | OCF3 | H |
| 227 | naphthalen-1-ylmethyl | H | H | CF3 | H |
| 228 | naphthalen-1-ylmethyl | H | H | Me | H |
| 229 | naphthalen-1-ylmethyl | H | H | F | H |
| 230 | naphthalen-1-ylmethyl | H | H | NO2 | H |
| 231 | naphthalen-1-ylmethyl | H | H | CN | H |
| 232 | naphthalen-1-ylmethyl | H | H | OH | H |
| 233 | 3-phenylpropyl | H | H | H | H |
| 234 | 3-phenylpropyl | H | H | Cl | H |

TABLE 5-continued
X = —CO—, q = 0, r = 0, Y = —S—
| Compound No. 5 | R1—(CH2)p— | R2 | R3 | R6 | R7 |
|---|---|---|---|---|---|
| 235 | 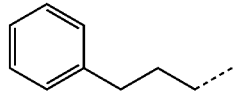 | H | H | COOMe | H |
| 236 | 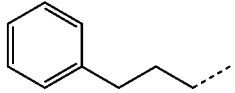 | H | H | OMe | H |
| 237 | 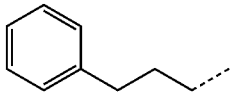 | H | H | OCF3 | H |
| 238 | 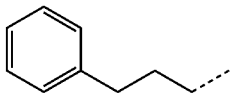 | H | H | CF3 | H |
| 239 | 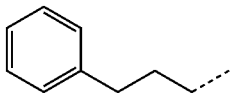 | H | H | Me | H |
| 240 | 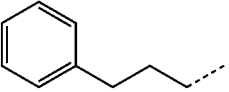 | H | H | F | H |
| 241 | 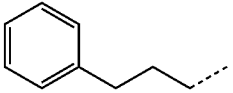 | H | H | NO2 | H |
| 242 | 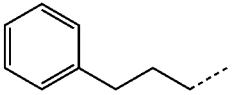 | H | H | CN | H |
| 243 | 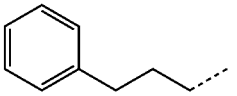 | H | H | OH | H |
| 244 | 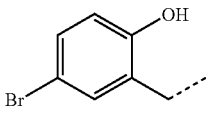 | H | H | H | H |
| 245 | 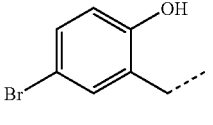 | H | H | Cl | H |
| 246 | 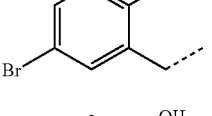 | H | H | COOMe | H |
| 247 | 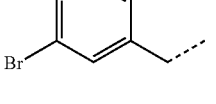 | H | H | OMe | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 248 | 5-Br, 2-OH-benzyl | H | H | OCF3 | H |
| 249 | 5-Br, 2-OH-benzyl | H | H | CF3 | H |
| 250 | 5-Br, 2-OH-benzyl | H | H | Me | H |
| 251 | 5-Br, 2-OH-benzyl | H | H | F | H |
| 252 | 5-Br, 2-OH-benzyl | H | H | NO2 | H |
| 253 | 5-Br, 2-OH-benzyl | H | H | CN | H |
| 254 | 5-Br, 2-OH-benzyl | H | H | OH | H |
| 255 | (1-Me-indol-3-yl)methyl | H | H | H | H |
| 256 | (1-Me-indol-3-yl)methyl | H | H | Cl | H |
| 257 | (1-Me-indol-3-yl)methyl | H | H | COOMe | H |
| 258 | (1-Me-indol-3-yl)methyl | H | H | OMe | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 259 | 1-methylindol-3-ylmethyl | H | H | OCF3 | H |
| 260 | 1-methylindol-3-ylmethyl | H | H | CF3 | H |
| 261 | 1-methylindol-3-ylmethyl | H | H | Me | H |
| 262 | 1-methylindol-3-ylmethyl | H | H | F | H |
| 263 | 1-methylindol-3-ylmethyl | H | H | NO2 | H |
| 264 | 1-methylindol-3-ylmethyl | H | H | CN | H |
| 265 | 1-methylindol-3-ylmethyl | H | H | OH | H |
| 266 | benzothiophen-3-ylmethyl | H | H | H | H |
| 267 | benzothiophen-3-ylmethyl | H | H | Cl | H |

TABLE 5-continued

X = —CO—, q = 0, r = 0, Y = —S—

| Compound No. 5 | R1—(CH2)p— | R2 | R3 | R6 | R7 |
|---|---|---|---|---|---|
| 268 | benzothiophen-3-yl | H | H | COOMe | H |
| 269 | benzothiophen-3-yl | H | H | OMe | H |
| 270 | benzothiophen-3-yl | H | H | OCF3 | H |
| 271 | benzothiophen-3-yl | H | H | CF3 | H |
| 272 | benzothiophen-3-yl | H | H | Me | H |
| 273 | benzothiophen-3-yl | H | H | F | H |
| 274 | benzothiophen-3-yl | H | H | NO2 | H |
| 275 | benzothiophen-3-yl | H | H | CN | H |
| 276 | benzothiophen-3-yl | H | H | OH | H |

TABLE 6

X = —CO—, q = 0, r = 0, Y = —N(R8)—

| Compound No. 6 | R1—(CH2)p— | R2 | R3 | R6 | R7 | R8 |
|---|---|---|---|---|---|---|
| 1 | 2,4-dichloro-6-hydroxyphenyl-CH2- (Cl, OH, Cl substituted benzyl) | H | H | H | H | Me |
| 2 | 3,4-dichlorobenzyl | H | H | H | H | Me |
| 3 | 3,4-dichlorobenzyl | H | H | H | H | Me |
| 4 | naphthalen-1-ylmethyl | H | H | H | H | Me |
| 5 | naphthalen-1-ylmethyl | H | H | H | H | Me |
| 6 | 2-chlorobenzyl | H | H | H | H | Me |
| 7 | 3-chlorobenzyl | H | H | H | H | Me |
| 8 | 4-chlorobenzyl | H | H | H | H | Me |
| 9 | 2-methoxybenzyl | H | H | H | H | Me |
| 10 | 4-methoxybenzyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 11 | 3-phenylpropyl | H | H | H | H | Me |
| 12 | 5-chloro-2-hydroxybenzyl | H | H | H | H | Me |
| 13 | 5-bromo-2-hydroxybenzyl | H | H | H | H | Me |
| 14 | 5-bromo-2-methoxybenzyl | H | H | H | H | Me |
| 15 | 5-bromo-2-fluorobenzyl | H | H | H | H | Me |
| 16 | 3-bromobenzyl | H | H | H | H | Me |
| 17 | 3-chloro-4-fluorobenzyl | H | H | H | H | Me |
| 18 | (1-methyl-1H-indol-3-yl)methyl | H | H | H | H | Me |
| 19 | benzo[b]thiophen-3-ylmethyl | H | H | H | H | Me |
| 20 | 2-hydroxy-5-methoxybenzyl | H | H | H | H | Me |
| 21 | 3-nitrobenzyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 22 | 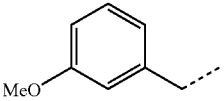 | H | H | H | H | Me |
| 23 | 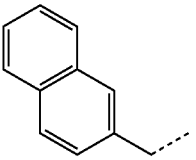 | H | H | H | H | Me |
| 24 | 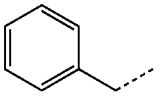 | H | H | H | H | Me |
| 25 | 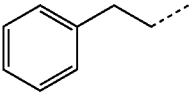 | H | H | H | H | Me |
| 26 | 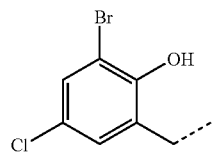 | H | H | H | H | Me |
| 27 | 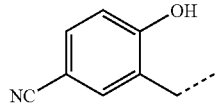 | H | H | H | H | Me |
| 28 | 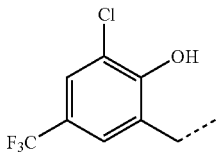 | H | H | H | H | Me |
| 29 | 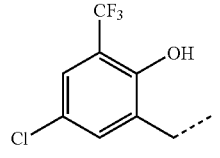 | H | H | H | H | Me |
| 30 | 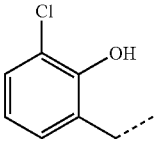 | H | H | H | H | Me |
| 31 | 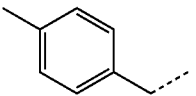 | H | H | H | H | Me |
| 32 | 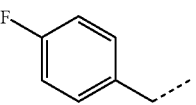 | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 33 | 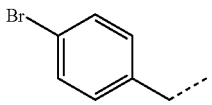 | H | H | H | H | Me |
| 34 | 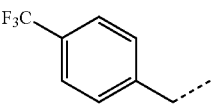 | H | H | H | H | Me |
| 35 | 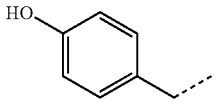 | H | H | H | H | Me |
| 36 | 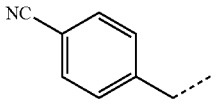 | H | H | H | H | Me |
| 37 | 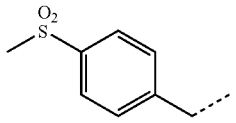 | H | H | H | H | Me |
| 38 | 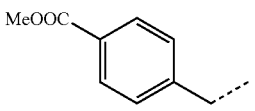 | H | H | H | H | Me |
| 39 | 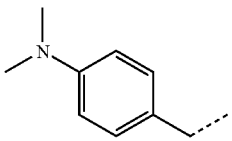 | H | H | H | H | Me |
| 40 | 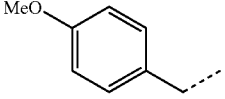 | H | H | H | H | Me |
| 41 | 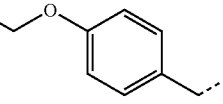 | H | H | H | H | Me |
| 42 | 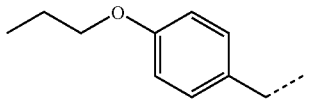 | H | H | H | H | Me |
| 43 | 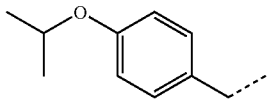 | H | H | H | H | Me |
| 44 | 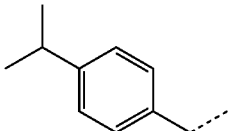 | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 45 | 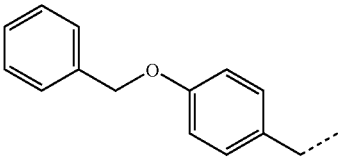 | H | H | H | H | Me |
| 46 | 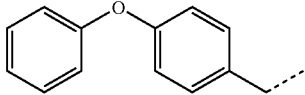 | H | H | H | H | Me |
| 47 | 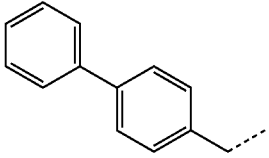 | H | H | H | H | Me |
| 48 | 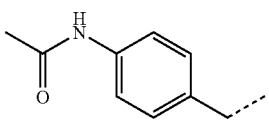 | H | H | H | H | Me |
| 49 | 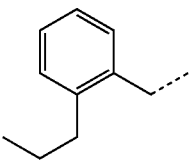 | H | H | H | H | Me |
| 50 | 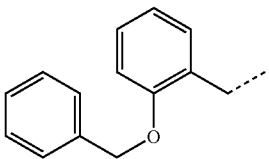 | H | H | H | H | Me |
| 51 | 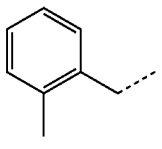 | H | H | H | H | Me |
| 52 | 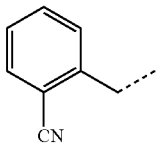 | H | H | H | H | Me |
| 53 | 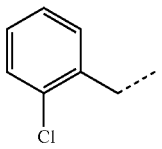 | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 54 | 2-methoxybenzyl | H | H | H | H | Me |
| 55 | 2-ethoxybenzyl | H | H | H | H | Me |
| 56 | 2-phenylbenzyl (biphenyl) | H | H | H | H | Me |
| 57 | 3-(trifluoromethyl)benzyl | H | H | H | H | Me |
| 58 | 3-chloro-2-fluorobenzyl | H | H | H | H | Me |
| 59 | 3,5-dichlorobenzyl | H | H | H | H | Me |
| 60 | 3-methylbenzyl | H | H | H | H | Me |
| 61 | 3-fluoro-5-(trifluoromethyl)benzyl | H | H | H | H | Me |
| 62 | 3-(trifluoromethoxy)benzyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 63 | 2-F, 5-MeO-benzyl | H | H | H | H | Me |
| 64 | 2-F, 5-O2N-benzyl | H | H | H | H | Me |
| 65 | 4-O2N-benzyl | H | H | H | H | Me |
| 66 | 2-Me, 3-F-benzyl | H | H | H | H | Me |
| 67 | 3-F3CS-benzyl | H | H | H | H | Me |
| 68 | 2,5-diCl-benzyl | H | H | H | H | Me |
| 69 | 3-F2HC-benzyl | H | H | H | H | Me |
| 70 | 2-F-benzyl | H | H | H | H | Me |
| 71 | 2-NO2-benzyl | H | H | H | H | Me |
| 72 | 2-COOH-benzyl | H | H | H | H | Me |
| 73 | 2-OEt, 4-Br-benzyl | H | H | H | H | Me |
| 74 | 2,3-diMe-benzyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 75 | 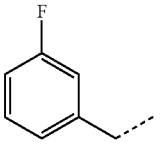 3-F-C6H4-CH2- | H | H | H | H | Me |
| 76 | 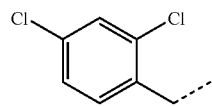 2,4-diCl-C6H3-CH2- | H | H | H | H | Me |
| 77 | 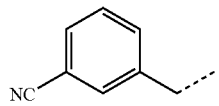 3-NC-C6H4-CH2- | H | H | H | H | Me |
| 78 | 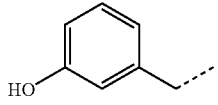 3-HO-C6H4-CH2- | H | H | H | H | Me |
| 79 | 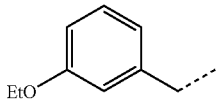 3-EtO-C6H4-CH2- | H | H | H | H | Me |
| 80 | 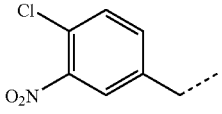 4-Cl-3-O2N-C6H3-CH2- | H | H | H | H | Me |
| 81 |  2,3-diCl-C6H3-CH2- | H | H | H | H | Me |
| 82 | 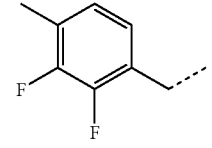 | H | H | H | H | Me |
| 83 | 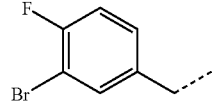 | H | H | H | H | Me |
| 84 | 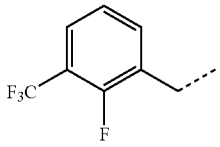 | H | H | H | H | Me |
| 85 | 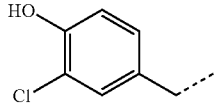 | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 86 | 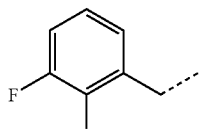 | H | H | H | H | Me |
| 87 | 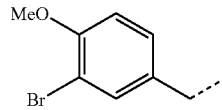 | H | H | H | H | Me |
| 88 | 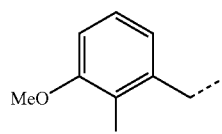 | H | H | H | H | Me |
| 89 | 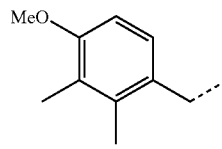 | H | H | H | H | Me |
| 90 | 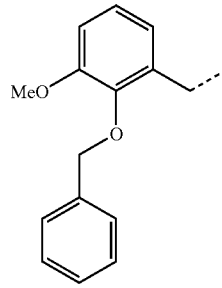 | H | H | H | H | Me |
| 91 | 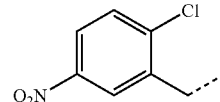 | H | H | H | H | Me |
| 92 | 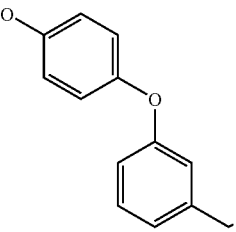 | H | H | H | H | Me |
| 93 | 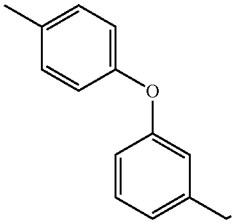 | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 94 | 4-Cl-C6H4-O-C6H4-CH2- (3-position) | H | H | H | H | Me |
| 95 | PhCH2-O-C6H4-CH2- (3-position) | H | H | H | H | Me |
| 96 | Ph-O-C6H4-CH2- (3-position) | H | H | H | H | Me |
| 97 | 3-HO-4-MeO-C6H3-CH2- | H | H | H | H | Me |
| 98 | 2-Cl-3-CF3-C6H3-CH2- | H | H | H | H | Me |
| 99 | 4-HO-3-O2N-C6H3-CH2- | H | H | H | H | Me |
| 100 | 2,3-(MeO)2-C6H3-CH2- | H | H | H | H | Me |
| 101 | 2-Me-3,6-(EtO)2-C6H2-CH2- | H | H | H | H | Me |
| 102 | 3-(HO-CH2CH2-O)-C6H4-CH2- | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 103 | 2,3,4-trimethoxybenzyl (MeO, OMe, OMe) | H | H | H | H | Me |
| 104 | 4-fluoro-3-phenoxybenzyl | H | H | H | H | Me |
| 105 | 2,3-dimethoxy-6-carboxybenzyl (MeO, OMe, COOH) | H | H | H | H | Me |
| 106 | 5-chloro-2-nitrobenzyl | H | H | H | H | Me |
| 107 | 3,5-dihydroxybenzyl | H | H | H | H | Me |
| 108 | 3-benzyloxy-4-methoxybenzyl | H | H | H | H | Me |
| 109 | 3,4-diethoxybenzyl | H | H | H | H | Me |
| 110 | 3-carboxybenzyl | H | H | H | H | Me |
| 111 | 3-hydroxy-4-methoxybenzyl | H | H | H | H | Me |
| 112 | 3-hydroxy-4-nitrobenzyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 113 | 3,5-bis(trifluoromethyl)benzyl | H | H | H | H | Me |
| 114 | 2-methoxy-3-nitrobenzyl | H | H | H | H | Me |
| 115 | (4-methylnaphthalen-1-yl)methyl | H | H | H | H | Me |
| 116 | (1-methyl-7-methyl-1H-indol-3-yl)methyl | H | H | H | H | Me |
| 117 | (2-methoxynaphthalen-1-yl)methyl | H | H | H | H | Me |
| 118 | benzofuran-2-ylmethyl | H | H | H | H | Me |
| 119 | (1,2-dimethyl-1H-indol-3-yl)methyl | H | H | H | H | Me |
| 120 | quinolin-8-ylmethyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 121 | 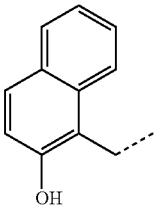 | H | H | H | H | Me |
| 122 | 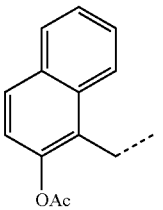 | H | H | H | H | Me |
| 123 | 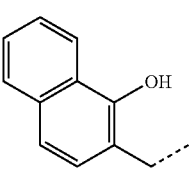 | H | H | H | H | Me |
| 124 | 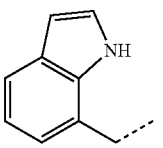 | H | H | H | H | Me |
| 125 | 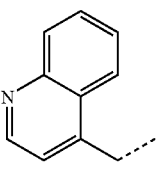 | H | H | H | H | Me |
| 126 | 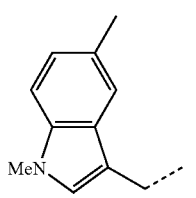 | H | H | H | H | Me |
| 127 | 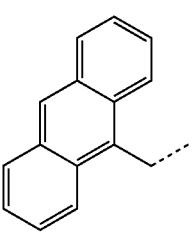 | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 128 | 2-methylnaphthalen-1-ylmethyl | H | H | H | H | Me |
| 129 | 2-ethoxynaphthalen-1-ylmethyl | H | H | H | H | Me |
| 130 | 1H-indol-3-ylmethyl | H | H | H | H | Me |
| 131 | 1,6-dimethyl-1H-indol-3-ylmethyl | H | H | H | H | Me |
| 132 | 1-methyl-1H-indol-2-ylmethyl | H | H | H | H | Me |
| 133 | 1,4-dimethyl-1H-indol-3-ylmethyl | H | H | H | H | Me |
| 134 | 1,2,5-trimethyl-1H-indol-3-ylmethyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 135 | 5-methoxy-1-methylindol-3-yl | H | H | H | H | Me |
| 136 | 4-methylbenzothiophen-3-yl | H | H | H | H | Me |
| 137 | 1-methylbenzimidazol-2-yl | H | H | H | H | Me |
| 138 | 1-methyl-2-phenylindol-3-yl | H | H | H | H | Me |
| 139 | 1-acetylindol-3-yl | H | H | H | H | Me |
| 140 | quinolin-2-yl | H | H | H | H | Me |
| 141 | 6-methoxy-1-methylindol-3-yl | H | H | H | H | Me |
| 142 | 3-methylbenzothiophen-2-yl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 143 | 4-MeO-naphthalen-1-ylmethyl | H | H | H | H | Me |
| 144 | phenanthren-9-ylmethyl | H | H | H | H | Me |
| 145 | 6-MeO-naphthalen-2-ylmethyl | H | H | H | H | Me |
| 146 | 1-Br-naphthalen-2-ylmethyl | H | H | H | H | Me |
| 147 | 4-(dimethylamino)naphthalen-1-ylmethyl | H | H | H | H | Me |
| 148 | 2,3-dihydro-1,4-benzodioxin-6-ylmethyl | H | H | H | H | Me |
| 149 | 2,2-dimethylchroman-6-ylmethyl | H | H | H | H | Me |
| 150 | 2,3-dihydrobenzofuran-5-ylmethyl | H | H | H | H | Me |
| 151 | 9-ethylcarbazol-3-ylmethyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 152 | 2,3-methylenedioxybenzyl | H | H | H | H | Me |
| 153 | 3,4-methylenedioxybenzyl | H | H | H | H | Me |
| 154 | 3-phenylpropyl | H | H | H | H | Me |
| 155 | 5-phenylpentyl | H | H | H | H | Me |
| 156 | cyclohexylmethyl | H | H | H | H | Me |
| 157 | 5-iodo-2-hydroxybenzyl | H | H | H | H | Me |
| 158 | 5-nitro-2-hydroxybenzyl | H | H | H | H | Me |
| 159 | 5-chloro-3-methyl-2-hydroxybenzyl | H | H | H | H | Me |
| 160 | 3-methyl-2-hydroxybenzyl | H | H | H | H | Me |
| 161 | 5-fluoro-2-hydroxybenzyl | H | H | H | H | Me |
| 162 | 3,5-diiodo-2-hydroxybenzyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 163 | 4-Cl-2-aminobenzyl (NH2 ortho, Cl para to CH2) | H | H | H | H | Me |
| 164 | 2-hydroxybenzyl | H | H | H | H | Me |
| 165 | 2-aminobenzyl | H | H | H | H | Me |
| 166 | 5-tert-butyl-2-hydroxybenzyl | H | H | H | H | Me |
| 167 | 5-trifluoromethoxy-2-hydroxybenzyl | H | H | H | H | Me |
| 168 | 3-methoxy-2-hydroxybenzyl | H | H | H | H | Me |
| 169 | 2,3-dihydroxybenzyl | H | H | H | H | Me |
| 170 | 3-ethoxy-2-hydroxybenzyl | H | H | H | H | Me |
| 171 | 3-carboxy-2-hydroxybenzyl | H | H | H | H | Me |
| 172 | 3-tert-butyl-2-hydroxybenzyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 173 | 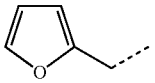 | H | H | H | H | Me |
| 174 | 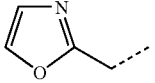 | H | H | H | H | Me |
| 175 | 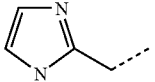 | H | H | H | H | Me |
| 176 | 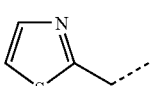 | H | H | H | H | Me |
| 177 | 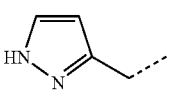 | H | H | H | H | Me |
| 178 | 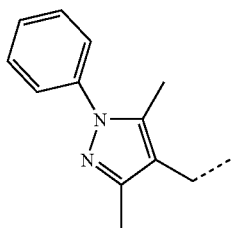 | H | H | H | H | Me |
| 179 | 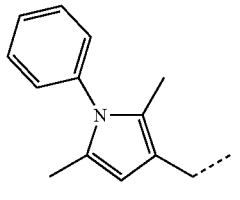 | H | H | H | H | Me |
| 180 | 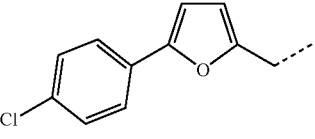 | H | H | H | H | Me |
| 181 | 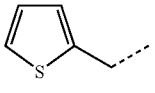 | H | H | H | H | Me |
| 182 | 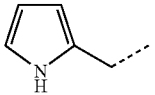 | H | H | H | H | Me |
| 183 | 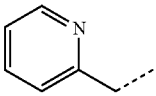 | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 184 | 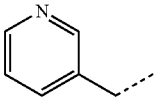 | H | H | H | H | Me |
| 185 | 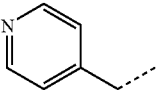 | H | H | H | H | Me |
| 186 | 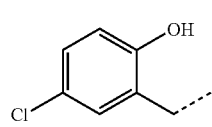 | H | H | H | H | Me |
| 187 | 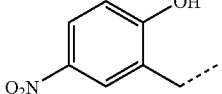 | H | H | H | H | Me |
| 188 | 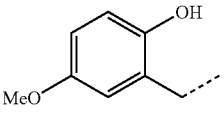 | H | H | H | H | Me |
| 189 | 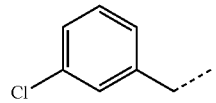 | H | H | H | H | Me |
| 190 | 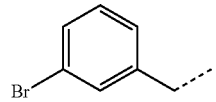 | H | H | H | H | Me |
| 191 | 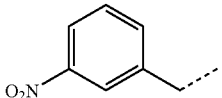 | H | H | H | H | Me |
| 192 | 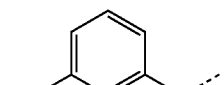 | H | H | H | H | Me |
| 193 | 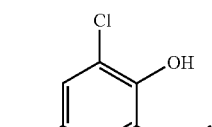 | H | H | H | H | Me |
| 194 | 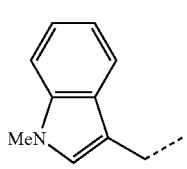 | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 195 | 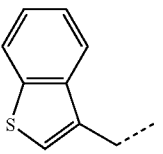 | H | H | H | H | Me |
| 196 | 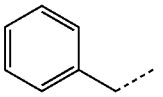 | H | H | H | H | Me |
| 197 | 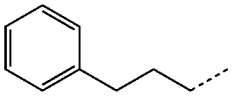 | H | H | H | H | Me |
| 198 | 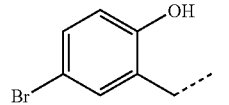 | H | H | H | H | Me |
| 199 | 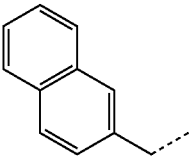 | H | H | H | H | Me |
| 200 | 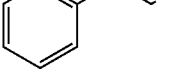 | H | H | H | H | Me |
| 201 | 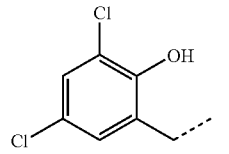 | H | H | Cl | H | Me |
| 202 | 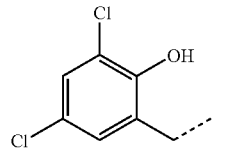 | H | H | COOMe | H | Me |
| 203 | 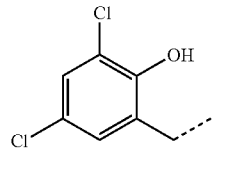 | H | H | OMe | H | Me |
| 204 | 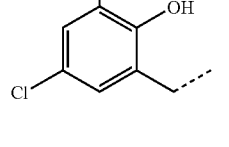 | H | H | OCF3 | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 205 | 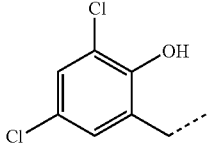 | H | H | CF3 | H | Me |
| 206 | 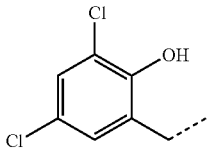 | H | H | Me | H | Me |
| 207 | 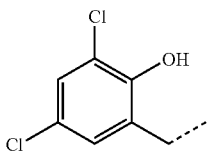 | H | H | F | H | Me |
| 208 | 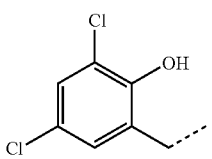 | H | H | NO2 | H | Me |
| 209 | 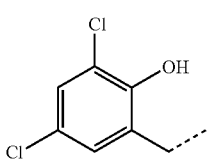 | H | H | CN | H | Me |
| 210 | 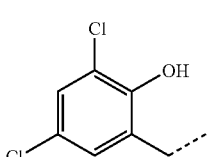 | H | H | OH | H | Me |
| 211 | 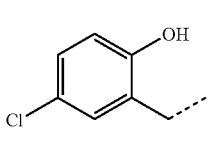 | H | H | H | H | Me |
| 212 | 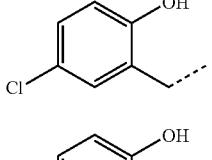 | H | H | Cl | H | Me |
| 213 | 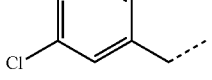 | H | H | COOMe | H | Me |
| 214 | 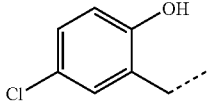 | H | H | OMe | H | Me |

TABLE 6-continued
| X = —CO—, q = 0, r = 0, Y = —N(R8)— | | | | | | |
|---|---|---|---|---|---|---|
| Compound No. 6 | R1—(CH2)p— | R2 | R3 | R6 | R7 | R8 |
| 215 | 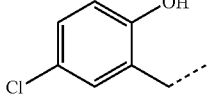 | H | H | OCF3 | H | Me |
| 216 | 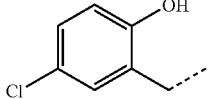 | H | H | CF3 | H | Me |
| 217 | 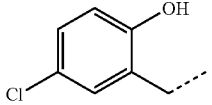 | H | H | Me | H | Me |
| 218 | 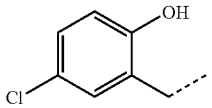 | H | H | F | H | Me |
| 219 | 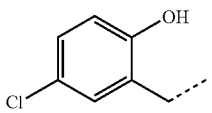 | H | H | NO2 | H | Me |
| 220 | 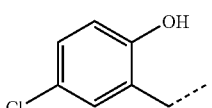 | H | H | CN | H | Me |
| 221 | 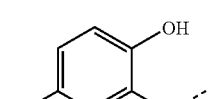 | H | H | OH | H | Me |
| 222 | 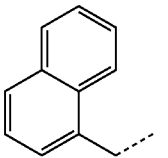 | H | H | H | H | Me |
| 223 | 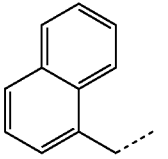 | H | H | Cl | H | Me |
| 224 | 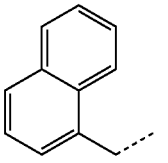 | H | H | COOMe | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 225 | naphthalen-1-ylmethyl | H | H | OMe | H | Me |
| 226 | naphthalen-1-ylmethyl | H | H | OCF3 | H | Me |
| 227 | naphthalen-1-ylmethyl | H | H | CF3 | H | Me |
| 228 | naphthalen-1-ylmethyl | H | H | Me | H | Me |
| 229 | naphthalen-1-ylmethyl | H | H | F | H | Me |
| 230 | naphthalen-1-ylmethyl | H | H | NO2 | H | Me |
| 231 | naphthalen-1-ylmethyl | H | H | CN | H | Me |
| 232 | naphthalen-1-ylmethyl | H | H | OH | H | Me |
| 233 | phenylpropyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 234 | 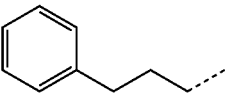 | H | H | Cl | H | Me |
| 235 | 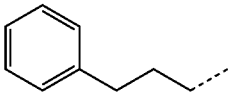 | H | H | COOMe | H | Me |
| 236 | 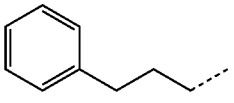 | H | H | OMe | H | Me |
| 237 | 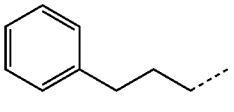 | H | H | OCF3 | H | Me |
| 238 | 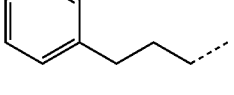 | H | H | CF3 | H | Me |
| 239 | 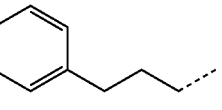 | H | H | Me | H | Me |
| 240 | 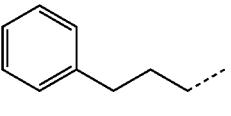 | H | H | F | H | Me |
| 241 | 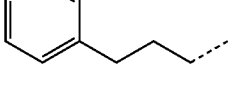 | H | H | NO2 | H | Me |
| 242 | 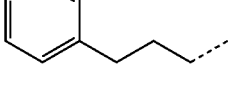 | H | H | CN | H | Me |
| 243 | 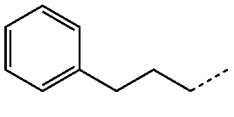 | H | H | OH | H | Me |
| 244 | 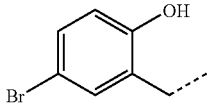 | H | H | H | H | Me |
| 245 | 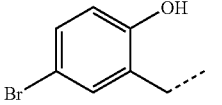 | H | H | Cl | H | Me |
| 246 | 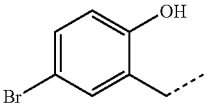 | H | H | COOMe | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 247 | 4-Br-2-(CH2)-phenol | H | H | OMe | H | Me |
| 248 | 4-Br-2-(CH2)-phenol | H | H | OCF3 | H | Me |
| 249 | 4-Br-2-(CH2)-phenol | H | H | CF3 | H | Me |
| 250 | 4-Br-2-(CH2)-phenol | H | H | Me | H | Me |
| 251 | 4-Br-2-(CH2)-phenol | H | H | F | H | Me |
| 252 | 4-Br-2-(CH2)-phenol | H | H | NO2 | H | Me |
| 253 | 4-Br-2-(CH2)-phenol | H | H | CN | H | Me |
| 254 | 4-Br-2-(CH2)-phenol | H | H | OH | H | Me |
| 255 | 1-Me-indol-3-yl-CH2 | H | H | H | H | Me |
| 256 | 1-Me-indol-3-yl-CH2 | H | H | Cl | H | Me |
| 257 | 1-Me-indol-3-yl-CH2 | H | H | COOMe | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 258 | 1-methylindol-3-ylmethyl | H | H | OMe | H | Me |
| 259 | 1-methylindol-3-ylmethyl | H | H | OCF3 | H | Me |
| 260 | 1-methylindol-3-ylmethyl | H | H | CF3 | H | Me |
| 261 | 1-methylindol-3-ylmethyl | H | H | Me | H | Me |
| 262 | 1-methylindol-3-ylmethyl | H | H | F | H | Me |
| 263 | 1-methylindol-3-ylmethyl | H | H | NO2 | H | Me |
| 264 | 1-methylindol-3-ylmethyl | H | H | CN | H | Me |
| 265 | 1-methylindol-3-ylmethyl | H | H | OH | H | Me |
| 266 | benzothiophen-3-ylmethyl | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 267 | benzothiophen-3-ylmethyl | H | H | Cl | H | Me |
| 268 | benzothiophen-3-ylmethyl | H | H | COOMe | H | Me |
| 269 | benzothiophen-3-ylmethyl | H | H | OMe | H | Me |
| 270 | benzothiophen-3-ylmethyl | H | H | OCF3 | H | Me |
| 271 | benzothiophen-3-ylmethyl | H | H | CF3 | H | Me |
| 272 | benzothiophen-3-ylmethyl | H | H | Me | H | Me |
| 273 | benzothiophen-3-ylmethyl | H | H | F | H | Me |
| 274 | benzothiophen-3-ylmethyl | H | H | NO2 | H | Me |
| 275 | benzothiophen-3-ylmethyl | H | H | CN | H | Me |

TABLE 6-continued
X=—CO—, q=0, r=0, Y=—N(R8)—
| Compound No. 6 | R1—(CH2)p— | R2 | R3 | R6 | R7 | R8 |
|---|---|---|---|---|---|---|
| 276 | 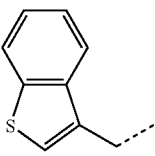 | H | H | OH | H | Me |
TABLE 7
X=—CO—, q=1, r=0, Y=—(R4)C=C(R5)—
| Compound No. 7 | R1—(CH2)p— | R2 | R3 | R4 | R5 | R6 | R7 |
|---|---|---|---|---|---|---|---|
| 1 | 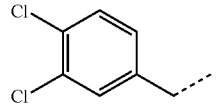 | H | H | H | H | H | H |
| 2 | 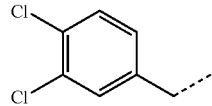 | H | H | H | Cl | H | H |
| 3 | 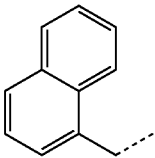 | H | H | H | H | H | H |
| 4 | 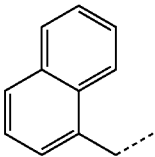 | H | H | H | Cl | H | H |
| 5 | 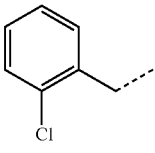 | H | H | H | H | H | H |
| 6 | 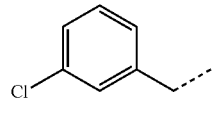 | H | H | H | H | H | H |
| 7 | 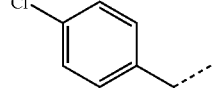 | H | H | H | H | H | H |
| 8 | 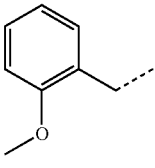 | H | H | H | H | H | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 9 | 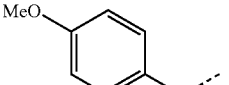 | H | H | H | H | H | H |
| 10 | 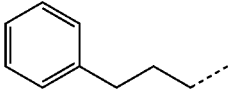 | H | H | H | H | H | H |
| 11 | 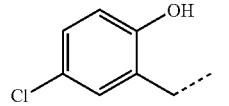 | H | H | H | H | H | H |
| 12 | 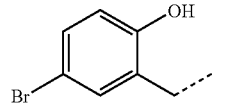 | H | H | H | H | H | H |
| 13 | 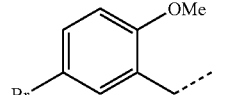 | H | H | H | H | H | H |
| 14 | 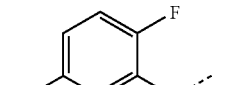 | H | H | H | H | H | H |
| 15 | 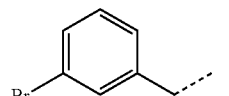 | H | H | H | H | H | H |
| 16 | 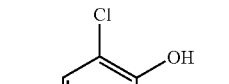 | H | H | H | H | H | H |
| 17 | 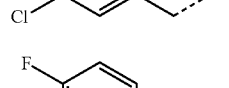 | H | H | H | H | H | H |
| 18 | 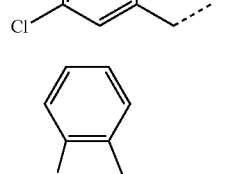 | H | H | H | H | H | H |
| 19 | 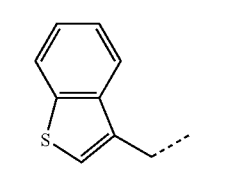 | H | H | H | H | H | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 20 | 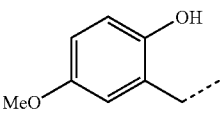 2-OH, 4-MeO benzyl | H | H | H | H | H | H |
| 21 | 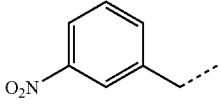 3-O₂N benzyl | H | H | H | H | H | H |
| 22 | 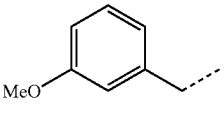 3-MeO benzyl | H | H | H | H | H | H |
| 23 | 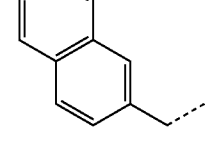 naphthylmethyl | H | H | H | H | H | H |
| 24 | 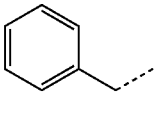 benzyl | H | H | H | H | H | H |
| 25 |  phenethyl | H | H | H | H | H | H |
| 26 | 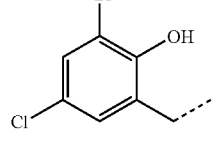 2-OH, 3-Br, 5-Cl benzyl | H | H | H | H | H | H |
| 27 | 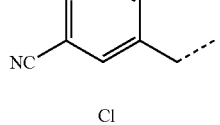 2-OH, 5-CN benzyl | H | H | H | H | H | H |
| 28 | 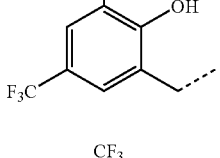 2-OH, 3-Cl, 5-CF₃ benzyl | H | H | H | H | H | H |
| 29 | 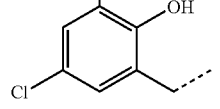 2-OH, 3-CF₃, 5-Cl benzyl | H | H | H | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 30 | 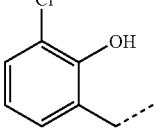 | H | H | H | H | H | H |
| 31 | 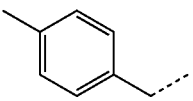 | H | H | H | H | H | H |
| 32 | 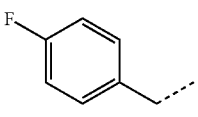 | H | H | H | H | H | H |
| 33 | 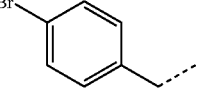 | H | H | H | H | H | H |
| 34 | 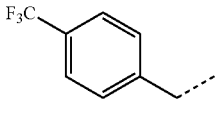 | H | H | H | H | H | H |
| 35 | 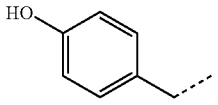 | H | H | H | H | H | H |
| 36 | 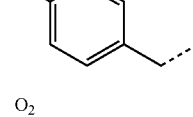 | H | H | H | H | H | H |
| 37 | 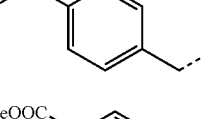 | H | H | H | H | H | H |
| 38 | 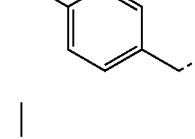 | H | H | H | H | H | H |
| 39 | 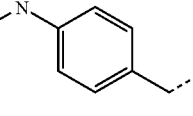 | H | H | H | H | H | H |
| 40 | 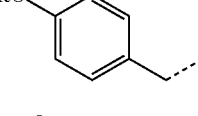 | H | H | H | H | H | H |
| 41 | 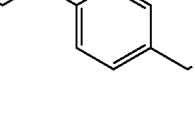 | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 42 | 4-propoxybenzyl | H | H | H | H | H | H |
| 43 | 4-isopropoxybenzyl | H | H | H | H | H | H |
| 44 | 4-isopropylbenzyl | H | H | H | H | H | H |
| 45 | 4-benzyloxybenzyl | H | H | H | H | H | H |
| 46 | 4-phenoxybenzyl | H | H | H | H | H | H |
| 47 | 4-biphenylmethyl | H | H | H | H | H | H |
| 48 | 4-acetamidobenzyl | H | H | H | H | H | H |
| 49 | 2-propylbenzyl | H | H | H | H | H | H |
| 50 | 2-benzyloxybenzyl | H | H | H | H | H | H |
| 51 | 2-methylbenzyl | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 52 | 2-CN-phenyl-CH2— | H | H | H | H | H | H |
| 53 | 2-Cl-phenyl-CH2— | H | H | H | H | H | H |
| 54 | 2-OMe-phenyl-CH2— | H | H | H | H | H | H |
| 55 | 2-OEt-phenyl-CH2— | H | H | H | H | H | H |
| 56 | 2-phenyl-phenyl-CH2— | H | H | H | H | H | H |
| 57 | 3-CF3-phenyl-CH2— | H | H | H | H | H | H |
| 58 | 3-Cl-2-F-phenyl-CH2— | H | H | H | H | H | H |
| 59 | 3,5-diCl-phenyl-CH2— | H | H | H | H | H | H |
| 60 | 3-Me-phenyl-CH2— | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 61 | 3-F,5-CF3-C6H3-CH2— | H | H | H | H | H | H |
| 62 | 3-(F3CO)-C6H4-CH2— | H | H | H | H | H | H |
| 63 | 2-F,4-MeO-C6H3-CH2— | H | H | H | H | H | H |
| 64 | 2-F,4-O2N-C6H3-CH2— | H | H | H | H | H | H |
| 65 | 4-O2N-C6H4-CH2— | H | H | H | H | H | H |
| 66 | 2-F,6-Me-C6H3-CH2— | H | H | H | H | H | H |
| 67 | 3-(F3CS)-C6H4-CH2— | H | H | H | H | H | H |
| 68 | 2,5-Cl2-C6H3-CH2— | H | H | H | H | H | H |
| 69 | 3-(F2HC)-C6H4-CH2— | H | H | H | H | H | H |
| 70 | 2-F-C6H4-CH2— | H | H | H | H | H | H |
| 71 | 2-NO2-C6H4-CH2— | H | H | H | H | H | H |
| 72 | 2-COOH-C6H4-CH2— | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 73 | 4-Br, 2-OEt phenyl | H | H | H | H | H | H |
| 74 | 2,3-dimethyl phenyl | H | H | H | H | H | H |
| 75 | 3-F phenyl | H | H | H | H | H | H |
| 76 | 2,4-diCl phenyl | H | H | H | H | H | H |
| 77 | 3-CN phenyl | H | H | H | H | H | H |
| 78 | 3-OH phenyl | H | H | H | H | H | H |
| 79 | 3-OEt phenyl | H | H | H | H | H | H |
| 80 | 4-Cl, 3-NO2 phenyl | H | H | H | H | H | H |
| 81 | 2,3-diCl phenyl | H | H | H | H | H | H |
| 82 | 4-Me, 2,3-diF phenyl | H | H | H | H | H | H |
| 83 | 4-F, 3-Br phenyl | H | H | H | H | H | H |

TABLE 7-continued

X = —CO—, q = 1, r = 0, Y = —(R4)C═C(R5)—

| Compound No. 7 | R1—(CH2)p— | R2 | R3 | R4 | R5 | R6 | R7 |
|---|---|---|---|---|---|---|---|
| 84 | 3-CF₃, 2-F phenyl | H | H | H | H | H | H |
| 85 | 4-OH, 3-Cl phenyl | H | H | H | H | H | H |
| 86 | 2,3-diF phenyl | H | H | H | H | H | H |
| 87 | 4-OMe, 3-Br phenyl | H | H | H | H | H | H |
| 88 | 3-OMe, 2-OEt phenyl | H | H | H | H | H | H |
| 89 | 4-OMe, 2,3-diMe phenyl | H | H | H | H | H | H |
| 90 | 3-OMe, 2-OBn phenyl | H | H | H | H | H | H |
| 91 | 4-Cl, 3-NO₂ phenyl... wait 4-NO2? | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 92 | 4-MeO-phenyl-O-(3-phenyl-CH2—) | H | H | H | H | H | H |
| 93 | 4-Me-phenyl-O-(3-phenyl-CH2—) | H | H | H | H | H | H |
| 94 | 4-Cl-phenyl-O-(3-phenyl-CH2—) | H | H | H | H | H | H |
| 95 | 3-(benzyloxy)phenyl-CH2— | H | H | H | H | H | H |
| 96 | 3-phenoxyphenyl-CH2— | H | H | H | H | H | H |
| 97 | 4-MeO-3-HO-phenyl-CH2— | H | H | H | H | H | H |
| 98 | 2-Cl-3-CF3-phenyl-CH2— | H | H | H | H | H | H |
| 99 | 4-HO-3-O2N-phenyl-CH2— | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
| --- | --- | --- | --- | --- | --- | --- | --- |
| 100 | 2,3-dimethoxybenzyl | H | H | H | H | H | H |
| 101 | 4-ethoxy-2-ethoxy-3-methylbenzyl | H | H | H | H | H | H |
| 102 | 3-(2-hydroxyethoxy)benzyl | H | H | H | H | H | H |
| 103 | 2,3,4-trimethoxybenzyl | H | H | H | H | H | H |
| 104 | 4-fluoro-3-phenoxybenzyl | H | H | H | H | H | H |
| 105 | 2,3-dimethoxy-6-(carboxy)benzyl | H | H | H | H | H | H |
| 106 | 4-chloro-2-nitrobenzyl | H | H | H | H | H | H |
| 107 | 3,5-dihydroxybenzyl | H | H | H | H | H | H |
| 108 | 3-benzyloxy-4-methoxybenzyl | H | H | H | H | H | H |
| 109 | 3,4-diethoxybenzyl | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 110 | 3-HOOC-C6H4-CH2- | H | H | H | H | H | H |
| 111 | 4-OMe-3-HO-C6H3-CH2- (2-OMe-5-HO benzyl) | H | H | H | H | H | H |
| 112 | 4-O2N-3-HO-C6H3-CH2- | H | H | H | H | H | H |
| 113 | 3,5-(CF3)2-C6H3-CH2- | H | H | H | H | H | H |
| 114 | 2-OMe-3-NO2-C6H3-CH2- | H | H | H | H | H | H |
| 115 | (4-methylnaphthalen-1-yl)-CH2- | H | H | H | H | H | H |
| 116 | (1-methyl-7-methyl-indol-3-yl)-CH2- | H | H | H | H | H | H |
| 117 | (2-methoxynaphthalen-1-yl)-CH2- | H | H | H | H | H | H |
| 118 | (benzofuran-2-yl)-CH2- | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 119 | 2-methyl-1-methyl-indol-3-yl-methyl | H | H | H | H | H | H |
| 120 | quinolin-8-yl-methyl | H | H | H | H | H | H |
| 121 | 2-hydroxy-naphthalen-1-yl-methyl | H | H | H | H | H | H |
| 122 | 2-acetoxy-naphthalen-1-yl-methyl | H | H | H | H | H | H |
| 123 | 1-hydroxy-naphthalen-2-yl-methyl | H | H | H | H | H | H |
| 124 | 1H-indol-7-yl-methyl | H | H | H | H | H | H |
| 125 | quinolin-4-yl-methyl | H | H | H | H | H | H |
| 126 | 5-methyl-1-methyl-indol-3-yl-methyl | H | H | H | H | H | H |

TABLE 7-continued

X = —CO—, q = 1, r = 0, Y = —(R4)C═C(R5)—

| Compound No. 7 | R1—(CH2)p— | R2 | R3 | R4 | R5 | R6 | R7 |
|---|---|---|---|---|---|---|---|
| 127 | (9-anthracenylmethyl) | H | H | H | H | H | H |
| 128 | (2-methyl-1-naphthylmethyl) | H | H | H | H | H | H |
| 129 | (2-ethoxy-1-naphthylmethyl) | H | H | H | H | H | H |
| 130 | (1H-indol-3-ylmethyl) | H | H | H | H | H | H |
| 131 | (6-methyl-1-methyl-1H-indol-3-ylmethyl) | H | H | H | H | H | H |
| 132 | (1-methyl-1H-indol-2-ylmethyl) | H | H | H | H | H | H |
| 133 | (4-methyl-1-methyl-1H-indol-3-ylmethyl) | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 134 | 2,5-dimethyl-1-methyl-indol-3-yl | H | H | H | H | H | H |
| 135 | 5-methoxy-1-methyl-indol-3-yl | H | H | H | H | H | H |
| 136 | 4-methyl-benzothiophen-3-yl | H | H | H | H | H | H |
| 137 | 1-methyl-benzimidazol-2-yl | H | H | H | H | H | H |
| 138 | 1-methyl-2-phenyl-indol-3-yl | H | H | H | H | H | H |
| 139 | 1-acetyl-indol-3-yl | H | H | H | H | H | H |
| 140 | quinolin-2-yl | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 141 | 6-MeO-1-Me-indol-3-ylmethyl | H | H | H | H | H | H |
| 142 | 3-methylbenzothiophen-2-ylmethyl | H | H | H | H | H | H |
| 143 | 4-methoxynaphthalen-1-ylmethyl | H | H | H | H | H | H |
| 144 | phenanthren-9-ylmethyl | H | H | H | H | H | H |
| 145 | 6-methoxynaphthalen-2-ylmethyl | H | H | H | H | H | H |
| 146 | 1-bromonaphthalen-2-ylmethyl | H | H | H | H | H | H |
| 147 | 4-(dimethylamino)naphthalen-1-ylmethyl | H | H | H | H | H | H |
| 148 | 2,3-dihydrobenzo[1,4]dioxin-6-ylmethyl | H | H | H | H | H | H |
| 149 | 2,2-dimethylchroman-6-ylmethyl | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 150 | 2,3-dihydrobenzofuran-5-ylmethyl | H | H | H | H | H | H |
| 151 | 9-ethyl-carbazol-3-ylmethyl | H | H | H | H | H | H |
| 152 | benzo[1,3]dioxol-4-ylmethyl | H | H | H | H | H | H |
| 153 | benzo[1,3]dioxol-5-ylmethyl | H | H | H | H | H | H |
| 154 | 4-phenylbutyl | H | H | H | H | H | H |
| 155 | 5-phenylpentyl | H | H | H | H | H | H |
| 156 | cyclohexylmethyl | H | H | H | H | H | H |
| 157 | 2-hydroxy-5-iodobenzyl | H | H | H | H | H | H |
| 158 | 2-hydroxy-5-nitrobenzyl | H | H | H | H | H | H |
| 159 | 5-chloro-2-hydroxy-3-methylbenzyl | H | H | H | H | H | H |
| 160 | 2-hydroxy-3-methylbenzyl | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 161 | 4-F, 2-(CH2)- phenol | H | H | H | H | H | H |
| 162 | 3,5-diiodo-2-hydroxybenzyl | H | H | H | H | H | H |
| 163 | 4-Cl, 2-(CH2)- aniline | H | H | H | H | H | H |
| 164 | 2-hydroxybenzyl | H | H | H | H | H | H |
| 165 | 2-aminobenzyl | H | H | H | H | H | H |
| 166 | 4-tert-butyl-2-hydroxybenzyl | H | H | H | H | H | H |
| 167 | 4-(trifluoromethoxy)-2-hydroxybenzyl | H | H | H | H | H | H |
| 168 | 3-methoxy-2-hydroxybenzyl | H | H | H | H | H | H |
| 169 | 2,3-dihydroxybenzyl | H | H | H | H | H | H |
| 170 | 3-ethoxy-2-hydroxybenzyl | H | H | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 171 | 3-(COOH)-2-(OH)-phenyl-CH2— | H | H | H | H | H | H |
| 172 | 3-(tBu)-2-(OH)-phenyl-CH2— | H | H | H | H | H | H |
| 173 | furan-2-yl-CH2— | H | H | H | H | H | H |
| 174 | oxazol-2-yl-CH2— | H | H | H | H | H | H |
| 175 | 1H-imidazol-2-yl-CH2— | H | H | H | H | H | H |
| 176 | thiazol-2-yl-CH2— | H | H | H | H | H | H |
| 177 | 1H-pyrazol-3-yl-CH2— | H | H | H | H | H | H |
| 178 | 1-phenyl-3,5-dimethyl-pyrazol-4-yl-CH2— | H | H | H | H | H | H |
| 179 | 1-phenyl-2,5-dimethyl-pyrrol-3-yl-CH2— | H | H | H | H | H | H |
| 180 | 5-(4-chlorophenyl)-furan-2-yl-CH2— | H | H | H | H | H | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 181 | 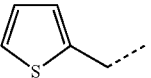 | H | H | H | H | H | H |
| 182 | 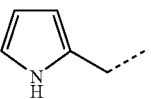 | H | H | H | H | H | H |
| 183 | 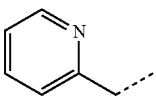 | H | H | H | H | H | H |
| 184 | 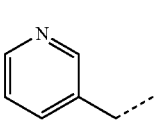 | H | H | H | H | H | H |
| 185 | 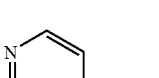 | H | H | H | H | H | H |
| 186 | 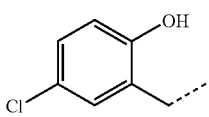 | H | H | H | Cl | H | H |
| 187 | 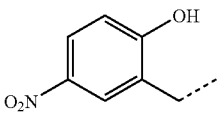 | H | H | H | Cl | H | H |
| 188 | 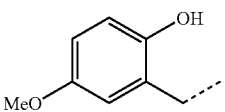 | H | H | H | Cl | H | H |
| 189 | 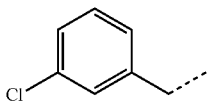 | H | H | H | Cl | H | H |
| 190 | 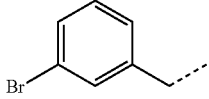 | H | H | H | Cl | H | H |
| 191 | 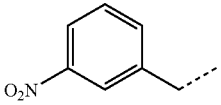 | H | H | H | Cl | H | H |
| 192 | 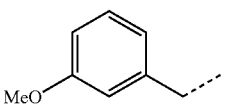 | H | H | H | Cl | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 193 | 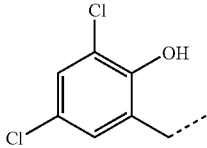 | H | H | H | Cl | H | H |
| 194 | 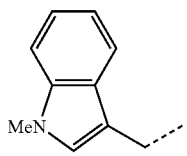 | H | H | H | Cl | H | H |
| 195 | 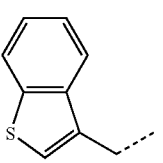 | H | H | H | Cl | H | H |
| 196 | 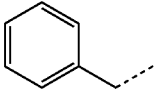 | H | H | H | Cl | H | H |
| 197 | 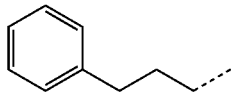 | H | H | H | Cl | H | H |
| 198 | 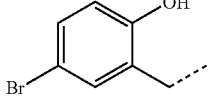 | H | H | H | Cl | H | H |
| 199 | 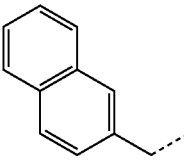 | H | H | H | Cl | H | H |
| 200 | 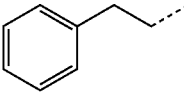 | H | H | H | Cl | H | H |
| 201 | 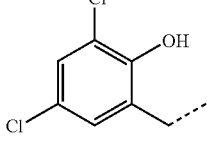 | H | H | Cl | H | H | H |
| 202 | 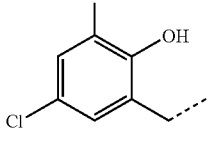 | H | H | H | OMe | H | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 203 | 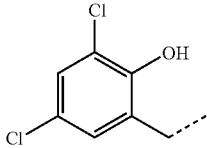 | H | H | H | COOMe | H | H |
| 204 | 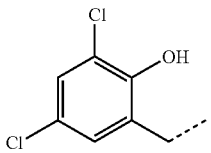 | H | H | H | H | Cl | H |
| 205 | 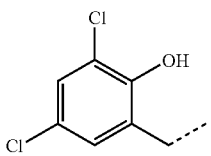 | H | H | H | H | COOMe | H |
| 206 | 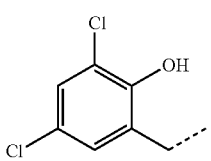 | H | H | H | H | H | Cl |
| 207 | 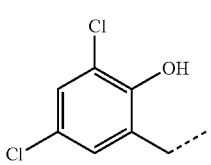 | H | H | H | OCF3 | H | H |
| 208 | 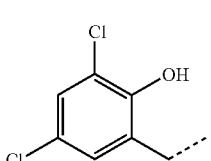 | H | H | COOMe | H | H | H |
| 209 | 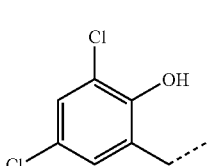 | H | H | H | CF3 | H | H |
| 210 | 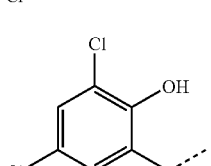 | H | H | H | Me | H | H |
| 211 | 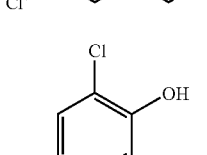 | H | H | H | F | H | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 212 | 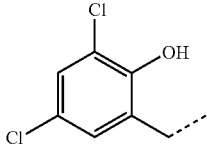 | H | H | H | OH | H | H |
| 213 | 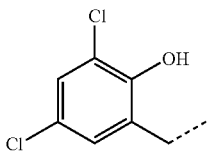 | H | H | H | NO2 | H | H |
| 214 | 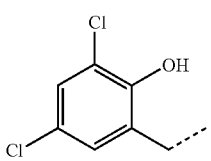 | H | H | H | F | F | H |
| 215 | 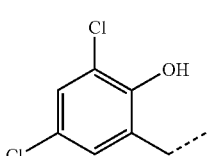 | H | H | F | H | H | H |
| 216 | 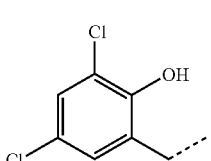 | H | H | Me | H | H | H |
| 217 | 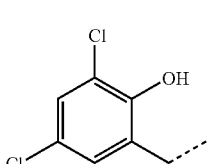 | H | H | H | CN | H | H |
| 218 | 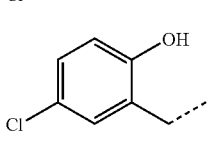 | H | H | Cl | H | H | H |
| 219 | 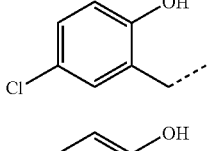 | H | H | H | OMe | H | H |
| 220 | 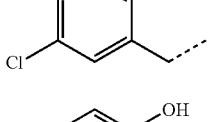 | H | H | H | COOMe | H | H |
| 221 | 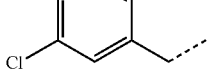 | H | H | H | H | Cl | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 222 | 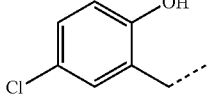 | H | H | H | H | COOMe | H |
| 223 | 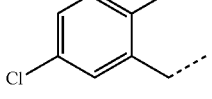 | H | H | H | H | H | Cl |
| 224 | 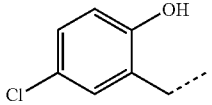 | H | H | H | OCF3 | H | H |
| 225 | 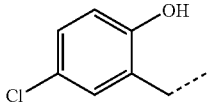 | H | H | COOMe | H | H | H |
| 226 | 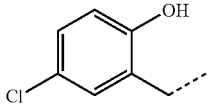 | H | H | H | CF3 | H | H |
| 227 | 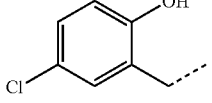 | H | H | H | Me | H | H |
| 228 | 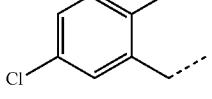 | H | H | H | F | H | H |
| 229 | 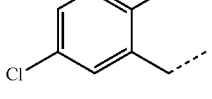 | H | H | H | OH | H | H |
| 230 | 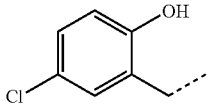 | H | H | H | NO2 | H | H |
| 231 | 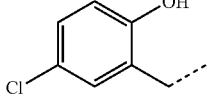 | H | H | H | F | F | H |
| 232 | 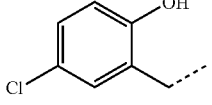 | H | H | F | H | H | H |
| 233 | 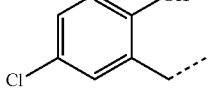 | H | H | Me | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 234 | 4-chloro-2-hydroxybenzyl (OH, Cl substituted) | H | H | H | CN | H | H |
| 235 | naphthalen-1-ylmethyl | H | H | Cl | H | H | H |
| 236 | naphthalen-1-ylmethyl | H | H | H | OMe | H | H |
| 237 | naphthalen-1-ylmethyl | H | H | H | COOMe | H | H |
| 238 | naphthalen-1-ylmethyl | H | H | H | H | Cl | H |
| 239 | naphthalen-1-ylmethyl | H | H | H | H | COOMe | H |
| 240 | naphthalen-1-ylmethyl | H | H | H | H | H | Cl |
| 241 | naphthalen-1-ylmethyl | H | H | H | OCF3 | H | H |
| 242 | naphthalen-1-ylmethyl | H | H | COOMe | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 243 | naphthalen-1-ylmethyl | H | H | H | CF3 | H | H |
| 244 | naphthalen-1-ylmethyl | H | H | H | Me | H | H |
| 245 | naphthalen-1-ylmethyl | H | H | H | F | H | H |
| 246 | naphthalen-1-ylmethyl | H | H | H | OH | H | H |
| 247 | naphthalen-1-ylmethyl | H | H | H | NO2 | H | H |
| 248 | naphthalen-1-ylmethyl | H | H | H | F | F | H |
| 249 | naphthalen-1-ylmethyl | H | H | F | H | H | H |
| 250 | naphthalen-1-ylmethyl | H | H | Me | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 251 | naphthyl-CH2- | H | H | H | CN | H | H |
| 252 | Ph-CH2CH2- | H | H | Cl | H | H | H |
| 253 | Ph-CH2CH2- | H | H | H | OMe | H | H |
| 254 | Ph-CH2CH2- | H | H | H | COOMe | H | H |
| 255 | Ph-CH2CH2- | H | H | H | H | Cl | H |
| 256 | Ph-CH2CH2- | H | H | H | H | COOMe | H |
| 257 | Ph-CH2CH2- | H | H | H | H | H | Cl |
| 258 | Ph-CH2CH2- | H | H | H | OCF3 | H | H |
| 259 | Ph-CH2CH2- | H | H | COOMe | H | H | H |
| 260 | Ph-CH2CH2- | H | H | H | CF3 | H | H |
| 261 | Ph-CH2CH2- | H | H | H | Me | H | H |
| 262 | Ph-CH2CH2- | H | H | H | F | H | H |
| 263 | Ph-CH2CH2- | H | H | H | OH | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 264 | 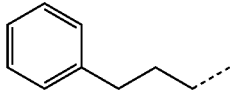 | H | H | H | NO2 | H | H |
| 265 | 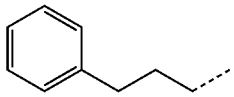 | H | H | H | F | F | H |
| 266 | 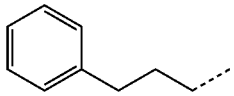 | H | H | F | H | H | H |
| 267 | 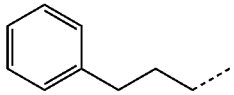 | H | H | Me | H | H | H |
| 268 | 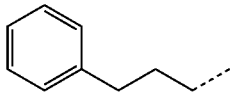 | H | H | H | CN | H | H |
| 269 | 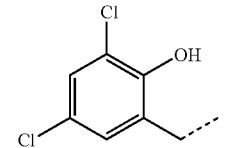 | H | H | H | H | H | COOMe |
| 270 | 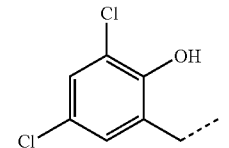 | H | H | H | H | F | H |
| 271 | 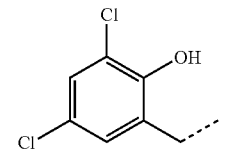 | H | H | H | H | H | F |
| 272 | 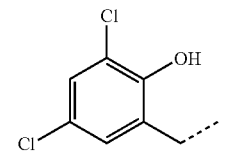 | H | H | H | H | Me | H |
| 273 | 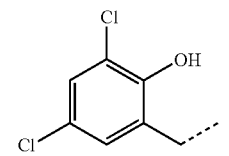 | H | H | H | H | H | Me |
| 274 | 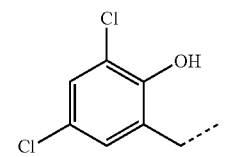 | H | H | OMe | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 275 | 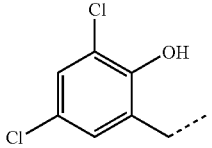 | H | H | H | H | OMe | H |
| 276 | 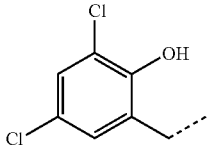 | H | H | H | H | H | OMe |
| 277 | 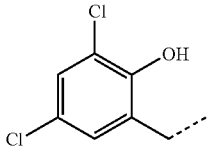 | H | H | CF3 | H | H | H |
| 278 | 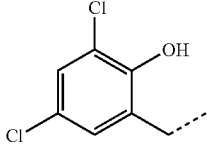 | H | H | H | H | CF3 | H |
| 279 | 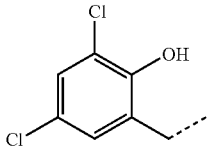 | H | H | H | H | H | CF3 |
| 280 | 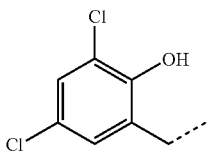 | H | H | OH | H | H | H |
| 281 | 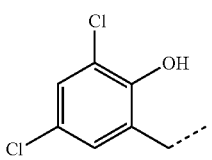 | H | H | H | H | OH | H |
| 282 | 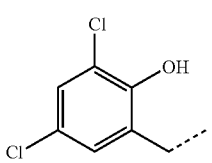 | H | H | H | H | H | OH |
| 283 | 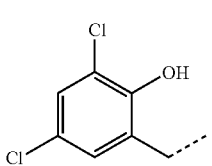 | H | H | OCF3 | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 284 | 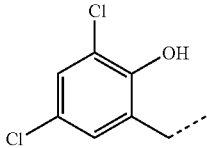 | H | H | H | H | OCF3 | H |
| 285 | 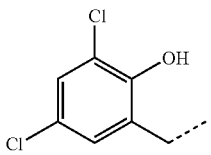 | H | H | H | H | H | OCF3 |
| 286 | 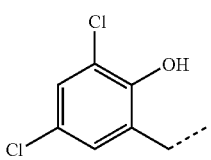 | H | H | NO2 | H | H | H |
| 287 | 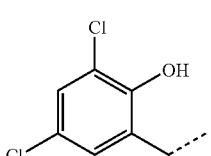 | H | H | H | H | NO2 | H |
| 288 | 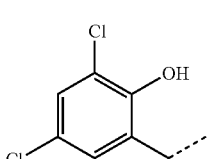 | H | H | H | H | H | NO2 |
| 289 | 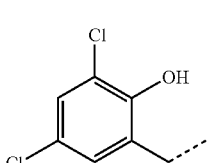 | H | H | CN | H | H | H |
| 290 | 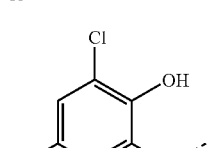 | H | H | H | H | CN | H |
| 291 | 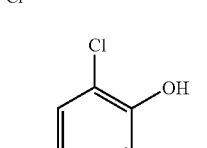 | H | H | H | H | H | CN |
| 292 | 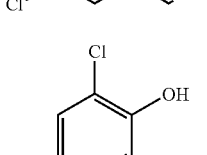 | H | H | Br | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 293 | 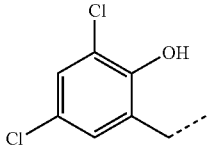 | H | H | H | Br | H | H |
| 294 | 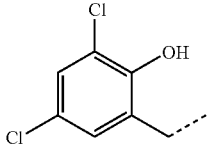 | H | H | H | H | Br | H |
| 295 | 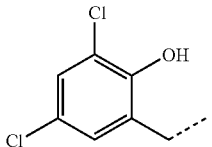 | H | H | H | H | H | Br |
| 296 | 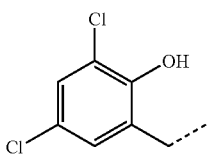 | H | H | COOH | H | H | H |
| 297 | 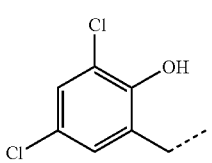 | H | H | H | COOH | H | H |
| 298 | 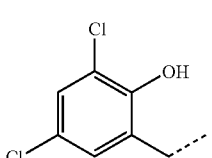 | H | H | H | H | COOH | H |
| 299 | 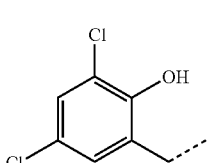 | H | H | H | H | H | COOH |
| 300 | 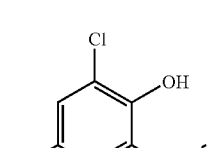 | H | H | NHCOMe | H | H | H |
| 301 | 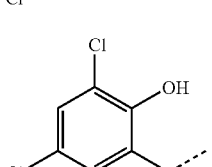 | H | H | H | NHCOMe | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 302 | 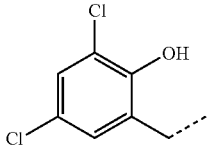 | H | H | H | H | NHCOMe | H |
| 303 | 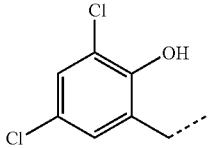 | H | H | H | H | H | NHCOMe |
| 304 | 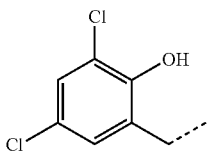 | H | H | SO2NH2 | H | H | H |
| 305 | 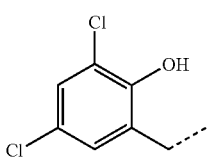 | H | H | H | SO2NH2 | H | H |
| 306 | 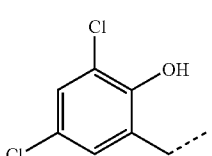 | H | H | H | H | SO2NH2 | H |
| 307 | 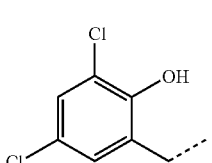 | H | H | H | H | H | SO2NH2 |
| 308 | 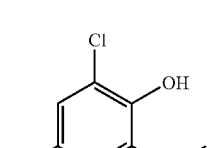 | H | H | Me | Me | H | H |
| 309 | 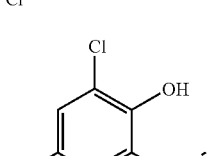 | H | H | Me | H | Me | H |
| 310 | 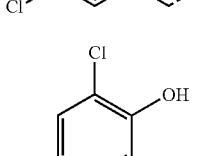 | H | H | H | Me | Me | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 311 | 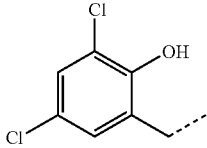 | H | H | F | F | H | H |
| 312 | 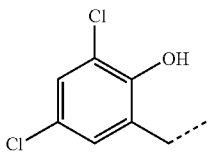 | H | H | F | H | F | H |
| 313 | 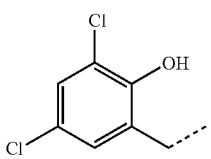 | H | H | H | F | F | H |
| 314 | 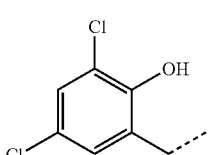 | H | H | Cl | Cl | H | H |
| 315 | 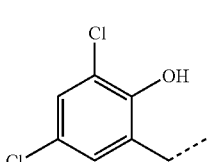 | H | H | Cl | H | Cl | H |
| 316 | 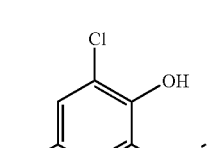 | H | H | H | Cl | Cl | H |
| 317 | 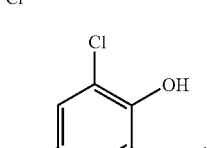 | H | H | Me | F | H | H |
| 318 | 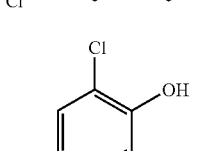 | H | H | Me | Cl | H | H |
| 319 | 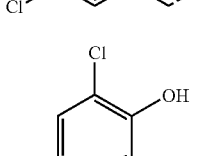 | H | H | Me | OH | H | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 320 | 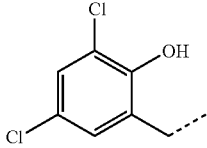 | H | H | Me | OMe | H | H |
| 321 | 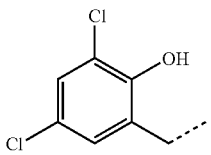 | H | H | F | Me | H | H |
| 322 | 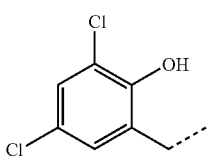 | H | H | F | Cl | H | H |
| 323 | 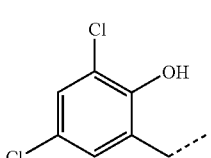 | H | H | F | OH | H | H |
| 324 | 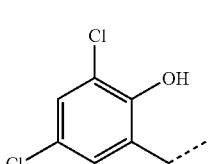 | H | H | F | OMe | H | H |
| 325 | 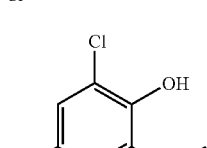 | H | H | Cl | Me | H | H |
| 326 | 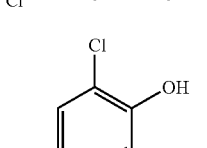 | H | H | Cl | F | H | H |
| 327 | 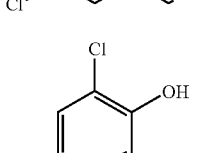 | H | H | Cl | OH | H | H |
| 328 | 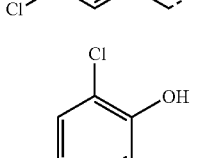 | H | H | Cl | OMe | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 329 | 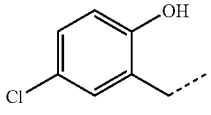 | H | H | H | H | H | COOMe |
| 330 | 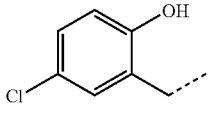 | H | H | H | H | F | H |
| 331 | 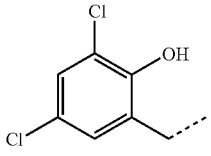 | H | H | H | H | H | F |
| 332 | 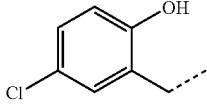 | H | H | H | H | Me | H |
| 333 | 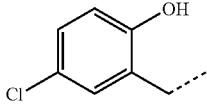 | H | H | H | H | H | Me |
| 334 | 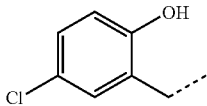 | H | H | OMe | H | H | H |
| 335 | 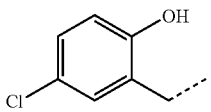 | H | H | H | H | OMe | H |
| 336 | 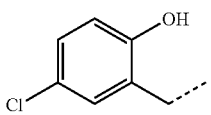 | H | H | H | H | H | OMe |
| 337 | 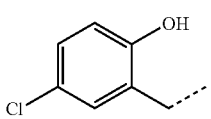 | H | H | CF3 | H | H | H |
| 338 | 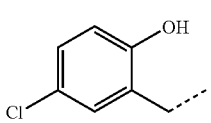 | H | H | H | H | CF3 | H |
| 339 | 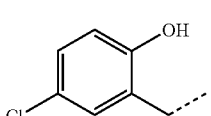 | H | H | H | H | H | CF3 |
| 340 | 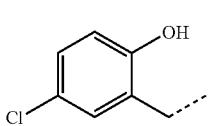 | H | H | OH | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 341 | 4-Cl, 2-OH-benzyl | H | H | H | H | OH | H |
| 342 | 4-Cl, 2-OH-benzyl | H | H | H | H | H | OH |
| 343 | 4-Cl, 2-OH-benzyl | H | H | OCF3 | H | H | H |
| 344 | 4-Cl, 2-OH-benzyl | H | H | H | H | OCF3 | H |
| 345 | 4-Cl, 2-OH-benzyl | H | H | H | H | H | OCF3 |
| 346 | 4-Cl, 2-OH-benzyl | H | H | NO2 | H | H | H |
| 347 | 4-Cl, 2-OH-benzyl | H | H | H | H | NO2 | H |
| 348 | 4-Cl, 2-OH-benzyl | H | H | H | H | H | NO2 |
| 349 | 4-Cl, 2-OH-benzyl | H | H | CN | H | H | H |
| 350 | 4-Cl, 2-OH-benzyl | H | H | H | H | CN | H |
| 351 | 4-Cl, 2-OH-benzyl | H | H | H | H | H | CN |
| 352 | 4-Cl, 2-OH-benzyl | H | H | Br | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 353 | 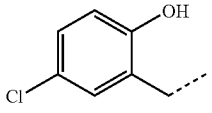 | H | H | H | Br | H | H |
| 354 | 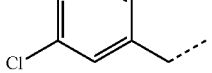 | H | H | H | H | Br | H |
| 355 | 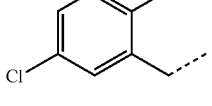 | H | H | H | H | H | Br |
| 356 | 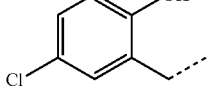 | H | H | COOH | H | H | H |
| 357 | 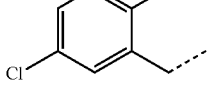 | H | H | H | COOH | H | H |
| 358 | 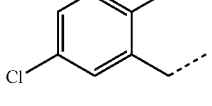 | H | H | H | H | COOH | H |
| 359 | 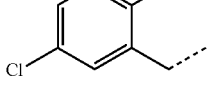 | H | H | H | H | H | COOH |
| 360 | 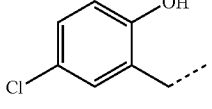 | H | H | NHCOMe | H | H | H |
| 361 | 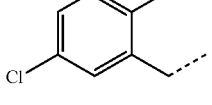 | H | H | H | NHCOMe | H | H |
| 362 | 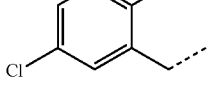 | H | H | H | H | NHCOMe | H |
| 363 | 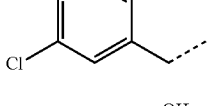 | H | H | H | H | H | NHCOMe |
| 364 | 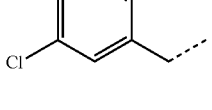 | H | H | SO2NH2 | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 365 | 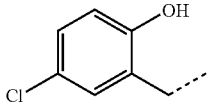 | H | H | H | SO2NH2 | H | H |
| 366 | 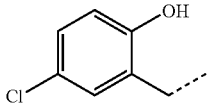 | H | H | H | H | SO2NH2 | H |
| 367 | 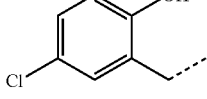 | H | H | H | H | H | SO2NH2 |
| 368 | 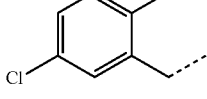 | H | H | Me | Me | H | H |
| 369 | 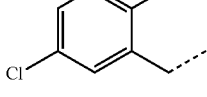 | H | H | Me | H | Me | H |
| 370 | 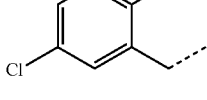 | H | H | H | Me | Me | H |
| 371 | 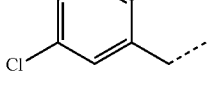 | H | H | F | F | H | H |
| 372 | 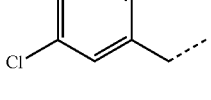 | H | H | F | H | F | H |
| 373 | 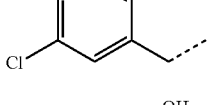 | H | H | H | F | F | H |
| 374 | 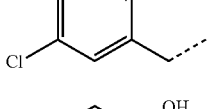 | H | H | Cl | Cl | H | H |
| 375 | 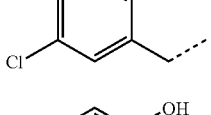 | H | H | Cl | H | Cl | H |
| 376 | 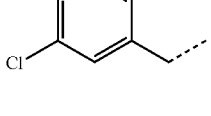 | H | H | H | Cl | Cl | H |

TABLE 7-continued
X = —CO—, q = 1, r = 0, Y = —(R4)C═C(R5)—
| Compound No. 7 | R1—(CH2)p— | R2 | R3 | R4 | R5 | R6 | R7 |
|---|---|---|---|---|---|---|---|
| 377 | 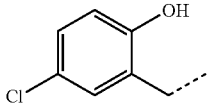 | H | H | Me | F | H | H |
| 378 | 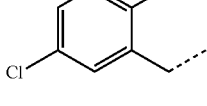 | H | H | Me | Cl | H | H |
| 379 | 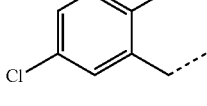 | H | H | Me | OH | H | H |
| 380 | 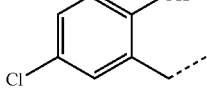 | H | H | Me | OMe | H | H |
| 381 | 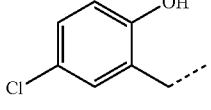 | H | H | F | Me | H | H |
| 382 | 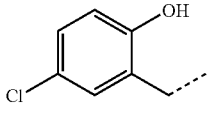 | H | H | F | Cl | H | H |
| 383 | 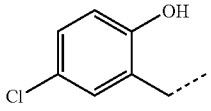 | H | H | F | OH | H | H |
| 384 | 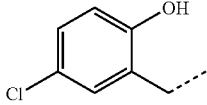 | H | H | F | OMe | H | H |
| 385 | 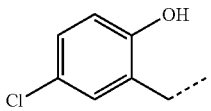 | H | H | Cl | Me | H | H |
| 386 | 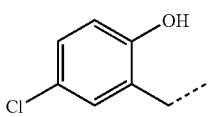 | H | H | Cl | F | H | H |
| 387 | 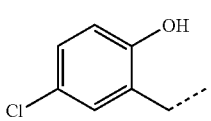 | H | H | Cl | OH | H | H |
| 388 | 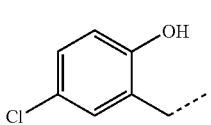 | H | H | Cl | OMe | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 389 | naphthalen-1-ylmethyl | H | H | H | H | H | COOMe |
| 390 | naphthalen-1-ylmethyl | H | H | H | H | F | H |
| 391 | naphthalen-1-ylmethyl | H | H | H | H | H | F |
| 392 | naphthalen-1-ylmethyl | H | H | H | H | Me | H |
| 393 | naphthalen-1-ylmethyl | H | H | H | H | H | Me |
| 394 | naphthalen-1-ylmethyl | H | H | OMe | H | H | H |
| 395 | naphthalen-1-ylmethyl | H | H | H | H | OMe | H |
| 396 | naphthalen-1-ylmethyl | H | H | H | H | H | OMe |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 397 | naphthyl-CH2— | H | H | CF3 | H | H | H |
| 398 | naphthyl-CH2— | H | H | H | H | CF3 | H |
| 399 | naphthyl-CH2— | H | H | H | H | H | CF3 |
| 400 | naphthyl-CH2— | H | H | OH | H | H | H |
| 401 | naphthyl-CH2— | H | H | H | H | OH | H |
| 402 | naphthyl-CH2— | H | H | H | H | H | OH |
| 403 | naphthyl-CH2— | H | H | OCF3 | H | H | H |
| 404 | naphthyl-CH2— | H | H | H | H | OCF3 | H |

TABLE 7-continued

X = —CO—, q = 1, r = 0, Y = —(R4)C═C(R5)—

| Compound No. 7 | R1—(CH2)p— | R2 | R3 | R4 | R5 | R6 | R7 |
|---|---|---|---|---|---|---|---|
| 405 | naphthyl-CH2— | H | H | H | H | H | OCF3 |
| 406 | naphthyl-CH2— | H | H | NO2 | H | H | H |
| 407 | naphthyl-CH2— | H | H | H | H | NO2 | H |
| 408 | naphthyl-CH2— | H | H | H | H | H | NO2 |
| 409 | naphthyl-CH2— | H | H | CN | H | H | H |
| 410 | naphthyl-CH2— | H | H | H | H | CN | H |
| 411 | naphthyl-CH2— | H | H | H | H | H | CN |
| 412 | naphthyl-CH2— | H | H | Br | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 413 | naphthalen-1-ylmethyl | H | H | H | Br | H | H |
| 414 | naphthalen-1-ylmethyl | H | H | H | H | Br | H |
| 415 | naphthalen-1-ylmethyl | H | H | H | H | H | Br |
| 416 | naphthalen-1-ylmethyl | H | H | COOH | H | H | H |
| 417 | naphthalen-1-ylmethyl | H | H | H | COOH | H | H |
| 418 | naphthalen-1-ylmethyl | H | H | H | H | COOH | H |
| 419 | naphthalen-1-ylmethyl | H | H | H | H | H | COOH |
| 420 | naphthalen-1-ylmethyl | H | H | NHCOMe | H | H | H |

TABLE 7-continued

X = —CO—, q = 1, r = 0, Y = —(R4)C═C(R5)—

| Compound No. 7 | R1—(CH2)p— | R2 | R3 | R4 | R5 | R6 | R7 |
|---|---|---|---|---|---|---|---|
| 421 | 1-naphthylmethyl | H | H | H | NHCOMe | H | H |
| 422 | 1-naphthylmethyl | H | H | H | H | NHCOMe | |
| 423 | 1-naphthylmethyl | H | H | H | H | H | NHCOMe |
| 424 | 1-naphthylmethyl | H | H | SO2NH2 | H | H | H |
| 425 | 1-naphthylmethyl | H | H | H | SO2NH2 | H | H |
| 426 | 1-naphthylmethyl | H | H | H | H | SO2NH2 | H |
| 427 | 1-naphthylmethyl | H | H | H | H | H | SO2NH2 |
| 428 | 1-naphthylmethyl | H | H | Me | Me | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 429 | naphthalen-1-ylmethyl | H | H | Me | H | Me | H |
| 430 | naphthalen-1-ylmethyl | H | H | H | Me | Me | H |
| 431 | naphthalen-1-ylmethyl | H | H | F | F | H | H |
| 432 | naphthalen-1-ylmethyl | H | H | F | H | F | H |
| 433 | naphthalen-1-ylmethyl | H | H | H | F | F | H |
| 434 | naphthalen-1-ylmethyl | H | H | Cl | Cl | H | H |
| 435 | naphthalen-1-ylmethyl | H | H | Cl | H | Cl | H |
| 436 | naphthalen-1-ylmethyl | H | H | H | Cl | Cl | H |

TABLE 7-continued

X = —CO—, q = 1, r = 0, Y = —(R4)C═C(R5)—

| Compound No. 7 | R1—(CH2)p— | R2 | R3 | R4 | R5 | R6 | R7 |
|---|---|---|---|---|---|---|---|
| 437 | naphthalen-1-ylmethyl | H | H | Me | F | H | H |
| 438 | naphthalen-1-ylmethyl | H | H | Me | Cl | H | H |
| 439 | naphthalen-1-ylmethyl | H | H | Me | OH | H | H |
| 440 | naphthalen-1-ylmethyl | H | H | Me | OMe | H | H |
| 441 | naphthalen-1-ylmethyl | H | H | F | Me | H | H |
| 442 | naphthalen-1-ylmethyl | H | H | F | Cl | H | H |
| 443 | naphthalen-1-ylmethyl | H | H | F | OH | H | H |
| 444 | naphthalen-1-ylmethyl | H | H | F | OMe | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 445 | naphthalen-1-ylmethyl | H | H | Cl | Me | H | H |
| 446 | naphthalen-1-ylmethyl | H | H | Cl | F | H | H |
| 447 | naphthalen-1-ylmethyl | H | H | Cl | OH | H | H |
| 448 | naphthalen-1-ylmethyl | H | H | Cl | OMe | H | H |
| 449 | 4-bromo-2-hydroxybenzyl | H | H | Cl | H | H | H |
| 450 | 4-bromo-2-hydroxybenzyl | H | H | H | OMe | H | H |
| 451 | 4-bromo-2-hydroxybenzyl | H | H | H | COOMe | H | H |
| 452 | 4-bromo-2-hydroxybenzyl | H | H | H | H | Cl | H |
| 453 | 4-bromo-2-hydroxybenzyl | H | H | H | H | COOMe | H |
| 454 | 4-bromo-2-hydroxybenzyl | H | H | H | H | H | Cl |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 455 | 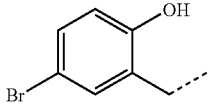 | H | H | H | OCF3 | H | H |
| 456 | 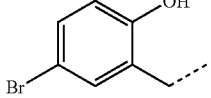 | H | H | COOMe | H | H | H |
| 457 | 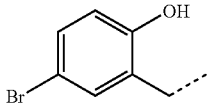 | H | H | H | CF3 | H | H |
| 458 | 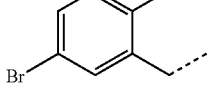 | H | H | H | Me | H | H |
| 459 | 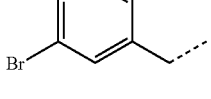 | H | H | H | F | H | H |
| 460 | 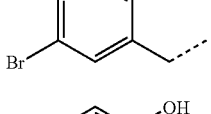 | H | H | H | OH | H | H |
| 461 | 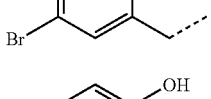 | H | H | H | NO2 | H | H |
| 462 | 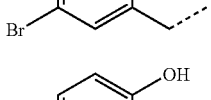 | H | H | H | F | F | H |
| 463 | 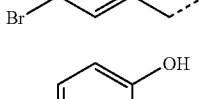 | H | H | F | H | H | H |
| 464 | 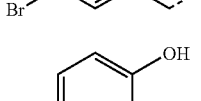 | H | H | Me | H | H | H |
| 465 |  | H | H | H | CN | H | H |
| 466 | 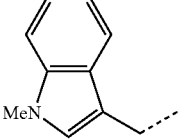 | H | H | Cl | H | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 467 | 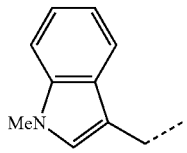 | H | H | H | OMe | H | H |
| 468 | 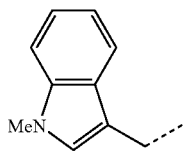 | H | H | H | COOMe | H | H |
| 469 | 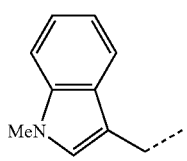 | H | H | H | H | Cl | H |
| 470 | 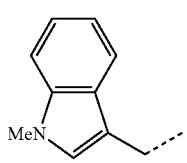 | H | H | H | H | COOMe | H |
| 471 | 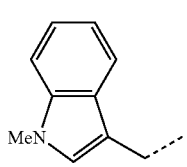 | H | H | H | H | H | Cl |
| 472 | 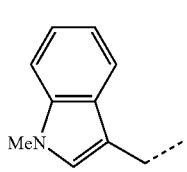 | H | H | H | OCF3 | H | H |
| 473 | 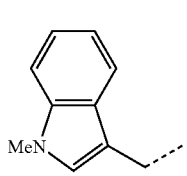 | H | H | COOMe | H | H | H |
| 474 | 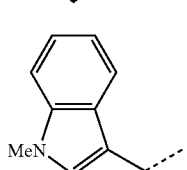 | H | H | H | CF3 | H | H |
| 475 | 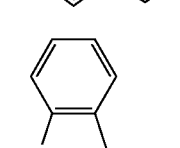 | H | H | H | Me | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 476 | 1-Me-indol-3-yl | H | H | H | F | H | H |
| 477 | 1-Me-indol-3-yl | H | H | H | OH | H | H |
| 478 | 1-Me-indol-3-yl | H | H | H | NO2 | H | H |
| 479 | 1-Me-indol-3-yl | H | H | H | F | F | H |
| 480 | 1-Me-indol-3-yl | H | H | F | H | H | H |
| 481 | 1-Me-indol-3-yl | H | H | Me | H | H | H |
| 482 | 1-Me-indol-3-yl | H | H | H | CN | H | H |
| 483 | benzothiophen-3-yl | H | H | Cl | H | H | H |
| 484 | benzothiophen-3-yl | H | H | H | OMe | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 485 | benzothiophen-3-ylmethyl | H | H | H | COOMe | H | H |
| 486 | benzothiophen-3-ylmethyl | H | H | H | H | Cl | H |
| 487 | benzothiophen-3-ylmethyl | H | H | H | H | COOMe | H |
| 488 | benzothiophen-3-ylmethyl | H | H | H | H | H | Cl |
| 489 | benzothiophen-3-ylmethyl | H | H | H | OCF3 | H | H |
| 490 | benzothiophen-3-ylmethyl | H | H | COOMe | H | H | H |
| 491 | benzothiophen-3-ylmethyl | H | H | H | CF3 | H | H |
| 492 | benzothiophen-3-ylmethyl | H | H | H | Me | H | H |
| 493 | benzothiophen-3-ylmethyl | H | H | H | F | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 494 | 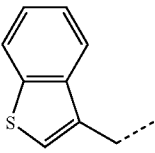 | H | H | H | OH | H | H |
| 495 | 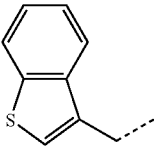 | H | H | H | NO2 | H | H |
| 496 | 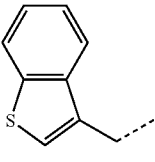 | H | H | H | F | F | H |
| 497 | 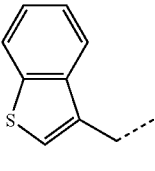 | H | H | F | H | H | H |
| 498 | 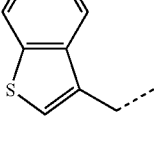 | H | H | Me | H | H | H |
| 499 | 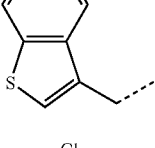 | H | H | H | CN | H | H |
| 500 | 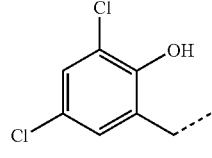 | H | Me | H | H | H | H |
| 501 | 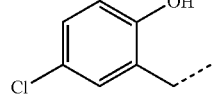 | H | Me | H | H | H | H |
| 502 | 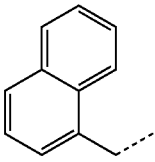 | H | Me | H | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 503 | 3-phenylpropyl | H | Me | H | H | H | H |
| 504 | 4-chloro-2-fluoro-6-(hydroxyphenyl)methyl | H | H | H | H | H | H |
| 505 | 4-chloro-2-fluoro-6-(hydroxyphenyl)methyl | H | H | F | H | H | H |
| 506 | 4-chloro-2-fluoro-6-(hydroxyphenyl)methyl | H | H | Cl | H | H | H |
| 507 | 4-chloro-2-fluoro-6-(hydroxyphenyl)methyl | H | H | Me | H | H | H |
| 508 | 4-chloro-2-fluoro-6-(hydroxyphenyl)methyl | H | H | Et | H | H | H |
| 509 | 4-chloro-2-fluoro-6-(hydroxyphenyl)methyl | H | H | OMe | H | H | H |
| 510 | 4-chloro-2-fluoro-6-(hydroxyphenyl)methyl | H | H | OEt | H | H | H |
| 511 | 4-chloro-2-fluoro-6-(hydroxyphenyl)methyl | H | H | CF3 | H | H | H |

TABLE 7-continued

X = —CO—, q = 1, r = 0, Y = —(R4)C=C(R5)—

| Compound No. 7 | R1—(CH2)p— | R2 | R3 | R4 | R5 | R6 | R7 |
|---|---|---|---|---|---|---|---|
| 512 | 4-Cl, 2-F, 6-OH-benzyl | H | H | OCF3 | H | H | H |
| 513 | 4-Cl, 2-F, 6-OH-benzyl | H | H | NO2 | H | H | H |
| 514 | 4-Cl, 2-F, 6-OH-benzyl | H | H | NH2 | H | H | H |
| 515 | 4-Cl, 2-F, 6-OH-benzyl | H | H | OH | H | H | H |
| 516 | 4-Cl, 2-F, 6-OH-benzyl | H | H | CN | H | H | H |
| 517 | 4-Cl, 2-F, 6-OH-benzyl | H | H | COMe | H | H | H |
| 518 | 4-Cl, 2-F, 6-OH-benzyl | H | H | COOMe | H | H | H |
| 519 | 4-Cl, 2-F, 6-OH-benzyl | H | H | H | F | H | H |
| 520 | 4-Cl, 2-F, 6-OH-benzyl | H | H | H | Cl | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 521 | 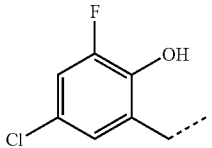 | H | H | H | Me | H | H |
| 522 | 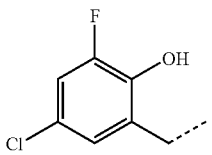 | H | H | H | Et | H | H |
| 523 | 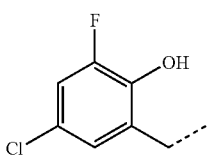 | H | H | H | OMe | H | H |
| 524 | 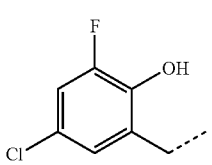 | H | H | H | OEt | H | H |
| 525 | 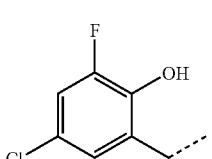 | H | H | H | CF3 | H | H |
| 526 | 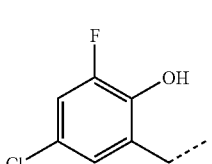 | H | H | H | OCF3 | H | H |
| 527 | 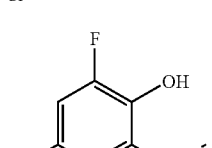 | H | H | H | NO2 | H | H |
| 528 | 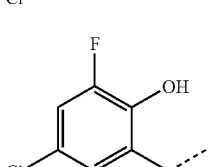 | H | H | H | NH2 | H | H |
| 529 | 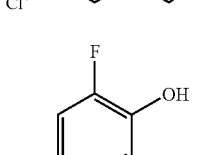 | H | H | H | OH | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 530 | 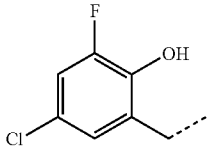 | H | H | H | CN | H | H |
| 531 | 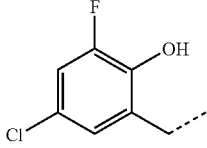 | H | H | H | COMe | H | H |
| 532 | 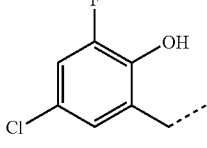 | H | H | H | COOMe | H | H |
| 533 | 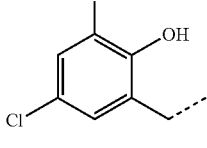 | H | H | F | F | H | H |
| 534 | 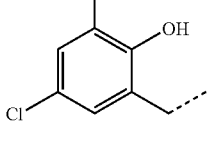 | H | H | F | Cl | H | H |
| 535 | 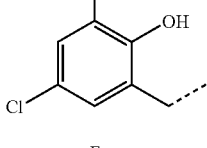 | H | H | F | Me | H | H |
| 536 | 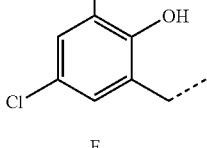 | H | H | F | Et | H | H |
| 537 | 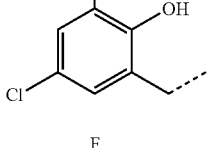 | H | H | F | OMe | H | H |
| 538 | 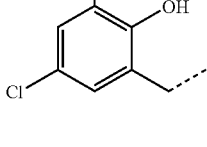 | H | H | F | OEt | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 539 | 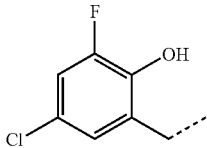 | H | H | F | CF3 | H | H |
| 540 | 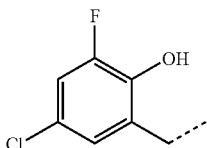 | H | H | F | OCF3 | H | H |
| 541 | 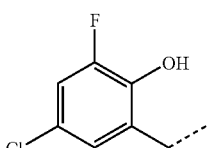 | H | H | Cl | F | H | H |
| 542 | 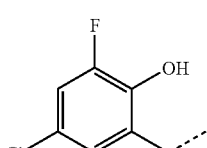 | H | H | Cl | Cl | H | H |
| 543 | 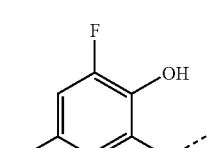 | H | H | Cl | Me | H | H |
| 544 | 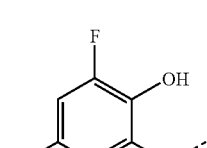 | H | H | Cl | Et | H | H |
| 545 | 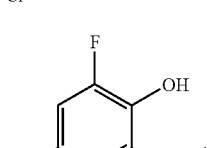 | H | H | Cl | OMe | H | H |
| 546 | 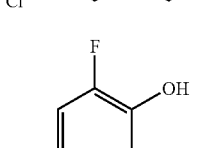 | H | H | Cl | OEt | H | H |
| 547 | 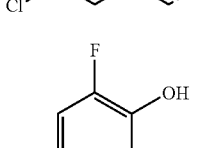 | H | H | Cl | CF3 | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 548 | 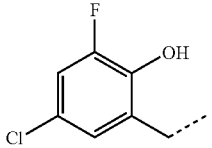 | H | H | Cl | OCF3 | H | H |
| 549 | 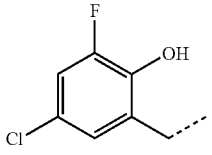 | H | H | Me | F | H | H |
| 550 | 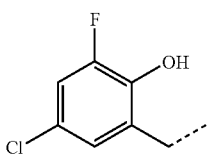 | H | H | Me | Cl | H | H |
| 551 | 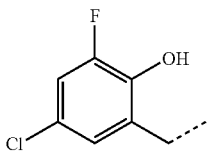 | H | H | Me | Me | H | H |
| 552 | 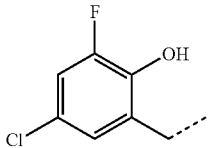 | H | H | Me | Et | H | H |
| 553 | 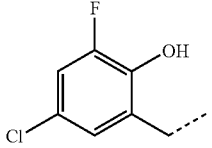 | H | H | Me | OMe | H | H |
| 554 | 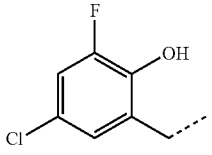 | H | H | Me | OEt | H | H |
| 555 | 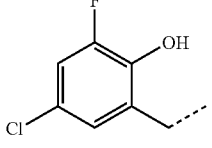 | H | H | Me | CF3 | H | H |
| 556 | 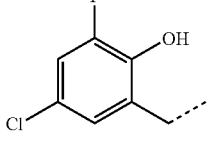 | H | H | Me | OCF3 | H | H |

TABLE 7-continued
X = —CO—, q = 1, r = 0, Y = —(R4)C=C(R5)—
| Compound No. 7 | R1—(CH2)p— | R2 | R3 | R4 | R5 | R6 | R7 |
|---|---|---|---|---|---|---|---|
| 557 | 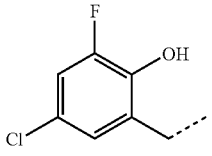 | H | H | OMe | F | H | H |
| 558 | 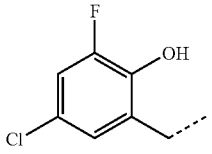 | H | H | OMe | Cl | H | H |
| 559 | 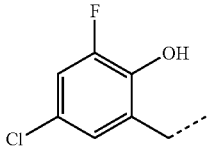 | H | H | OMe | Me | H | H |
| 560 | 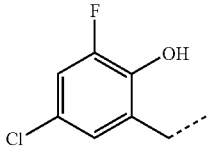 | H | H | OMe | Et | H | H |
| 561 | 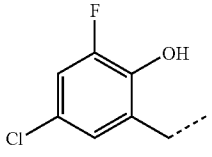 | H | H | OMe | OMe | H | H |
| 562 | 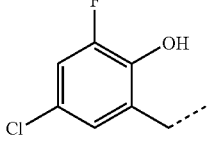 | H | H | OMe | OEt | H | H |
| 563 | 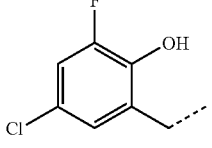 | H | H | OMe | CF3 | H | H |
| 564 | 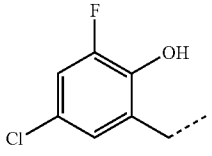 | H | H | OMe | OCF3 | H | H |

TABLE 8

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 1 | 3,4-dichlorobenzyl | H | H | H | H | H | H |
| 2 | 3,4-dichlorobenzyl | H | H | H | Cl | H | H |
| 3 | naphthalen-1-ylmethyl | H | H | H | H | H | H |
| 4 | naphthalen-1-ylmethyl | H | H | H | Cl | H | H |
| 5 | 2-chlorobenzyl | H | H | H | H | H | H |
| 6 | 3-chlorobenzyl | H | H | H | H | H | H |
| 7 | 4-chlorobenzyl | H | H | H | H | H | H |
| 8 | 2-methoxybenzyl | H | H | H | H | H | H |
| 9 | 4-methoxybenzyl | H | H | H | H | H | H |
| 10 | 3-phenylpropyl | H | H | H | H | H | H |
| 11 | 4-chloro-2-hydroxybenzyl | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 12 | 4-Br-2-hydroxybenzyl | H | H | H | H | H | H |
| 13 | 4-Br-2-methoxybenzyl | H | H | H | H | H | H |
| 14 | 4-Br-2-fluorobenzyl | H | H | H | H | H | H |
| 15 | 3-Br-benzyl | H | H | H | H | H | H |
| 16 | 3,5-dichloro-2-hydroxybenzyl | H | H | H | H | H | H |
| 17 | 3-chloro-4-fluorobenzyl | H | H | H | H | H | H |
| 18 | (1-methyl-1H-indol-3-yl)methyl | H | H | H | H | H | H |
| 19 | (benzo[b]thiophen-3-yl)methyl | H | H | H | H | H | H |
| 20 | 4-methoxy-2-hydroxybenzyl | H | H | H | H | H | H |
| 21 | 3-nitrobenzyl | H | H | H | H | H | H |
| 22 | 3-methoxybenzyl | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 23 | 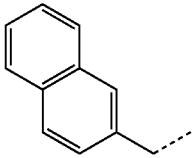 | H | H | H | H | H | H |
| 24 | 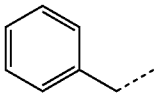 | H | H | H | H | H | H |
| 25 | 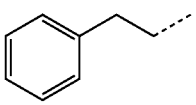 | H | H | H | H | H | H |
| 26 | 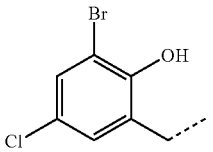 | H | H | H | H | H | H |
| 27 | 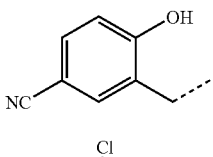 | H | H | H | H | H | H |
| 28 | 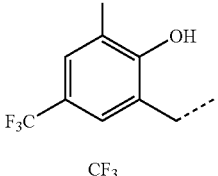 | H | H | H | H | H | H |
| 29 | 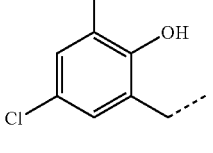 | H | H | H | H | H | H |
| 30 | 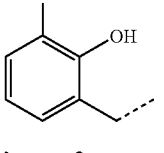 | H | H | H | H | H | H |
| 31 | 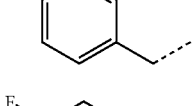 | H | H | H | H | H | H |
| 32 | 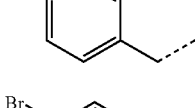 | H | H | H | H | H | H |
| 33 | 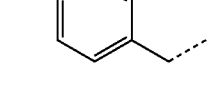 | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 34 | 4-(F₃C)C₆H₄-CH₂- | H | H | H | H | H | H |
| 35 | 4-(HO)C₆H₄-CH₂- | H | H | H | H | H | H |
| 36 | 4-(NC)C₆H₄-CH₂- | H | H | H | H | H | H |
| 37 | 4-(MeSO₂)C₆H₄-CH₂- | H | H | H | H | H | H |
| 38 | 4-(MeOOC)C₆H₄-CH₂- | H | H | H | H | H | H |
| 39 | 4-(Me₂N)C₆H₄-CH₂- | H | H | H | H | H | H |
| 40 | 4-(MeO)C₆H₄-CH₂- | H | H | H | H | H | H |
| 41 | 4-(EtO)C₆H₄-CH₂- | H | H | H | H | H | H |
| 42 | 4-(n-PrO)C₆H₄-CH₂- | H | H | H | H | H | H |
| 43 | 4-(i-PrO)C₆H₄-CH₂- | H | H | H | H | H | H |
| 44 | 4-(i-Pr)C₆H₄-CH₂- | H | H | H | H | H | H |
| 45 | 4-(PhCH₂O)C₆H₄-CH₂- | H | H | H | H | H | H |

TABLE 8-continued

X = —CS—, q = 0, r = 0, Y = —(R4)C=C(R5)—

| Compound No. 8- R1—(CH2)p— | | R2 | R3 | R4 | R5 | R6 | R7 |
|---|---|---|---|---|---|---|---|
| 46 | (phenoxyphenyl-CH2) | H | H | H | H | H | H |
| 47 | (biphenyl-CH2) | H | H | H | H | H | H |
| 48 | (4-acetamidophenyl-CH2) | H | H | H | H | H | H |
| 49 | (2-propylphenyl-CH2) | H | H | H | H | H | H |
| 50 | (2-benzyloxyphenyl-CH2) | H | H | H | H | H | H |
| 51 | (2-methylphenyl-CH2) | H | H | H | H | H | H |
| 52 | (2-cyanophenyl-CH2) | H | H | H | H | H | H |
| 53 | (2-chlorophenyl-CH2) | H | H | H | H | H | H |
| 54 | (2-methoxyphenyl-CH2) | H | H | H | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 55  2-ethoxybenzyl | H | H | H | H | H | H |
| 56  2-biphenylmethyl | H | H | H | H | H | H |
| 57  3-(trifluoromethyl)benzyl | H | H | H | H | H | H |
| 58  3-chloro-2-fluorobenzyl | H | H | H | H | H | H |
| 59  3,5-dichlorobenzyl | H | H | H | H | H | H |
| 60  3-methylbenzyl | H | H | H | H | H | H |
| 61  3-fluoro-5-(trifluoromethyl)benzyl | H | H | H | H | H | H |
| 62  3-(trifluoromethoxy)benzyl | H | H | H | H | H | H |
| 63  4-fluoro-3-methoxybenzyl (MeO at 5) | H | H | H | H | H | H |
| 64  4-fluoro-5-nitrobenzyl | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 65 | 4-O$_2$N-C$_6$H$_4$-CH$_2$- | H | H | H | H | H | H |
| 66 | 2-F-6-methyl-C$_6$H$_3$-CH$_2$- | H | H | H | H | H | H |
| 67 | 3-F$_3$CS-C$_6$H$_4$-CH$_2$- | H | H | H | H | H | H |
| 68 | 2,5-diCl-C$_6$H$_3$-CH$_2$- | H | H | H | H | H | H |
| 69 | 3-F$_2$HC-C$_6$H$_4$-CH$_2$- | H | H | H | H | H | H |
| 70 | 2-F-C$_6$H$_4$-CH$_2$- | H | H | H | H | H | H |
| 71 | 2-NO$_2$-C$_6$H$_4$-CH$_2$- | H | H | H | H | H | H |
| 72 | 2-COOH-C$_6$H$_4$-CH$_2$- | H | H | H | H | H | H |
| 73 | 4-Br-2-OEt-C$_6$H$_3$-CH$_2$- | H | H | H | H | H | H |
| 74 | 2,3-dimethyl-C$_6$H$_3$-CH$_2$- | H | H | H | H | H | H |
| 75 | 3-F-C$_6$H$_4$-CH$_2$- | H | H | H | H | H | H |
| 76 | 2,4-diCl-C$_6$H$_3$-CH$_2$- | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 77 | 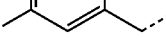 | H | H | H | H | H | H |
| 78 | 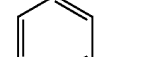 | H | H | H | H | H | H |
| 79 |  | H | H | H | H | H | H |
| 80 | 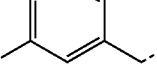 | H | H | H | H | H | H |
| 81 | 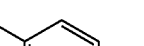 | H | H | H | H | H | H |
| 82 | 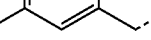 | H | H | H | H | H | H |
| 83 | 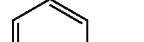 | H | H | H | H | H | H |
| 84 |  | H | H | H | H | H | H |
| 85 | 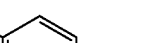 | H | H | H | H | H | H |
| 86 | 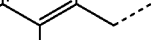 | H | H | H | H | H | H |
| 87 |  | H | H | H | H | H | H |

TABLE 8-continued

X = —CS—, q = 0, r = 0, Y = —(R4)C=C(R5)—

| Compound No. 8- R1—(CH2)p— | | R2 | R3 | R4 | R5 | R6 | R7 |
|---|---|---|---|---|---|---|---|
| 88 | 2-MeO, 3-OEt phenyl | H | H | H | H | H | H |
| 89 | 4-MeO, 2,3-dimethyl phenyl | H | H | H | H | H | H |
| 90 | 3-MeO, 2-OBn phenyl | H | H | H | H | H | H |
| 91 | 4-Cl, 3-NO2 phenyl | H | H | H | H | H | H |
| 92 | 3-(4-MeO-phenoxy)phenyl | H | H | H | H | H | H |
| 93 | 3-(4-methyl-phenoxy)phenyl | H | H | H | H | H | H |
| 94 | 3-(4-Cl-phenoxy)phenyl | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 95 | 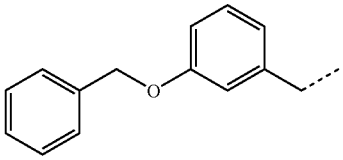 | H | H | H | H | H | H |
| 96 | 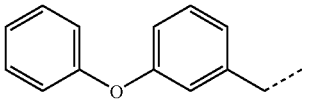 | H | H | H | H | H | H |
| 97 | 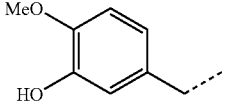 | H | H | H | H | H | H |
| 98 | 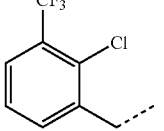 | H | H | H | H | H | H |
| 99 | 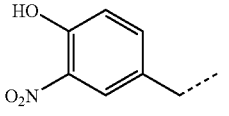 | H | H | H | H | H | H |
| 100 | 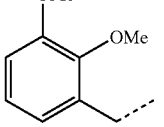 | H | H | H | H | H | H |
| 101 | 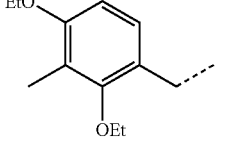 | H | H | H | H | H | H |
| 102 | 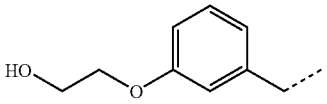 | H | H | H | H | H | H |
| 103 | 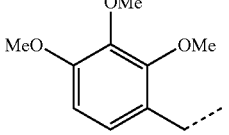 | H | H | H | H | H | H |
| 104 | 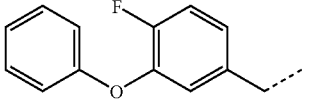 | H | H | H | H | H | H |

TABLE 8-continued

| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 105 | 2,3-dimethoxy-6-COOH-benzyl (MeO, OMe, COOH substituted phenyl-CH2-) | H | H | H | H | H | H |
| 106 | 4-Cl-2-NO2-benzyl | H | H | H | H | H | H |
| 107 | 3,5-dihydroxybenzyl | H | H | H | H | H | H |
| 108 | 4-MeO-3-benzyloxy-benzyl | H | H | H | H | H | H |
| 109 | 3,4-diethoxybenzyl | H | H | H | H | H | H |
| 110 | 3-COOH-benzyl | H | H | H | H | H | H |
| 111 | 4-MeO-2-HO-benzyl (ortho-OMe, para-OH relative) | H | H | H | H | H | H |
| 112 | 4-NO2-3-HO-benzyl | H | H | H | H | H | H |
| 113 | 3,5-bis(CF3)-benzyl | H | H | H | H | H | H |
| 114 | 2-OMe-3-NO2-benzyl | H | H | H | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 115 4-methylnaphthalen-1-ylmethyl | H | H | H | H | H | H |
| 116 7-methyl-1-methyl-1H-indol-3-ylmethyl (MeN) | H | H | H | H | H | H |
| 117 2-methoxynaphthalen-1-ylmethyl (OMe) | H | H | H | H | H | H |
| 118 benzofuran-2-ylmethyl | H | H | H | H | H | H |
| 119 1,2-dimethyl-1H-indol-3-ylmethyl (MeN) | H | H | H | H | H | H |
| 120 quinolin-8-ylmethyl | H | H | H | H | H | H |
| 121 2-hydroxynaphthalen-1-ylmethyl (OH) | H | H | H | H | H | H |
| 122 2-acetoxynaphthalen-1-ylmethyl (OAc) | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 123 | naphthalene-1-ol-2-yl-CH2 | H | H | H | H | H | H |
| 124 | 1H-indol-7-yl-CH2 | H | H | H | H | H | H |
| 125 | quinolin-4-yl-CH2 | H | H | H | H | H | H |
| 126 | 1-methyl-5-methyl-1H-indol-3-yl-CH2 | H | H | H | H | H | H |
| 127 | anthracen-9-yl-CH2 | H | H | H | H | H | H |
| 128 | 2-methylnaphthalen-1-yl-CH2 | H | H | H | H | H | H |
| 129 | 2-ethoxynaphthalen-1-yl-CH2 | H | H | H | H | H | H |
| 130 | 1H-indol-3-yl-CH2 | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 131 | 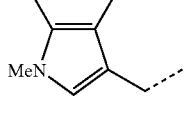 | H | H | H | H | H | H |
| 132 | 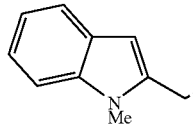 | H | H | H | H | H | H |
| 133 | 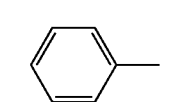 | H | H | H | H | H | H |
| 134 | 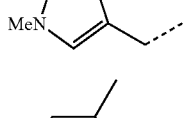 | H | H | H | H | H | H |
| 135 | 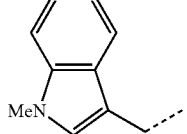 | H | H | H | H | H | H |
| 136 | 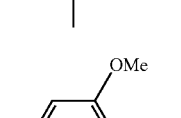 | H | H | H | H | H | H |
| 137 | 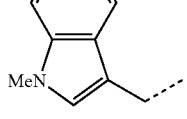 | H | H | H | H | H | H |
| 138 | 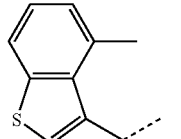 | H | H | H | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 139 (1-acetyl-indol-3-yl) | H | H | H | H | H | H |
| 140 (quinolin-2-yl) | H | H | H | H | H | H |
| 141 (6-methoxy-1-methyl-indol-3-yl) | H | H | H | H | H | H |
| 142 (3-methyl-benzothiophen-2-yl) | H | H | H | H | H | H |
| 143 (4-methoxy-naphthalen-1-yl) | H | H | H | H | H | H |
| 144 (phenanthren-9-yl) | H | H | H | H | H | H |
| 145 (2-methoxy-naphthalen-6-yl) | H | H | H | H | H | H |
| 146 (1-bromo-naphthalen-2-yl) | H | H | H | H | H | H |

TABLE 8-continued

| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 147 | [4-(dimethylamino)naphthalen-1-yl]methyl | H | H | H | H | H | H |
| 148 | (2,3-dihydro-1,4-benzodioxin-6-yl)methyl | H | H | H | H | H | H |
| 149 | (2,2-dimethylchroman-6-yl)methyl | H | H | H | H | H | H |
| 150 | (2,3-dihydro-1-benzofuran-5-yl)methyl | H | H | H | H | H | H |
| 151 | (9-ethyl-9H-carbazol-3-yl)methyl | H | H | H | H | H | H |
| 152 | (1,3-benzodioxol-4-yl)methyl | H | H | H | H | H | H |
| 153 | (1,3-benzodioxol-5-yl)methyl | H | H | H | H | H | H |
| 154 | 3-phenylpropyl | H | H | H | H | H | H |
| 155 | 4-phenylbutyl | H | H | H | H | H | H |
| 156 | cyclohexylmethyl | H | H | H | H | H | H |
| 157 | (2-hydroxy-5-iodophenyl)methyl | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 158 | 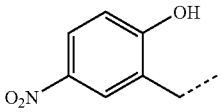 | H | H | H | H | H | H |
| 159 | 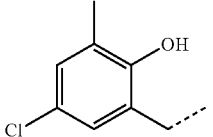 | H | H | H | H | H | H |
| 160 | 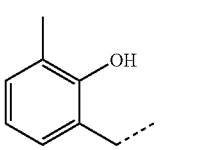 | H | H | H | H | H | H |
| 161 | 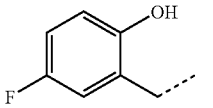 | H | H | H | H | H | H |
| 162 | 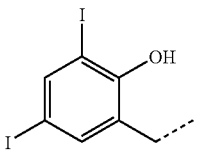 | H | H | H | H | H | H |
| 163 | 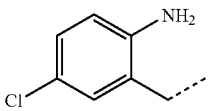 | H | H | H | H | H | H |
| 164 | 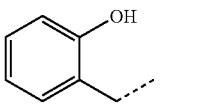 | H | H | H | H | H | H |
| 165 | 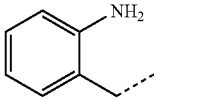 | H | H | H | H | H | H |
| 166 | 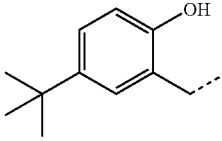 | H | H | H | H | H | H |
| 167 | 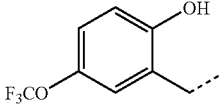 | H | H | H | H | H | H |
| 168 | 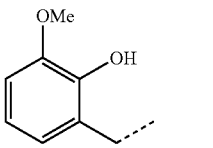 | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 169 | 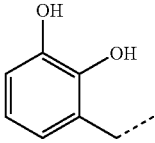 | H | H | H | H | H | H |
| 170 | 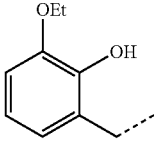 | H | H | H | H | H | H |
| 171 | 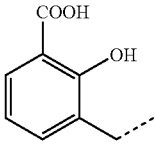 | H | H | H | H | H | H |
| 172 | 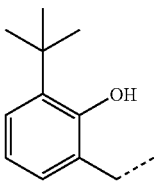 | H | H | H | H | H | H |
| 173 | 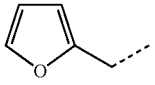 | H | H | H | H | H | H |
| 174 | 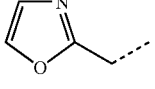 | H | H | H | H | H | H |
| 175 | 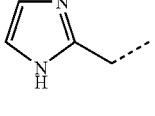 | H | H | H | H | H | H |
| 176 | 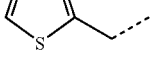 | H | H | H | H | H | H |
| 177 | 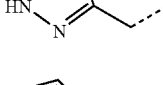 | H | H | H | H | H | H |
| 178 | 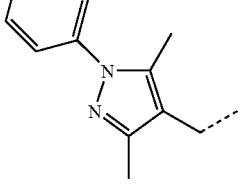 | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 179 | 1-phenyl-2,5-dimethylpyrrol-3-ylmethyl | H | H | H | H | H | H |
| 180 | 5-(4-chlorophenyl)furan-2-ylmethyl | H | H | H | H | H | H |
| 181 | thiophen-2-ylmethyl | H | H | H | H | H | H |
| 182 | 1H-pyrrol-2-ylmethyl | H | H | H | H | H | H |
| 183 | pyridin-2-ylmethyl | H | H | H | H | H | H |
| 184 | pyridin-3-ylmethyl | H | H | H | H | H | H |
| 185 | pyridin-4-ylmethyl | H | H | H | H | H | H |
| 186 | 5-chloro-2-hydroxybenzyl | H | H | H | Cl | H | H |
| 187 | 2-hydroxy-5-nitrobenzyl | H | H | H | Cl | H | H |
| 188 | 2-hydroxy-5-methoxybenzyl | H | H | H | Cl | H | H |
| 189 | 3-chlorobenzyl | H | H | H | Cl | H | H |
| 190 | 3-bromobenzyl | H | H | H | Cl | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 191 3-nitrobenzyl | H | H | H | Cl | H | H |
| 192 3-methoxybenzyl | H | H | H | Cl | H | H |
| 193 2,4-dichloro-6-hydroxybenzyl | H | H | H | Cl | H | H |
| 194 (1-methylindol-3-yl)methyl | H | H | H | Cl | H | H |
| 195 benzothiophen-3-ylmethyl | H | H | H | Cl | H | H |
| 196 benzyl | H | H | H | Cl | H | H |
| 197 3-phenylpropyl | H | H | H | Cl | H | H |
| 198 4-bromo-2-hydroxybenzyl | H | H | H | Cl | H | H |
| 199 naphthalen-2-ylmethyl | H | H | H | Cl | H | H |
| 200 phenethyl | H | H | H | Cl | H | H |
| 201 2,4-dichloro-6-hydroxybenzyl | H | H | Cl | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 202 | 2,4-dichloro-6-hydroxyphenyl-CH2 | H | H | H | OMe | H | H |
| 203 | 2,4-dichloro-6-hydroxyphenyl-CH2 | H | H | H | COOMe | H | H |
| 204 | 2,4-dichloro-6-hydroxyphenyl-CH2 | H | H | H | H | Cl | H |
| 205 | 2,4-dichloro-6-hydroxyphenyl-CH2 | H | H | H | H | COOMe | H |
| 206 | 2,4-dichloro-6-hydroxyphenyl-CH2 | H | H | H | H | H | Cl |
| 207 | 2,4-dichloro-6-hydroxyphenyl-CH2 | H | H | H | OCF3 | H | H |
| 208 | 2,4-dichloro-6-hydroxyphenyl-CH2 | H | H | COOMe | H | H | H |
| 209 | 2,4-dichloro-6-hydroxyphenyl-CH2 | H | H | H | CF3 | H | H |
| 210 | 2,4-dichloro-6-hydroxyphenyl-CH2 | H | H | H | Me | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 211 | 2,4-dichloro-6-hydroxyphenyl-CH< | H | H | H | F | H | H |
| 212 | 2,4-dichloro-6-hydroxyphenyl-CH< | H | H | H | OH | H | H |
| 213 | 2,4-dichloro-6-hydroxyphenyl-CH< | H | H | H | NO2 | H | H |
| 214 | 2,4-dichloro-6-hydroxyphenyl-CH< | H | H | H | F | F | H |
| 215 | 2,4-dichloro-6-hydroxyphenyl-CH< | H | H | F | H | H | H |
| 216 | 2,4-dichloro-6-hydroxyphenyl-CH< | H | H | Me | H | H | H |
| 217 | 2,4-dichloro-6-hydroxyphenyl-CH< | H | H | H | CN | H | H |
| 218 | 4-chloro-2-hydroxyphenyl-CH< | H | H | Cl | H | H | H |
| 219 | 4-chloro-2-hydroxyphenyl-CH< | H | H | H | OMe | H | H |
| 220 | 4-chloro-2-hydroxyphenyl-CH< | H | H | H | COOMe | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 221 | 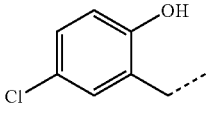 | H | H | H | H | Cl | H |
| 222 | 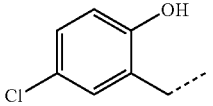 | H | H | H | H | COOMe | H |
| 223 | 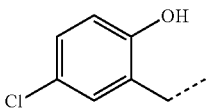 | H | H | H | H | H | Cl |
| 224 | 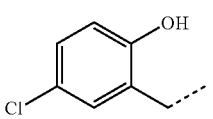 | H | H | H | OCF3 | H | H |
| 225 | 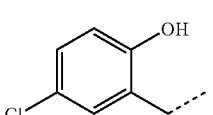 | H | H | COOMe | H | H | H |
| 226 | 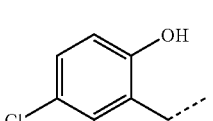 | H | H | H | CF3 | H | H |
| 227 | 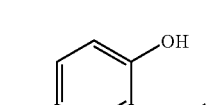 | H | H | H | Me | H | H |
| 228 | 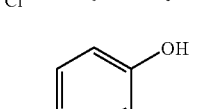 | H | H | H | F | H | H |
| 229 | 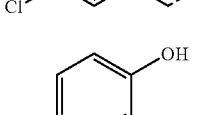 | H | H | H | OH | H | H |
| 230 | 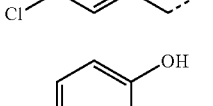 | H | H | H | NO2 | H | H |
| 231 | 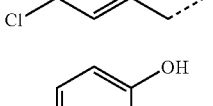 | H | H | H | F | F | H |
| 232 | 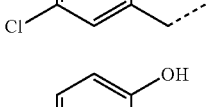 | H | H | F | H | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 233 | 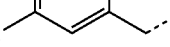 | H | H | Me | H | H | H |
| 234 | 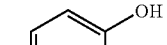 | H | H | H | CN | H | H |
| 235 | 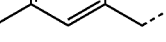 | H | H | Cl | H | H | H |
| 236 | 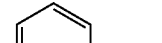 | H | H | H | OMe | H | H |
| 237 | 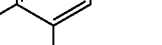 | H | H | H | COOMe | H | H |
| 238 | 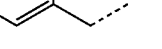 | H | H | H | H | Cl | H |
| 239 | 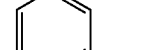 | H | H | H | H | COOMe | H |
| 240 |  | H | H | H | H | H | Cl |
| 241 | 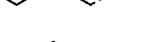 | H | H | H | OCF3 | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 242 | 1-naphthylmethyl | H | H | COOMe | H | H | H |
| 243 | 1-naphthylmethyl | H | H | H | CF3 | H | H |
| 244 | 1-naphthylmethyl | H | H | H | Me | H | H |
| 245 | 1-naphthylmethyl | H | H | H | F | H | H |
| 246 | 1-naphthylmethyl | H | H | H | OH | H | H |
| 247 | 1-naphthylmethyl | H | H | H | NO2 | H | H |
| 248 | 1-naphthylmethyl | H | H | H | F | F | H |
| 249 | 1-naphthylmethyl | H | H | F | H | H | H |
| 250 | 1-naphthylmethyl | H | H | Me | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 251 naphthalen-1-ylmethyl | H | H | H | CN | H | H |
| 252 phenylpropyl | H | H | Cl | H | H | H |
| 253 phenylpropyl | H | H | H | OMe | H | H |
| 254 phenylpropyl | H | H | H | COOMe | H | H |
| 255 phenylpropyl | H | H | H | H | Cl | H |
| 256 phenylpropyl | H | H | H | H | COOMe | H |
| 257 phenylpropyl | H | H | H | H | H | Cl |
| 258 phenylpropyl | H | H | H | OCF3 | H | H |
| 259 phenylpropyl | H | H | COOMe | H | H | H |
| 260 phenylpropyl | H | H | H | CF3 | H | H |
| 261 phenylpropyl | H | H | H | Me | H | H |
| 262 phenylpropyl | H | H | H | F | H | H |
| 263 phenylpropyl | H | H | H | OH | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 264 (phenylpropyl) | H | H | H | NO2 | H | H |
| 265 (phenylpropyl) | H | H | H | F | F | H |
| 266 (phenylpropyl) | H | H | F | H | H | H |
| 267 (phenylpropyl) | H | H | Me | H | H | H |
| 268 (phenylpropyl) | H | H | H | CN | H | H |
| 269 (3,5-dichloro-2-hydroxybenzyl) | H | H | H | H | H | COOMe |
| 270 (3,5-dichloro-2-hydroxybenzyl) | H | H | H | H | F | H |
| 271 (3,5-dichloro-2-hydroxybenzyl) | H | H | H | H | H | F |
| 272 (3,5-dichloro-2-hydroxybenzyl) | H | H | H | H | Me | H |
| 273 (3,5-dichloro-2-hydroxybenzyl) | H | H | H | H | H | Me |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 274 2,4-dichloro-6-hydroxybenzyl | H | H | OMe | H | H | H |
| 275 2,4-dichloro-6-hydroxybenzyl | H | H | H | H | OMe | H |
| 276 2,4-dichloro-6-hydroxybenzyl | H | H | H | H | H | OMe |
| 277 2,4-dichloro-6-hydroxybenzyl | H | H | CF3 | H | H | H |
| 278 2,4-dichloro-6-hydroxybenzyl | H | H | H | H | CF3 | H |
| 279 2,4-dichloro-6-hydroxybenzyl | H | H | H | H | H | CF3 |
| 280 2,4-dichloro-6-hydroxybenzyl | H | H | OH | H | H | H |
| 281 2,4-dichloro-6-hydroxybenzyl | H | H | H | H | OH | H |
| 282 2,4-dichloro-6-hydroxybenzyl | H | H | H | H | H | OH |

TABLE 8-continued

X = —CS—, q = 0, r = 0, Y = —(R4)C═C(R5)—

| Compound No. 8- R1—(CH2)p— | R2 | R3 | R4 | R5 | R6 | R7 |
|---|---|---|---|---|---|---|
| 283 [2,4-dichloro-6-hydroxyphenyl-CH2—] | H | H | OCF3 | H | H | H |
| 284 [2,4-dichloro-6-hydroxyphenyl-CH2—] | H | H | H | H | OCF3 | H |
| 285 [2,4-dichloro-6-hydroxyphenyl-CH2—] | H | H | H | H | H | OCF3 |
| 286 [2,4-dichloro-6-hydroxyphenyl-CH2—] | H | H | NO2 | H | H | H |
| 287 [2,4-dichloro-6-hydroxyphenyl-CH2—] | H | H | H | H | NO2 | H |
| 288 [2,4-dichloro-6-hydroxyphenyl-CH2—] | H | H | H | H | H | NO2 |
| 289 [2,4-dichloro-6-hydroxyphenyl-CH2—] | H | H | CN | H | H | H |
| 290 [2,4-dichloro-6-hydroxyphenyl-CH2—] | H | H | H | H | CN | H |
| 291 [2,4-dichloro-6-hydroxyphenyl-CH2—] | H | H | H | H | H | CN |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 292 2,4-dichloro-6-hydroxybenzyl | H | H | Br | H | H | H |
| 293 2,4-dichloro-6-hydroxybenzyl | H | H | H | Br | H | H |
| 294 2,4-dichloro-6-hydroxybenzyl | H | H | H | H | Br | H |
| 295 2,4-dichloro-6-hydroxybenzyl | H | H | H | H | H | Br |
| 296 2,4-dichloro-6-hydroxybenzyl | H | H | COOH | H | H | H |
| 297 2,4-dichloro-6-hydroxybenzyl | H | H | H | COOH | H | H |
| 298 2,4-dichloro-6-hydroxybenzyl | H | H | H | H | COOH | H |
| 299 2,4-dichloro-6-hydroxybenzyl | H | H | H | H | H | COOH |
| 300 2,4-dichloro-6-hydroxybenzyl | H | H | NHCOMe | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 301  2,4-dichloro-6-hydroxybenzyl | H | H | H | NHCOMe | H | H |
| 302  2,4-dichloro-6-hydroxybenzyl | H | H | H | H | NHCOMe | |
| 303  2,4-dichloro-6-hydroxybenzyl | H | H | H | H | H | NHCOMe |
| 304  2,4-dichloro-6-hydroxybenzyl | H | H | SO2NH2 | H | H | H |
| 305  2,4-dichloro-6-hydroxybenzyl | H | H | H | SO2NH2 | H | H |
| 306  2,4-dichloro-6-hydroxybenzyl | H | H | H | H | SO2NH2 | H |
| 307  2,4-dichloro-6-hydroxybenzyl | H | H | H | H | H | SO2NH2 |
| 308  2,4-dichloro-6-hydroxybenzyl | H | H | Me | Me | H | H |
| 309  2,4-dichloro-6-hydroxybenzyl | H | H | Me | H | Me | H |

TABLE 8-continued

X = —CS—, q = 0, r = 0, Y = —(R4)C═C(R5)—

| Compound No. 8- R1—(CH2)p— | R2 | R3 | R4 | R5 | R6 | R7 |
|---|---|---|---|---|---|---|
| 310 2,4-dichloro-6-hydroxybenzyl | H | H | H | Me | Me | H |
| 311 2,4-dichloro-6-hydroxybenzyl | H | H | F | F | H | H |
| 312 2,4-dichloro-6-hydroxybenzyl | H | H | F | H | F | H |
| 313 2,4-dichloro-6-hydroxybenzyl | H | H | H | F | F | H |
| 314 2,4-dichloro-6-hydroxybenzyl | H | H | Cl | Cl | H | H |
| 315 2,4-dichloro-6-hydroxybenzyl | H | H | Cl | H | Cl | H |
| 316 2,4-dichloro-6-hydroxybenzyl | H | H | H | Cl | Cl | H |
| 317 2,4-dichloro-6-hydroxybenzyl | H | H | Me | F | H | H |
| 318 2,4-dichloro-6-hydroxybenzyl | H | H | Me | Cl | H | H |

TABLE 8-continued

X = —CS—, q = 0, r = 0, Y = —(R4)C=C(R5)—

| Compound No. 8- R1—(CH2)p— | | R2 | R3 | R4 | R5 | R6 | R7 |
|---|---|---|---|---|---|---|---|
| 319 | 2,4-diCl-phenol-CH2 | H | H | Me | OH | H | H |
| 320 | 2,4-diCl-phenol-CH2 | H | H | Me | OMe | H | H |
| 321 | 2,4-diCl-phenol-CH2 | H | H | F | Me | H | H |
| 322 | 2,4-diCl-phenol-CH2 | H | H | F | Cl | H | H |
| 323 | 2,4-diCl-phenol-CH2 | H | H | F | OH | H | H |
| 324 | 2,4-diCl-phenol-CH2 | H | H | F | OMe | H | H |
| 325 | 2,4-diCl-phenol-CH2 | H | H | Cl | Me | H | H |
| 326 | 2,4-diCl-phenol-CH2 | H | H | Cl | F | H | H |
| 327 | 2,4-diCl-phenol-CH2 | H | H | Cl | OH | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 328 | 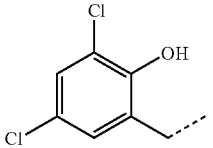 | H | H | Cl | OMe | H | H |
| 329 | 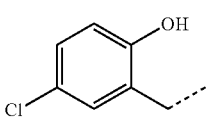 | H | H | H | H | H | COOMe |
| 330 | 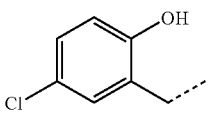 | H | H | H | H | F | H |
| 331 | 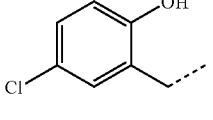 | H | H | H | H | H | F |
| 332 | 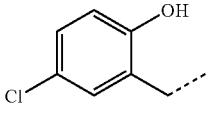 | H | H | H | H | Me | H |
| 333 | 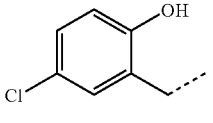 | H | H | H | H | H | Me |
| 334 | 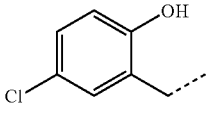 | H | H | OMe | H | H | H |
| 335 | 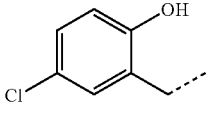 | H | H | H | H | OMe | H |
| 336 | 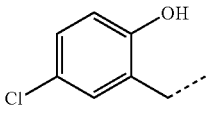 | H | H | H | H | H | OMe |
| 337 | 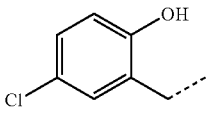 | H | H | CF3 | H | H | H |
| 338 | 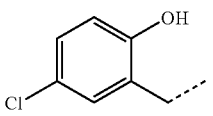 | H | H | H | H | CF3 | H |
| 339 | 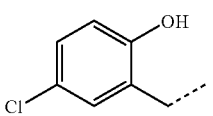 | H | H | H | H | H | CF3 |

TABLE 8-continued

X = —CS—, q = 0, r = 0, Y = —(R4)C=C(R5)—

| Compound No. 8- R1—(CH2)p— | | R2 | R3 | R4 | R5 | R6 | R7 |
|---|---|---|---|---|---|---|---|
| 340 | 4-Cl-2-OH-benzyl | H | H | OH | H | H | H |
| 341 | 4-Cl-2-OH-benzyl | H | H | H | H | OH | H |
| 342 | 4-Cl-2-OH-benzyl | H | H | H | H | H | OH |
| 343 | 4-Cl-2-OH-benzyl | H | H | OCF3 | H | H | H |
| 344 | 4-Cl-2-OH-benzyl | H | H | H | H | OCF3 | H |
| 345 | 4-Cl-2-OH-benzyl | H | H | H | H | H | OCF3 |
| 346 | 4-Cl-2-OH-benzyl | H | H | NO2 | H | H | H |
| 347 | 4-Cl-2-OH-benzyl | H | H | H | H | NO2 | H |
| 348 | 4-Cl-2-OH-benzyl | H | H | H | H | H | NO2 |
| 349 | 4-Cl-2-OH-benzyl | H | H | CN | H | H | H |
| 350 | 4-Cl-2-OH-benzyl | H | H | H | H | CN | H |
| 351 | 4-Cl-2-OH-benzyl | H | H | H | H | H | CN |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 352 | 4-Cl-2-HO-C6H3-CH2- | H | H | Br | H | H | H |
| 353 | 4-Cl-2-HO-C6H3-CH2- | H | H | H | Br | H | H |
| 354 | 4-Cl-2-HO-C6H3-CH2- | H | H | H | H | Br | H |
| 355 | 4-Cl-2-HO-C6H3-CH2- | H | H | H | H | H | Br |
| 356 | 4-Cl-2-HO-C6H3-CH2- | H | H | COOH | H | H | H |
| 357 | 4-Cl-2-HO-C6H3-CH2- | H | H | H | COOH | H | H |
| 358 | 4-Cl-2-HO-C6H3-CH2- | H | H | H | H | COOH | H |
| 359 | 4-Cl-2-HO-C6H3-CH2- | H | H | H | H | H | COOH |
| 360 | 4-Cl-2-HO-C6H3-CH2- | H | H | NHCOMe | H | H | H |
| 361 | 4-Cl-2-HO-C6H3-CH2- | H | H | H | NHCOMe | H | H |
| 362 | 4-Cl-2-HO-C6H3-CH2- | H | H | H | H | NHCOMe | H |
| 363 | 4-Cl-2-HO-C6H3-CH2- | H | H | H | H | H | NHCOMe |

TABLE 8-continued

X = —CS—, q = 0, r = 0, Y = —(R4)C═C(R5)—

| Compound No. 8- | R1—(CH2)p— | R2 | R3 | R4 | R5 | R6 | R7 |
|---|---|---|---|---|---|---|---|
| 364 | 4-Cl-2-(OH)-C6H3-CH2- | H | H | SO2NH2 | H | H | H |
| 365 | 4-Cl-2-(OH)-C6H3-CH2- | H | H | H | SO2NH2 | H | H |
| 366 | 4-Cl-2-(OH)-C6H3-CH2- | H | H | H | H | SO2NH2 | H |
| 367 | 4-Cl-2-(OH)-C6H3-CH2- | H | H | H | H | H | SO2NH2 |
| 368 | 4-Cl-2-(OH)-C6H3-CH2- | H | H | Me | Me | H | H |
| 369 | 4-Cl-2-(OH)-C6H3-CH2- | H | H | Me | H | Me | H |
| 370 | 4-Cl-2-(OH)-C6H3-CH2- | H | H | H | Me | Me | H |
| 371 | 4-Cl-2-(OH)-C6H3-CH2- | H | H | F | F | H | H |
| 372 | 4-Cl-2-(OH)-C6H3-CH2- | H | H | F | H | F | H |
| 373 | 4-Cl-2-(OH)-C6H3-CH2- | H | H | H | F | F | H |
| 374 | 4-Cl-2-(OH)-C6H3-CH2- | H | H | Cl | Cl | H | H |
| 375 | 4-Cl-2-(OH)-C6H3-CH2- | H | H | Cl | H | Cl | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 376 | 4-Cl-2-(OH)-C6H3-CH2- | H | H | H | Cl | Cl | H |
| 377 | 4-Cl-2-(OH)-C6H3-CH2- | H | H | Me | F | H | H |
| 378 | 4-Cl-2-(OH)-C6H3-CH2- | H | H | Me | Cl | H | H |
| 379 | 4-Cl-2-(OH)-C6H3-CH2- | H | H | Me | OH | H | H |
| 380 | 4-Cl-2-(OH)-C6H3-CH2- | H | H | Me | OMe | H | H |
| 381 | 4-Cl-2-(OH)-C6H3-CH2- | H | H | F | Me | H | H |
| 382 | 4-Cl-2-(OH)-C6H3-CH2- | H | H | F | Cl | H | H |
| 383 | 4-Cl-2-(OH)-C6H3-CH2- | H | H | F | OH | H | H |
| 384 | 4-Cl-2-(OH)-C6H3-CH2- | H | H | F | OMe | H | H |
| 385 | 4-Cl-2-(OH)-C6H3-CH2- | H | H | Cl | Me | H | H |
| 386 | 4-Cl-2-(OH)-C6H3-CH2- | H | H | Cl | F | H | H |
| 387 | 4-Cl-2-(OH)-C6H3-CH2- | H | H | Cl | OH | H | H |

TABLE 8-continued
X = —CS—, q = 0, r = 0, Y = —(R4)C═C(R5)—
| Compound No. 8- | R1—(CH2)p— | R2 | R3 | R4 | R5 | R6 | R7 |
|---|---|---|---|---|---|---|---|
| 388 | 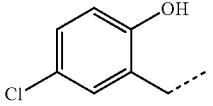 | H | H | Cl | OMe | H | H |
| 389 | 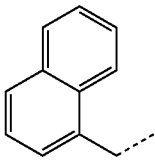 | H | H | H | H | H | COOMe |
| 390 | 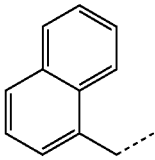 | H | H | H | H | F | H |
| 391 | 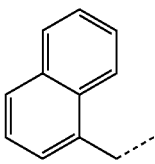 | H | H | H | H | H | F |
| 392 | 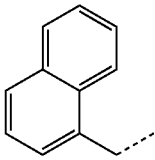 | H | H | H | H | Me | H |
| 393 | 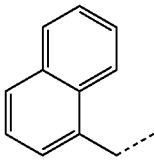 | H | H | H | H | H | Me |
| 394 | 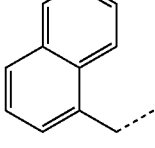 | H | H | OMe | H | H | H |
| 395 | 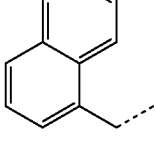 | H | H | H | H | OMe | H |
| 396 | 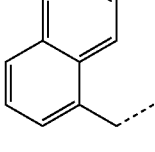 | H | H | H | H | H | OMe |

TABLE 8-continued
X = —CS—, q = 0, r = 0, Y = —(R4)C═C(R5)—
| Compound No. 8- | R1—(CH2)p— | R2 | R3 | R4 | R5 | R6 | R7 |
|---|---|---|---|---|---|---|---|
| 397 | 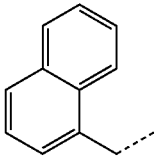 | H | H | CF3 | H | H | H |
| 398 | 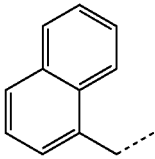 | H | H | H | H | CF3 | H |
| 399 | 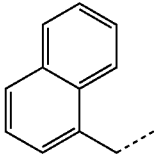 | H | H | H | H | H | CF3 |
| 400 | 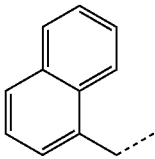 | H | H | OH | H | H | H |
| 401 | 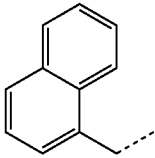 | H | H | H | H | OH | H |
| 402 | 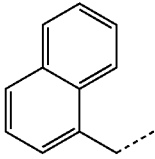 | H | H | H | H | H | OH |
| 403 | 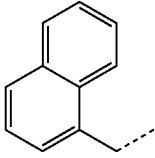 | H | H | OCF3 | H | H | H |
| 404 | 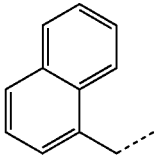 | H | H | H | H | OCF3 | H |
| 405 | 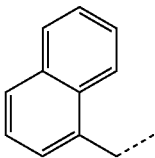 | H | H | H | H | H | OCF3 |

TABLE 8-continued
| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 406 | 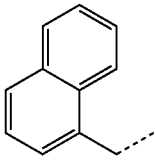 | H | H | NO2 | H | H | H |
| 407 | 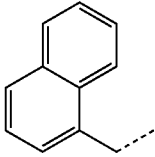 | H | H | H | H | NO2 | H |
| 408 | 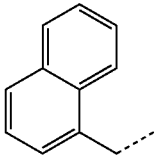 | H | H | H | H | H | NO2 |
| 409 | 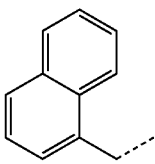 | H | H | CN | H | H | H |
| 410 | 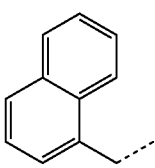 | H | H | H | H | CN | H |
| 411 | 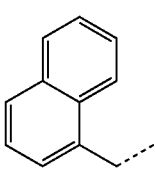 | H | H | H | H | H | CN |
| 412 | 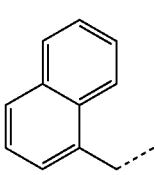 | H | H | Br | H | H | H |
| 413 | 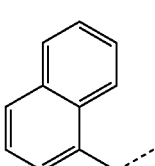 | H | H | H | Br | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 414 | 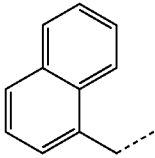 | H | H | H | H | Br | H |
| 415 | 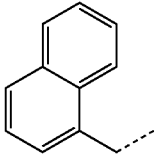 | H | H | H | H | H | Br |
| 416 | 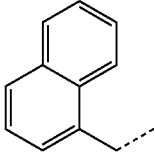 | H | H | COOH | H | H | H |
| 417 | 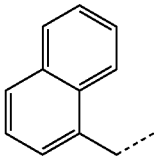 | H | H | H | COOH | H | H |
| 418 | 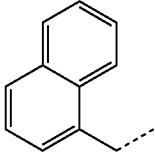 | H | H | H | H | COOH | H |
| 419 | 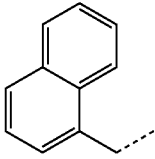 | H | H | H | H | H | COOH |
| 420 | 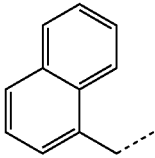 | H | H | NHCOMe | H | H | H |
| 421 | 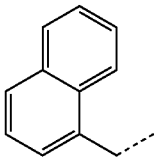 | H | H | H | NHCOMe | H | H |
| 422 | 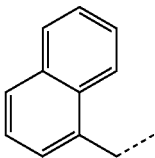 | H | H | H | H | NHCOMe | |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 423 (1-naphthylmethyl) | H | H | H | H | H | NHCOMe |
| 424 (1-naphthylmethyl) | H | H | SO2NH2 | H | H | H |
| 425 (1-naphthylmethyl) | H | H | H | SO2NH2 | H | H |
| 426 (1-naphthylmethyl) | H | H | H | H | SO2NH2 | H |
| 427 (1-naphthylmethyl) | H | H | H | H | H | SO2NH2 |
| 428 (1-naphthylmethyl) | H | H | Me | Me | H | H |
| 429 (1-naphthylmethyl) | H | H | Me | H | Me | H |
| 430 (1-naphthylmethyl) | H | H | H | Me | Me | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
| --- | --- | --- | --- | --- | --- | --- |
| 431 naphthalen-1-ylmethyl | H | H | F | F | H | H |
| 432 naphthalen-1-ylmethyl | H | H | F | H | F | H |
| 433 naphthalen-1-ylmethyl | H | H | H | F | F | H |
| 434 naphthalen-1-ylmethyl | H | H | Cl | Cl | H | H |
| 435 naphthalen-1-ylmethyl | H | H | Cl | H | Cl | H |
| 436 naphthalen-1-ylmethyl | H | H | H | Cl | Cl | H |
| 437 naphthalen-1-ylmethyl | H | H | Me | F | H | H |
| 438 naphthalen-1-ylmethyl | H | H | Me | Cl | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 439 | 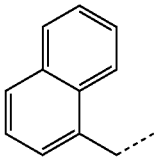 | H | H | Me | OH | H | H |
| 440 | 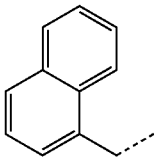 | H | H | Me | OMe | H | H |
| 441 | 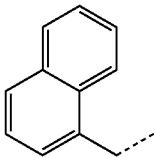 | H | H | F | Me | H | H |
| 442 | 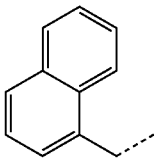 | H | H | F | Cl | H | H |
| 443 | 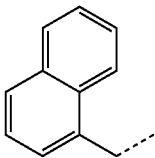 | H | H | F | OH | H | H |
| 444 | 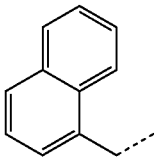 | H | H | F | OMe | H | H |
| 445 | 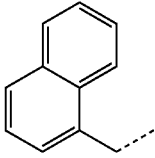 | H | H | Cl | Me | H | H |
| 446 | 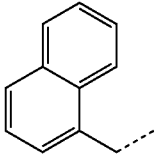 | H | H | Cl | F | H | H |
| 447 | 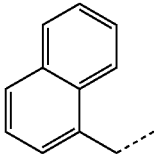 | H | H | Cl | OH | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 448 | naphthalen-1-ylmethyl | H | H | Cl | OMe | H | H |
| 449 | 5-bromo-2-hydroxybenzyl | H | H | Cl | H | H | H |
| 450 | 5-bromo-2-hydroxybenzyl | H | H | H | OMe | H | H |
| 451 | 5-bromo-2-hydroxybenzyl | H | H | H | COOMe | H | H |
| 452 | 5-bromo-2-hydroxybenzyl | H | H | H | H | Cl | H |
| 453 | 5-bromo-2-hydroxybenzyl | H | H | H | H | COOMe | H |
| 454 | 5-bromo-2-hydroxybenzyl | H | H | H | H | H | Cl |
| 455 | 5-bromo-2-hydroxybenzyl | H | H | H | OCF3 | H | H |
| 456 | 5-bromo-2-hydroxybenzyl | H | H | COOMe | H | H | H |
| 457 | 5-bromo-2-hydroxybenzyl | H | H | H | CF3 | H | H |
| 458 | 5-bromo-2-hydroxybenzyl | H | H | H | Me | H | H |
| 459 | 5-bromo-2-hydroxybenzyl | H | H | H | F | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 460 | 4-Br, 2-(CH2)- phenol | H | H | H | OH | H | H |
| 461 | 4-Br, 2-(CH2)- phenol | H | H | H | NO2 | H | H |
| 462 | 4-Br, 2-(CH2)- phenol | H | H | H | F | F | H |
| 463 | 4-Br, 2-(CH2)- phenol | H | H | F | H | H | H |
| 464 | 4-Br, 2-(CH2)- phenol | H | H | Me | H | H | H |
| 465 | 4-Br, 2-(CH2)- phenol | H | H | H | CN | H | H |
| 466 | 1-Me-indol-3-yl-(CH2)- | H | H | Cl | H | H | H |
| 467 | 1-Me-indol-3-yl-(CH2)- | H | H | H | OMe | H | H |
| 468 | 1-Me-indol-3-yl-(CH2)- | H | H | H | COOMe | H | H |
| 469 | 1-Me-indol-3-yl-(CH2)- | H | H | H | H | Cl | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 470 | 3-(N-methylindolyl)methyl | H | H | H | H | COOMe | H |
| 471 | 3-(N-methylindolyl)methyl | H | H | H | H | H | Cl |
| 472 | 3-(N-methylindolyl)methyl | H | H | H | OCF3 | H | H |
| 473 | 3-(N-methylindolyl)methyl | H | H | COOMe | H | H | H |
| 474 | 3-(N-methylindolyl)methyl | H | H | H | CF3 | H | H |
| 475 | 3-(N-methylindolyl)methyl | H | H | H | Me | H | H |
| 476 | 3-(N-methylindolyl)methyl | H | H | H | F | H | H |
| 477 | 3-(N-methylindolyl)methyl | H | H | H | OH | H | H |
| 478 | 3-(N-methylindolyl)methyl | H | H | H | NO2 | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 479 (3-methylindol-3-yl-methyl) | H | H | H | F | F | H |
| 480 (N-methylindol-3-yl-methyl) | H | H | F | H | H | H |
| 481 (N-methylindol-3-yl-methyl) | H | H | Me | H | H | H |
| 482 (N-methylindol-3-yl-methyl) | H | H | H | CN | H | H |
| 483 (benzothiophen-3-yl-methyl) | H | H | Cl | H | H | H |
| 484 (benzothiophen-3-yl-methyl) | H | H | H | OMe | H | H |
| 485 (benzothiophen-3-yl-methyl) | H | H | H | COOMe | H | H |
| 486 (benzothiophen-3-yl-methyl) | H | H | H | H | Cl | H |
| 487 (benzothiophen-3-yl-methyl) | H | H | H | H | COOMe | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 488 benzothiophen-3-ylmethyl | H | H | H | H | H | Cl |
| 489 benzothiophen-3-ylmethyl | H | H | H | OCF3 | H | H |
| 490 benzothiophen-3-ylmethyl | H | H | COOMe | H | H | H |
| 491 benzothiophen-3-ylmethyl | H | H | H | CF3 | H | H |
| 492 benzothiophen-3-ylmethyl | H | H | H | Me | H | H |
| 493 benzothiophen-3-ylmethyl | H | H | H | F | H | H |
| 494 benzothiophen-3-ylmethyl | H | H | H | OH | H | H |
| 495 benzothiophen-3-ylmethyl | H | H | H | NO2 | H | H |
| 496 benzothiophen-3-ylmethyl | H | H | H | F | F | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 497 benzothiophen-3-ylmethyl | H | H | F | H | H | H |
| 498 benzothiophen-3-ylmethyl | H | H | Me | H | H | H |
| 499 benzothiophen-3-ylmethyl | H | H | H | Cn | H | H |
| 500 3,5-dichloro-2-hydroxybenzyl | H | Me | H | H | H | H |
| 501 5-chloro-2-hydroxybenzyl | H | Me | H | H | H | H |
| 502 naphthalen-1-ylmethyl | H | Me | H | H | H | H |
| 503 3-phenylpropyl | H | Me | H | H | H | H |
| 504 5-chloro-3-fluoro-2-hydroxybenzyl | H | H | H | H | H | H |
| 505 5-chloro-3-fluoro-2-hydroxybenzyl | H | H | F | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 506 (4-Cl-2-F-6-OH-phenyl)methyl | H | H | Cl | H | H | H |
| 507 (4-Cl-2-F-6-OH-phenyl)methyl | H | H | Me | H | H | H |
| 508 (4-Cl-2-F-6-OH-phenyl)methyl | H | H | Et | H | H | H |
| 509 (4-Cl-2-F-6-OH-phenyl)methyl | H | H | OMe | H | H | H |
| 510 (4-Cl-2-F-6-OH-phenyl)methyl | H | H | OEt | H | H | H |
| 511 (4-Cl-2-F-6-OH-phenyl)methyl | H | H | CF3 | H | H | H |
| 512 (4-Cl-2-F-6-OH-phenyl)methyl | H | H | OCF3 | H | H | H |
| 513 (4-Cl-2-F-6-OH-phenyl)methyl | H | H | NO2 | H | H | H |
| 514 (4-Cl-2-F-6-OH-phenyl)methyl | H | H | NH2 | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 515 4-Cl-2-F-6-OH-benzyl | H | H | OH | H | H | H |
| 516 4-Cl-2-F-6-OH-benzyl | H | H | CN | H | H | H |
| 517 4-Cl-2-F-6-OH-benzyl | H | H | COMe | H | H | H |
| 518 4-Cl-2-F-6-OH-benzyl | H | H | COOMe | H | H | H |
| 519 4-Cl-2-F-6-OH-benzyl | H | H | H | F | H | H |
| 520 4-Cl-2-F-6-OH-benzyl | H | H | H | Cl | H | H |
| 521 4-Cl-2-F-6-OH-benzyl | H | H | H | Me | H | H |
| 522 4-Cl-2-F-6-OH-benzyl | H | H | H | Et | H | H |
| 523 4-Cl-2-F-6-OH-benzyl | H | H | H | OME | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 524 | 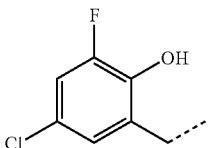 | H | H | H | OEt | H | H |
| 525 | 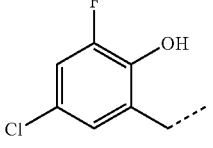 | H | H | H | CF3 | H | H |
| 526 | 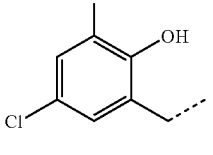 | H | H | H | OCF3 | H | H |
| 527 | 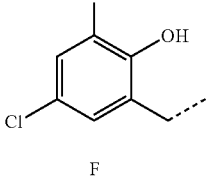 | H | H | H | NO2 | H | H |
| 528 | 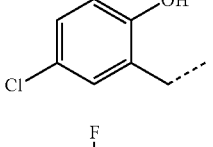 | H | H | H | NH2 | H | H |
| 529 | 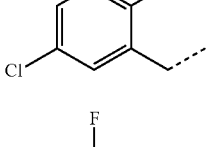 | H | H | H | OH | H | H |
| 530 | 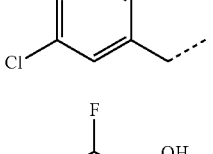 | H | H | H | CN | H | H |
| 531 | 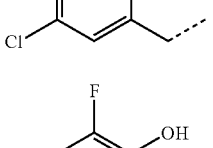 | H | H | H | COMe | H | H |
| 532 | 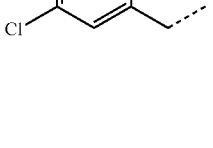 | H | H | H | COOMe | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 533 | 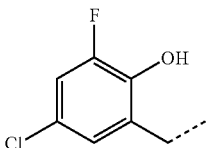 | H | H | F | F | H | H |
| 534 | 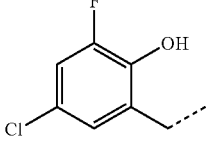 | H | H | F | Cl | H | H |
| 535 | 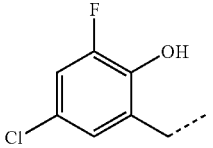 | H | H | F | Me | H | H |
| 536 | 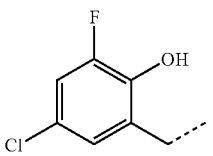 | H | H | F | Et | H | H |
| 537 | 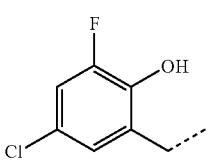 | H | H | F | OMe | H | H |
| 538 | 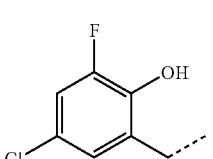 | H | H | F | OEt | H | H |
| 539 | 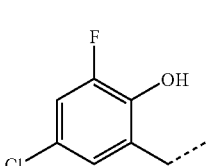 | H | H | F | CF3 | H | H |
| 540 | 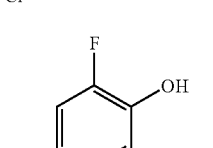 | H | H | F | OCF3 | H | H |
| 541 | 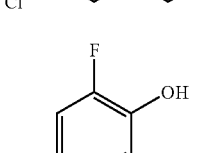 | H | H | Cl | F | H | H |

TABLE 8-continued
| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 542 | 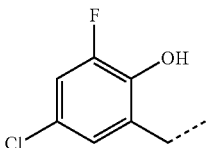 | H | H | Cl | Cl | H | H |
| 543 | 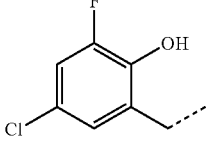 | H | H | Cl | Me | H | H |
| 544 | 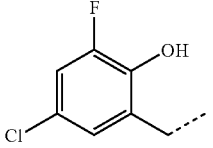 | H | H | Cl | Et | H | H |
| 545 | 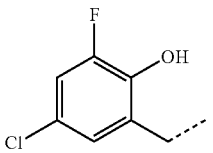 | H | H | Cl | OMe | H | H |
| 546 | 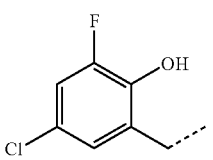 | H | H | Cl | OEt | H | H |
| 547 | 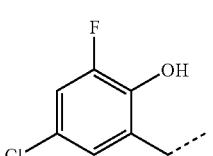 | H | H | Cl | CF3 | H | H |
| 548 | 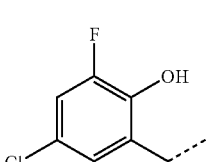 | H | H | Cl | OCF3 | H | H |
| 549 | 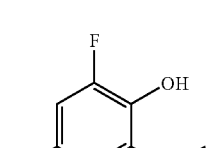 | H | H | Me | F | H | H |
| 550 | 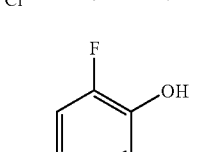 | H | H | Me | Cl | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 551 | 4-Cl, 2-F, 6-OH-phenyl-CH2- | H | H | Me | Me | H | H |
| 552 | 4-Cl, 2-F, 6-OH-phenyl-CH2- | H | H | Me | Et | H | H |
| 553 | 4-Cl, 2-F, 6-OH-phenyl-CH2- | H | H | Me | OMe | H | H |
| 554 | 4-Cl, 2-F, 6-OH-phenyl-CH2- | H | H | Me | OEt | H | H |
| 555 | 4-Cl, 2-F, 6-OH-phenyl-CH2- | H | H | Me | CF3 | H | H |
| 556 | 4-Cl, 2-F, 6-OH-phenyl-CH2- | H | H | Me | OCF3 | H | H |
| 557 | 4-Cl, 2-F, 6-OH-phenyl-CH2- | H | H | OMe | F | H | H |
| 558 | 4-Cl, 2-F, 6-OH-phenyl-CH2- | H | H | OMe | Cl | H | H |
| 559 | 4-Cl, 2-F, 6-OH-phenyl-CH2- | H | H | OMe | Me | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 560 | 4-Cl-2-F-6-(CH2)-phenol (F ortho to OH, Cl para) | H | H | OMe | Et | H | H |
| 561 | 4-Cl-2-F-6-(CH2)-phenol | H | H | OMe | OMe | H | H |
| 562 | 4-Cl-2-F-6-(CH2)-phenol | H | H | OMe | OEt | H | H |
| 563 | 4-Cl-2-F-6-(CH2)-phenol | H | H | OMe | CF3 | H | H |
| 564 | 4-Cl-2-F-6-(CH2)-phenol | H | H | OMe | OCF3 | H | H |

The present invention also encompasses pharmaceutically acceptable acid adducts of the aforementioned piperidine compounds. As examples of suitable acids there may be mentioned inorganic acids such as hydrochloric acid, hydrobromic acid, sulfuric acid, phosphoric acid and carbonic acid, or organic acids such as maleic acid, citric acid, malic acid, tartaric acid, fumaric acid, methanesulfonic acid, trifluoroacetic acid and formic acid.

The invention further encompasses $C_1$-$C_6$ alkyl adducts of cyclic amine compounds such as, for example, 1-(4-chlorobenzyl)-1-methyl-4-[{2-benzimidazolyl}aminomethyl]piperidinium iodide. As preferred examples of alkyl groups for $C_1$-$C_6$ alkyl adducts there may be mentioned methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, 2-methylpentyl and 1-ethylbutyl, among which methyl and ethyl are especially preferred. As preferred examples of counter anions to the ammonium cation there may be mentioned halide anions such as fluoride, chloride, bromide and iodide.

The compounds represented by formula (I) of the invention may contain optically active carbons, and therefore include racemic forms and all possible optically active forms.

When $R^3$ of the compound represented by formula (I) is hydrogen, the structure represented by formula (I) will be indistinguishable from the structure represented by formula (II) below, and formulas (I) and (II) will represent the same compound. When $R^3$ is hydrogen, therefore, the invention includes both the structures of formula (I) and formula (II).

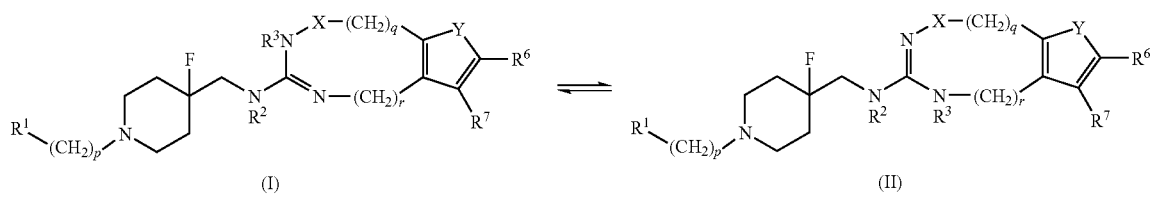

The compounds represented by formula (I) may be produced by any of the general production processes described below.

<Production Process 1>

One equivalent of a compound represented by the following formula (III):

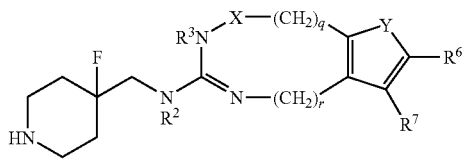

(wherein $R^2, R^3, X, q, r, Y, R^6$ and $R^7$ have the same definitions as in formula (I))

is treated with 0.1-10 equivalents of an alkylating reagent represented by the following formula (IV):

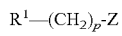

$$R^1-(CH_2)_p-Z \quad (IV)$$

(wherein $R^1$ and p have the same definitions as in formula (I), and Z represents a halogen, alkylsulfonyloxy or arylsulfonyloxy)

in the presence or in the absence of a solvent, to produce a compound represented by formula (I).

The reaction of Production Process 1 may be smoothly carried out using a base containing an inorganic salt such as potassium carbonate, calcium carbonate or sodium hydrogen carbonate, an amine such as triethylamine, diisopropylethylamine or pyridine, or a polymer supporting base such as (piperidinomethyl)polystyrene, (morpholinomethyl)polystyrene, (diethylaminomethyl)polystyrene or poly(4-vinylpyridine).

The reaction of Production Process 1 will sometimes be accelerated by addition of an iodide such as potassium iodide or sodium iodide.

The compounds of formula (III) may be synthesized by known processes described in the relevant literature.

<Production Process 2>

One equivalent of an aldehyde represented by the following formula (V):

$$R^1-(CH_2)_{p-1}-CHO \quad (V)$$

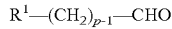

(where $R^1$ and p have the same respective definitions as in formula (I))

is treated with 0.1-10 equivalents of a compound represented by formula (III), in the presence or in the absence of a solvent, to produce a compound represented by formula (I).

The reaction of Production Process 2 is generally referred to as reductive amination, and the reaction may be conducted under conditions with a catalyst containing a metal such as palladium, platinum, nickel or rhodium, a hydride complex such as aluminum lithium hydride, sodium borohydride, sodium cyanoborohydride or sodium triacetoxyborohydride, catalytic hydrogenation with borane, or electrolytic reduction.

<Production Process 3>

One equivalent of a compound represented by the following formula (VI):

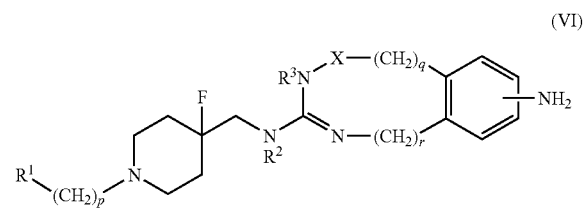

(wherein $R^1, p, R^2, R^3, X, q$ and r have the same definitions as in formula (I))

is treated with 0.1-10 equivalents of a carboxylic acid or its reactive derivative, in the presence or in the absence of a solvent, to produce a compound represented by formula (I).

Reactive derivatives of carboxylic acids include highly reactive carboxylic acid derivatives ordinarily used in organic synthetic chemistry, such as, for example, acid halides, acid anhydrides or mixed anhydrides.

The reaction of Production Process 3 may be smoothly carried out using an appropriate amount of a dehydrating agent such as molecular sieve and a condensation agent such as dicyclohexylcarbodiimide (DCC), N-ethyl-N'-(3-dimethylaminopropyl)carbodiimide (EDCI or WSC), carbodiimidazole (CDI), N-hydroxysuccinimide (HOSu), N-hydroxybenzotriazole (HOBT), benzotriazol-1-yloxytris(pyrrolidino)phosphonium, hexafluorophosphate (PyBOP), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(5-norbornane-2,3-dicarboxyimide)-1,1,3,3-tetramethyluronium tetrafluoroborate (TNTU), O-(N-succinimidyl)-1,1,3,3-tetramethyluronium tetrafluoroborate (TSTU) or bromotris(pyrrolidino)phosphonium hexafluorophosphate (PyBrop).

The reaction of Production Process 3 may be smoothly carried out using a base indicated for Production Process 1.

The compounds of formula (VI) may be synthesized by known processes described in the relevant literature.

<Production Process 4>

One equivalent of a compound represented by the following formula (VII):

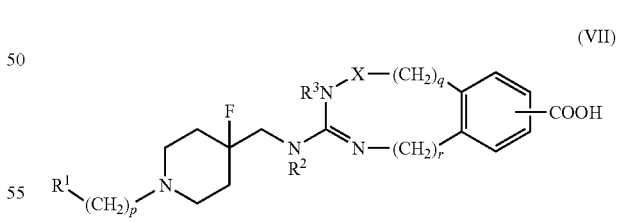

(wherein $R^1, p, R^2, R^3, X, q$ and r have the same definitions as in formula (I))

is treated with 0.1-10 equivalents of an amine, in the presence or in the absence of a solvent, to produce a compound represented by formula (I).

The reaction of Production Process 4 can proceed smoothly by using appropriate amounts of the same dehydrating agents, condensation agents or bases used in Production Process 3.

The compounds of formula (VII) may be synthesized by known processes described in the relevant literature.

<Production Process 5>

One equivalent of a compound represented by the following formula (VIII):

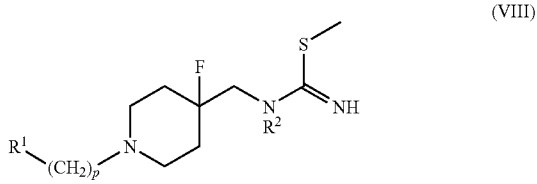

(wherein $R^1$, $R^2$ and p have the same definitions as in formula (I))

is treated with 0.1-10 equivalents of an acid anhydride represented by the following formula (IX):

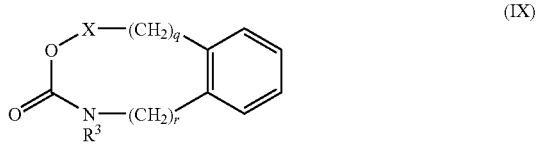

(wherein $R^3$, q and r have the same definitions as in formula (I), and X represents CO)

in the presence or in the absence of a solvent, to produce a compound represented by formula (I).

The reaction of Production Process 5 may be smoothly carried out using a base indicated for Production Process 1.

The compounds of formula (VIII) and (IX) may be synthesized by known processes described in the relevant literature.

<Production Process 6>

One equivalent of a compound represented by the following formula (X):

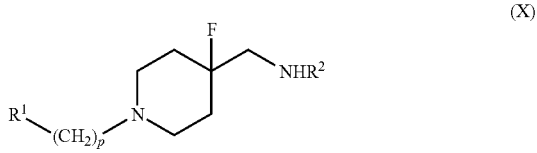

(wherein $R^1$, $R^2$ and p have the same definitions as in formula (I))

is treated with 0.1-10 equivalents of a sulfanyl or sulfinyl compound represented by the following formula (XI):

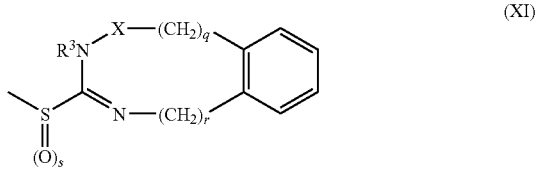

(wherein $R^3$, X, q and r have the same definitions as in formula (I), and s represents 0 or 1), in the presence or in the absence of a solvent, to produce a compound represented by formula (I).

The reaction of Production Process 6 may be smoothly carried out using a base indicated for Production Process 1, or a suitable acid (hydrochloric acid, sulfuric acid, acetic acid, benzoic acid, toluenesulfonic acid, methanesulfonic acid or the like).

The compounds of formula (X) and (XI) may be synthesized by known processes described in the relevant literature.

When the compounds of each of Production Processes 1-6 contain functional groups which react with the substrates used under the respective reaction conditions or functional groups which generally can adversely affect reactions in organic synthetic chemistry, such functional groups may be protected with appropriate known protective groups, and then subjected to the reaction of the production processes and subsequently deprotected using known steps, to obtain the compounds of formula (I).

The compounds of the invention may also be produced by utilizing known reactions ordinarily employed in organic synthetic chemistry, such as alkylation, acylation or reduction, for further conversion of (one or more of) the substituents of the compounds produced by Production Processes 1-6.

In each of Production Processes 1-6, the reaction may be conducted using a halogenated carbon compound such as dichloromethane or chloroform, an aromatic hydrocarbon such as benzene or toluene, an ether such as diethyl ether or tetrahydrofuran, an ester such as ethyl acetate, an aprotic polar solvent such as dimethylformamide, dimethylsulfoxide or acetonitrile, or an alcohol such as methanol, ethanol or isopropyl alcohol.

In each of Production Processes 1-6 the reaction temperature is in the range of −78° C. and +150° C., and preferably between 0° C. and 100° C. Upon completion of the reaction, ordinary separation and purification procedures such as concentration, filtration, extraction, solid phase extraction, recrystallization or chromatography may be employed to isolate the piperidine derivatives represented by formula (I). These may then be converted to pharmaceutically acceptable acid adducts or $C_1$-$C_6$ alkyl adducts by ordinary methods.

The compounds represented by formula (I), their pharmaceutically acceptable acid adducts or their pharmaceutically acceptable $C_1$-$C_6$ alkyl adducts may be used in therapeutically effective doses together with pharmaceutically acceptable carriers and/or diluents for preparation of pharmaceutical compositions, as drugs for inhibiting binding of CCR3 ligands such as eotaxins to CCR3 on target cells, as drugs with activity of inhibiting the physiological effects of binding of CCR3 ligands such as eotaxins to their target cells, and as therapeutic and/or prophylactic agents for diseases believed to be associated with CCR3. Specifically, the 4,4-(disubstituted)piperidine derivatives represented by formula (I), their pharmaceutically acceptable acid adducts or their pharmaceutically acceptable $C_1$-$C_6$ alkyl adducts may be administered orally or parenterally, such as intravenously, subcutaneously, intramuscularly, percutaneously or intrarectally.

The dosage form for oral administration may be, for example, tablets, pills, granules, powder, a solution, a suspension, capsules or the like.

Tablets may be molded by an ordinary method using, for example, an excipient such as lactose, starch or microcrystalline cellulose, a binder such as carboxymethyl cellulose, methyl cellulose or polyvinylpyrrolidone and a disintegrator such as sodium alginate, sodium hydrogen-carbonate or lauryl sodium sulfate.

Pills, powders or granules may also be molded by ordinary methods using the aforementioned excipients and the like. Solutions and suspensions may be formed by ordinary methods using, for example, glycerin esters such as tricaprylin or triacetin and/or alcohols such as ethanol. Capsules may be prepared by filling capsules made of gelatin or the like with granules, powders and/or solutions.

Dosage forms for subcutaneous, intramuscular or intravenous administration include injections in the form of aqueous or non-aqueous solutions. Aqueous solutions may employ, for example, physiological saline. Non-aqueous solutions may employ, for example, propylene glycol, polyethylene glycol, olive oil or ethyl oleate, with addition of antiseptic agents and/or stabilizers or the like as necessary. Injections are sterilized by appropriate filtration through a bacteria-capturing filter or treatment with addition of a sterilizing agent.

As examples of dosage forms for percutaneous administration there may be mentioned ointments and creams, among which ointments may be formed using fats and oils such as castor oil or olive oil, or vaseline, and creams may be formed by ordinary methods using emulsifying agents such as fatty oils or diethylene glycol or sorbitan monofatty acid esters.

For intrarectal administration there may be used ordinary suppositories such as gelatin soft capsules.

The dosage of a piperidine derivative of the invention, its pharmaceutically acceptable acid adduct or its pharmaceutically acceptable $C_1$-$C_6$ alkyl adduct will differ depending on the type of disease, the route of administration, the age and gender of the patient and the severity of the disease, but it will normally be 1-500 mg/day per adult.

EXAMPLES

The present invention will now be explained in greater detail through the following examples. The invention, however, is not limited to the compounds listed in the examples. The compound numbers referred to in the examples are those assigned to the compounds listed as preferred examples in the tables. The example numbers correspond to the compound numbers of the compounds produced in those examples.

Reference Example 1

Synthesis of
6-aza-1-oxaspiro[2.5]octane-6-carboxylic acid tert-butyl ester

After dissolving 60% NaH-in-oil (5.28 g, 132 mmol) in DMSO (dimethylsulfoxide) (250 mL) cooled to 0° C., trimethylsulfonium iodide (29.0 g, 132 mmol) was added. The reaction mixture was then raised to room temperature and the mixture was stirred for 40 minutes. N-Boc-piperidone (Boc=tert-butoxycarbonyl) (25.0 g, 125 mmol) was added to the reaction mixture, which was then stirred at room temperature for 1 hour and then at 55° C. for 1.5 hours. Next, the reaction mixture was poured into ice-cooled water (500 mL) and was extracted with AcOEt (ethyl acetate) (500 ml×3 times). The organic layer obtained by combining the ethyl acetate layers was washed with water and then with saturated brine, and then dried over anhydrous $Na_2SO_4$. After filtration, the filtrate was concentrated to obtain 6-aza-1-oxaspiro[2.5]octane-6-carboxylic acid tert-butyl ester. The compound was identified by $^1$H-NMR. The yield was 26.4 g (99%).

$^1$H-NMR (270 MHz, $CDCl_3$): 1.40-1.49(m,2H), 1.46(s, 9H), 1.74-1.85(m,2H), 2.69(s,2H), 3.37-3.48(m,2H), 3.68-3.77(m,2H).

Reference Example 2

Synthesis of
4-fluoro-4-(hydroxymethyl)piperidinecarboxylic acid tert-butyl ester A mixed solution of 6-aza-1-oxaspiro[2.5]octane-6-carboxylic acid tert-butyl ester (10.0 g, 46.9 mmol) in benzene-ether (2:1) (750 mL) was cooled to 0° C., and after adding $BF_3.OEt_2$ (29.6 mL, 234 mmol) to the solution, it was stirred 1 hour. The reaction mixture was poured into ice-cooled 1N NaOH (500 ml) and stirred. After extraction with AcOEt (500 ml×3 times), the extract was washed with water and then with saturated brine, and finally dried over anhydrous $MgSO_4$. The solvent was distilled off, and the crude product was purified by silica gel column chromatography (30% AcOEt/hexane) to obtain 4-fluoro-4-(hydroxymethyl)piperidinecarboxylic acid tert-butyl ester. The compound was identified by $^1$H-NMR. The yield was 4.26 g (39%).

$^1$H-NMR (270 MHz, $CDCl_3$): 1.45-1.70(m,2H), 1.46(s, 9H), 1.83-1.93(m,2H), 3.10(brt,2H,J=11.3 Hz), 3.60(d,2H, J=20.3 Hz), 3.94(brd,2H,J=11.3 Hz)

Reference Example 3

Synthesis of
4-(aminomethyl)-4-fluoropiperidinecarboxylic acid tert-butyl ester

After dissolving 4-fluoro-4-(hydroxymethyl)piperidinecarboxylic acid tert-butyl ester (4.26 g, 18.3 mmol) in THF (183 mL), the solution was cooled to 0° C. Triphenylphosphine (7.19 g, 27.4 mmol) and DIAD (diisopropyl azodicarboxylate) (5.39 mL, 27.4 mmol) were then added to the solution. After stirring for 20 minutes, phthalimide (4.03 g, 27.4 mmol) was added and the mixture was stirred at room temperature for 2.5 hours. The reaction mixture was concentrated, and the crude product was crudely purified by silica gel column chromatography (20% AcOEt/hexane) to obtain 4-[(1,3-dioxoisoindolin-2-yl)methyl]-4-fluoropiperidinecarboxylic acid tert-butyl ester.

The 4-[(1,3-dioxoisoindolin-2-yl)methyl]-4-fluoropiperidinecarboxylic acid tert-butyl ester was dissolved in ethanol (200 mL), and then hydrazine monohydrate (10.0 mL) was added. After stirring at room temperature for 2 hours, the precipitated solid was filtered out and the filtrate was concentrated under reduced pressure. The obtained crudely purified product was further purified by silica gel column chromatography (5% MeOH/$CH_2Cl_2$) to obtain 4-(aminomethyl)-4-fluoropiperidinecarboxylic acid tert-butyl ester. The compound was identified by $^1$H-NMR. The yield was 3.23 g (76%).

$^1$H-NMR (270 MHz, $CDCl_3$): 1.36-1.70(m,4H), 1.46(s, 9H), 1.80-1.93(m,2H), 2.79(d,2H,J=20.3 Hz), 3.08(brt,2H, J=11.0 Hz), 3.95(brd,2H,J=11.0 Hz).

<Synthesis of Benzimidazole Derivatives>

Reference Example 4

Synthesis of 4-fluoro-4-({[5-(methoxycarbonyl)benzimidazol-2-yl]amino}methyl)piperidinecarboxylic acid tert-butyl ester 4-(Aminomethyl)-4-fluoropiperidinecarboxylic acid tert-butyl ester (3.23 g, 13.9 mmol) was dissolved in acetonitrile (50 ml). A solution of thiocarbonyldiimidazole (2.73 g, 15.3 mmol) and triethylamine (4.27 ml, 30.6 mmol) in acetonitrile (20 ml) was then added dropwise at 0° C. of a period of 3 minutes. After stirring at room temperature for 1 hour, 3,4-diaminobenzoic acid methyl ester dihydrochloride (3.66 g, 15.3 mmol) was added to the reaction mixture, and the mixture was stirred at 50° C. for 5.5 hours. Diisopropylcarbodiimide (0.32 ml, 15.3 mmol) was further added and the mixture was stirred overnight at 50° C. Saturated brine was added to the obtained reaction mixture, extraction was performed with ethyl acetate (200 ml), and the organic layer was dried overnight over anhydrous sodium sulfate. After filtration with a desiccant (anhydrous sodium sulfate) and concentration of the filtrate, the obtained brown oil was purified by silica gel column chromatography ($CH_2Cl_2$/MeOH=49:1→19:1) to obtain 4-fluoro-4-({[5-(methoxycarbonyl)benzimidazol-2-yl]amino}methyl)piperidinecarboxylic acid tert-butyl ester. The yield was 0.838 g (60%).

$^1$H-NMR (270 MHz, $CDCl_3$): δ1.43-1.95(m,5H), 1.45(s, 9H), 3.06(brt,2H,J=11.3 Hz), 3.50(s,3H), 3.67(d,2H,J=21.6 Hz), 3.83-3.96(m,2H), 3.90(s,2H), 7.28(d,1H,J=8.4 Hz), 7.81(dd,1H,J=1.6, 8.4 Hz), 7.90(brs,1H).

Reference Example 5

Synthesis of 2-{[(4-fluoro-4-piperidyl)methyl]amino} benzimidazole-5-carboxylic acid methyl ester hydrochloride After dissolving 4-fluoro-4-({[5-(methoxycarbonyl)benzimidazol-2-yl]amino}methyl)piperidinecarboxylic acid tert-butyl ester (1.2 g, 2.95 mmol) in MeOH (6 ml), a 4N hydrogen chloride/1,4-dioxane solution (3.7 ml, 14.7 mmol) was added and the mixture was stirred at room temperature overnight. The reaction mixture was concentrated to obtain 2-{[(4-fluoro-4-piperidyl)methyl]amino}benzimidazole-5-carboxylic acid methyl ester hydrochloride. The compound was identified by LC-MS.

Yield: 1.14 g (quantitative), M+1=307.1

Example 1-1

Synthesis of 2-[({1-[(3,5-dichloro-2-hydroxyphenyl) methyl]4-fluoro-4-piperidyl}methyl)amino]benzimidazole-5-carboxylic acid methyl ester (Compound No. 1-1)

After adding 3,5-dichloro-2-hydroxybenzaldehyde (57.3 mg, 0.3 mmol) and sodium triacetoxyborohydride (64 mg, 0.3 mmol) to a solution of 2-{[(4-fluoro-4-piperidyl)methyl] amino}benzimidazole-5-carboxylic acid methyl ester hydrochloride (30 mg, 0.1 mmol) in DMF-acetic acid (10:1) (1.0 ml), the mixture was stirred at room temperature overnight. Methanol (1.0 ml) was added to the reaction mixture to suspend the reaction, and after stirring for 1 hour, the solution was passed through SCX (Bond Elute SCX500MG: cationic ion-exchange resin, Varian). The SCX was washed with methanol and then with a mixed solution of chloroform/methanol (1/1), and elution was performed with a 0.5 N ammonia-dioxane solution to obtain 2-[({1-[(3,5-dichloro-2-hydroxyphenyl)methyl]4-fluoro-4-piperidyl}methyl)amino] benzimidazole-5-carboxylic acid methyl ester. The compound was identified by LC-MS.

Yield: 5.1 mg (11%), M+1=481.1

Examples 1-2, 1-3, 1-4, 1-5, 1-6

Compound Nos. 1-2, 1-3, 1-4, 1-5, and 1-6 were synthesized in the same manner as Example 1-1 using the corresponding reactants. The results are shown in Table 9.

TABLE 9

| Compound No. 1- | Yield (mg) | Yield: (%) | MW | M + 1 |
| --- | --- | --- | --- | --- |
| 1 | 5.1 | 11 | 480.1 | 481.1 |
| 2 | 3.8 | 9 | 446.2 | 447.1 |
| 3 | 4.5 | 10 | 446.2 | 447.2 |
| 4 | 10.4 | 24 | 424.2 | 425.2 |
| 5 | 20.3 | 45 | 449.2 | 450.2 |
| 6 | 9.3 | 21 | 452.2 | 453.1 |

<Synthesis of quinazolin-4-one Derivatives (1)>

Reference Example 6

Synthesis of 4-[({[(fluoren-9-ylmethoxy)carbonylamino]thioxomethyl}amino)methyl]-4-fluoropiperidinecarboxylic acid tert-butyl ester After dissolving 4-(aminomethyl)-4-fluoropiperidinecarboxylic acid tert-butyl ester (1071 mg, 4.61 mmol) in tetrahydrofuran (10 ml), FmocNCS (9-fluorenylmethoxycarbonyl isothiocyanate) (1425 mg, 5.07 mmol) was added and the mixture was stirred at room temperature overnight. After completion of the reaction, the mixture was concentrated and purified by silica gel column chromatography (hexane/ethyl acetate=10/1-5/1) to obtain 4-[({[(fluoren-9-ylmethoxy)carbonylamino] thioxomethyl}amino)methyl]-4-fluoropiperidinecarboxylic acid tert-butyl ester. The compound was identified by LC-MS.

Yield: 1896 mg (80%), M+1=514.2

Reference Example 7

Synthesis of 4-{[(aminothioxomethyl)amino]methyl}-4-fluoropiperidinecarboxylic acid tert-butyl ester After dissolving 4-[({[(fluoren-9-ylmethoxy)carbonylamino]thioxomethyl}amino)methyl]-4-fluoropiperidinecarboxylic acid tert-butyl ester (1896 mg, 3.69 mmol) in DMF (15 ml), piperidine (1.8 ml, 18.5 mmol) was added and the mixture was stirred at room temperature overnight. After completion of the reaction, water (100 ml) was added and extraction was performed with ethyl acetate (100 ml×3 times). The extracted organic layer was washed with water (300 ml×2 times) and then with saturated brine; dried over anhydrous sodium sulfate, and then filtered and concentrated. It was subsequently purified by silica gel column chromatography (hexane/ethyl acetate=1/1, ethyl acetate) to obtain 4-{[(aminothioxomethyl)amino]methyl}-4-fluoropiperidinecarboxylic acid tert-butyl ester. The compound was identified by LC-MS. Yield: 900 mg (84%), M+1=292.1

Reference Example 8

Synthesis of 4-((2Z)-3-amino-2-aza-3-methylthioprop-2-enyl)-4-fluoropiperidinecarboxylic acid tert-butyl ester hydroiodide After dissolving 4-{[(aminothioxomethyl)amino]methyl}-4-fluoropiperidinecarboxylic acid tert-butyl ester (900 mg, 3.09 mmol) in tetrahydrofuran (15 ml) and adding methyl iodide (202 μl, 3.24 mmol), the mixture was stirred at room temperature overnight. After completion of the reaction, the mixture was concentrated and dried under reduced pressure in a desiccator to obtain 4-((2Z)-3-amino-2-aza-3-methylthioprop-2-enyl)-4-fluoropiperidinecarboxylic acid tert-butyl ester hydroiodide. The compound was identified by LC-MS.
Yield: 1280 mg (96%), M+1=306.1

Reference Example 9

Synthesis of 4-fluoro-4-{[(4-oxohydroquinazolin-2-yl)amino]methyl}piperidinecarboxylic acid tert-butyl ester After dissolving 4-((2Z)-3-amino-2-aza-3-methylthioprop-2-enyl)-4-fluoropiperidinecarboxylic acid tert-butyl ester hydroiodide (1280 mg, 2.95 mmol) in DMA (15 ml), triethylamine (0.616 ml, 4.42 mmol) and isatoic anhydride (1440 mg, 8.85 mmol) were added and the mixture was stirred at 80° C. for 2 hours. A 2N sodium hydroxide aqueous solution (10 ml) was then added to suspend the reaction. Water (100 ml) was added and extraction was performed with ethyl acetate (100 ml×3 times). The extracted organic layer was washed with water (100 ml×2) and then with saturated brine, dried over anhydrous sodium sulfate, and subsequently filtered and concentrated. It was then purified by silica gel column chromatography (hexane/ethyl acetate=1/1-1/2) to obtain 4-fluoro-4-{[(4-oxohydroquinazolin-2-yl)amino]methyl}piperidinecarboxylic acid tert-butyl ester. The compound was identified by LC-MS.
Yield: 473 mg (42%), M+1=377.1

Reference Example 10

Synthesis of 2-{[(4-fluoro-4-piperidyl)methyl]amino}hydroquinazolin-4-one hydrochloride 2-{[(4-Fluoro-4-piperidyl)methyl]amino} hydroquinazolin-4-one hydrochloride was obtained from 4-fluoro-4-{[(4-oxohydroquinazolin-2-yl)amino]methyl} piperidinecarboxylic acid tert-butyl ester in the same manner as Reference Example 5
Yield: 183 mg (83%), M+1=277.1

Example 2-1

Synthesis of 2-[({1-[(3,5-dichloro-2-hydroxyphenyl)methyl]-4-fluoro-4-piperidyl}methyl)amino]hydroquinazolin-4-one (Compound No. 2-1)

2-[({1-[(3,5-Dichloro-2-hydroxyphenyl)methyl]-4-fluoro-4-piperidyl}methyl)amino]hydroquinazolin-4-one was obtained from 2-{[(4-fluoro-4-piperidyl)methyl]amino}hydroquinazolin-4-one hydrochloride in the same manner as Example 1.
Yield: 5.2 mg (38%), M+1=451.1

Example 2-2-2-4

Compound Nos. 2-2, 2-3 and 2-4 were synthesized in the same manner as Example 2-1 using the corresponding reactants. The results are shown in Table 10.

TABLE 10

| Compound No. 2- | Yield (mg) | Yield (%) | MW | M + 1 |
|---|---|---|---|---|
| 1 | 5.2 | 38 | 450.1 | 451.1 |
| 2 | 6.0 | 48 | 416.1 | 417.1 |
| 3 | 1.4 | 17 | 416.2 | 417.1 |
| 4 | 2.8 | 18 | 394.2 | 395.1 |
| 210 | 18.0 | 37 | 465.4 | 465.1 |
| 211 | 37.0 | 50 | 469.3 | 469.1 |
| 227 | 29.0 | 62 | 430.9 | 431.1 |
| 228 | 29.0 | 60 | 434.9 | 435.1 |
| 275 | 226 | 30 | 530.2 | 529.2 |
| 283 | 300 | 94 | 508.4 | 508.3 |
| 290 | 120 | 35 | 479.4 | 479.2 |
| 291 | 80 | 28 | 479.4 | 479.1 |
| 292 | 120 | 43 | 479.4 | 479.1 |
| 299 | 95 | 30 | 483.3 | 483.2 |
| 302 | 11 | 3 | 495.4 | 495.1 |
| 511 | 7.0 | 23 | 452.9 | 453.1 |
| 513 | 7.0 | 23 | 448.9 | 449.1 |
| 596 | 95 | 28 | 544.3 | 545.1 |
| 600 | 160 | 55 | 483.3 | 483.1 |
| 603 | 170 | 60 | 479.4 | 479.1 |
| 604 | 52 | 18 | 495.4 | 495.1 |
| 607 | 32 | 40 | 466.3 | 466.3 |
| 610 | 68 | 24 | 479.4 | 479.1 |
| 613 | 116 | 40 | 493.4 | 493.1 |
| 619 | 20 | 41 | 495.4 | 495.1 |
| 628 | 60 | 19 | 529.4 | 529.3 |
| 636 | 120 | 34 | 591.5 | 591.1 |
| 648 | 95 | 30 | 558.5 | 558.1 |

<Synthesis of Substituted Isatoic Anhydrides (1)>

Reference Example 11

Synthesis of 6-fluoroisatoic anhydride

After dissolving 5-fluoroanthranilic acid (2.03 g, 13.09 mmol) in THF (40 mL), triphosgene (4.08 g) was added and the mixture was stirred at room temperature overnight. After completion of the reaction, the solvent was removed and the residue was dried over under reduced pressure. The residue obtained after drying under reduced pressure was washed with acetone and then with hexane, and subsequently dried under reduced pressure in a desiccator to obtain 6-fluoroisatoic anhydride. The compound was identified by LC-MS.
Yield: 1.516 g (61%), M+1=181.9.

The following isatoic anhydride derivatives were synthesized in the same manner as Reference Example 11 using the corresponding reactants.

6-Methylisatoic anhydride: Yield=1.251 g (70%), M+1=178.0.

6-Nitroisatoic anhydride: Yield=0.889 g (43%), M+1=208.9.

6-Methylisatoic anhydride: Yield=1.251 g (70%), M+1=178.0.

5-Carboxylisatoic anhydride: Yield=1.352 g (65%), M+1=208.0.

6-Fluoroisatoic anhydride: M+1=182.0.

6-Hydroxyisatoic anhydride: M+1=180.0.

6-Methoxyisatoic anhydride: M+1=194.0.

5-Methylisatoic anhydride: M+1=178.0.

6-Acetamideisatoic anhydride: Yield=0.4 g (9%),
$^1$H-NMR (200 MHz, DMSO): δ2.05(s,3H), 7.05(d,1H), 7.85(dd,1H), 8.25(d,1H), 10.15(s,1H).

Reference Example 12

Synthesis of 2-{[(4-fluoro-4-piperidyl)methyl]amino}hydroquinazolin-4-one hydrochloride analog The isatoic anhydride synthesized in Reference Example 11 was used to synthesize the following analogs, in the same manner as Reference Example 9 and Reference Example 10.

6-Fluoro-2-{[(4-fluoro-4-piperidyl)methyl]amino}hydroquinazolin-4-one hydrochloride
Yield: 310 mg (95%), M+1=295.0.
6-Methyl-2-{[(4-fluoro-4-piperidyl)methyl]amino}hydroquinazolin-4-one hydrochloride
Yield: 257 mg (62%), M+1=291.1.

Examples 2-210, 2-211, 2-227, 2-228, 2-511 and 2-513

Compound Nos. 2-210, 2-211, 2-227, 2-228, 2-511 and 2-513 were synthesized in the same manner as Example 1, using the corresponding 2-{[(4-fluoro-4-piperidyl)methyl]amino}hydroquinazolin-4-one hydrochloride analogs obtained in Reference Example 12. The results are shown in Table 10.

<Synthesis of quinazolin-4-one derivatives (2)>

Reference Example 13

Synthesis of 2-(4-fluoro-piperidin-4-ylmethyl)-isoindole-1,3-dione

Trifluoroacetic acid (30 ml) was added to a solution of 4-[(1,3-dioxoisoindolin-2-yl)methyl]-4-fluoropiperidinecarboxylic acid tert-butyl ester (23 g) in dichloromethane (250 ml), and the mixture was stirred at room temperature for 5 hours. The obtained solution was concentrated, and the residue was recrystallized from ether to obtain a trifluoroacetic acid salt of 2-(4-fluoro-piperidin-4-ylmethyl)-isoindole-1,3-dione.

Yield: 22.6 g
$^1$H-NMR (200 MHz, DMSO): δ1.90-2.20(m,4H), 3.00(m, 2H), 3.35(m,2H), 3.85(d,2H,J=20 Hz), 7.92(m,4H), 8.75(bs, 1H), 9.05(bs,1H)

Reference Example 14

Synthesis of 2-[1-(3,5-dichloro-2-hydroxy-benzyl)-4-fluoro-piperidin-4-ylmethyl]-isoindole-1,3-dione Triethylamine (9 ml) was added to a solution of a trifluoroacetic acid salt of 2-(4-fluoro-piperidin-4-ylmethyl)-isoindole-1,3-dione (22.6 g) in dichloromethane (300 ml). The obtained solution was stirred for 5 minutes, and then 3,5-dichloro-2-hydroxy-benzaldehyde (12.4 g) and NaBH(OAc)$_3$ (19 g) were added and the mixture was stirred at room temperature for 3 hours. The obtained solution was washed with a saturated aqueous solution of sodium hydrogen carbonate, the dichloromethane was concentrated out, and the residue was recrystallized from ether to obtain 2-[1-(3,5-dichloro-2-hydroxy-benzyl)-4-fluoro-piperidin-4-ylmethyl]-isoindole-1,3-dione.

Yield: 20.7 g
$^1$H-NMR (200 MHz, DMSO): δ1.80-2.20(m,4H), 2.30(m, 2H), 2.78(m,2H), 3.74(s,2H), 3.85(d,2H,J=20 Hz), 7.10(d, 1H,J=3 Hz), 7.35(d,1H,J=3 Hz), 7.92(m,4H).

Reference Example 15

Synthesis of 2-(4-aminomethyl-4-fluoro-piperidin-1-ylmethyl)-4,6-dichlorophenol

Hydrazine (10 ml) was added to a solution of 2-[1-(3,5-dichloro-2-hydroxy-benzyl)-4-fluoro-piperidin-4-ylmethyl]-isoindole-1,3-dione (20.7 g) in ethanol (600 ml). The obtained solution was stirred for 5 hours while heating to reflux, and then subjected to heated filtration. The filtrate was concentrated, water was added to the residue, and then extraction with dichloromethane was followed by concentration. The obtained residue was recrystallized from isopropyl ether-pentane to obtain 2-(4-aminomethyl-4-fluoro-piperidin-1-ylmethyl)-4,6-dichlorophenol.

Yield: 12.7 g
$^1$H-NMR (200 MHz, DMSO): δ1.60-1.75(m,1H), 1.75-1.95(m,3H), 2.30-2.40(m,2H), 2.50-2.85(m,4H), 3.80(d,2H, J=20 Hz), 7.15(d,1H,J=3 Hz), 7.45(d,1H,J=3 Hz).

Reference Example 16

Synthesis of N-{[({1-[(3,5-dichloro-2-hydroxyphenyl)methyl](4-piperidyl)}methyl)amino]thioxomethyl}(fluoren-9-ylmethoxy)carboxamide N-{[({1-[(3,5-Dichloro-2-hydroxyphenyl)methyl](4-piperidyl)}methyl)amino]thioxomethyl}(fluoren-9-ylmethoxy)carboxamide was obtained in the same manner as Reference Example 6 using 2-(4-aminomethyl-4-fluoro-piperidin-1-ylmethyl)-4,6-dichlorophenol (6 g).

Yield: 9.1 g
$^1$H-NMR (200 MHz, DMSO): δ1.75-1.85(m,4H), 2.35(m, 2H), 2.80(m,2H), 3.75(s,2H), 4.00(dd,2H), 4.35(dd,2H), 7.15(d,1H), 7.40(m,5H), 7.90(m,4H), 10.15(t,1H), 11.5(s, 1H).

Reference Example 17

Synthesis of [1-(3,5-dichloro-2-hydroxy-benzyl)-4-fluoropiperidin-4-ylmethyl]-thiourea

[1-(3,5-Dichloro-2-hydroxy-benzyl)-4-fluoropiperidin-4-ylmethyl]-thiourea was obtained in the same manner as Reference Example 7 using N-{[({1-[(3,5-dichlorb-2-hydroxyphenyl)methyl](4-piperidyl)}methyl)amino]thioxomethyl}(fluoren-9-ylmethoxy)carboxamide (9.1 g).

Yield: 4.95 g
$^1$H-NMR (200 MHz, DMSO): δ1.75-1.85(m,4H), 2.35-2.45(m,2H), 2.75-2.85(m,2H), 3.75(dd,2H), 3.80(s,2H), 6.45(bs,2H), 7;10(bs,1H), 7.15(d,1H), 7.45(d,1H), 7.80(t,1H).

Reference Example 18

Synthesis of 1-[1-(3,5-dichloro-2-hydroxy-benzyl)-4-fluoropiperidin-4-ylmethyl]-2-methyl-isothiourea 1-[1-(3,5-Dichloro-2-hydroxy-benzyl)-4-fluoropiperidin-4-ylmethyl]-2-methyl-isothiourea was obtained in the same manner as Reference Example 8 using [1-(3,5-dichloro-2-hydroxy-benzyl)-4-fluoropiperidin-4-ylmethyl]-thiourea (4.95 g).

$^1$H-NMR (200 MHz, DMSO): δ1.75-1.85(m,4H), 2.35-2.40(m,2H), 2.55(s,3H), 2.75-2.85(m,2H), 3.70(dd,2H), 3.85(s,2H), 6.15(bs,2H), 7.15(d,1H), 7.40(d,1H), 9.20(bs,2H).

Examples 2-283

Triethylamine (0.15 ml) and 6-acetamideisatoic anhydride (0.32 g, 0.63 mmol) were added to a solution of 1-[1-(3,5-dichloro-2-hydroxybenzyl)-4-fluoropiperidin-4-ylmethyl]-2-methyl-isothiourea (0.5 g, 0.98 mmol) in THF (50 ml), and the mixture was stirred for 24 hours while heating to reflux. Water was added to the obtained solution, and the obtained precipitate was filtered out and washed with methanol to obtain Compound No. 2-283.

Yield: 300 mg (94%), M+1=508.3.

$^1$H-NMR (200 MHz, DMSO-d6): 1.75-1.85(m,4H), 2.05 (s,3H), 2.35-2.40(m,2H), 2.75-2.85(m,2H), 3.65(dd,2H), 3.85(s,2H), 6.40(bs,1H), 7.15(d,1H), 7.20(d,1H), 7.40(d, 1H), 7.75(d,1H), 8.25(s,1H), 10.0(bs,1H), 10.95(bs,1H).

Examples 2-607

Concentrated hydrochloric acid (3 ml) was added to a solution of the compound (Example No. 2-283) (90 mg, 0.17 mmol) in ethanol, and the mixture was stirred for 6 hours while heating to reflux. Aqueous ammonia was added to the obtained solution, and extraction was performed with dichloromethane. The obtained precipitate was filtered out and washed with methanol to obtain Compound No. 2-607.

Yield: 3.2 mg (40%), M+1=466.3.

$^1$H-NMR (200 MHz, DMSO-d6): 1.85-2.00(m,4H), 2.75-2.85(m,2H), 3.05-3.15(m,2H), 3.65(dd,2H), 4.15(s,2H), 6.50 (bs,1H), 6.95(d,1H), 7.00(d,1H), 7.45(d,1H), 7.55(d,1H).

<Synthesis of Substituted Isatoic Anhydrides (2)>

Reference Example 19

Synthesis of N-(3,4-dimethylphenyl)-2-hydroxyimino-acetamide

An aqueous solution (500 ml) of hydroxylamine (90 g, 0.41 mmol) was added to a mixture of an aqueous solution (2.5 ml) containing chloral (73.8 g, 0.41 mol) and sodium sulfate (1066 g), and an aqueous solution (600 ml) containing 3,4-dimethylamine (50 g, 0.41 mol) and concentrated hydrochloric acid (35.4 ml), and the mixture was stirred for 1 hour while heating to reflux. The obtained heated solution was filtered, and the obtained precipitate was washed with water and then with dichloromethane to obtain N-(3,4-dimethylphenyl)-2-hydroxyimino-acetamide.

Yield: 63 g (80%)

Reference Example 20

Synthesis of 4,5-dimethyl-1H-indole-2,3-dione

N-(3,4-Dimethylphenyl)-2-hydroxyimino-acetamide (30 g, 0.156 mmol) was slowly added to an aqueous solution (17 ml) of concentrated sulfuric acid (85 ml), and the mixture was stirred at 85° C. for 2 hours. The obtained solution was poured into ice-cooled water, and the precipitated orange solid was filtered out. The obtained solid was dissolved in a 10% aqueous sodium hydroxide solution, activated carbon was added, and the mixture was stirred. The obtained solution was filtered, and acetic acid was used to adjust the pH to 3 to obtain 4,5-dimethyl-1H-indole-2,3-dione as crystals.

Yield: 9.8 g (30%)

$^1$H-NMR (200 MHz, DMSO-d6): 2.25(s,3H), 2.55(s,3H), 6.95(d,2H), 7.50(d,2H), 10.55(bs,1H).

Reference Example 21

Synthesis of 6-amino-2,3-dimethylbenzoic acid

An aqueous solution (80 ml) containing 4,5-dimethyl-1H-indole-2,3-dione (9.8 g, 0.056 mmol) and sodium hydroxide (8.1 g, 0.2 mol) was heated to 85° C., and then 10% aqueous hydrogen peroxide (43 ml) was slowly added. The obtained solution was stirred at 85° C. for 2 hours, cooled to room temperature, and filtered. The filtrate was adjusted to pH 1 using sulfuric acid, to obtain 6-amino-2,3-dimethylbenzoic acid as crystals.

Yield: 3.6 g (38%)

$^1$H-NMR (200 MHz, DMSO-d6): 2.05(s,3H), 2.15(s,3H), 6.50(d,2H), 6.92(d,2H).

Reference Example 22

Synthesis of 5,6-dimethylisatoic anhydride 5,6-Dimethylisatoic anhydride was synthesized in the same manner as Reference Example 11, using 6-amino-2,3-dimethylbenzoic acid (1 g, 6 mmol).

Yield: 500 mg (92%)

$^1$H-NMR (200 MHz, DMSO): 2.25(s,3H), 2.55(s,3H), 6.92(d,2H), 7.50(d,2H), 10.65(bs,1H).

The following isatoic anhydrides were synthesized in the same manner as Reference Examples 19-22, using the corresponding reactants.

5-Methyl-6-fluoro-isatoic anhydride
$^1$H-NMR (200 MHz, DMSO-d6): 2.45(s,3H), 6.75(dd, 1H), 7.45(dd,1H), 11.0(bs,1H).

5-Methyl-6-bromo-isatoic anhydride
$^1$H-NMR (200 MHz, DMSO): 2.75(s,3H), 6.85(d,1H), 7.95(d,1H), 10.75(bs,1H).

6-(N,N-Dimethylamino-sulfonyl)-isatoic anhydride
$^1$H-NMR (200 MHz, DMSO-d6): 2.65(s,6H), 7.35(d,1H), 8.05(s,1H), 8.15(d,1H), 11.2(bs,1H).

6-Methoxy-7-methyl-isatoic anhydride
M+1=208.0

5-Methyl-6-methoxy-isatoic anhydride
M+1=208.0

6,7-Dimethyl-isatoic anhydride
$^1$H-NMR (200 MHz, DMSO): 2.24(s,3H), 2.29(s,3H), 6.91(s,1H), 7.66(s,1H), 10.60(bs,1H).

5,7-Dimethyl-isatoic anhydride
$^1$H-NMR (200 MHz, DMSO): 6.91(s,1H), 6.79(s,1H), 2.56(s,3H), 2.32(s,3H).

6-Ethyl-isatoic anhydride
$^1$H-NMR (200 MHz, DMSO): 7.73(s,1H), 7.65(d,1H), 7.09(d,1H), 2.64(q,2H); 1.18(t,3H)

6-Ethoxy-isatoic anhydride
$^1$H-NMR (200 MHz, DMSO): 1.35(t,3H), 4.05(q,2H), 7.05(d,1H), 7.35(d,1H), 7.45(dd,1H), 10.5(bs,1H).

5-Methyl-8-fluoro-isatoic anhydride
$^1$H-NMR (200 MHz, DMSO-d6): 2.56(s,3H), 7.05(dd, 1H), 7.55(dd,1H)

5,8-Dimethyl-isatoic anhydride
$^1$H-NMR (200 MHz, DMSO-d6): 2.27(s,3H), 2.56(s,3H), 7.00(d,1H), 7.45(d,1H).

6-Isopropyl-isatoic anhydride
$^1$H-NMR (200 MHz, DMSO): 7.73 (s, 1H), 7.65 (d, 1H), 7.10 (d, 1H), 2.95 (h, 1H), 1.20 (d, 6H)

6-Sulfonylphenyl-isatoic anhydride
$^1$H-NMR (200 MHz, DMSO-d6—): 7.35(d,1H), 7.65(m, 3H), 8.00 (m, 2H), 8.25 (dd, 1H), 8.35 (d, 1H), 11.30 (s, 1H)

Examples 2-290, 291, 292, 299, 302, 596, 600, 603, 604, 610, 613, 619, 636, 648

Compound Nos. 2-290, 2-291, 2-292, 2-299, 2-302, 2-596, 2-600, 2-603, 2-604, 2-610, 2-613, 2-619, 2-636, 2-648 were synthesized in the same manner as Example 2-283, using the corresponding isatoic anhydrides obtained in Reference Example 22, and 1-[1-(3,5-dichloro-2-hydroxy-benzyl)-4-fluoropiperidin-4-ylmethyl]-2-methyl-isothiourea.

Compound No. 2-290: Yield=120 mg (35%), M+1=479.2.
$^1$H-NMR (200 MHz, DMSO-d6): 1.85-1.95(m,4H), 2.15 (s,3H), 2.35-2.40(m,2H), 2.65(s,3H), 2.75-2.85(m,2H), 3.65 (dd,2H), 3.75(s,2H), 6.32(bs,1H), 7.10(d,1H), 7.15(d,1H), 7.35(d,1H), 7.40(d,1H), 10.50(bs,1H).

Compound No. 2-291: Yield=80 mg (28%), M+1=479.1
$^1$H-NMR (200 MHz, DMSO-d6): 1.69-1.90(m,4H), 2.30 (s,3H), 2.45-2.33(m,2H), 2.63(s,3H), 2.76-2.82(m,2H), 3.57 (t,1H), 3.68(d,1H), 3.81(s,2H), 6.34(brs,1H), 6.69(s,1H), 6.93(s,1H), 7.15(d,1H), 7.39(d,1H).

Compound No. 2-292: Yield=120 mg (43%), M+1=479.1.
$^1$H-NMR (200 MHz, DMSO-d6): 1.82-1.99(m,2H), 2.24-2.27(d,4H), 2.39(m,1H), 2.50(s,3H), 2.76-2.81(m,2H), 3.56 (d,1H), 3.67(d,1H), 3.80(s,2H), 6.35(bs,1H), 7.10(s,1H), 7.15(d,1H), 7.39(d,1H), 7.62(s,1H), 10.60(bs,1H).

Compound No. 2-299: Yield=95 mg (30%), M+1=483.2.
$^1$H-NMR (200 MHz, DMSO-d6): 1.85-1.95(m,4H), 2.35-2.45(m,2H), 2.55(s,3H), 2.75-2.85(m,2H), 3.65(dd,2H), 3.85 (s,2H), 6.40(bs,1H), 7.10(m,2H), 7.35(d,1H), 7.4(dd,1H), 10.10(bs,1H).

Compound No. 2-302: Yield=11 mg (3%), M+1=495.1.
$^1$H-NMR (200 MHz, DMSO-d6): 1.85-2.05(m,4H), 2.49 (s,3H), 3.05-3.25(m,2H), 3.25-3.48(m,2H), 3.12-3.86(s,5H), 4.34(bs,2H), 7.23(d,1H), 7.49(s,1H), 7.66(s,1H).

Compound No. 2-596: Yield=95 mg (28%), M+1=545.1.
$^1$H-NMR (200 MHz, DMSO-d6): 1.85-1.95(m,4H), 2.35-2.40(m,2H), 2.55(s,3H), 2.75-2.85(m,2H), 3.65(dd,2H), 3.85 (s,2H), 6.50(bs,1H), 7.10(d,1H), 7.15(d,1H), 7.45(d,1H), 7.70(d,1H), 10.80(bs,1H)

Compound No. 2-600: Yield=160 mg (55%), M+1=483.1.
$^1$H-NMR (200 MHz, DMSO-d6): 1.85-1.95(m,4H), 2.3.5-2.40(m,2H), 2.65(s,3H), 2.75-2.85(m,2H), 3.7(dd,2H), 3.8(s, 2H), 6.6(m,1H), 6.85(dd,1H), 7.15(d,1H), 7.35(dd,1H), 7.40 (d,1H).

Compound No. 2-603: Yield=170 mg (60%), M+1=479.1.
$^1$H-NMR (200 MHz, DMSO-d6): 1.85-1.95(m,4H), 2.35 (s,3H), 2.35-2.40(m,2H), 2.6(s,3H), 2.75-2.85(m,2H), 3.70 (dd,2H), 3.8(s,2H), 6.4(m,1H), 6.75(d,1H), 7.15(d,1H), 7.35 (d,1H), 7.40(d,1H).

Compound No. 2-604: Yield=52 mg (18%), M+1=495.1.
$^1$H-NMR (200 MHz, DMSO-d6): 1.85-2.05(m,4H), 2.05 (s,3H), 2.35-2.40(m,2H), 2.75-2.85(m,2H), 3.65(dd,2H), 3.80-3.87(brs,5H), 6.28(brs,1H), 7.13(brs,2H), 7.30(s,1H), 7.40(s,1H), 10.66(brs,1H).

Compound No. 2-610: Yield=68 mg (24%), M+1=479.1.
$^1$H-NMR (200 MHz, DMSO-d6): 1.21(t,3H), 1.65-2.00 (m,4H), 2.30-2.55(m,2H), 2.65(q,2H), 2.75-2.90(m,2H), 3.70(dd,2H), 3.84(s,2H), 6.30(brs,1H), 7.13(s,1H), 7.22(d, 1H), 7.37-7.50(m,2H).

Compound No. 2-613: Yield=116 mg (40%), M+1=493.1.
$^1$H-NMR (200 MHz, DMSO-d6): 1.21(d,6H), 1.65-2.00 (m,4H), 2.30-2.55(m,2H), 2.70-3.00(m,3H), 3.70(dd,2H), 3.84(s,2H), 6.40(bs,1H), 7.13(s,1H), 7.22(d,1H), 7.40(s,1H), 7.50(d,1H).

Compound No. 2-619: Yield=20 mg (41%), M+1=495.1.
$^1$H-NMR (200 MHz, DMSO-d6): 1.25(t,3H), 1.85-1.95 (m,4H), 2.35-2.45(m,2H), 2.75-2.85(m,2H), 3.60(dd,2H), 3.80(s,2H), 4.05(q,2H), 6.30(bs,1H), 7.15(s,1H), 7.20(m, 2H), 7.25(d,1H), 7.40(d,1H), 10.80(bs,1H).

Compound No. 2-636: Yield=120 mg (34%), M+1=591.1.
$^1$H-NMR (200 MHz, DMSO-d6): 1.75-2.00(m,4H), 2.30-2.55(m,2H), 2.70-2.80(m,2H), 3.70(dd,2H), 3.75(s,2H), 6.80 (bs,1H), 7.13(s,1H), 7.45(m,2H), 7.65(m,3H), 7.90(m,3H), 8.85(s,1H).

Compound No. 2-648: Yield=95 mg (30%), M+1=558.1.
$^1$H-NMR (200 MHz, DMSO-d6): 1.85-2.05(m,4H), 2.50-2.60(m,2H), 2.75(s,6H), 2.75-2.95(m,2H), 3.65(s,2H), 3.75 (dd,2H), 6.75(bs,1H), 6.80(d,1H), 7.25(d,1H), 7.50(d,1H), 7.95(d,1H), 8.45(d,1H), 11.50(bs,1H).

<Synthesis of Substituted Isatoic Anhydrides (3)>

Reference Example 23

Synthesis of 2-amino-5-methylsulfanylbenzoic acid

A 4N aqueous sodium hydroxide solution (42 m) was added to an aqueous solution (500 ml) containing 5-chloro-2-nitrobenzoic acid (50 g, 0.25 mmol). After adding an aqueous solution (150 ml) containing Na$_2$S (66 g, 0.8 mol), the mixture was stirred at 55° C. for 2.5 hours. Next, a 20% aqueous sodium hydroxide solution (50 ml) and dimethylsulfuric acid (63 ml, 0.66 mmol) were added to the obtained solution, and the mixture was stirred at 80° C. for 1 hour. Hydrochloric acid was added to the obtained solution, and the separated precipitate was filtered out and washed with ether to obtain 2-amino-5-methylsulfanylbenzoic acid.
Yield: 14 g (26%)

Reference Example 24

Synthesis of 2-amino-5-methylsulfonylbenzoic acid m-Chloro-perbenzoic acid (42.7 g, 0.165 mmol) was added to a solution of 2-amino-5-methylsulfanylbenzoic acid (12 g, 0.055 mol) in dichloromethane and acetone, and the mixture was stirred at room temperature for 3 hours. The precipitated solid was filtered out and washed with ether and dichloromethane to obtain 2-amino-5-methylsulfonylbenzoic acid.
Yield: 4 g (30%)
$^1$H-NMR (200 MHz, DMSO-d6): 3.15(s,3H), 6.95(dd, 1H), 7.55(bs,2H), 7.77(dd,1H), 8.25(d,1H).

Reference Example 25

Synthesis of 6-methanesulfonyl-isatoic anhydride

6-Methanesulfonyl-isatoic anhydride was synthesized in the same manner as Reference Example 11 using 2-amino-5-methylsulfonylbenzoic acid (2 g, 9.6 mmol).
Yield: 1500 mg (66%)
$^1$H-NMR (200 MHz, DMSO-d6): 3.35(s,3H), 7.35(d,1H), 8.25(dd,1H), 8.35(d,1H), 9.90(s,1H).

Example 2-628

Compound No. 2-628 was synthesized in the same manner as Example 2-607, using the isatoic anhydride obtained in Reference Example 25, and 1-[1-(3,5-dichloro-2-hydroxy-benzyl)-4-fluoropiperidin-4-ylmethyl]-2-methyl-isothiourea.
Yield: 60 mg (19%), M+1=529.3.
$^1$H-NMR (200 MHz, DMSO-d6): 1.85-2.05(m,4H), 2.45-2.55(m,2H), 2.75-2.85(m,2H), 3.15(s,3H), 3.75(s,2H), 3.85 (dd,2H,6.80(bs,1H), 7.20(m,2H), 7.45(d,1H), 8.0(d,1H).

<Synthesis of quinazolin-4-one derivatives (3)>

Reference Example 26

Synthesis of
6-bromo-2-thioxo-2,3-dihydro-1H-quinazolin-4-one

Thionyl chloride (20 ml) was added to 2-amino-5-bromobenzoic acid (4.3 g, 19 mmol), and the mixture was stirred for 1 hour while heating to reflux. The thionyl chloride was removed under reduced pressure, and acetone (50 ml) was added to the residue. Ammonium thiocyanate (2.2 g) was added to the obtained solution, and the mixture was stirred at room temperature for 4 hours. The separated precipitate was filtered out and washed with acidic water and then with acetone to obtain 6-bromo-2-thioxo-2,3-dihydro-1H-quinazolin-4-one.
Yield: 3.95 g (80%)

Reference Example 27

Synthesis of
6-bromo-2-methylsulfanyl-3H-quinazolin-4-one

A saturated aqueous sodium hydroxide solution was added to an aqueous solution (50 ml) containing 6-bromo-2-thioxo-2,3-dihydro-1H-quinazolin-4-one (4.3 g, 16.7 mmol), and the mixture was stirred at room temperature for 5 hours. The separated precipitate was filtered out and washed with acetone to obtain 6-bromo-2-methylsulfanyl-3H-quinazolin-4-one.
Yield: 2.5 g (55%)
$^1$H-NMR (200 MHz, DMSO-d6): 2.65(s,3H), 7.45(d,1H), 7.85(d,1H), 8.05(s,1H), 11.55(bs,1H).

Reference Example 28

Synthesis of
6-bromo-2-methylsulfinyl-3H-quinazolin-4-one m-Chloro-perbenzoic acid (3.3 g, 19 mmol) was added to a solution of 6-bromo-2-methylsulfanyl-3H-quinazolin-4-one (2.5 g, 9.2 mmol) in dichloromethane (200 ml), and the mixture was stirred at room temperature for 24 hours. The obtained solution was washed with an aqueous potassium carbonate solution and then concentrated, and the precipitated solid was filtered out and washed with aqueous hydrochloric acid to obtain 6-bromo-2-methylsulfinyl-3H-quinazolin-4-one.
Yield: 0.4 g (15%)
$^1$H-NMR (200 MHz, DMSO-d6): 2.95(s,3H), 7.45(d,1H), 8.00(d,1H), 8.25(s,1H), 11.55(bs,1H).

Example 2-275

6-Bromo-2-methylsulfinyl-3H-quinazolin-4-one (0.4 g, 1.39 mmol) was added to a solution of 2-(4-aminomethyl-4-fluoropiperidin-1-ylmethyl)-4,6-dichlorophenol (0.43 g, 1.4 mmol) in DMF, and the mixture was stirred for 8 hours while heating to reflux. Water was added to the obtained solution, and the separated precipitate was filtered out and recrystallized from methanol to synthesize Compound No. 2-275.
Yield: 226 mg (30%), M+1=529.2.
$^1$H-NMR (200 MHz, DMSO-d6): 1.80-1.90(m,4H), 2.35-2.40(m,2H), 2.80(m,2H), 3.65(dd,2H), 3.80(s,2H), 6.65(bs, 1H), 7.15(d,1H), 7.20(d,1H), 7.42(d,1H), 7.70(d,1H), 7.95(d,1H).

<Synthesis of benzothiadiazine-1,1-dione derivatives>

Reference Example 29

Synthesis of 7-fluoro-2H,4H-benzo[e]1,2,4-thiadiazine-1,1,3-trione

After dissolving chlorosulfonyl isocyanate (3.29 mL, 37.8 mmol) in nitroethane (45 mL), the mixture was cooled to −80° C. A solution of 4-fluoroaniline (3.50 g, 31.5 mmol) in nitromethane (5 mL) was then added dropwise thereto over a period of 10 minutes. The reaction mixture was raised to 0° C., and aluminum chloride (5.33 g, 40.0 mmol) was added. After heating to reflux for 30 minutes, the reaction mixture was cooled to room temperature and poured into ice water (120 mL). The precipitated crystals were filtered out and dried to obtain 7-fluoro-2H,4H-benzo[e]1,2,4-thiadiazine-1,1,3-trione.
Yield: 3.72 g (55%), M+1=217.0.
The following 2H,4H-benzo[e]1,2,4-thiadiazine-1,1,3-trione derivative was synthesized in the same manner as Reference Example 29.
7-methyl-2H,4H-benzo[e]1,2,4-thiadiazine-1,1,3-trione: Yield: 4.24 g (67%), M+1=213.0.

Reference Example 30

Synthesis of 2-amino-5-fluorobenzenesulfonamide

After suspending 7-fluoro-2H,4H-benzo[e]1,2,4-thiadiazine-1,1,3-trione (3.00 g, 13.9 mmol) in 50% sulfuric acid (90 mL), the mixture was stirred at 130° C. for 1 hour. The reaction mixture was cooled in an ice bath while adding 40% aqueous sodium hydroxide for neutralization. The aqueous solution was concentrated under reduced pressure to 200 mL, and the precipitate was filtered out. It was then suspended in ethyl acetate (100 mL), and the insoluble portion was filtered out. The filtrate was concentrated under reduced pressure and dried to obtain 2-amino-5-fluorobenzenesulfonamide.
Yield: 2.27 g (86%), M+1=191.0.
The following 2-amino-benzenesulfonamide derivative was synthesized in the same manner as Reference Example 30. 2-Amino-5-methylbenzenesulfonamide: Yield 958 mg (55%), M+1=187.0.

Reference Example 31

Synthesis of 2-bromo-4,5-dimethylnitrobenzene

After measuring out 10.02 g of 4,5-dimethyl-2-nitroaniline (60.3 mmol) into a 300 mL round-bottomed flask equipped with a magnetic stirrer, 30 mL of 48% aqueous hydrobromic acid and 30 mL of water were added, and the mixture was vigorously stirred. The suspension was orange. The orange suspension was cooled on an ice water-salt bath, and then an aqueous solution of 4.422 g of sodium nitrite (64.1 mmol) in 24 mL of water was added dropwise to the suspension while keeping the liquid temperature from exceeding 5° C. Completion of the dropwise addition resulted in conversion of the reaction mixture to a brown solution. Stirring was continued on the ice water bath.

Next, 30 mL of 48% aqueous hydrobromic acid and 11.85 g of copper(I) bromide (82.6 mmol) were placed in a 1 L Erlenmeyer flask equipped with a magnetic stirrer, and the previously obtained brown solution was added dropwise over a period of 5 minutes while cooling and stirring on an ice water bath. After completion of the dropwise addition, the mixture was stirred for 20 minutes on the ice-water bath, and then heated on a 80° C. oil bath while vigorously stirring.

Heating was terminated after 1 hour, and upon stirring overnight at room temperature, the reaction mixture was extracted with ethyl acetate (300 mL×2 times), and the extracted organic layers were combined and washed with 5N hydrochloric acid, saturated sodium bicarbonate water and saturated brine in that order. The organic layer was dried over anhydrous sodium sulfate, and then the desiccant was removed by filtration under reduced pressure and the filtrate was concentrated to obtain a yellowish brown solid. The yellowish brown solid was purified by silica gel column chromatography (Hex-EtOAc/10:1) to obtain brown needle-like crystals. The brown needle-like crystals were recrystallized from hexane to obtain yellow needle-like crystals. Yield: 6.637 g (47.9%)

$^1$H-NMR (270 MHz, CDCl$_3$): δ2.29(3H,s), 2.31(3H,s), 7.49(1H,s), 7.69(1H,s).

Reference Example 32

Synthesis of 2-bromo-4,5-dimethylaniline

After measuring out 1.006 g of 2-bromo-4,5-dimethylnitrobenzene (4.375 mmol) into a 100 mL round-bottomed flask equipped with a magnetic stirrer, 10 mL of 2-methoxyethanol and 10 mL of water were added and the mixture was stirred to create a suspension. After adding 2.799 g of sodium hydrosulfite (10.07 mmol) to the suspension, it was heated on a 100° C. oil bath while vigorously stirring. After 2.5 hours, the resulting faint yellow suspension was heated and stirred, while adding 10 mL of water until the insoluble portion disappeared to produce a faint yellow solution. To the faint yellow solution there was added dropwise 10 mL of concentrated hydrochloric acid over a period of 5 minutes, after which the mixture was refluxed for 20 minutes.

Next, the temperature of the reaction mixture was lowered to room temperature, and upon adding sodium carbonate in powder form to neutralize the reaction mixture, a faint brownish white precipitate separated at approximately pH 7-8. The collected precipitate was dried to obtain the target substance as a white solid.

Yield: 0.832 g (95.0%).

$^1$H-NMR (270 MHz, CDCl$_3$): δ2.13(6H,s), 6.59 (1H,s), 7.16(1H,s).

Reference Example 33

Synthesis of 5-bromo-7,8-dimethyl-2H,4H-benzo[e] 1,2,4-thiadiazine-1,1,3-trione

The title compound was obtained in the same manner as Reference Example 29.

Yield: 5.27 g (83%), M+1=304.9.

$^1$H-NMR (270 MHz, CD$_3$OD): δ7.69(1H,s), 2.55(3H,s), 2.31(3H,s).

Reference Example 34

Synthesis of 7,8-dimethyl-2H,4H-benzo[e]1,2,4-thiadiazine-1,1,3-trione

5-Bromo-7,8-dimethyl-2H,4H-benzo[e]1,2,4-thiadiazine-1,1,3-trione (5.27 g, 17.3 mmol) was suspended in methanol (60 mL), and then ammonium formate (5.45 g, 86.5 mmol, 5 eq) was added and nitrogen substitution was performed. Next, 10% palladium-carbon powder (1.84 g, 1.73 mmol, 10 mol %) was added and the mixture was heated to reflux for 4 hours. The reaction mixture was cooled to room temperature and filtered through celite. The filtrate was cooled on ice and the precipitated crystals were filtered out and dried to obtain the title compound.

Yield: 3.66 g (94%), M+1=227.0.

$^1$H-NMR (270 MHz, CD$_3$OD): δ7.19(1H,d,J=8.3 Hz), 6.78(1H,d,J=8.3 Hz), 2.57(3H,s), 2.26(3H,s).

Reference Example 35

Synthesis of 2-amino-5,6-dimethylbenzenesulfonamide

The title compound was obtained in the same manner as Reference Example 30.

Yield: 1.98 g (61%), M+1=201.1.

$^1$H-NMR (270 MHz, DMSO-d6): δ7.20(2H,s), 6.98(1H,d, J=8.4 Hz), 6.55(1H,d,J=8.4 Hz), 5.98(2H,s), 2.39(3H,s), 2.10 (3H,s).

2-Amino-6-methylbenzenesulfonamide was synthesized in the same manner as Reference Examples 30-35, using 4-methyl-2-nitroaniline as the starting material.

Yield: 555 mg (45%).

$^1$H-NMR (270 MHz, DMSO): δ2.48(3H,s), 6.12(2H,s), 6.40(1H,d,J=7.0 Hz), 6.62(1H,d, J=8.1 Hz), 6.99-7.04(1H, dd,J=8.1 Hz,J=7.0 Hz), 7.19(2H,s).

Reference Example 36

Synthesis of 4-fluoro-4-{[(7-fluoro-1,1-dioxo-4H-benzo[e]1,2,4-thiadiazine-3-yl)amino] methyl}piperidinecarboxylic acid tert-butyl ester The 4-(aminomethyl)-4-fluoropiperidinecarboxylic acid tert-butyl ester (1.0 g, 4.30 mmol) synthesized in Reference Example 3 was dissolved in acetonitrile (30.0 mL), and the solution was cooled to 0° C. A solution of 1,1'-thiocarbonyldiimidazole (844 mg, 4.73 mmol) and imidazole (88 mg, 1.30 mmol) in acetonitrile (10 mL) was added dropwise thereto, and the mixture was stirred at room temperature for 2 hours. Next, 2-amino-5-fluorobenzenesulfonamide (981 mg, 5.16 mmol) and dimethylaminopyridine (630 mg, 5.16 mmol) were added to the reaction mixture which was then stirred at 80° C. overnight. Diisopropylcarbodiimide (0.662 mL, 4.30 mmol) was added thereto, and the mixture was stirred for 1 hour. The reaction mixture was cooled to room temperature and then concentrated under reduced pressure, and the residue was dissolved in ethyl acetate (50 mL). This was washed with water (20 mL) and saturated brine (20 mL), and then dried over anhydrous sodium sulfate. The residue obtained by concentration under reduced pressure was purified by silica gel column chromatography (n-hexane:ethyl acetate=3: 2→2:3) to obtain 4-fluoro-4-{[(7-fluoro-1,1-dioxo-4H-benzo[e]1,2,4-thiadiazine-3-yl)amino] methyl}piperidinecarboxylic acid tert-butyl ester.

Yield: 1.27 g (69%), M-Boc+2H=331.1.

The following compounds were synthesized in the same manner as Reference Example 36, using the corresponding 2-aminobenzenesulfonamide derivatives.

4-Fluoro-4-{[(7-methyl-1,1-dioxo-4H-benzo[e]1,2,4-thiadiazine-3-yl)amino]methyl}piperidinecarboxylic acid tert-butyl ester: Yield=133 mg (56%), M+1=327.1.

4-Fluoro-4-{[(8-methyl-1,1-dioxo-4H-benzo[e]1,2,4-thiadiazine-3-yl)amino]methyl}piperidinecarboxylic acid tert-butyl ester: Yield=989 mg (54%), M-Boc+2H=327.0.

4-Fluoro-4-{[(7,8-dimethyl-1,1-dioxo-4H-benzo[e]1,2,4-thiadiazine-3-yl)amino]methyl}piperidinecarboxylic acid tert-butyl ester: Yield=121 mg (42%), M+1=341.1.

Reference Example 37

Synthesis of 7-fluoro-3-{[(4-fluoro-4-piperidylmethyl)amino]-4H-benzo[e]1,2,4-thiadiazine-1,1-dione hydrochloride The title compound was obtained in the same manner as Reference Example 5, from 4-fluoro-4-{[(7-fluoro-1,1-dioxo-4H-benzo[e]1,2,4-thiadiazine-3-yl)amino]methyl}piperidinecarboxylic acid tert-butyl ester.

Yield: 689 mg (58%), M+1=331.0.

The following compounds were synthesized in the same manner as Reference Example 37.

7-Methyl-3-[(4-fluoro-4-piperidylmethyl)amino]-4H-benzo[e]1,2,4-thiadiazine-1,1-dione hydrochloride: Yield=136 mg (98%), M+1=327.1.

8-Methyl-3-[(4-fluoro-4-piperidylmethyl)amino]-4H-benzo[e]1,2,4-thiadiazine-1,1-dione hydrochloride: Yield=730 mg (79%), M+1=327.0.

7,8-Dimethyl-3-[(4-fluoro-4-piperidylmethyl)amino]-4H-benzo[e]1,2,4-thiadiazine-1,1-dione hydrochloride: Yield=62 mg (67%), M+1=341.1.

Examples 3-5, 3-6, 3-8, 3-9, 3-220, 3-235, 3-368, 3-507, 3-519 and 3-551

Compound Nos. 3-5, 3-6, 3-8, 3-9, 3-220, 3-235, 3-368, 307, 3-519 and 3-551 were synthesized in the same manner as Example 1, using the corresponding reactants for the 3-}[(4-fluoro-4-piperidylmethyl)amino]-4H-benzo[e]1,2,4-thiadiazine-1,1-dione hydrochloride derivatives obtained in Reference Example 37. The results are shown in Table 11.

TABLE 11

| Compound No. 3- | Yield (mg) | Yield (%) | MW | M + 1 |
| --- | --- | --- | --- | --- |
| 5 | 33.5 | 97 | 501.4 | 501.0 |
| 6 | 18.4 | 57 | 467.0 | 467.1 |
| 8 | 30.4 | 89 | 505.4 | 505.0 |
| 9 | 24.9 | 78 | 470.9 | 471.1 |
| 220 | 22.0 | 35 | 501.4 | 501.1 |
| 235 | 16.6 | 41 | 467.0 | 467.1 |
| 368 | 4.3 | 21 | 481.0 | 481.1 |
| 507 | 20.0 | 33 | 485.0 | 485.1 |
| 519 | 10.0 | 34 | 488.9 | 489.0 |
| 551 | 36.0 | 75 | 499.0 | 499.1 |

Example 4

Measurement of Inhibiting Power of Test Compounds Against Eotaxin-Induced Intracellular Calcium Concentration Increase in CCR3-Expressing Cells K562 cells stably expressing CCR3 receptor were used in the following method for measurement of the inhibiting power of compounds of the invention against intracellular calcium concentration increase.

The CCR3-expressing K562 cells' were suspended in HBSS solution (Hanks' Balanced Salt Solution, Gibco BRL) containing 10 mM HEPES (N-[2-hydroxyethyl]piperazine-N'-[2-ethanesulfonic acid]), and then 1 mM Fura-2 acetoxymethyl ester (product of Dojin Kagaku) was added and the mixture was incubated at 37° C. for 30 minutes. It was then excited at 340 nm and 380 nm, and the 340/380 ratio was monitored to measure the intracellular calcium concentration. Human eotaxin (product of Genzyme Techne) (0.5 µg/ml) was used as an agonist, and the inhibiting power of the test compound was determined by measuring the intracellular calcium concentration upon treatment of the CCR3-expressing K562 cells with the test compound 5 minutes before eotaxin stimulation, and calculating the suppression by the following formula.

Suppression(%)={1−(A−B)/(C−B)}×100

(A: Intracellular calcium concentration upon stimulation with eotaxin after treatment with test compound, B: Intracellular calcium concentration without stimulation, C: Intracellular calcium concentration upon stimulation with eotaxin without treatment with test compound)

The inhibiting power of cyclic amine derivatives of the invention was measured, and the following compounds demonstrated inhibiting power of 80% or greater at 2 µM concentration.

Compound No. 1-: 1-6

Compound No. 2-: 1-3, 210, 211, 227, 228, 275, 283, 290, 291, 299, 302, 511, 513, 596, 600, 604, 607, 610, 613, 619, 628, 636, 648.

Compound No. 3-: 5, 6, 8, 9, 220, 235, 368, 507, 519, 551

Example 5

Measurement of Inhibiting Power Against Eotaxin Binding to CCR3-Expressing Cell Membrane Fractions Human CCR3-expressing L1.2 cells were suspended in assay buffer [RPMI1640 (phenol red free), 25 mM HEPES (pH7.4), 0.1% NaN$_3$, 0.1% gelatin, 0.08% CHAPS] to prepare a 5×10$^5$/mL cell suspension. A solution of the test compound diluted with assay buffer was prepared as the test compound solution. A solution of [$^{125}$I]-labeled human eotaxin (Amersham) diluted with assay buffer to 1 µCi/mL was prepared as the labeled ligand solution. After dispensing 25 µL of the test compound solution, 25 µL of the labeled ligand solution and 50 µL of the membrane fraction suspension in that order into each well of a 96-well microplate (Falcon) covered with 0.5% BSA and stirring (100 µL of reaction solution), incubation was performed at 25° C. for 90 minutes.

After completion of the reaction, a 96-well filter plate (Millipore) containing filters immersed in 0.5% polyethyleneimine solution was used for filter filtration of the reaction mixture, with washing of the filters four times with 150 µL of cold washing buffer (assay buffer+0.5 M NaCl) (filtering was performed after adding 150 µL of cold washing buffer). The filters were blow-dried, and then 25 µL of liquid scintillator (MicroScient-O, Packard) was added to each well and the radioactivity incorporated in each membrane fraction on the filter was measured by a Top Count (Packard).

The count upon addition of 100 ng of unlabeled human eotaxin instead of the test compound was subtracted as the non-specific adsorption, to calculate the inhibiting power of the test compound against binding of human eotaxin to the CCR3 membrane fraction, with 100% as the count with no addition of the test compound.

Inhibiting power(%)={1−(A−B)/(C−B)}×100

(A: Count upon addition of test compound, B: Count upon addition of 100 ng of unlabeled human eotaxin, C: Count upon addition of [$^{125}$I]-labeled human eotaxin alone)

Example 6

Measurement of Inhibiting Power of Test Compounds on Eotaxin-Induced Cell Migration of CCR3-Expressing Cells L1.2 cells stably expressing CCR3 receptor were used to measure the inhibiting power of compounds of the invention against cell migration, by the following method.

The test compound was suspended in 0.5% BSA-containing RPMI1640 (Gibco BRL) solution and human eotaxin (product of Genzyme Techne) (20 ng/mL) was added as an agonist, and then the mixture was placed in the lower compartment of a chemotaxis chamber (Neuro Probe, Inc.) and a special filter was inserted in the upper compartment. After adding the same test compound and CCR3-expressing L1.2 cells to the upper compartment, incubation was performed at 37° C. for 2 hours.

Upon completion of the reaction, the special filter was stained with a screening blood staining solution (Diff-Quick, Kokusai Shiyaku Co., Ltd.), the absorbance at 550 nm was measured, and the suppression (%) was calculated according to the following formula.

Suppression(%)={1−(A−B)/(C−B)}×100

(A: Cell migration upon eotaxin stimulation of CCR3-expressing L1.2 cells treated with test compound, B: cell migration without stimulation, C: cell migration upon eotaxin stimulation without treatment with test compound)

Upon measurement of the suppression rates of several of the compounds of the invention in Examples 5 and 6, the inhibiting power was found to be essentially the same as in Example 4.

INDUSTRIAL APPLICABILITY

The compounds represented by formula (I) of the present invention exhibit activity which inhibits binding of CCR3 ligands such as eotaxins to their target cells and activity of inhibiting the physiological effects of binding of CCR3 ligands such as eotaxins to their target cells, and can therefore be utilized as CCR3 antagonists such as, for example, therapeutic and/or prophylactic agents for diseases at least partly caused by binding of CCR3 ligands such as eotaxins to CCR3 on target cells.

What is claimed is:

1. A 4,4-(disubstituted)piperidine derivative represented by the following formula (I):

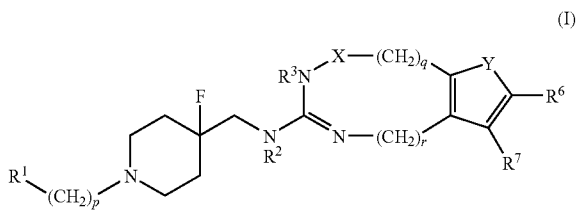

wherein $R^1$ represents phenyl, $C_3$-$C_8$ cycloalkyl or an aromatic heterocyclic group having 1-3 atoms selected from the group consisting of oxygen, sulfur and nitrogen as hetero atoms, the phenyl or aromatic heterocyclic group of $R^1$ may optionally fuse with a benzene ring or aromatic heterocyclic group having 1-3 atoms selected from the group consisting of oxygen, sulfur and nitrogen as hetero atoms to form a fused ring, the phenyl, $C_3$-$C_8$ cycloalkyl or aromatic heterocyclic group, or fused ring, in $R^1$ may be unsubstituted, or substituted with one or more substituents selected from the group consisting of halogens, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_1$-$C_6$ alkylsulfonyl, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, piperidylcarbonyl, morpholinylcarbonyl, pyrrolidinylcarbonyl, piperazinylcarbonyl, N-methoxycarbamoyl, (formyl)amino and ureido, and the substituent of the phenyl, $C_3$-$C_8$ cycloalkyl or aromatic heterocyclic group, or fused ring, of $R^1$ may be unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, $C_1$-$C_6$ alkylthio, amino, mono($C_1$-$C_6$ alkyl)amino, di($C_1$-$C_6$ alkyl)amino, pyrrolidinyl, piperidyl, $C_3$-$C_7$ lactam, carbamoyl, $C_2$-$C_7$ N-alkylcarbamoyl, $C_2$-$C_7$ alkoxycarbonyl, carboxyl, hydroxy, benzoyl, cyano, trifluoromethyl, halogen and tert-butoxycarbonylamino, provided that when $R^1$ is $C_3$-$C_8$ cycloalkyl, the substituent does not include amino, mono($C_1$-$C_6$ alkyl)amino or di($C_1$-$C_6$ alkyl)amino;

p represents an integer of 1-6;

$R^2$ and $R^3$ may be the same or different and each independently represents hydrogen, $C_1$-$C_6$ alkyl or phenyl, where the $C_1$-$C_6$ alkyl or phenyl group of $R^2$ and $R^3$ may be unsubstituted, or substituted with one or more substituents selected from the group consisting of halogens, hydroxy, $C_1$-$C_6$ alkyl, $C_2$-$C_7$ alkoxycarbonyl, amino, carbamoyl, carboxyl, cyano and $C_1$-$C_6$ alkoxy;

X represents —CO—, —SO$_2$—, —CH$_2$—, —CS— or a single bond;

q represents 0 or 1;

r represents 0 or 1;

Y represents —(R$^4$)C═C(R$^5$)—, —S— or —NR$^8$—;

R$^4$, R$^5$, R$^6$ and R$^7$ may be the same or different, and each independently represents hydrogen, a halogen, hydroxy, cyano, nitro, carboxyl, C$_1$-C$_6$ alkyl, C$_3$-C$_8$ cycloalkyl, C$_2$-C$_6$ alkenyl, C$_1$-C$_6$ alkoxy, C$_1$-C$_6$ alkylthio, C$_3$-C$_5$ alkylene, C$_2$-C$_4$ alkyleneoxy, C$_1$-C$_3$ alkylenedioxy, phenyl, phenoxy, phenylthio, phenylsulfonyl, benzyl, benzyloxy, benzoylamino, formyl, C$_2$-C$_7$ alkanoyl, C$_2$-C$_7$ alkoxycarbonyl, C$_2$-C$_7$ alkanoyloxy, C$_2$-C$_7$ alkanoylamino, C$_4$-C$_{10}$ cycloalkanoylamino, C$_3$-C$_7$ alkenoylamino, C$_1$-C$_6$ alkylsulfonyl, C$_1$-C$_6$ alkylsulfonylamino, C$_3$-C$_8$ (alkoxycarbonyl)methyl, amino, mono(C$_1$-C$_6$ alkyl)amino, di(C$_1$-C$_6$ alkyl)amino, carbamoyl, C$_2$-C$_7$ N-alkylcarbamoyl, C$_4$-C$_9$ N-cycloalkylcarbamoyl, N-phenylcarbamoyl, N-(C$_7$-C$_{12}$ phenylalkyl)carbamoyl, piperidylcarbonyl, morpholinylcarbonyl, pyrrolidinylcarbonyl, piperazinylcarbonyl, N-methoxycarbamoyl, sulfamoyl, C$_1$-C$_6$ N-alkylsulfamoyl, (formyl)amino, (thioformyl)amino, ureido or thioureido, where the aforementioned groups of R$^4$, R$^5$, R$^6$ and R$^7$ each may be independently unsubstituted, or substituted with one or more substituents selected from the group consisting of C$_1$-C$_6$ alkyl, C$_2$-C$_6$ alkenyl, C$_2$-C$_6$ alkynyl, phenyl, C$_3$-C$_5$ alkylene, C$_3$-C$_8$ cycloalkyl, C$_3$-C$_8$ cycloalkenyl, C$_1$-C$_6$ alkoxy, (C$_1$-C$_6$ alkoxy) (C$_1$-C$_6$ alkoxy), phenyl (C$_1$-C$_6$ alkoxy), C$_1$-C$_6$ alkylthio, amino, mono(C$_1$-C$_6$ alkyl)amino, di(C$_1$-C$_6$ alkyl)amino, pyrrolidinyl, piperidyl, (C$_2$-C$_7$ alkanoyl)piperidyl, C$_3$-C$_7$ lactam, carbamoyl, C$_2$-C$_7$ N-alkylcarbamoyl, C$_4$-C$_9$ N-cycloalkylcarbamoyl, N-phenylcarbamoyl, N—(C$_7$-C$_{12}$ phenylalkyl)carbamoyl, C$_2$-C$_7$ alkanoylamino, C$_2$-C$_7$ alkoxycarbonyl, carboxyl, hydroxy, benzoyl, cyano, trifluoromethyl, halogens, tert-butoxycarbonylamino, C$_1$-C$_6$ alkylsulfonyl and heterocycles or aromatic heterocycles where a heterocycle or aromatic heterocycle has 1-3 atoms selected from the group consisting of oxygen, sulfur and nitrogen as hetero atoms, and may be substituted with C$_1$-C$_6$ alkyl; and R$^8$ represents hydrogen or C$_1$-C$_6$ alkyl, where the C$_1$-C$_6$ alkyl group of R$^8$ may be unsubstituted, or substituted with one or more substituents selected from the group consisting of halogens, hydroxy, cyano, nitro, carboxyl, carbamoyl, mercapto, guanidino, C$_3$-C$_8$ cycloalkyl, C$_1$-C$_6$ alkoxy, C$_1$-C$_6$ alkylthio, phenyl where phenyl may be substituted, or substituted with one or more substituents selected from the group consisting of halogens, hydroxy, C$_1$-C$_6$ alkyl, C$_1$-C$_6$ alkoxy and benzyloxy), phenoxy, benzyloxy, benzyloxycarbonyl, C$_2$-C$_7$ alkanoyl, C$_2$-C$_7$ alkoxycarbonyl, C$_2$-C$_7$ alkanoyloxy, C$_2$-C$_7$ alkanoylamino, C$_2$-C$_7$ N-alkylcarbamoyl, C$_2$-C$_6$ alkylsulfonyl, amino, mono(C$_1$-C$_6$ alkyl)amino, di(C$_1$-C$_6$ alkyl)amino and ureido, a pharmaceutically acceptable acid adduct thereof, or a pharmaceutically acceptable C$_1$-C$_6$ alkyl adduct thereof.

2. A 4,4-(disubstituted)piperidine derivative according to claim 1, a pharmaceutically acceptable acid adduct thereof, or a pharmaceutically acceptable C$_1$-C$_6$ alkyl adduct thereof, wherein X in formula (I) is —SO$_2$—.

3. A 4,4-(disubstituted)piperidine derivative according to claim 1, a pharmaceutically acceptable acid adduct thereof, or a pharmaceutically acceptable C$_1$-C$_6$ alkyl adduct thereof, wherein X in formula (I) is —CO—.

4. A 4,4-(disubstituted)piperidine derivative according to claim 1, a pharmaceutically acceptable acid adduct thereof, or a pharmaceutically acceptable C$_1$-C$_6$ alkyl adduct thereof, wherein X in formula (I) is —CH$_2$—.

5. A 4,4-(disubstituted)piperidine derivative according to claim 1, a pharmaceutically acceptable acid adduct thereof, or a pharmaceutically acceptable C$_1$-C$_6$ alkyl adduct thereof, wherein X in formula (I) is —CS—.

6. A 4,4-(disubstituted)piperidine derivative according to claim 1, a pharmaceutically acceptable acid adduct thereof, or a pharmaceutically acceptable C$_1$-C$_6$ alkyl adduct thereof, wherein X in formula (I) is a single bond.

7. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein Y in formula (I) is —(R$^4$)C═C(R$^5$)—.

8. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein Y in formula (I) is —S—.

9. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein Y in formula (I) is —NR$^8$—.

10. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein R$^1$ in formula (I) is substituted or unsubstituted phenyl.

11. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein R$^2$ in formula (I) is hydrogen.

12. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein R$^3$ in formula (I) is hydrogen.

13. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein q=0 and r=0 in formula (I).

14. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein q=1 and r=0 in formula (I).

15. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein q=0 and r=1 in formula (I).

16. A 4,4-(disubstituted)piperidine derivative according to any one of claims 1 to 6, a pharmaceutically acceptable acid adduct thereof, or a pharmaceutically acceptable C$_1$-C$_6$ alkyl adduct thereof, wherein p=1 in formula (I).

17. A 4,4-(disubstituted)piperidine derivative according to claim 2, a pharmaceutically acceptable acid adduct thereof, or a pharmaceutically acceptable C$_1$-C$_6$ alkyl adduct thereof, wherein Y is —(R$^4$)C═C(R$^5$)—, R$^1$ is substituted or unsubstituted phenyl, R$^2$ is hydrogen, R$^3$ is hydrogen, q=0, r=0 and p=1 in formula (I).

18. A 4,4-(disubstituted)piperidine derivative according to claim 3, a pharmaceutically acceptable acid adduct thereof, or a pharmaceutically acceptable C$_1$-C$_6$ alkyl adduct thereof, wherein Y is —(R$^4$)C═C(R$^5$)—, R$^1$ is substituted or unsubstituted phenyl, R$^2$ is hydrogen, R$^3$ is hydrogen, q=0, r=0 and p=1 in formula (I).

19. A 4,4-(disubstituted)piperidine derivative according to claim 4, a pharmaceutically acceptable acid-adduct thereof, or a pharmaceutically acceptable C$_1$-C$_6$ alkyl adduct thereof, wherein Y is —(R$^4$)C═C(R$^5$)—, R$^1$ is substituted or unsubstituted phenyl, R$^2$ is hydrogen, R$^3$ is hydrogen, q=0, r=0 and p=1 in formula (I).

20. A 4,4-(disubstituted)piperidine derivative according to claim 6, a pharmaceutically acceptable acid adduct thereof, or a pharmaceutically acceptable $C_1$-$C_6$ alkyl adduct thereof, wherein Y is —($R^4$)C═C($R^5$)—, $R^1$ is substituted or unsubstituted phenyl, $R^2$ is hydrogen, $R^3$ is hydrogen, q=0, r=0 and p=1 in formula (I).

21. A 4,4-(disubstituted)piperidine derivative according to any one of claims 17 to 20, a pharmaceutically acceptable acid adduct thereof, or a pharmaceutically acceptable $C_1$-$C_6$ alkyl adduct thereof, wherein $R^4$ and $R^5$ in formula (I) may be the same or different and each is independently hydrogen, a halogen, hydroxy, cyano, nitro, carboxyl, $C_1$-$C_6$ alkyl, $C_1$-$C_6$ alkoxy, $C_2$-$C_7$ alkoxycarbonyl, $C_2$-$C_7$ alkanoylamino, $C_1$-$C_6$ alkylsulfonyl, amino, carbamoyl, $C_2$-$C_7$ N-alkylcarbamoyl, sulfamoyl or $C_1$-$C_6$ N-alkylsulfamoyl.

22. A 4,4-(disubstituted)piperidine derivative according to any one of claims 17 to 20, a pharmaceutically acceptable acid adduct thereof, or a pharmaceutically acceptable $C_1$-$C_6$ alkyl adduct thereof, wherein $R^4$ and $R^5$ in formula (I) may be the same or different and each is independently a halogen, hydroxy, cyano, nitro, $C_1$-$C_6$ alkyl, $C_1$-$C_6$ alkoxy, $C_2$-$C_7$ alkoxycarbonyl, $C_1$-$C_6$ alkylsulfonyl or $C_1$-$C_6$ N-alkylsulfamoyl.

23. A 4,4-(disubstituted)piperidine derivative according to any one of claims 17 to 20, a pharmaceutically acceptable acid adduct thereof, or a pharmaceutically acceptable $C_1$-$C_6$ alkyl adduct thereof, wherein each $R^1$ in formula (I) above may be the same or different and is independently hydrogen, a halogen, hydroxy, cyano, nitro, $C_1$-$C_6$ alkyl or $C_1$-$C_6$ alkoxy.

24. A pharmaceutical composition with CCR3 antagonism, which comprises as an effective ingredient thereof a 4,4-(disubstituted)piperidine derivative represented by formula (I) above according to any one of claims 1 to 6, a pharmaceutically acceptable acid adduct thereof; or a pharmaceutically acceptable $C_1$-$C_6$ alkyl adduct thereof; and a pharmaceutically acceptable carrier.

25. A method for treatment of a disease or condition selected from the group consisting of bronchial asthma, allergic rhinitis, atopic dermatitis, urticaria, contact dermatitis, allergic conjunctivitis, inflammatory bowel disease, Acquired Immune Deficiency Syndrome, eosinophilia, eosinophilic gastroenteritis, eosinophilic enteropathy, eosinophilic fasciitis, eosiniphilic granuloma, eosinophilic pustular folliculitis, eosinophilic pneumonia and eosinophilic leukemia comprising administering an effective amount of a compound represented by formula (I) according to any one of claims 1 to 6, a pharmaceutically acceptable acid adduct thereof or a pharmaceutically acceptable $C_1$-$C_6$ alkyl adduct thereof.

* * * * *